United States Patent
Qiao et al.

(10) Patent No.: US 11,502,260 B2
(45) Date of Patent: Nov. 15, 2022

(54) IRIDIUM COMPLEXES AND THEIR APPLICATIONS, AS WELL AS ORGANIC ELECTROLUMINESCENT DEVICES

(71) Applicant: TSINGHUA UNIVERSITY, Beijing (CN)

(72) Inventors: Juan Qiao, Beijing (CN); Jie Xue, Beijing (CN)

(73) Assignee: TSINGHUA UNIVERSITY, Beijing (CN)

( * ) Notice: Subject to any disclaimer, the term of this patent is extended or adjusted under 35 U.S.C. 154(b) by 367 days.

(21) Appl. No.: 16/479,578

(22) PCT Filed: Dec. 12, 2017

(86) PCT No.: PCT/CN2017/115586
§ 371 (c)(1),
(2) Date: Jul. 19, 2019

(87) PCT Pub. No.: WO2018/133579
PCT Pub. Date: Jul. 26, 2018

(65) Prior Publication Data
US 2019/0372028 A1    Dec. 5, 2019

(30) Foreign Application Priority Data

Jan. 22, 2017 (CN) .......................... 201710046271.4

(51) Int. Cl.
*H01L 51/00* (2006.01)
*C07F 15/00* (2006.01)
(Continued)

(52) U.S. Cl.
CPC ...... *H01L 51/0085* (2013.01); *C07F 15/0033* (2013.01); *C09K 11/06* (2013.01);
(Continued)

(58) Field of Classification Search
CPC ............. H01L 51/0085; H01L 51/0052; H01L 51/0058; H01L 51/0067; H01L 51/0072;
(Continued)

(56) References Cited

U.S. PATENT DOCUMENTS

| 4,763,966 A | 8/1988 | Suzuki et al. |
| 2010/0270916 A1* | 10/2010 | Xia ........................ H05B 33/14 546/10 |
| 2015/0218441 A1 | 8/2015 | Cho et al. |

FOREIGN PATENT DOCUMENTS

| CN | 101200635 A | 6/2008 |
| CN | 104004026 A | 8/2014 |

(Continued)

OTHER PUBLICATIONS

English language translation of CN104804045A, pp. 1-37, Sep. 14, 2021.*
(Continued)

*Primary Examiner* — Alexander C Kollias
(74) *Attorney, Agent, or Firm* — Maschoff Brennan

(57) ABSTRACT

Irridium complexes with molecular formula of $L_3Ir$, together with application thereof and organic electroluminescent devices, wherein Ir is the central metal atom and L is a ligand. The structure of these complexes is of the following formula (I):

(Continued)

The device configurations of OLED.

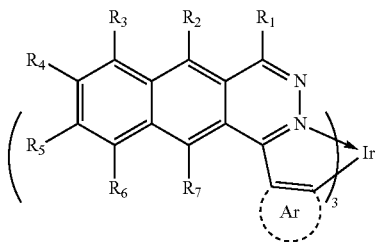

(I)

Ar is selected from substituted or unsubstituted aryl groups with 6 to 30 carbon atoms, and substituted or unsubstituted heterocyclic aryl groups with 4 to 30 carbon atoms. R1 to R7 are each independently selected from atoms or groups described herein. The substituent group on above-mentioned Ar or R1 to R7 is independently selected from F, Cl, Br, I, CHO, CN, substituted or unsubstituted alkyl or cycloalkyl groups with 1 to 30 carbon atoms, fluoroalkyl groups, alkoxy groups, and thioalkoxy groups.

12 Claims, 3 Drawing Sheets

(51) Int. Cl.
  *C09K 11/06* (2006.01)
  *H01L 51/50* (2006.01)
(52) U.S. Cl.
  CPC .............. *C09K 2211/1051* (2013.01); *C09K 2211/185* (2013.01); *H01L 51/5016* (2013.01)

(58) Field of Classification Search
  CPC . H01L 51/0074; H01L 51/5012; C09K 11/06; C09K 11/025
  See application file for complete search history.

(56) References Cited

FOREIGN PATENT DOCUMENTS

| | | | |
|---|---|---|---|
| CN | 104193783 A | 12/2014 | |
| CN | 104804045 A | 7/2015 | |
| JP | 2001-247859 A | 9/2001 | |
| JP | 2002338588 A | 11/2002 | |
| JP | 2015534547 A | 12/2015 | |
| WO | 2013/174075 A1 | 11/2013 | |

OTHER PUBLICATIONS

Xue et al. "Homoleptic Facial Ir(III) Complexes via Facile Synthesis for High-Efficiency and Low-Roll-Off Near-Infrared Organic Light Emitting Diodes over 750 nm" Chem. Mater. vol. 29, pp. 4775-4782, especially figures 1-6, (May 21, 2017).

Xin, Lijun, et al.,Efficient near-infrared-emitting cationic iridium complexes based on highly conjugated cyclometalated benzo[ g ] phthalazine derivatives. RSC Advances, Issue 53, 2015, 42354-42361.

JP Office Action in Application No. 2019-539753 dated Mar. 1, 2021.

Drechsel et al., "Influence of Material Purification by Vacuum Sublimation on Organic Optoelectronic Device Performance," SID Symposium Digest of Technical Papers, Jun. 1, 2016, vol. 37, No. 1, pp. 1692-1695.

Xue et al., "Homoleptic Facial Ir(III) Complexes via Facile Synthesis for High-Efficiency and Low-Roll-Off Near-Infrared Organic Light-Emitting Diodes over 750 nm," Chemistry of Materials, Jun. 13, 2017, vol. 29, No. 11, pp. 4775-4782.

\* cited by examiner

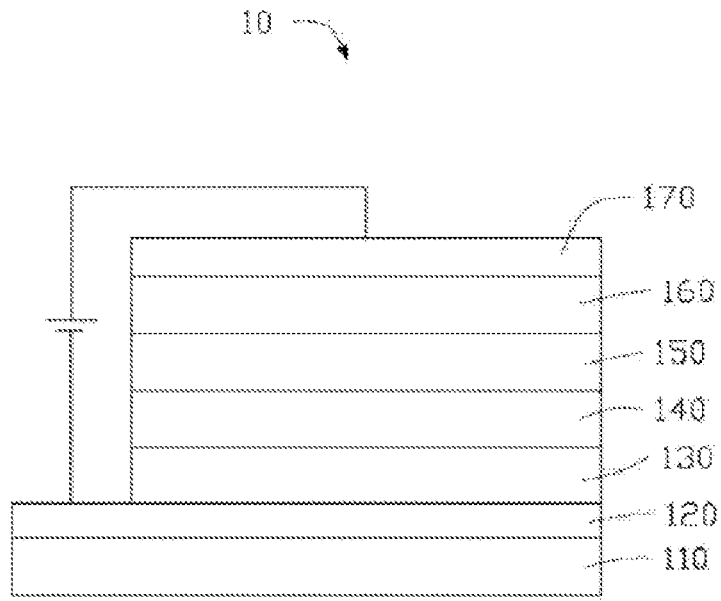
Figure 1. The device configurations of OLED.
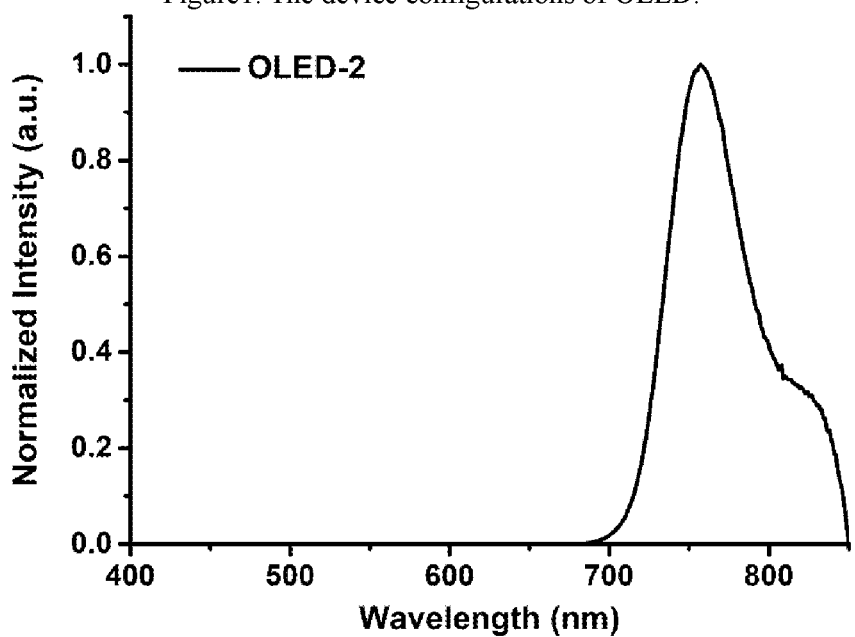
Figure 2. Electroluminescent spectrum of device OLED-2.

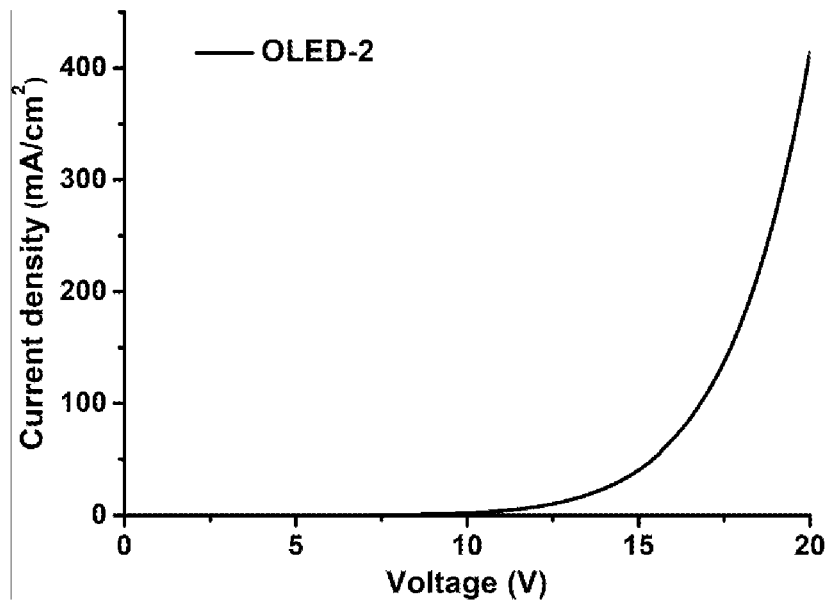
Figure 3. Current density (*J*)−voltage (*V*) characteristics of device OLED-2.
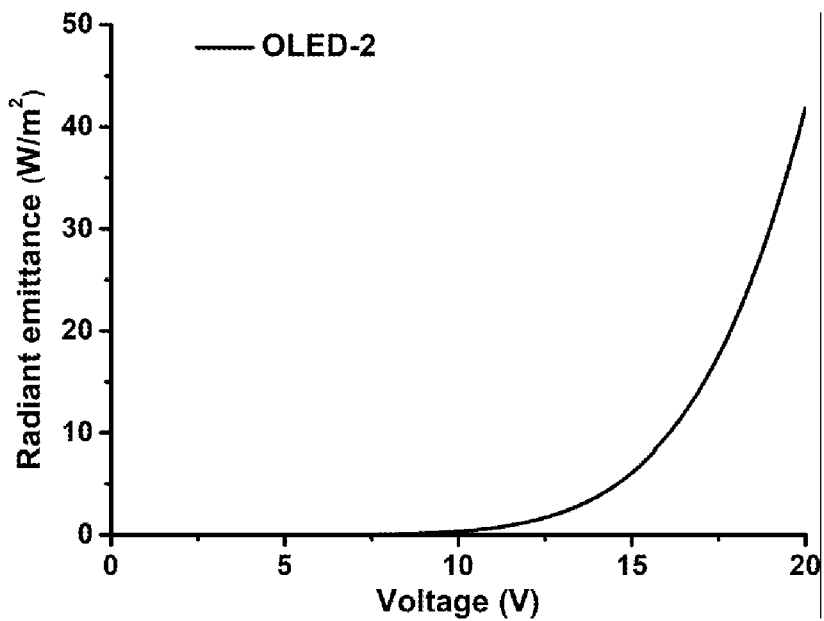
Figure 4. Radiant emittance (*R*)−voltage (*V*) characteristics of device OLED-2.

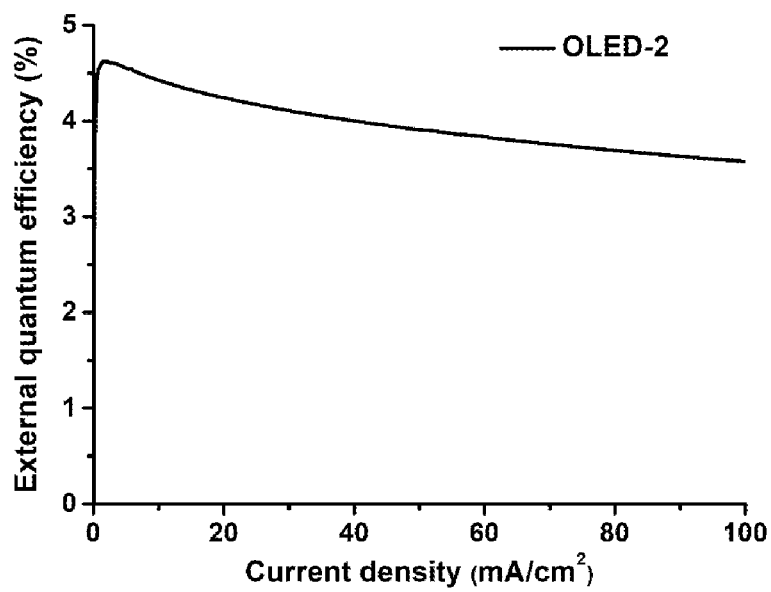
Figure 5. External quantum efficiency (EQE)–current density (*J*) characteristics of device OLED-2.

IRIDIUM COMPLEXES AND THEIR APPLICATIONS, AS WELL AS ORGANIC ELECTROLUMINESCENT DEVICES

TECHNICAL FIELD

This invention relates to a sort of novel iridium complexes, which in particular involve in near-infrared light emission and application, as well as organic electroluminescent devices.

BACKGROUND ART

Near-infrared region refers to the spectral range from 700 nm to 2500 nm. Recent years, near-infrared materials and technologies have attracted great attentions from scientific community. In terms of military demand, near-infrared technology could be used as heat source target locking, regional defense, night vision equipment, missile positioning and target tracking; in civil applications, near-infrared technology can be used for thermal efficiency analysis, temperature remote sensing transmission, short-range wireless communication and weather forecasting. In biological tissues and cells, near-infrared light can penetrate the skin into the living tissues, and can avoid the interference of the biological autofluorescence signal. Consequently, near-infrared spectrum is the best biological analysis window. Meanwhile, near-infrared spectrum is also the window of optical fiber communications because near-infrared light source with wavelengths of 1.31 and 1.55 μm can minimize the energy loss of light in the optical fiber. In addition, nearly 50% of the solar energy falls in the near-infrared region, so in order to make full use of them, it is also necessary to develop new type of near-infrared photovoltaic materials.

Iridium complexes are excellent phosphorescent dyes due to their rich photophysical properties, and have been widely used in organic light-emitting devices, sensors, and lasers. At present, Iridium complexes with visible light emission have been successfully developed and applied. However, high-efficiency near-infrared iridium complexes are still rare, which could be ascribed to the contradiction between the red shift of the emission wavelength and improvement of near-infrared luminescence efficiency. In order to make the emission wavelength of near-infrared materials red-shifted, it is necessary to reduce the energy gap between HOMO and LUMO by modifying the molecular structure. However, according to the energy gap law, the reduction of optical energy gap would lead to exponentially increased non-radiative decay rate, and thus resulting in a decrease in luminescence efficiency. How to solve the abovementioned contradiction is the key issue to develop high-efficiency iridium complexes with pure near-infrared. Especially, at present, most of the iridium complexes are heteroleptiadvised, and very few homoleptic iridium complexes have been reported in the near-infrared region.

SUMMARY OF THE INVENTION

In order to solve the abovementioned problems, this invention provides a sort of near-infrared iridium complexes with high color purity and luminescence efficiency.

The iridium complexes of this invention have a molecular formula of $L_3Ir$, wherein Ir is the central atom and L is the ligand. The specific structural formula of the iridium complexes in this invention is represented in formula (I):

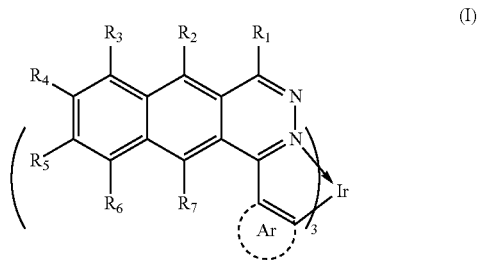

In formula (I), Ar is selected from substituted or unsubstituted aryl groups with 6 to 30 carbon atoms, as well as substituted or unsubstituted heterocyclic aryl groups with 4 to 30 carbon atoms.

Furthermore, Ar is preferably substituted or unsubstituted aryl groups with 6 to 18 carbon atoms, as well as substituted or unsubstituted heterocyclic aryl groups with 5 to 18 carbon atoms.

The heterocyclic aryl group means a monocyclic or fused ring aromatic group containing one or more hetero atoms selected from B, N, O, S, P, P=O, Si and P with 4 to 30 ring carbon atoms.

The substituent groups on aryl or heteroaryl group are independently selected from F, Cl, Br, I, CHO, CN, substituted or unsubstituted alkyl or cycloalkyl groups with 1 to 30 carbon atoms, fluoroalkyl groups, alkoxy groups or thioalkoxy groups. Furthermore, the substituent group is preferably and independently selected from F, Cl, or substituted or unsubstituted alkyl or cycloalkyl groups with 1 to 10 carbon atoms, fluoroalkyl groups, alkoxy groups or thioalkoxy groups.

Further, Ar mentioned above may preferably be the following substituted or unsubstituted groups: thiophene, benzothiophene, benzene, naphthalene, anthracene, phenanthrene, pyrene, furan, benzofuran, thiazole, benzothiazole, isothiazole, benzoisothiazole, pyrrole, benzopyrrole, imidazole, benzimidazole, pyrazole, benzopyrazole, oxazole, benzoxazole, isoxazole, benzisoxazole, pyridine, pyrimidine, benzopyrimidine, pyrazine, benzopyrazine, pyridazine, benzopyridazine, quinoline, isoquinoline, purine, pteridine, indole.

In formula (I), $R_1$ to $R_7$ are each independently selected from hydrogen atoms, halogen atoms, cyano groups, nitro groups, hydroxyl groups, substituted or unsubstituted alkyl or cycloalkyl groups with 1 to 30 carbon atoms, fluoroalkyl groups, chloroalkyl groups, alkoxy groups, thioalkoxy groups, carboxyl groups with 1 to 30 carbon atoms, ester groups with 1 to 30 carbon atoms, acyl groups with 1 to 30 carbon atoms, substituted or unsubstituted amino groups with 1 to 30 carbon atoms, substituted or unsubstituted aryl groups with 6 to 30 carbon atoms, substituted or unsubstituted heterocyclic aryl groups with 4 to 30 carbon atoms.

The above heterocyclic aryl group means a monocyclic or fused ring aryl group containing one or more hetero atoms selected from B, N, O, S, P, P=O, Si and P with 4 to 30 ring carbon atoms.

Further, $R_1$ to $R_7$ are each independently selected from hydrogen atoms, halogen atoms, cyano groups, nitro groups, hydroxyl groups, substituted or unsubstituted alkyl groups with 1 to 20 carbon atoms, cycloalkyl groups, fluoroalkyl groups, chloroalkyl groups, alkoxy groups, thioalkoxy groups, carboxyl groups with 1 to 20 carbon atoms, ester groups with 1 to 20 carbon atoms, acyl groups with 1 to 20 carbon atoms, substituted or unsubstituted amino groups with 1 to 20 carbon atoms, substituted or unsubstituted aryl groups with 6 to 18 carbon atoms, substituted or unsubstituted heterocyclic aryl groups with 4 to 18 carbon atoms.

When a substituent group is present on the above-mentioned $R_1$ to $R_7$, the substituent group is independently selected from F, Cl, Br, I, CHO, CN, substituted or unsubstituted alkyl or ring with 1 to 30 carbon atoms, fluoroalkyl, chloroalkyl, alkoxy or thioalkoxy groups. Further, it is preferred that the substituted group is selected from F, Cl, Br, substituted or unsubstituted alkyl or cycloalkyl groups with 1 to 20 carbon atoms, fluoroalkyl groups, alkoxy groups, or thioalkoxy groups.

Further, $R_1$ to $R_7$ can each be preferably and independently selected from hydrogen atoms or following substituted or unsubstituted groups: thiophene, benzothiophene, benzene, naphthalene, anthracene, phenanthrene, pyrene, furan, benzofuran, thiazole, benzothiazole, isothiazole, benzisothiazole, pyrrole, benzopyrrole, imidazole, benzimidazole, pyrazole, benzopyrazole, oxazole, benzoxazole, isoxazole, benzisoxazole, pyridine, pyrimidine, benzopyrimidine, pyrazine, benzopyrazine, pyridazine, benzopyridazine, quinoline, isoquinoline, purine, pteridine, indole, carbazole, diphenylamine, phenoxy, diphenyl boron, diphenylphosphine, diphenylphosphine oxide, triphenyl silicon. Further, the substituent group is most preferably selected from F, Cl, substituted or unsubstituted alkyl or cycloalkyl groups with 1 to 10 carbon atoms, fluoroalkyl groups, alkoxy groups or thioalkyl groups.

Furthermore, $R_2$ to $R_7$ can preferably be hydrogen atoms; $R_1$ is selected from following substituted or unsubstituted groups: thiophene, benzothiophene, benzene, naphthalene, anthracene, phenanthrene, pyrene, furan, benzofuran, thiazole, benzothiazole, isothiazole, benzisothiazole, pyrrole, benzopyrrole, imidazole, benzimidazole, pyrazole, benzopyrazole, oxazole, benzoxazole, isoxazole, benzisoxazole, pyridine, pyrimidine, benzopyrimidine, pyrazine, benzopyrazine, pyridazine, benzopyridazine, quinoline, isoquinoline, purine, pteridine, indole, carbazole, diphenylamine, phenoxy, diphenyl boron, diphenyl phosphine, diphenylphosphine oxide, triphenyl silicon. Moreover, the substituent group is most preferably selected from F, Cl, substituted or unsubstituted alkyl or cycloalkyl groups with 1 to 10 carbon atoms, fluoroalkyl groups, alkoxy groups, thioalkyl groups.

In the ligand L of the iridium complexes, three aromatic rings fused to form a large 7-conjugation system, and two electron-withdrawing nitrogen atoms are introduced in the ortho-position at the same time, thereby effectively reducing energy gap between HOMO and LUMO and realizing redshift of emission. Furthermore, the rigid structure could suppress the geometric isomerization and molecular rotations of the iridium complexes, thus improving the luminescence efficiency of corresponding iridium complexes. At the same time, quenching between the triplet excitons of the Iridium complexes can be reduced, therefore contributing to negligible efficiency roll-off at high current density.

More importantly, the sterically hindered groups corresponding to coordinated N atom and C atom are located at same sides, which would not hinder the coordination reaction. Meanwhile, compared to the previously reported C^N═CH type ligands, the two nitrogen atoms of our C^N═N type benzo[g]pyridazine ligands are in adjacent positions without steric hindrance effect caused by ortho carbon atom. Consequently, this kind of ligands has stronger coordination ability, and is more preferable to form a stable homoleptic configuration.

Preferred compounds with specific structures in the present invention include CT1-CT48, CBT1-CBT48, CBF1-CBF48, and CP1-CP48. Preferred compounds of this invention are not limited to these specific structures listed below.

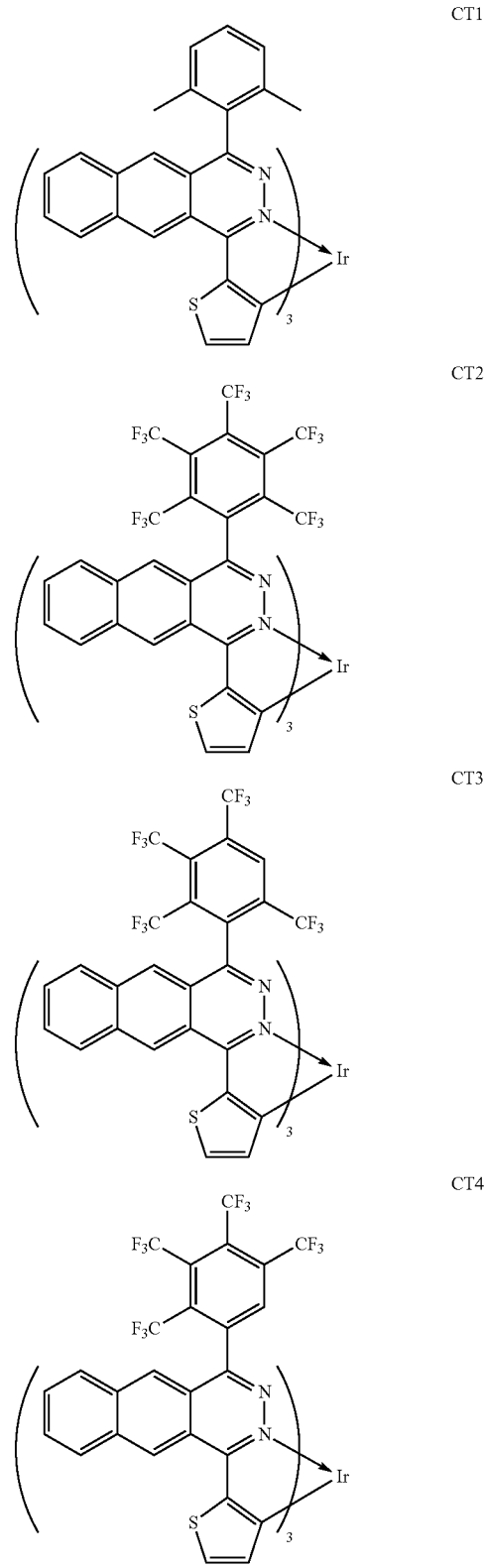

CT5
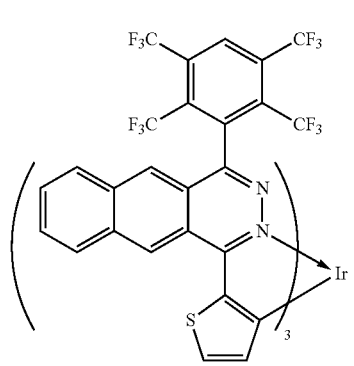
CT6
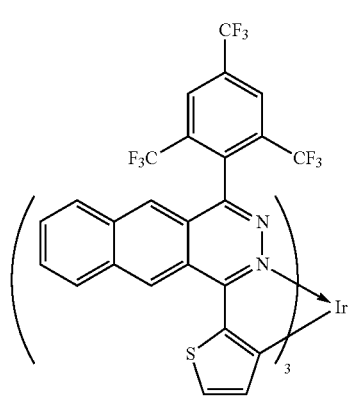
CT7
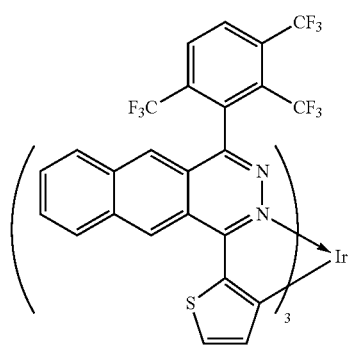
CT8
CT9
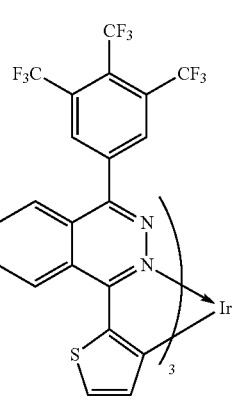
CT10
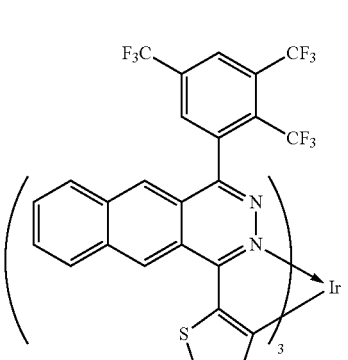
CT11
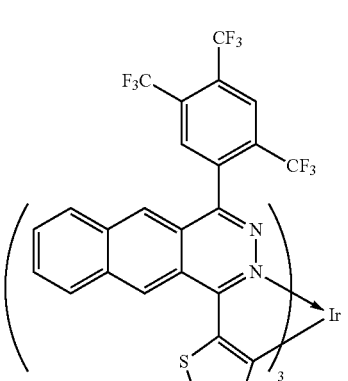
CT12
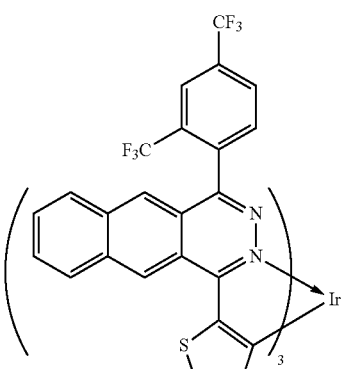

CT13
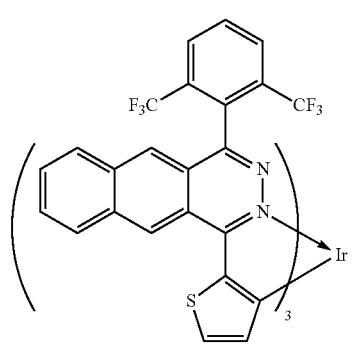
CT14
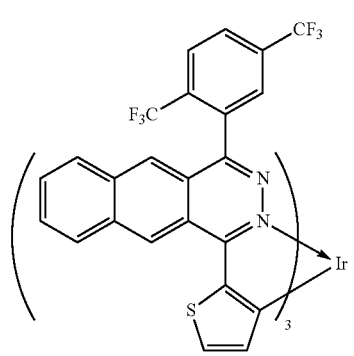
CT15
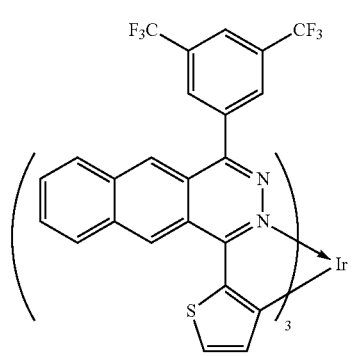
CT16
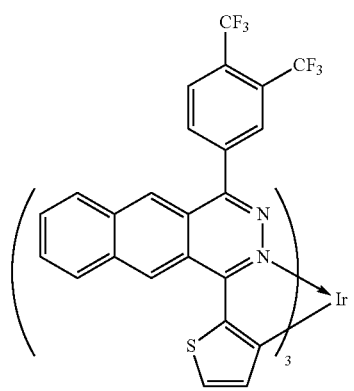
CT17
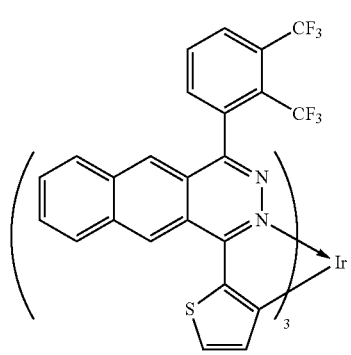
CT18
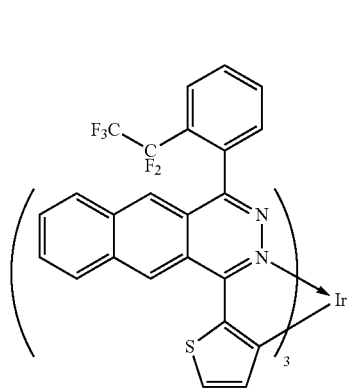
CT19
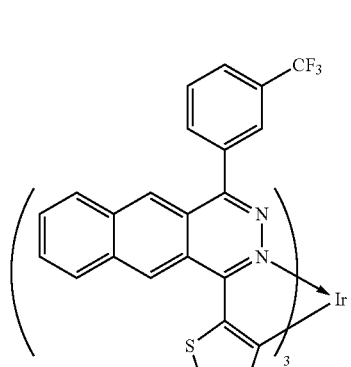
CT20
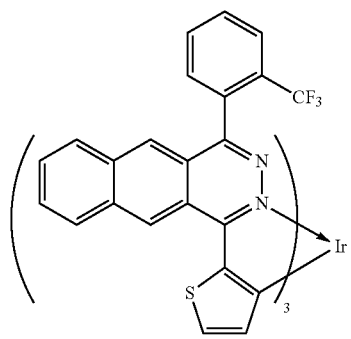

CT21
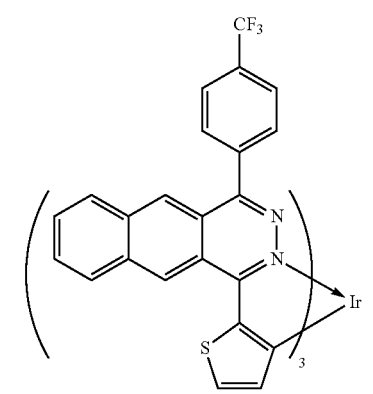
CT22
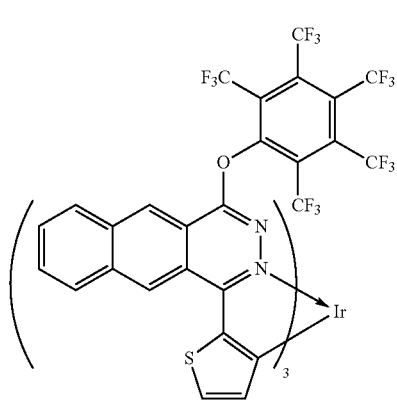
CT23
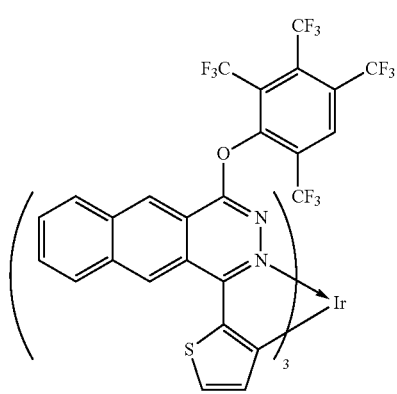
CT24
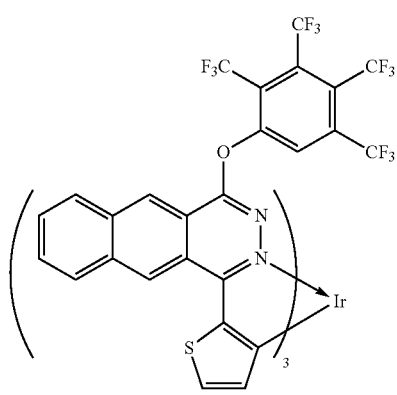
CT25
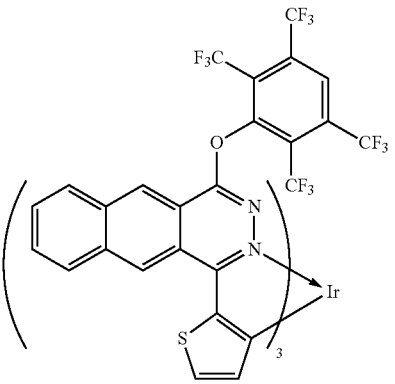
CT26
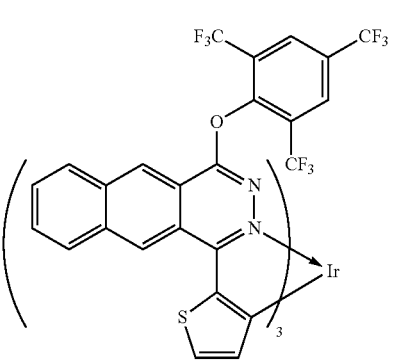
CT27
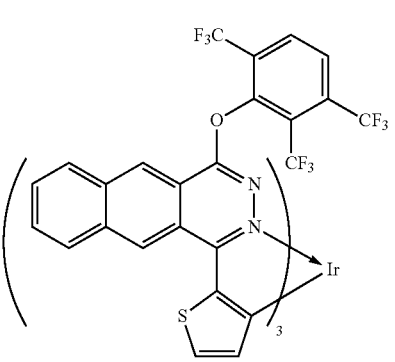
CT28
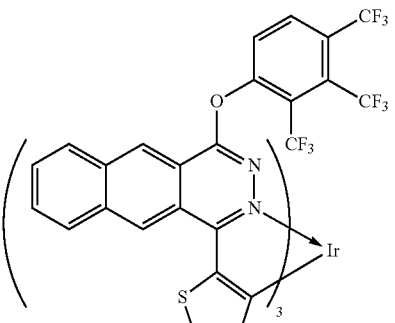

CT29
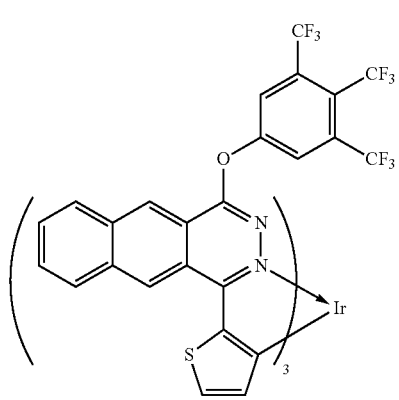
CT30
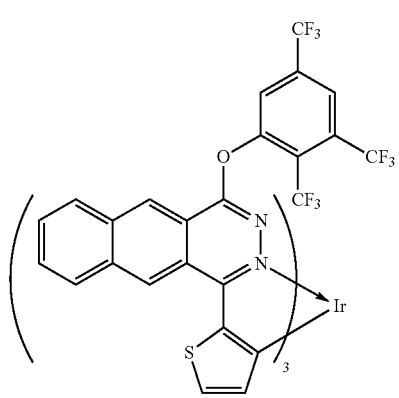
CT31
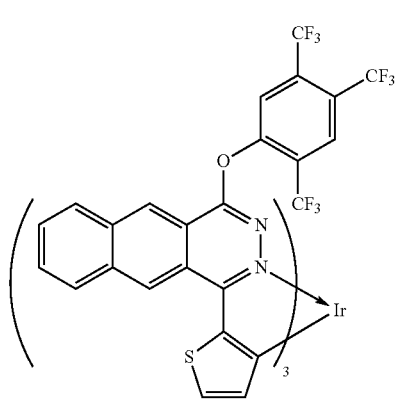
CT32
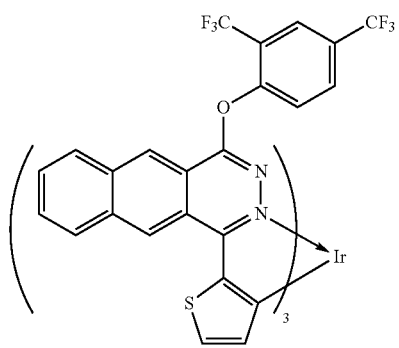
CT33
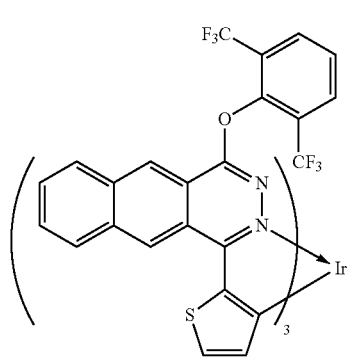
CT34
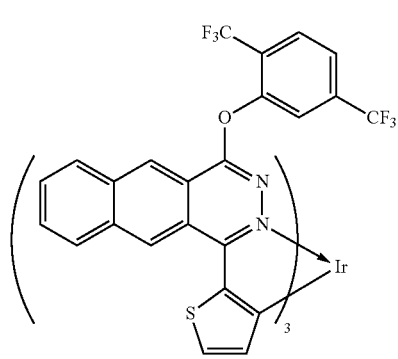
CT35
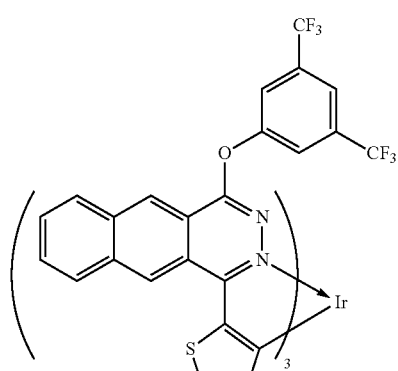
CT36
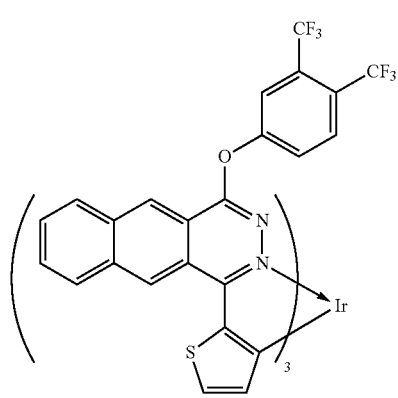

-continued
CT37
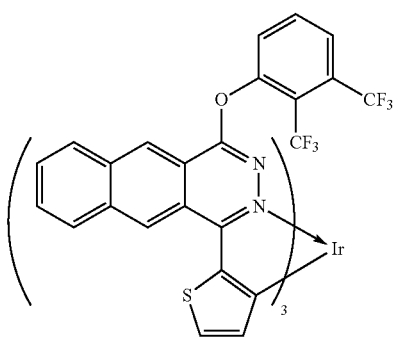
CT41
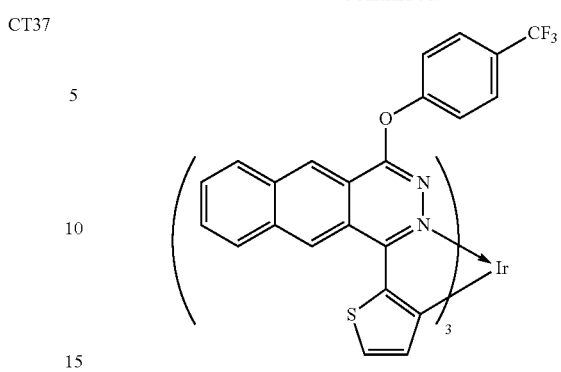
CT38
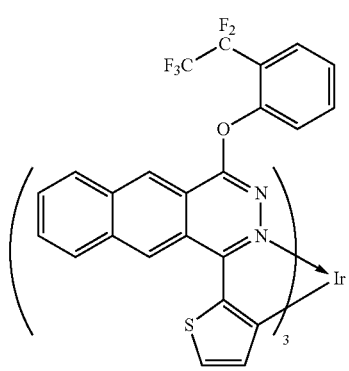
CT42
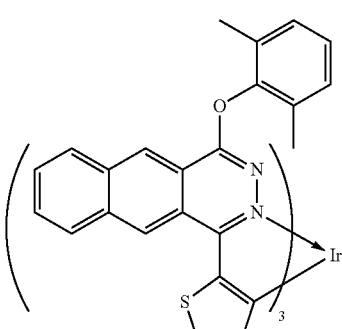
CT39
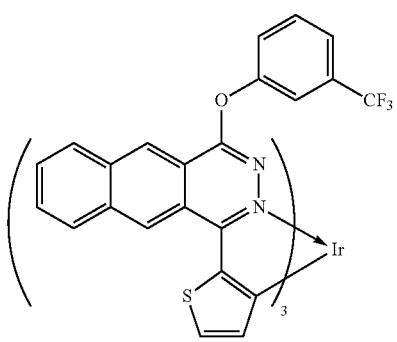
CT43
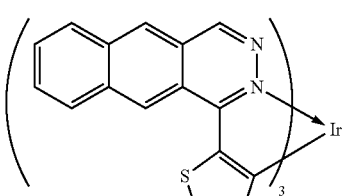
CT44
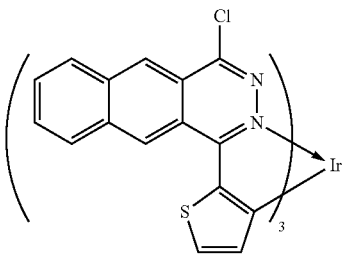
CT40
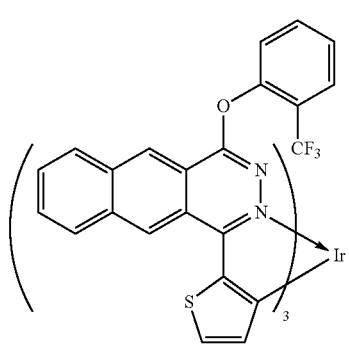
CT45
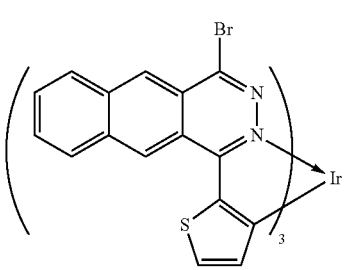

-continued
CT46
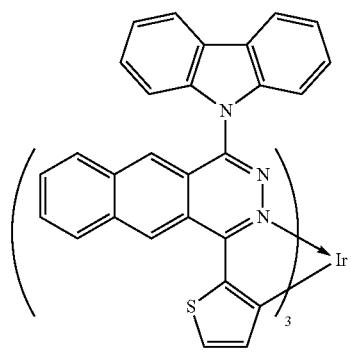
CT47
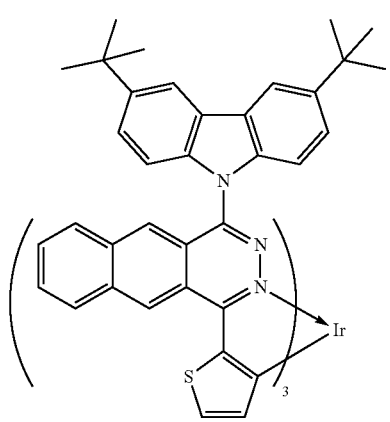
CT48
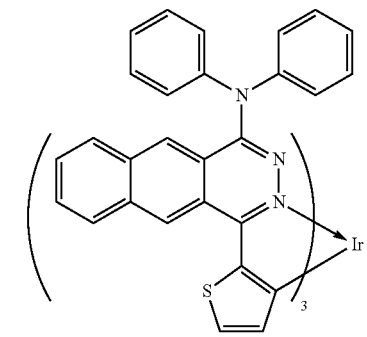
CBT1
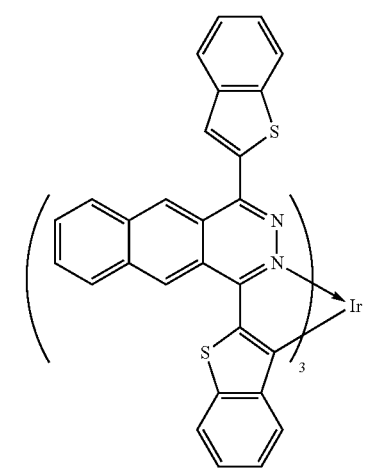
-continued
CBT2
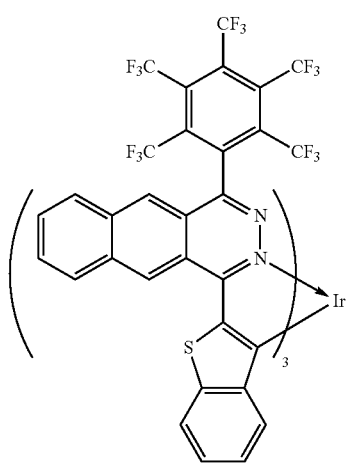
CBT3
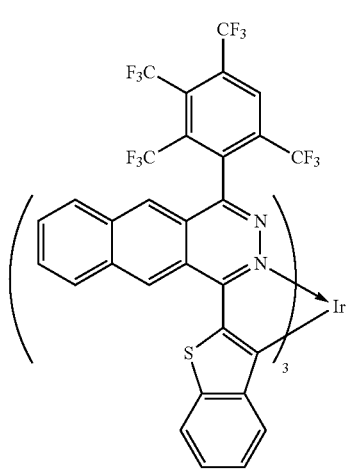
CBT4
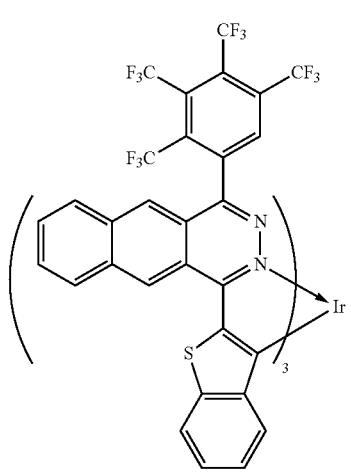

-continued
CBT5
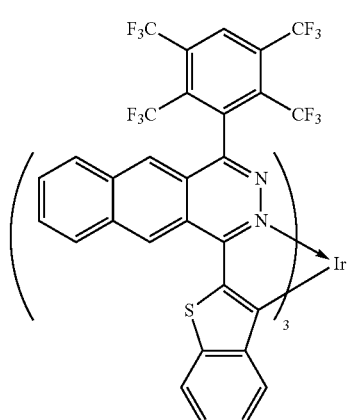
CBT6
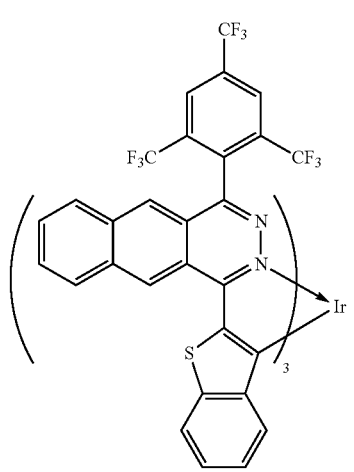
CBT7
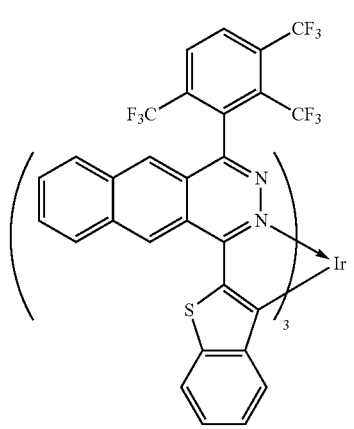
-continued
CBT8
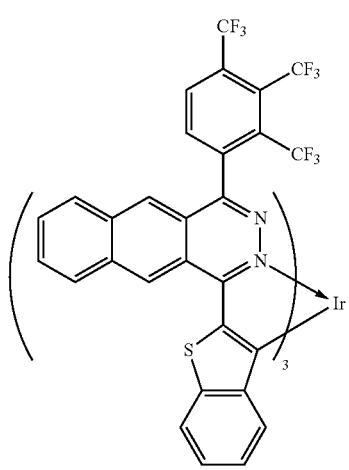
CBT9
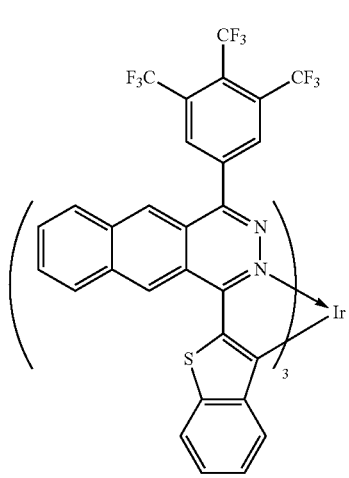
CBT10
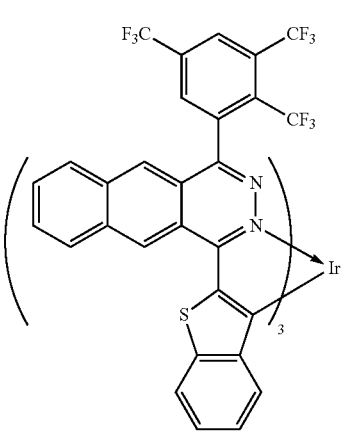

CBT11
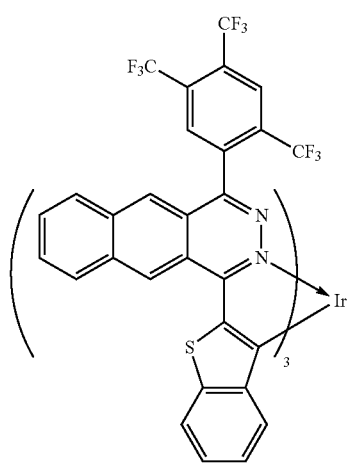
CBT12
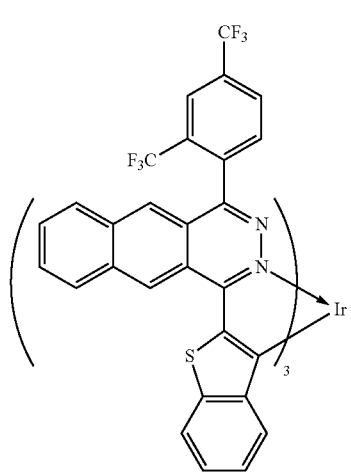
CBT13
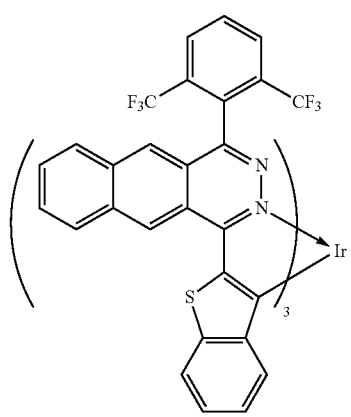
CBT14
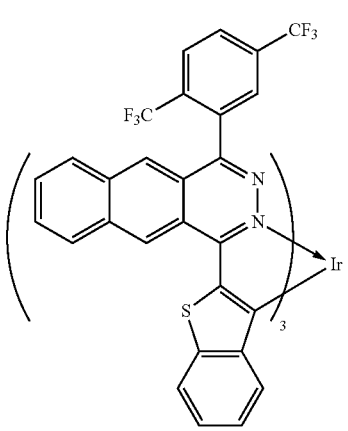
CBT15
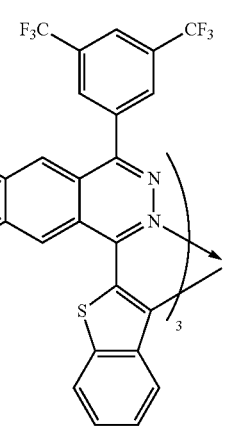
CBT16
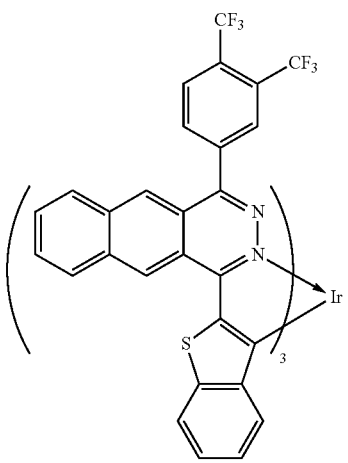

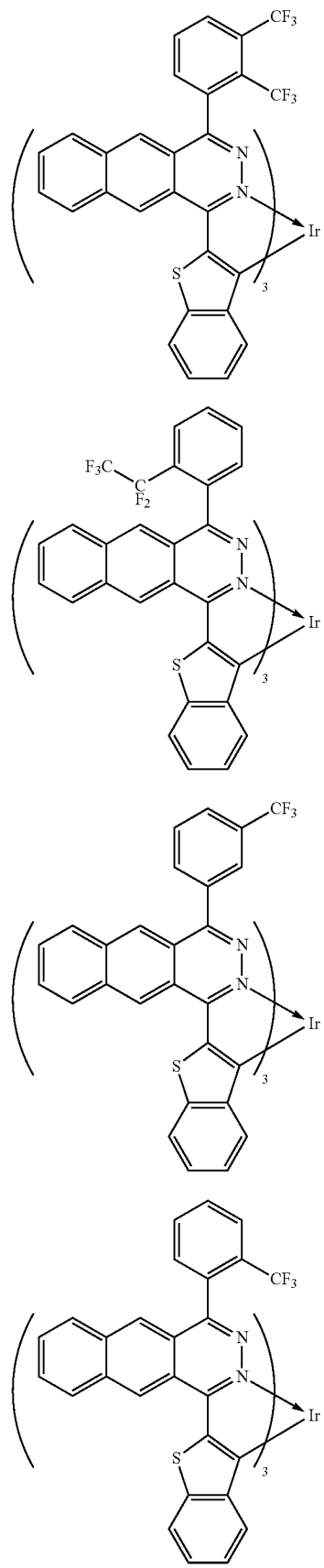
CBT17
CBT18
CBT19
CBT20
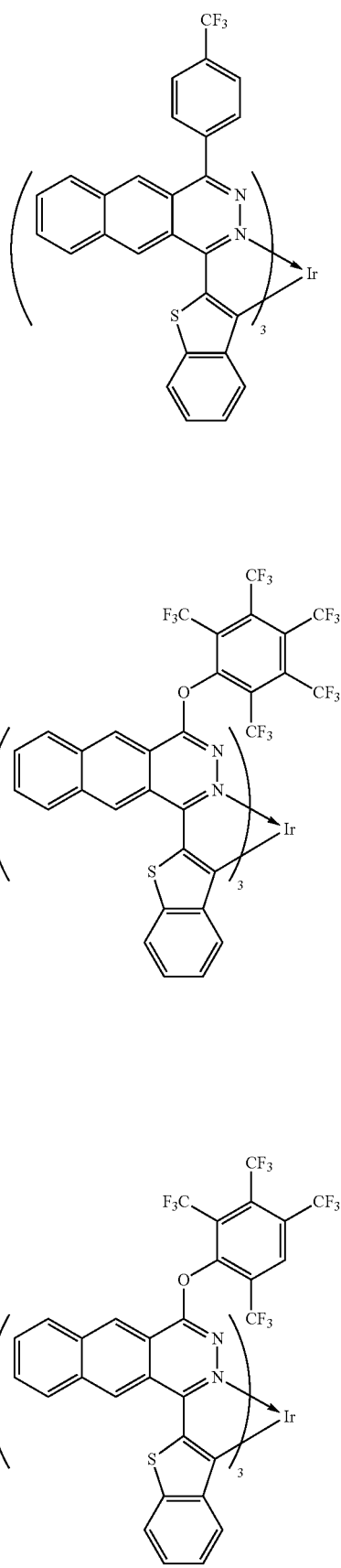
CBT21
CBT22
CBT23

-continued
CBT24
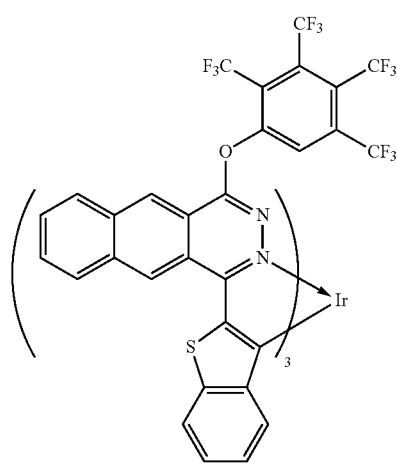
CBT25
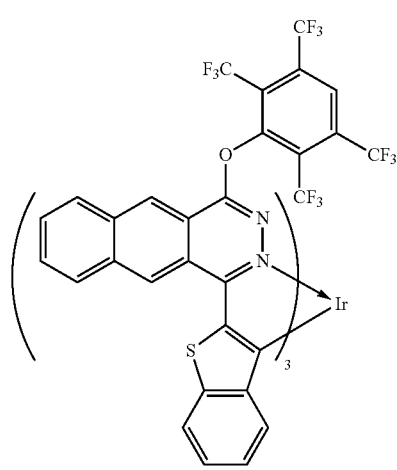
CBT26
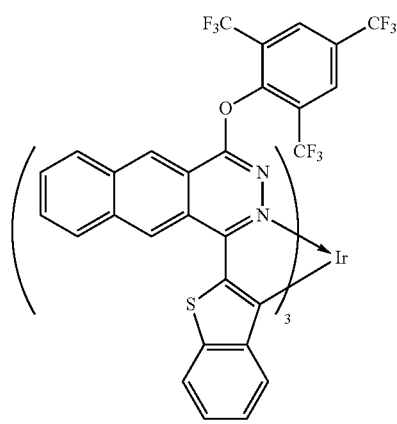
-continued
CBT27
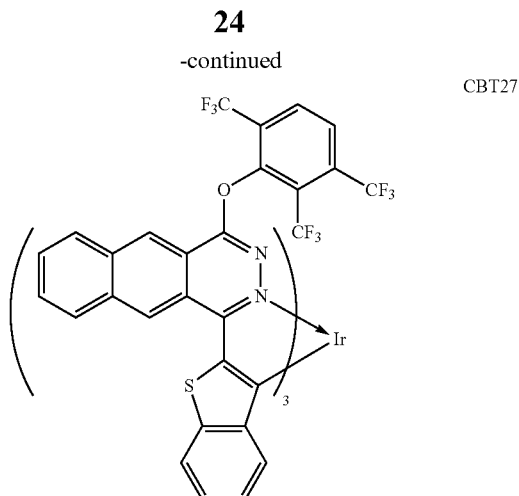
CBT28
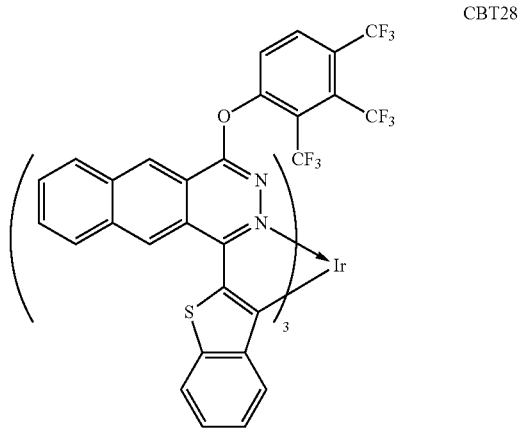
CBT29
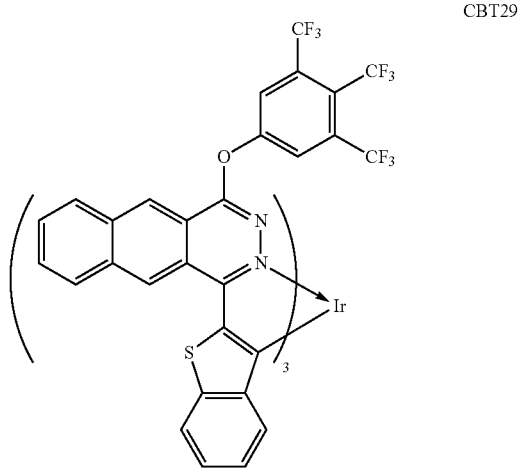

CBT30
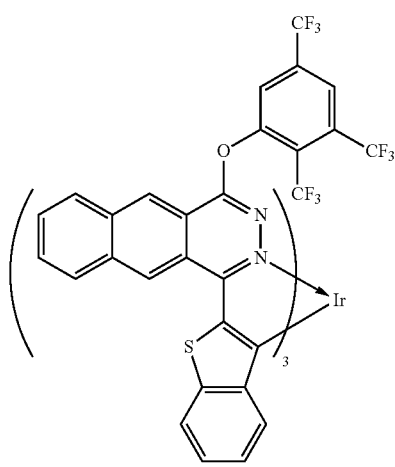
CBT31
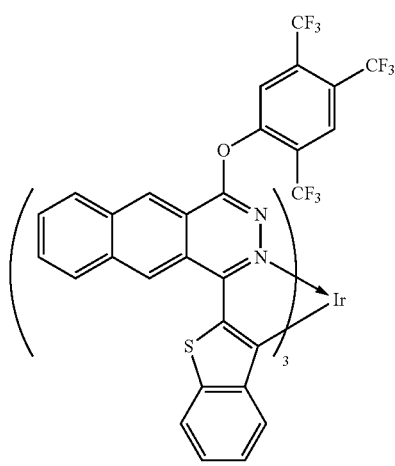
CBT32
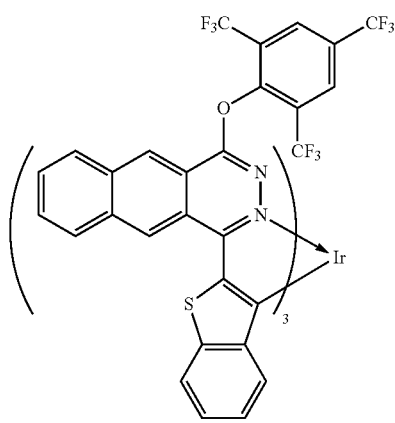
CBT33
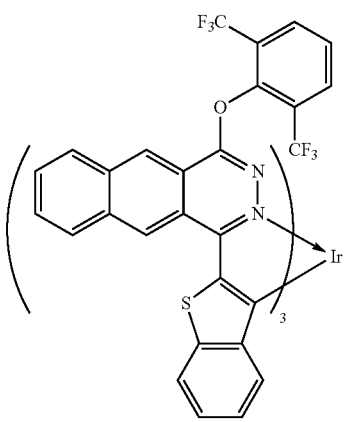
CBT34
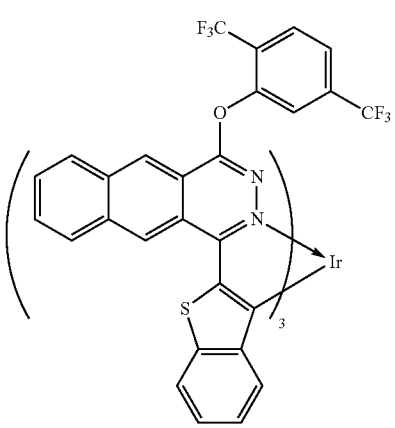
CBT35
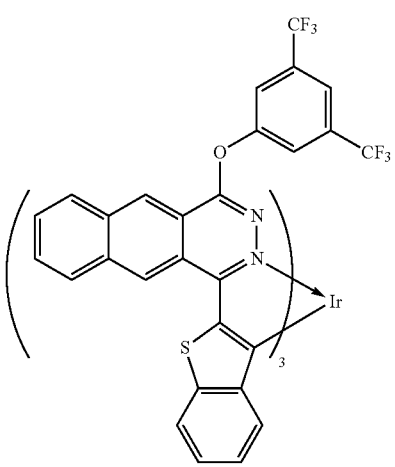

CBT36
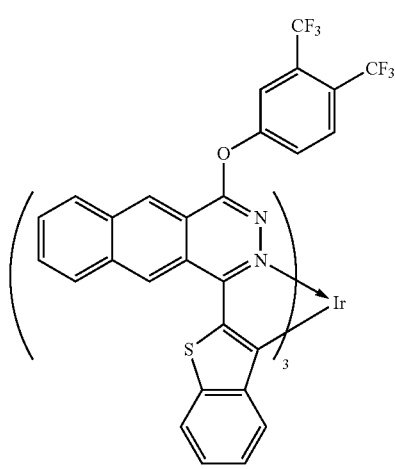
CBT37
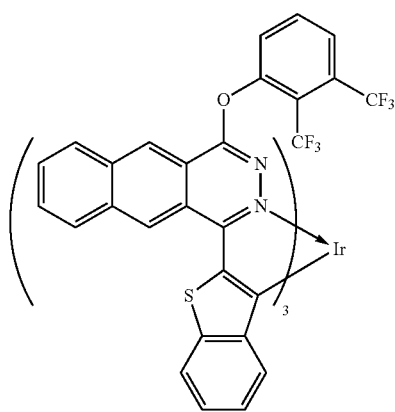
CBT38
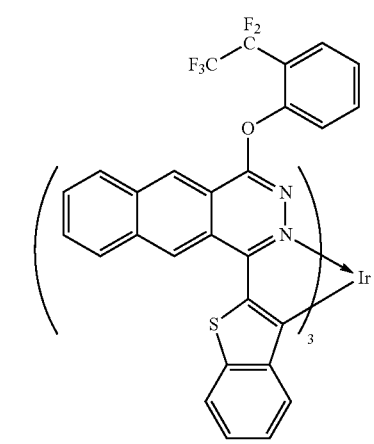
CBT39
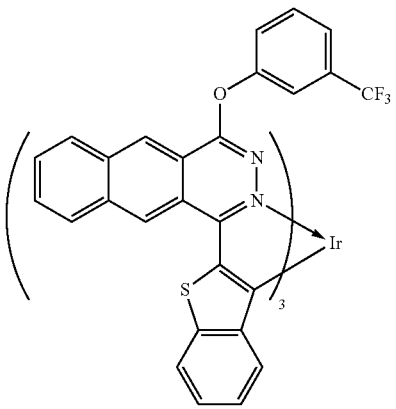
CBT40
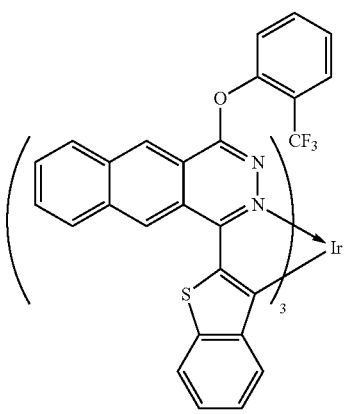
CBT41
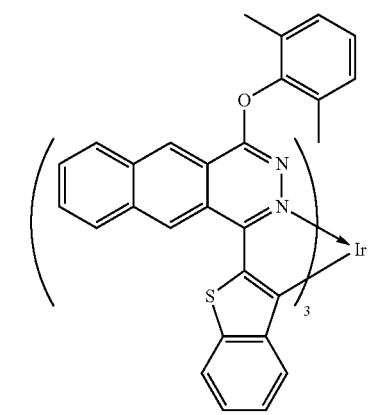
CBT42

CBT43
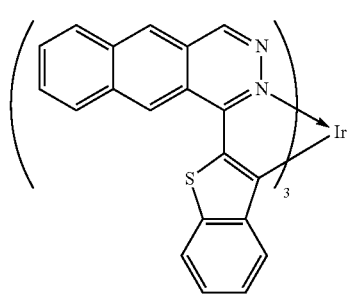
CBT44
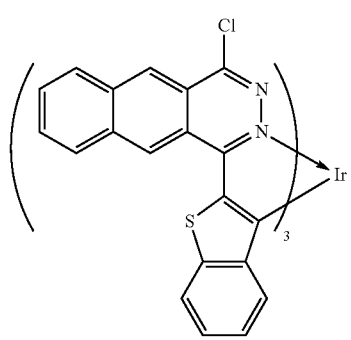
CBT45
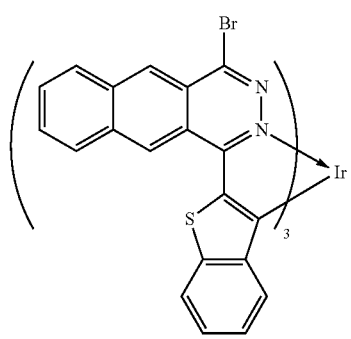
CBT46
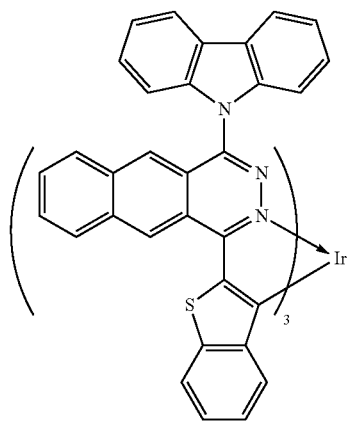
CBT47
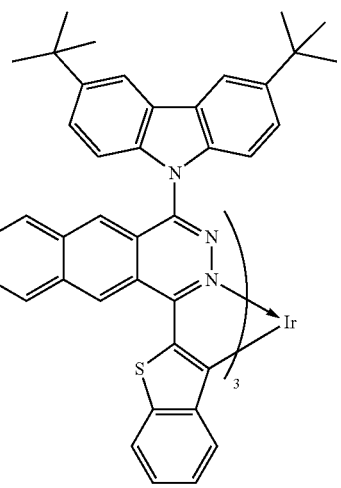
CBT48
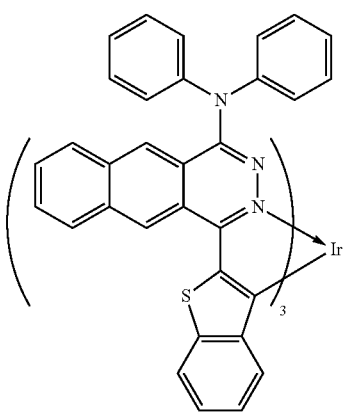
CBF1
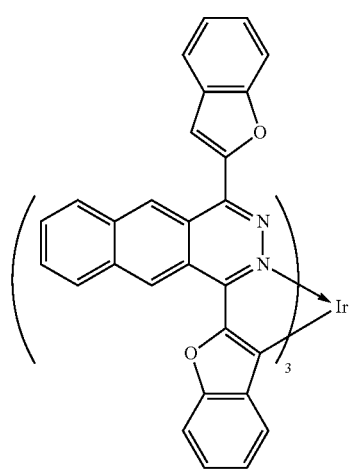

CBF2
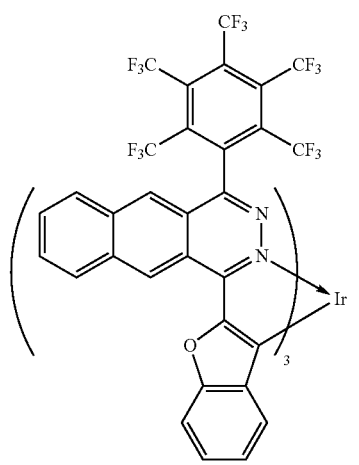
CBF3
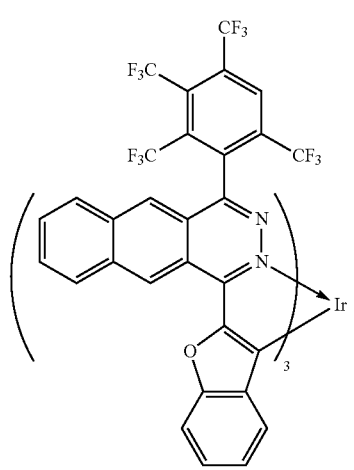
CBF4
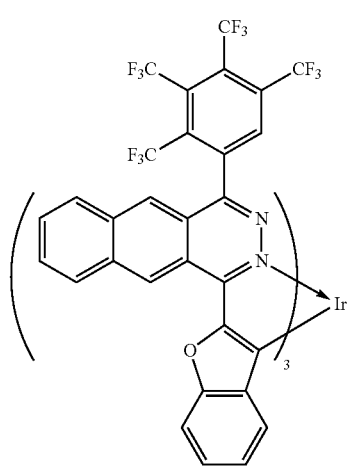
CBF5
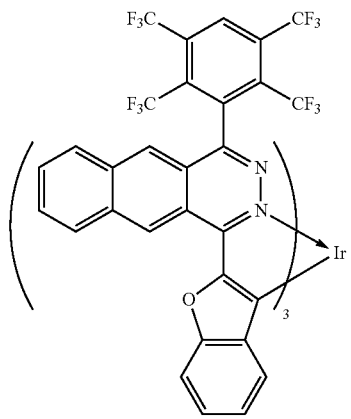
CBF6
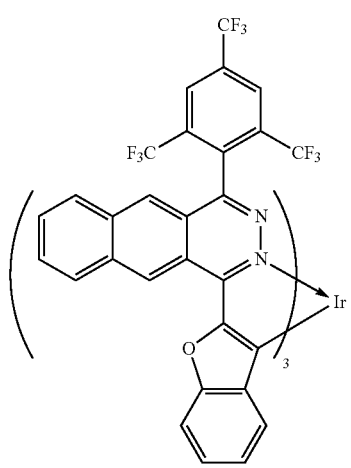
CBF7
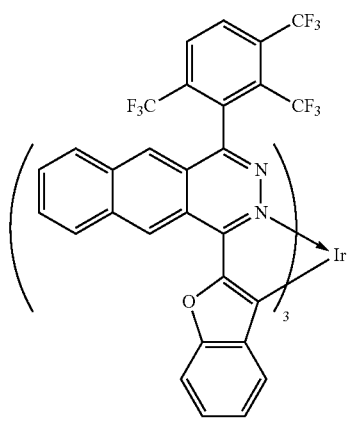

CBF8
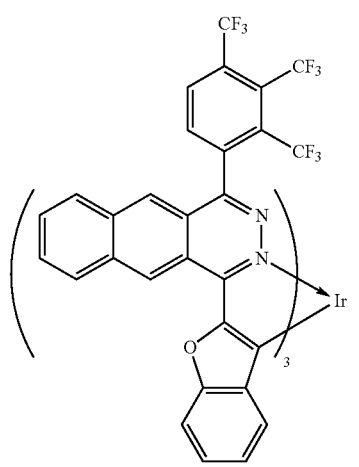
CBF9
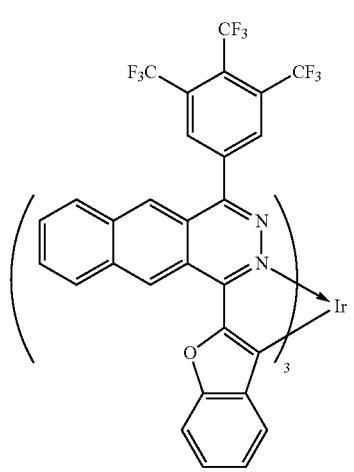
CBF10
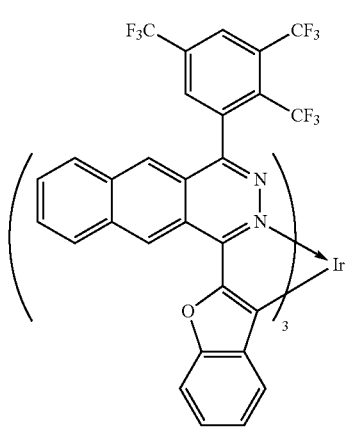
CBF11
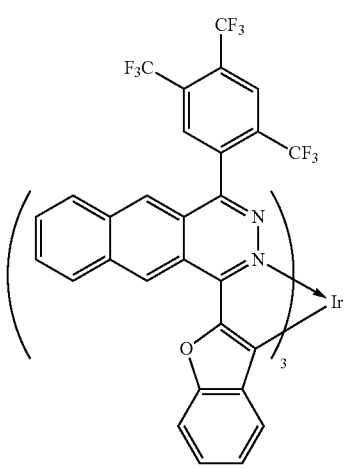
CBF12
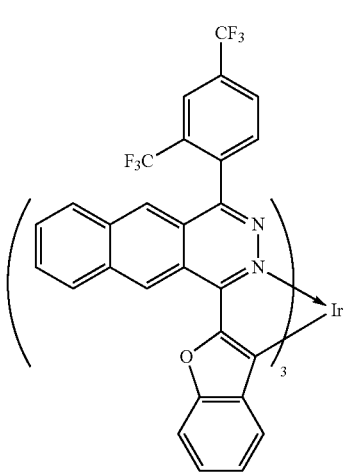
CBF13
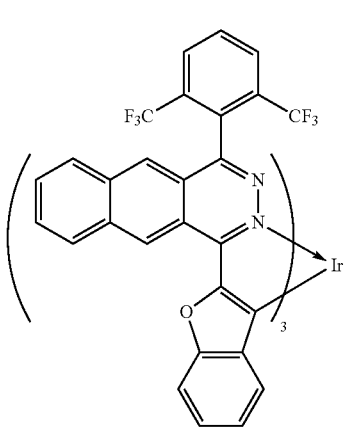

CBF14
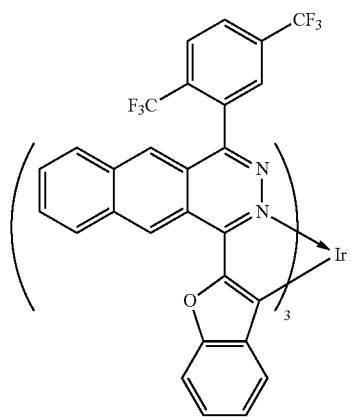
CBF15
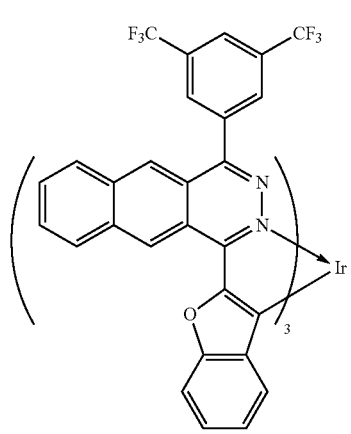
CBF16
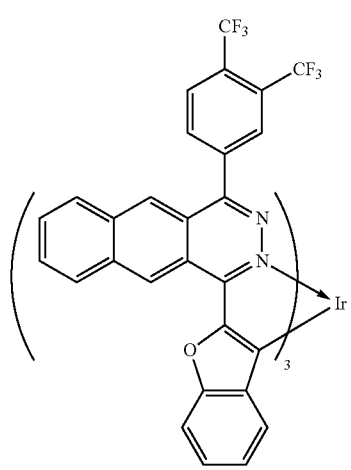
CBF17
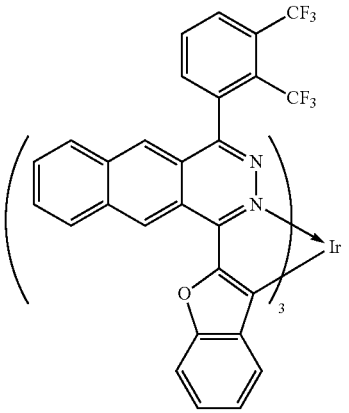
CBF18
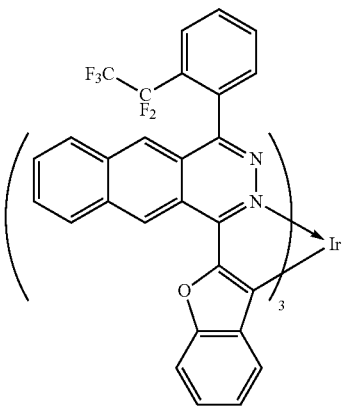
CBF19
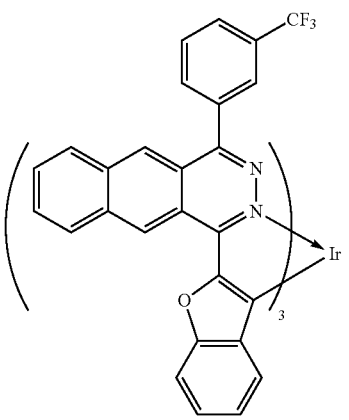
CBF20
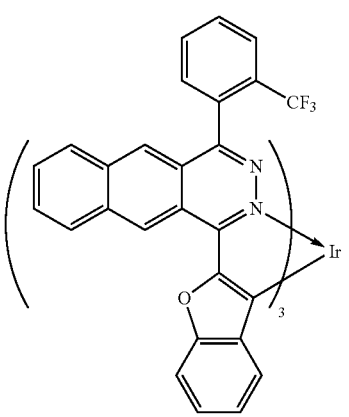

CBF21 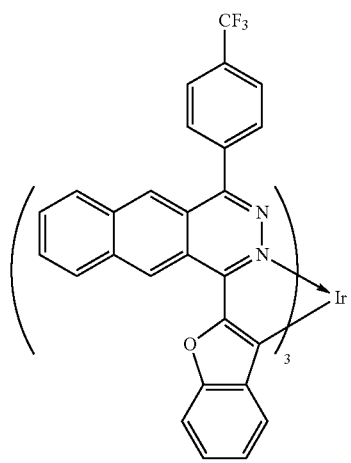
CBF22 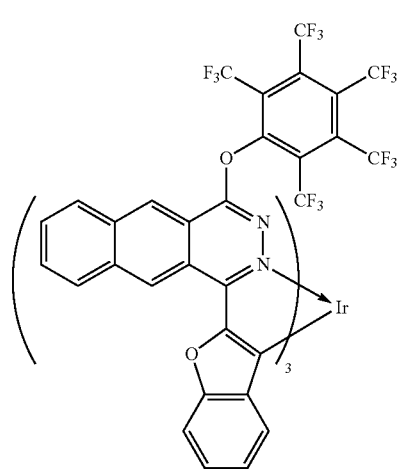
CBF23 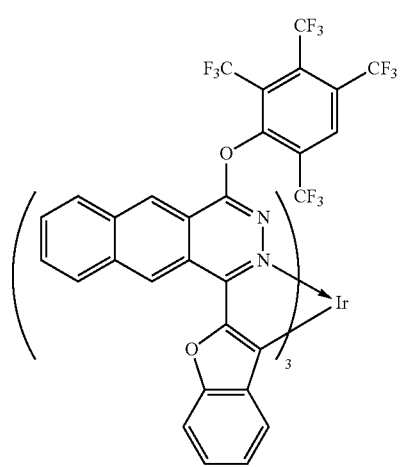
CBF24 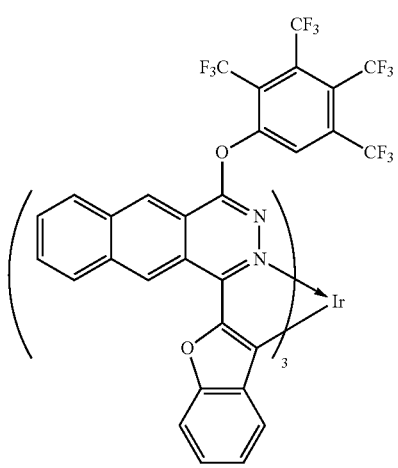
CBF25 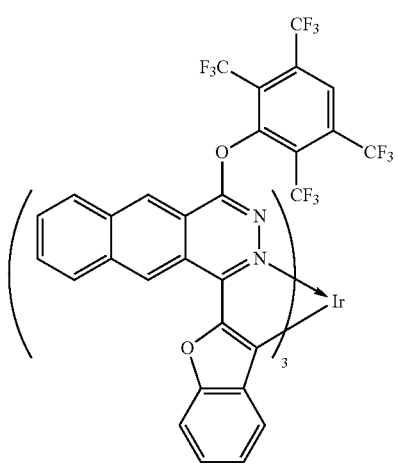
CBF26 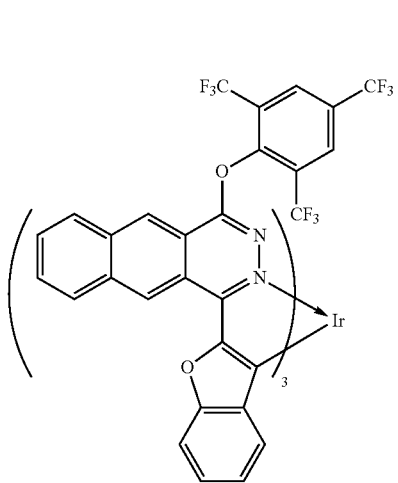

-continued
CBF27
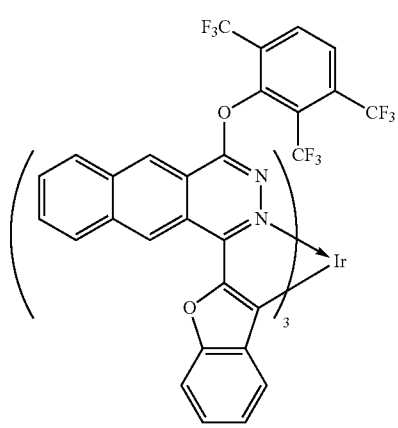
CBF30
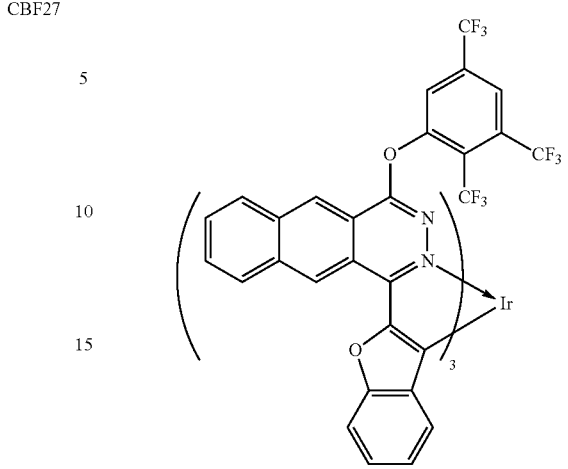
CBF28
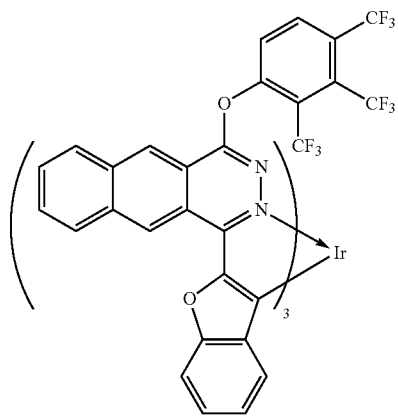
CBF31
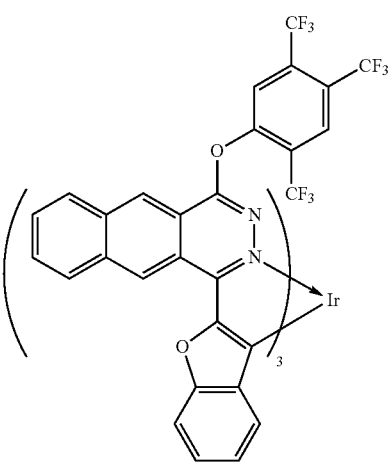
CBF29
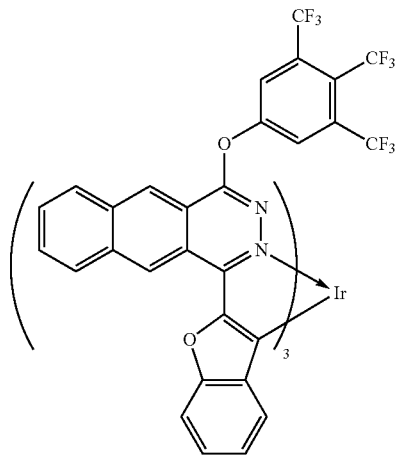
CBF32
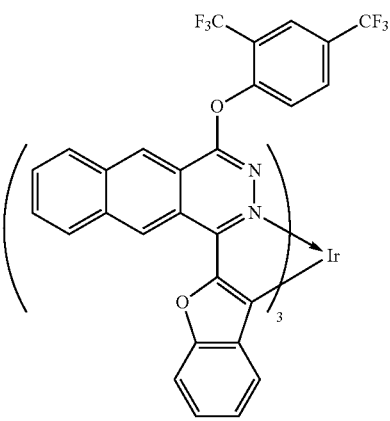

CBF33
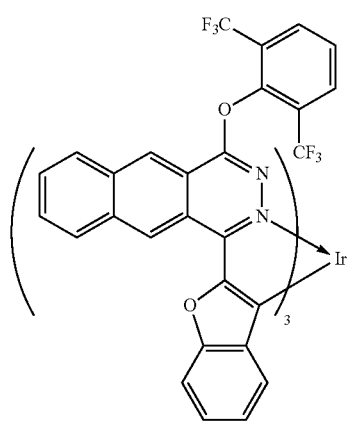
CBF34
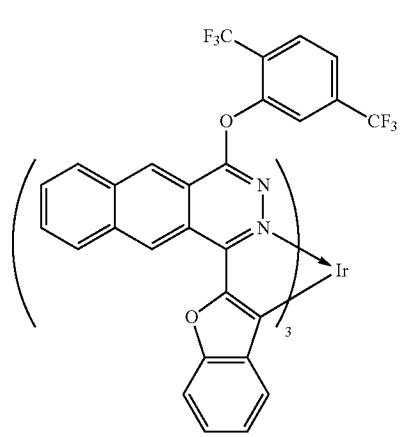
CBF35
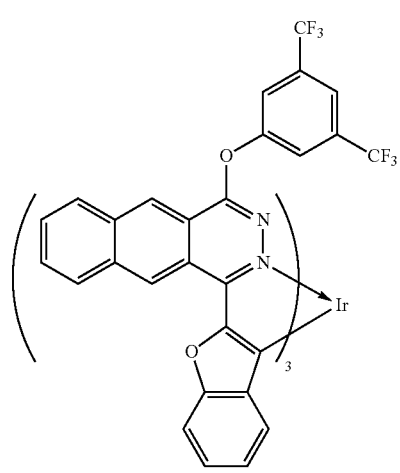
CBF36
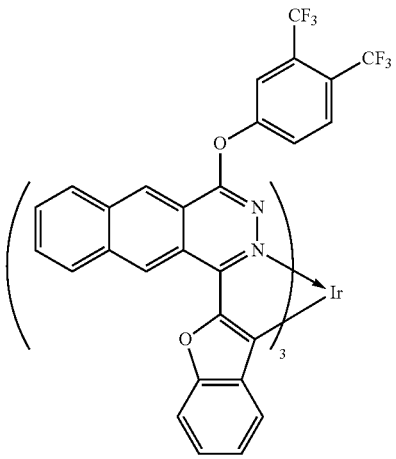
CBF37
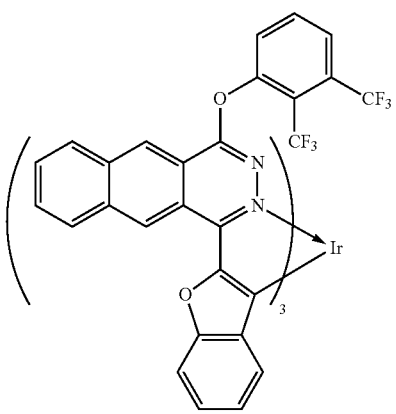
CBF38
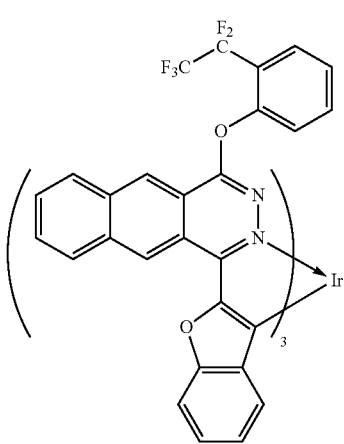

CBF39
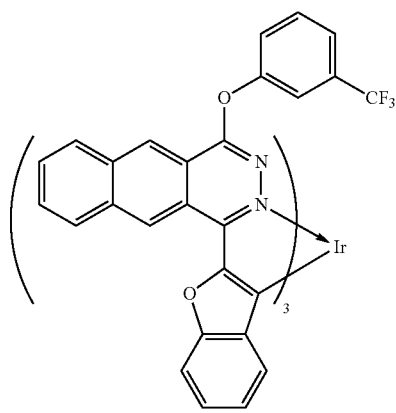
CBF40
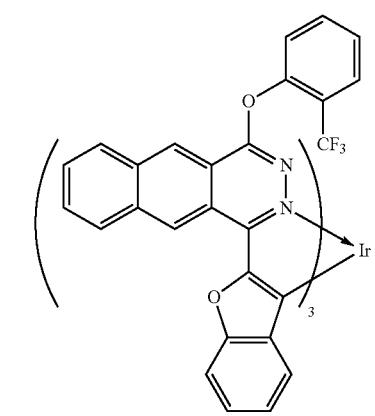
CBF41
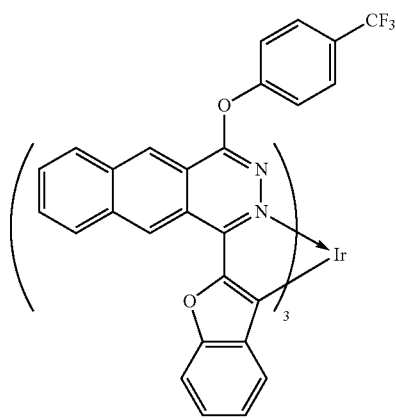
CBF42
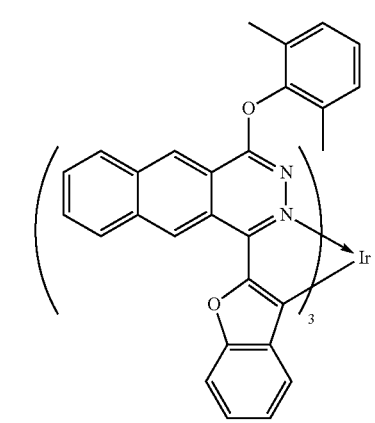
CBF43
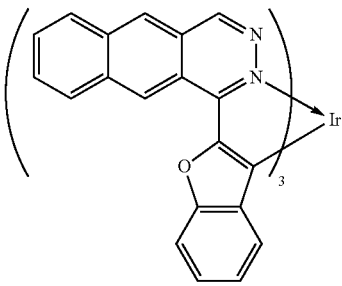
CBF44
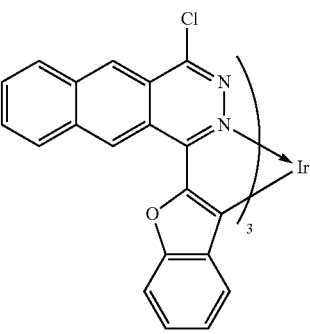
CBF45
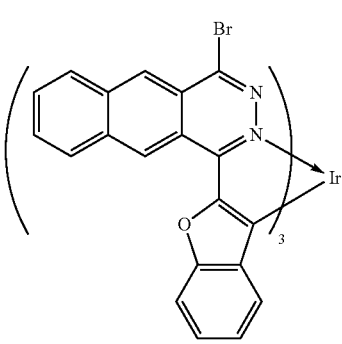
CBF46
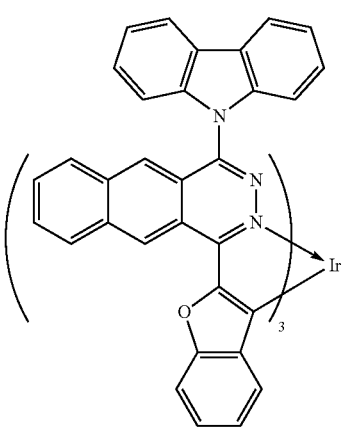

CBF47
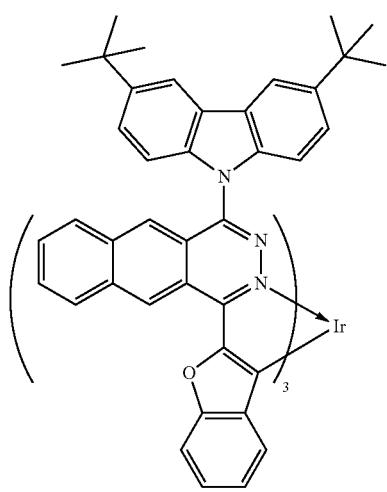
CBF48
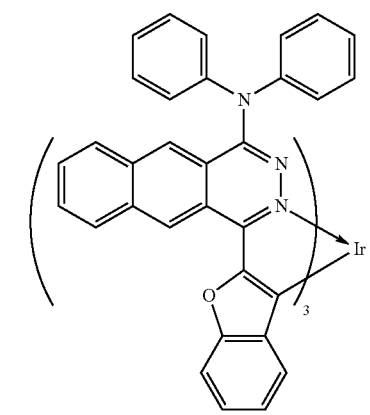
CP1
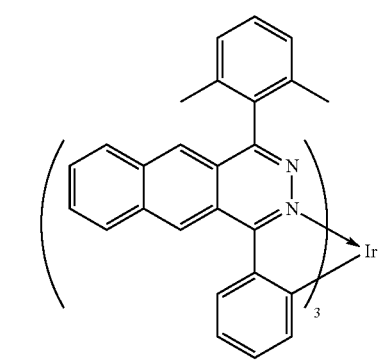
CP2
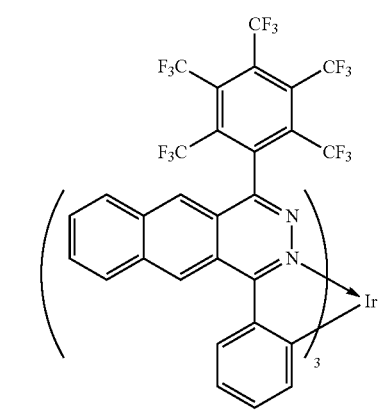
CP3
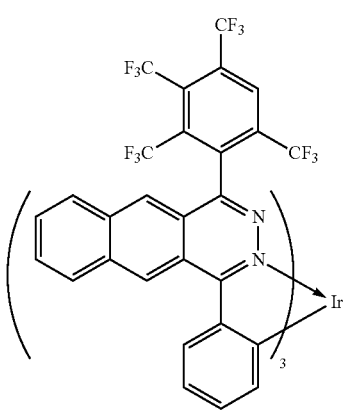
CP4
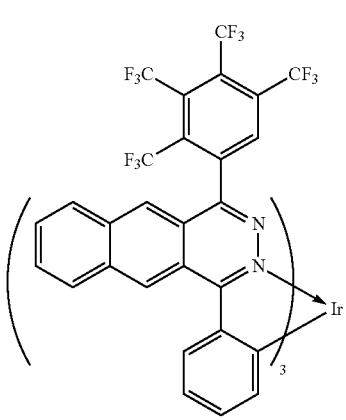
CP5
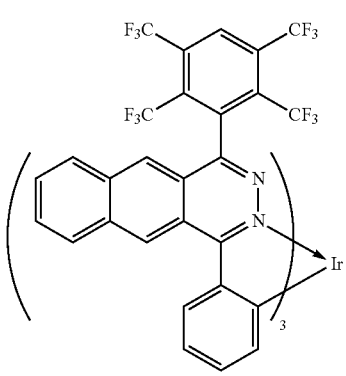
CP6
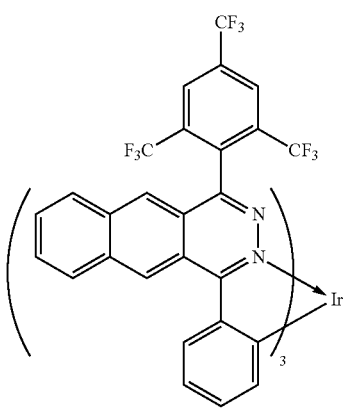

CP7
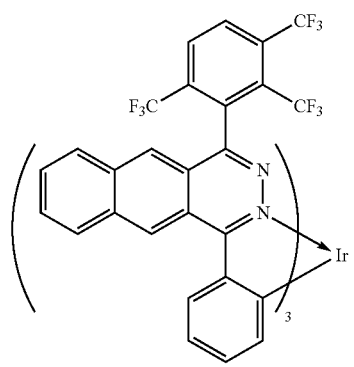
CP8
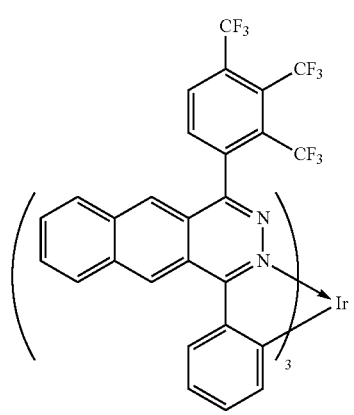
CP9
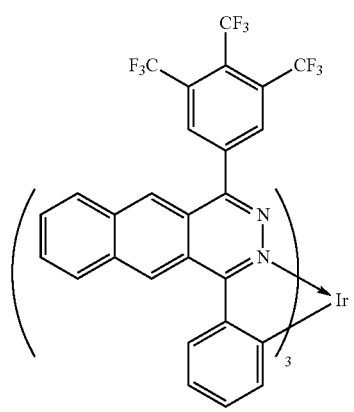
CP10
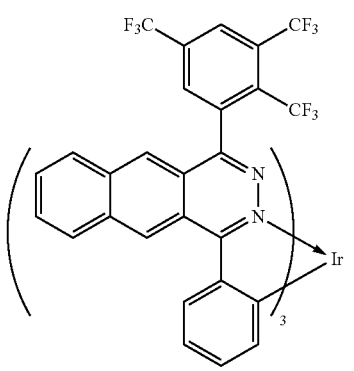
CP11
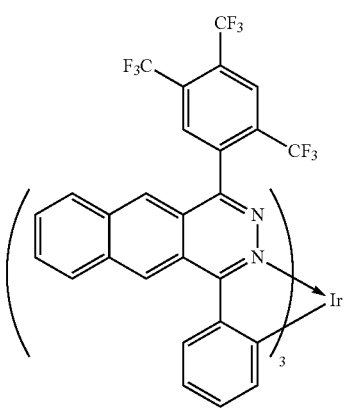
CP12
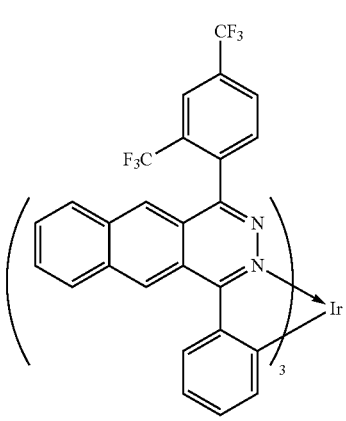
CP13
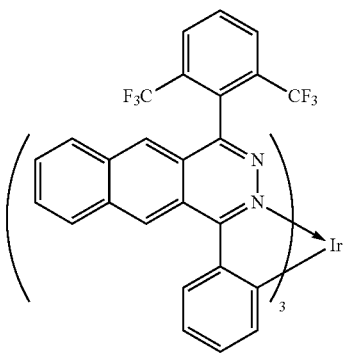
CP14
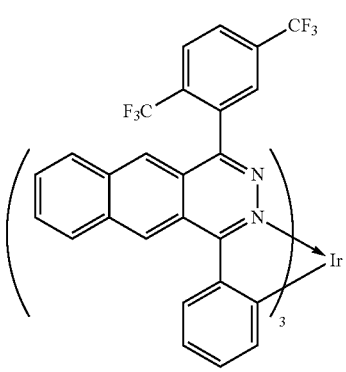

CP15
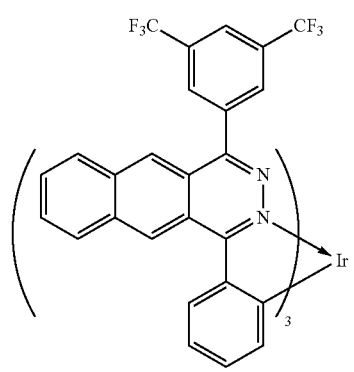
CP16
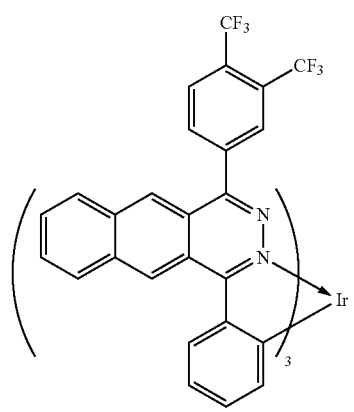
CP17
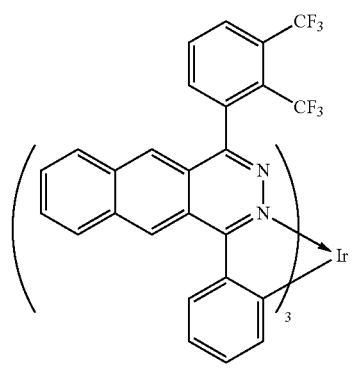
CP18
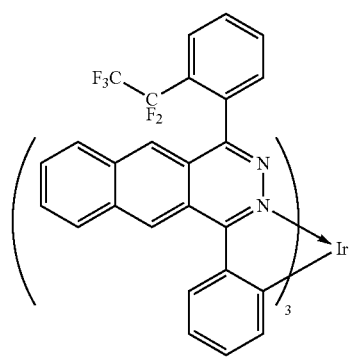
CP19
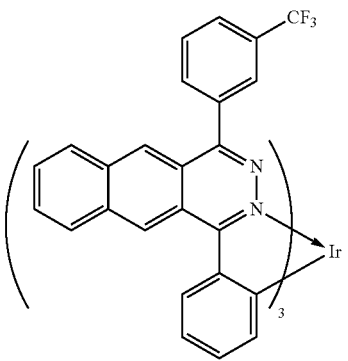
CP20
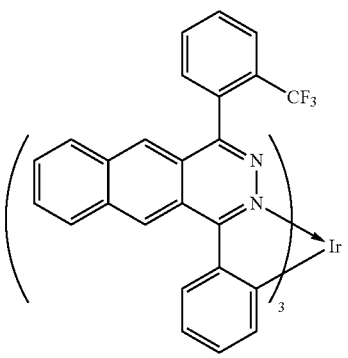
CP21
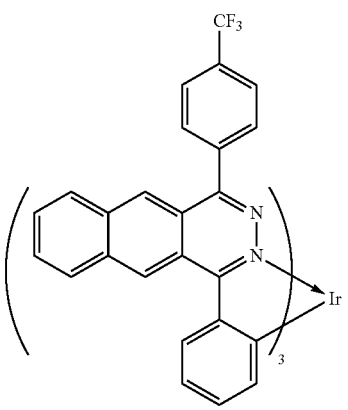
CP22
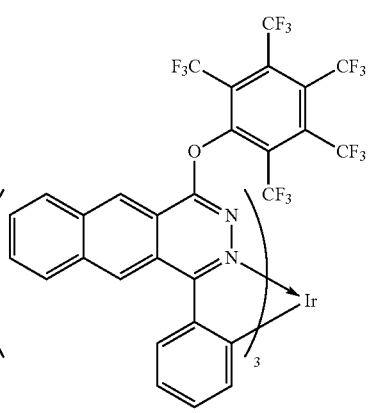

CP23 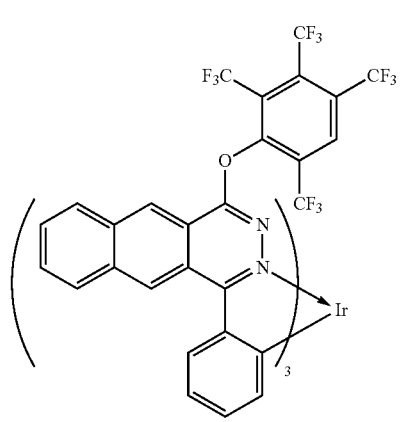
CP24 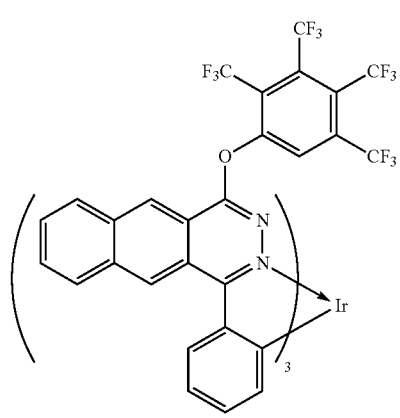
CP25 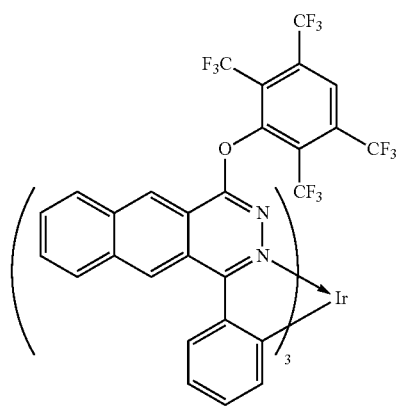
CP26 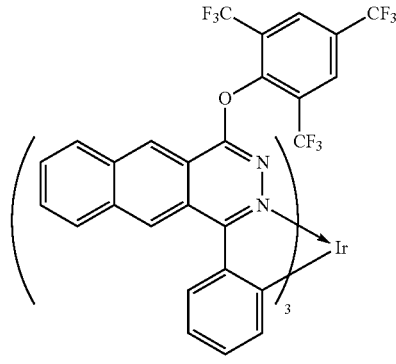
CP27 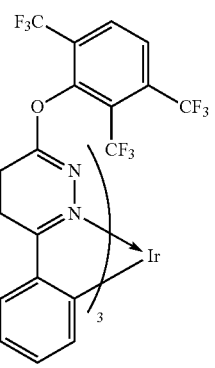
CP28 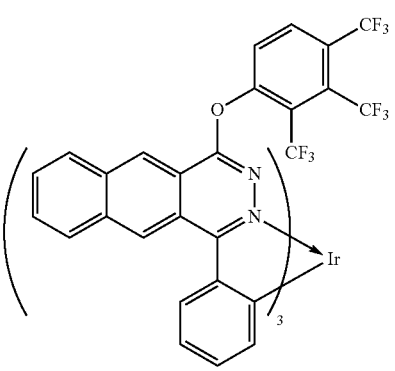
CP29 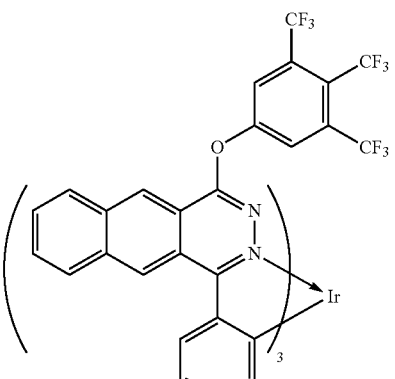
CP30 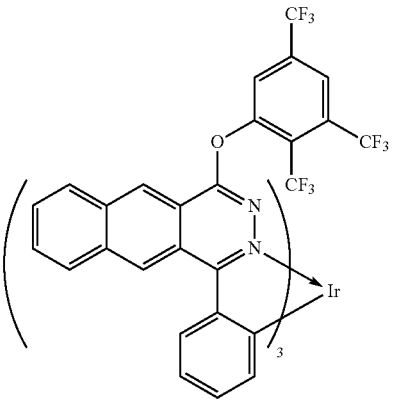

CP31 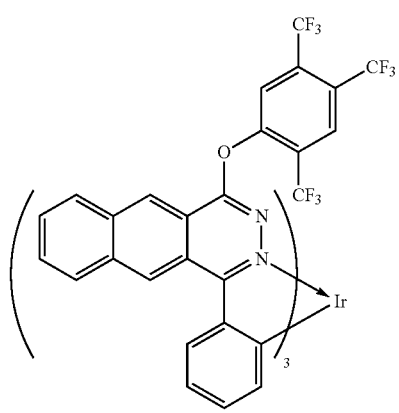
CP32 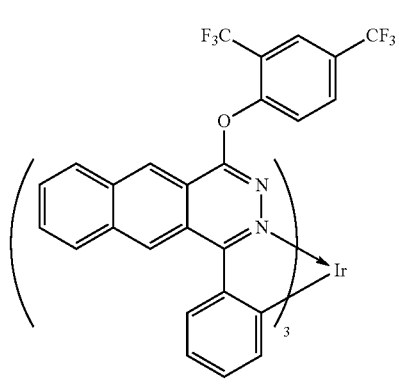
CP33 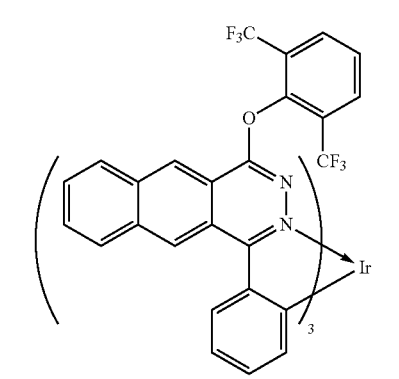
CP34 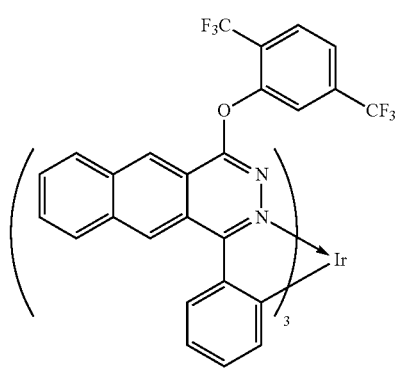
CP35 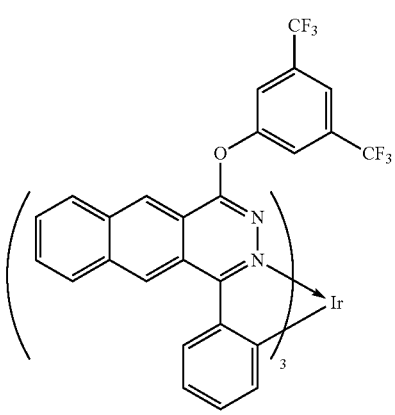
CP36 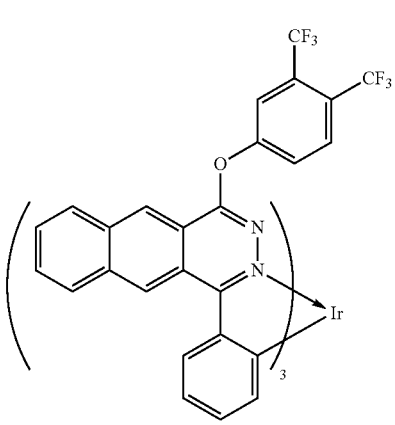
CP37 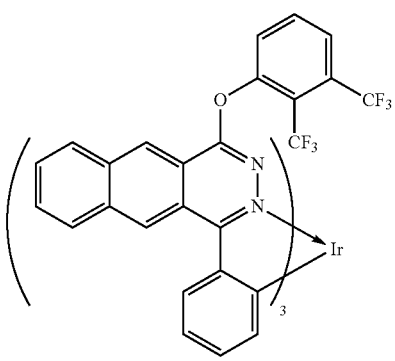
CP38 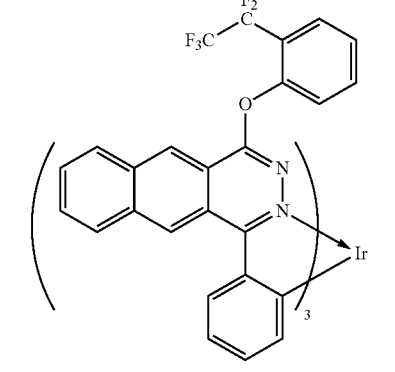

CP39
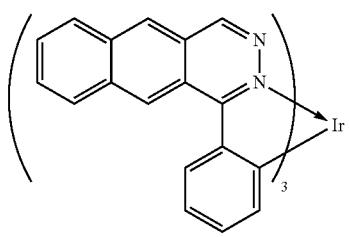
CP40
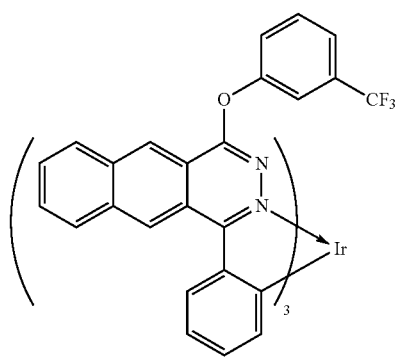
CP41
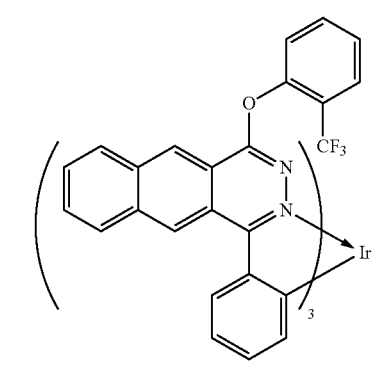
CP42
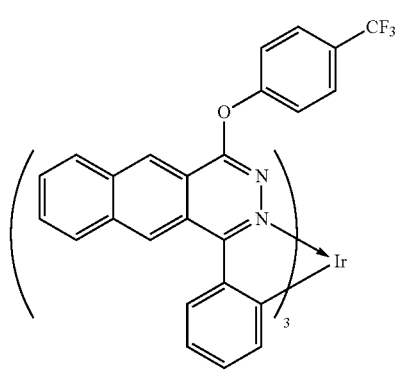
CP43
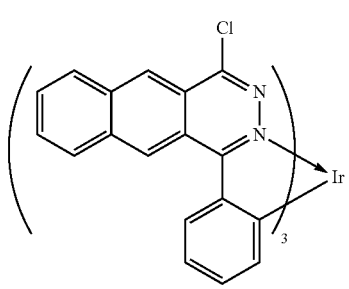
CP44
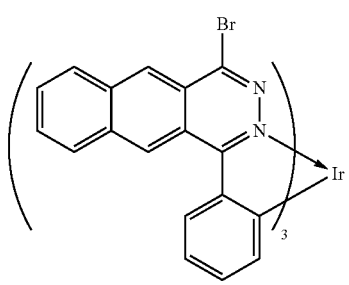
CP45
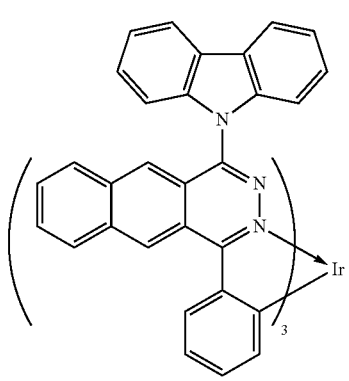
CP46
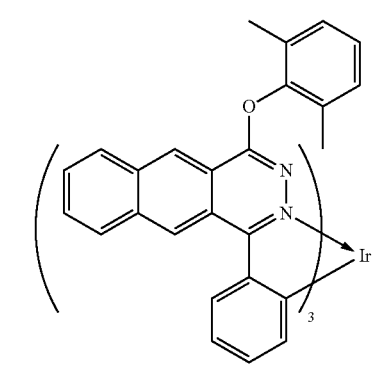
CP47
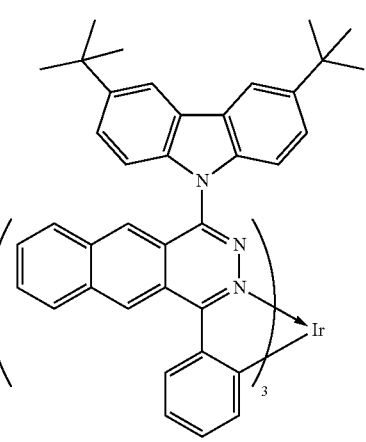

-continued

CP48

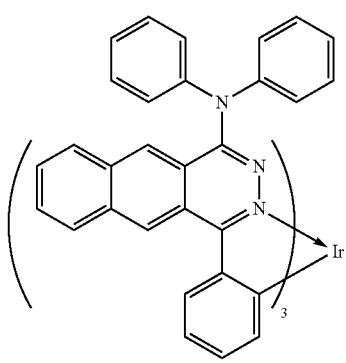

The iridium complexes provided by this invention have following advantages:

Firstly, in the L ligand, a large conjugated benzo[g] pyridazine-based heteroaryl ligands are used to reduce HOMO and LUMO splitting, therefore the iridium complexes achieved red-shifted emission and then can be used as near-infrared luminescent materials.

Secondly, the L ligand with a rigid structure can effectively suppress the geometric isomerization of the iridium complexes and limit the intramolecular motion, improving the luminescence efficiency of corresponding iridium complexes, and alleviate efficiency roll-off of corresponding organic electroluminescent device by reducing the quenching between triplet excitons at high current density.

Thirdly, the N atoms and C atoms coordinating with iridium are not hindered by the sterically hindered group during coordination reaction, which contribute to strong coordinate bond and stable iridium complexes. The lifetime of organic electroluminescent devices based on these iridium complexes could be improved.

Fourthly, since the iridium complexes are homoleptic, there is no ligand-ligand charge-transfer excited state and other additional non-radiative decay transitions caused by auxiliary ligands, which contribute to highly efficient emission.

Another propose of this present invention is to provide an application of the above mentioned iridium complexes in organic electroluminescent devices.

This present invention also provides a type of organic electroluminescent devices comprising a first electrode, a second electrode, and one or more organic layers between the first electrode and the second electrode. The organic layer includes one kind of Iridium Complexes as shown by general formula (I), which have a molecular formula of $L_3Ir$, wherein Ir is the central metal atom and L is the ligand:

(I)

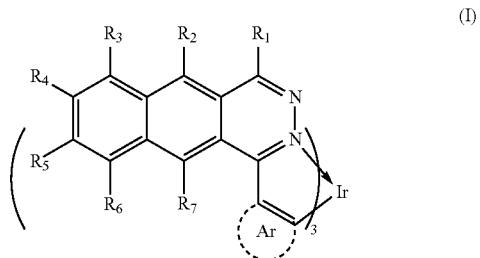

Wherein, Ar is selected from substituted or unsubstituted aryl groups with 6 to 30 carbon atoms, and substituted or unsubstituted heterocyclic aryl groups with 4 to 30 carbon atoms.

$R_1$ to $R_7$ can each be independently selected from hydrogen atoms, halogen atoms, cyano groups, nitro groups, hydroxyl groups, substituted or unsubstituted alkyl or cycloalkyl groups with 1 to 30 carbon atoms, fluoroalkyl groups, chloroalkyl groups, alkoxy groups, thioalkoxy groups, carboxyl groups with 1 to 30 carbon atoms, ester groups with 1 to 30 carbon atoms, acyl groups with 1 to 30 carbon atoms, substituted or unsubstituted amino groups with 1 to 30 carbon atoms, substituted or unsubstituted aryl groups with 6 to 30 carbon atoms, substituted or unsubstituted heterocyclic aryl groups with 4 to 30 carbon atoms.

The above heterocyclic aryl group means a monocyclic or fused ring aryl group containing one or more hetero atoms selected from B, N, O, S, P, P=O, Si and P with 4 to 30 ring carbon atoms.

The substituent group on above-mentioned Ar or $R_1$ to $R_7$ is independently selected from F, Cl, Br, I, CHO, CN, substituted or unsubstituted alkyl or cycloalkyl groups with 1 to 30 carbon atoms, fluoroalkyl groups, alkoxy groups, and thioalkoxy groups.

DESCRIPTION OF DRAWINGS

The above and other objects, features and advantages of the present invention will become apparent from the following description of preferred embodiments given in conjunction with the accompanying drawings, in which:

FIG. 1 is the device configurations prepared with the compound of this present invention;

FIG. 2 is the electroluminescent spectrum of the device OLED-2 prepared in Example 194 of this present invention;

FIG. 3 is current density-voltage characteristics of the device OLED-2 prepared in Example 194 of this present invention;

FIG. 4 is radiant emittance-voltage characteristics of the device OLED-2 prepared in Example 194 of this present invention;

FIG. 5 is external quantum efficiency-current density characteristics of the device OLED-2 prepared in Example 194 of this present invention.

DETAILED DESCRIPTION OF THE INVENTION

In order to be better understood by the researchers and technicians in this area, this present invention will be further described in detail below with accompanying drawings and specific embodiments.

Compound synthesis procedure:

The compounds with no synthetic methods mentioned in the examples are all commercially available raw materials.

The preparation method of the L ligand in iridium complexes is described below by introducing the preparation methods of the following three ligands as an example: ligand 1, ligand 2 and ligand 3.

Ligand 1

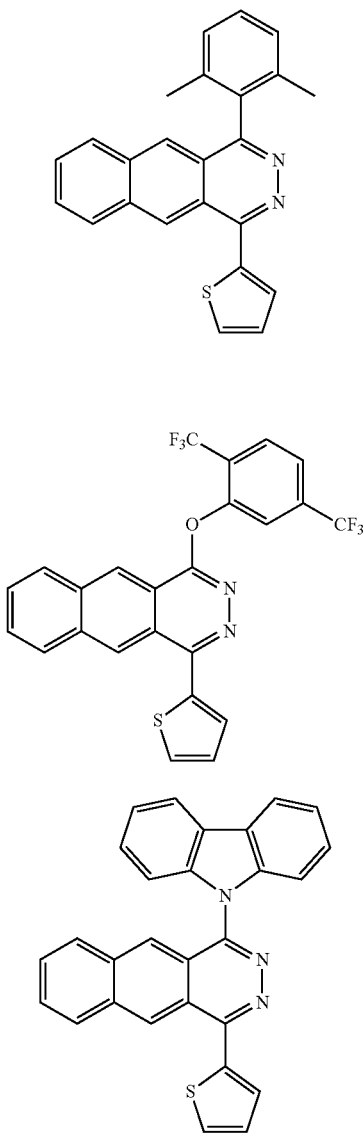

Ligand 2

Ligand 3

When the L ligand is selected from ligand 1, ligand 2 or ligand 3, respectively, the L ligand can be prepared according to the following route:

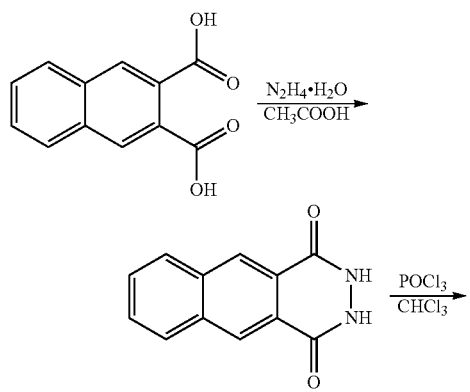

-continued

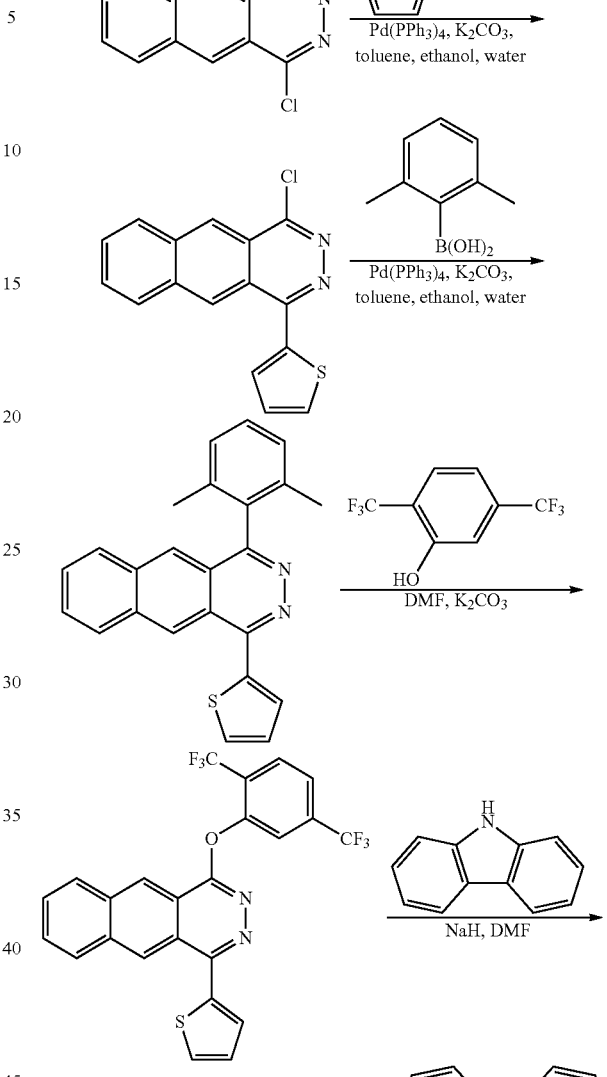

Process characteristics:

This process is versatile. Carbon-carbon coupling, carbon-oxygen coupling and carbon-nitrogen coupling on both sides can be processed, so that symmetric and asymmetric ligands can be constructed.

Process summary:

First, 2,3-naphthalene dicarboxylic acid (1 equivalent) and hydrazine hydrate (0.5-100 equivalents) conduct a dehydration condensation reaction in a solvent (0.5-1000 equivalents) to obtain benzo[g]phthaloyl hydrazide. Then, benzo[g]phthalic acid hydrazide (1 equivalent) conducts a chlorination reaction in phosphorus oxychloride (0.5-100 equivalents) to obtain 1,4-dichlorobenzo[g]pyridazine. Thereafter, 1,4-dichlorobenzo[g]pyridazine (1 equivalent) and arylboronic acid (0.5-100 equivalents) conduct carbon-carbon coupling to obtain the corresponding side substitution ligand in the presence of a catalyst (0.5-10 equivalents) and a base (0.5-1000 equivalents) in a solvent (0.5-1000 equivalents) by Suzuki reaction. Or 1,4-dichlorobenzo[g]pyridazine (1 equivalent) and aromatic phenols (0.5-100 equivalents) conduct carbon-oxygen coupling to obtain a corresponding one-side substituted ligand in a solvent (0.5-1000 equivalents) in the presence of a base (0.5-1000 equivalents). Or 1,4-Dichlorobenzo[g]pyridazine (1 equivalent) and aromatic amine (0.5-100 equivalents) conduct carbon-nitrogen coupling to obtain a corresponding one-side substituted ligand in the presence of NaH (0.5-100 equivalents) in a solvent (0.5-1000 equivalents). Finally, 1-chloro-4-(2-thienyl)-benzo[g]pyridazine (1 equivalent) and arylboronic acid (0.5-100 equivalents) conduct carbon-carbon coupling to obtain the corresponding ligand by Suzuki reaction in the presence of a catalyst (0.5-10 equivalents) and a base (0.5-1000 equivalents) in a solvent (0.5-1000 equivalents). Or 1-chloro-4-(2-thienyl)-benzo[g]pyridazine (1 equivalent) and aromatic phenols (0.5-100 equivalents) conduct carbon-oxygen coupling to obtain the corresponding ligand in the presence of a base (0.5-1000 equivalents) in a solvent (0.5-1000 equivalents). Or 1-chloro-4-(2-thienyl)-benzo[g]pyridazine (1 equivalent) and aromatic amines (0.5-100 equivalents) conduct carbon-nitrogen coupling to obtain the corresponding ligand in the presence of NaH (0.5-100 equivalents) in a solvent (0.5-1000 equivalents).

The specific preferred process steps are as follows:

10 mmol of 2,3-naphthalene dicarboxylic acid and 12 mmol of 80% hydrazine hydrate were refluxed in acetic acid under nitrogen atmosphere for 16 h. The reaction solution was then cooled at 0° C. overnight, then suction filtered, rinsed with water and methanol, and finally recrystallized from methanol to gain white benzo[g]phthalic acid hydrazide in 70% yield.

10 mmol benzo[g]phthaloyl hydrazide and 40 mmol phosphorus oxychloride were mixed together and refluxed under nitrogen atmosphere for 5 h. After complete reaction, the mixture was poured into ice water, basified with aqueous ammonia, and stirred for 15 minutes, then suction filtered, rinsed with water and petroleum ether. After drying, yellow 1,4-dichlorobenzo[g]pyridazine was obtained in a yield of 80%.

0.512 g (4 mmol) 2-thiopheneboronic acid and 0.462 g (0.4 mmol) tetrakis(triphenylphosphine)palladium, 1.66 g (12 mmol) potassium carbonate, 20 ml toluene, 16 ml ethanol and 10 ml distilled water were added to a 100 ml round bottom flask. The mixture was stirred under reflux for 24 h under nitrogen atmosphere. After cooling to room temperature, it was extracted with dichloromethane, then the organic layer was washed with water, and the organic layer was dried by anhydrous magnesium sulfate. After concentration, it was purified by silica gel column chromatography. Yellow 1-chloro-(2-thienyl)-benzo[g]pyridazine was obtained in a yield of 70%.

4 mmol 1-chloro-4-(2-thienyl)-benzo[g]pyridazine, 4.8 mmol 2-thiopheneboronic acid, 0.4 mmol tetrakis(triphenylphosphine)palladium, 12 mmol potassium carbonate, 20 ml toluene, 16 ml ethanol and 10 ml distilled water were placed in a 100 ml round bottom flask, and stirred under reflux for 24 hours under nitrogen atmosphere. After cooling to room temperature, it was extracted with dichloromethane, then the organic layer was washed with water, and the organic layer was dried by anhydrous magnesium sulfate. After concentration, it was purified by silica gel column chromatography. A yellow 1,4-bis(2-thienyl)benzo[g]pyridazine solid was obtained in a yield of 70%. 4 mmol 1-chloro-4-(2-thienyl)-benzo[g]pyridazine, 4.8 mmol 2,5-bistrifluoromethylphenol and 12 mmol potassium carbonate in potassium carbonate were added to a 100 ml round bottom. The flask was stirred under nitrogen atmosphere and reacted at 110° C. for 5 h. After cooling, the reaction solution was poured into water, then suction filtered, dried and purified by silica gel column chromatography. A yellow 1-(2,5-bistrifluoromethylphenoxy)-4-(2-thienyl)-benzo[g]pyridazine solid was obtained in a yield of 60%.

4 mmol carbazole was added to 20 ml anhydrous DMF. After dissolution by stirring under nitrogen atmosphere, 4 mmol 60% NaH (in mineral oil) was added. After stirring for 1 hour, anhydrous DMF solution containing 4 mmol 1-chloro-(2-thienyl)-benzo[g]pyridazine was added under nitrogen atmosphere. Then the solution was stirred at room temperature for 12 h to give the corresponding 1-(9-carbazolyl)-4-(2-thienyl)-benzo[g]pyridazine solid with a yield of 60%.

It can be seen from above that the $R_2$-$R_7$ moiety in structural general formula (I) of the iridium complexes in this present invention can be controlled by replacing the starting carboxylic acid raw material, and the Ar and R1 moieties in structural general formula (I) can be controlled by replacing the subsequent coupling raw material.

The following Examples 1 to 192 illustrate the preparation methods of Iridium Complexes CT1-CT48, CBT1-CBT48, CBF1-CBF48 and CP1-CP48, respectively.

EXAMPLE 1

Preparation of Iridium Complex CT1

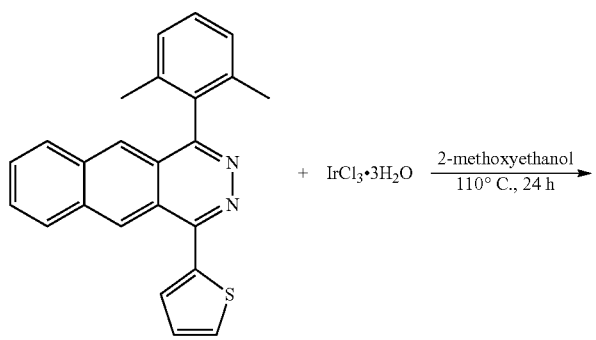

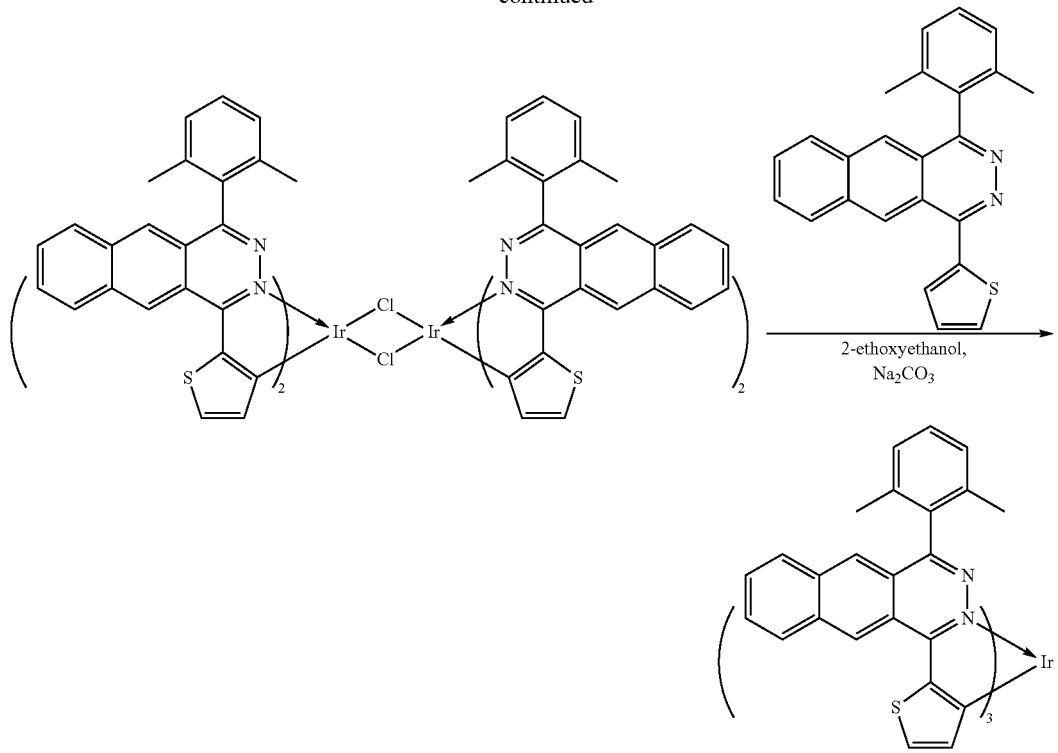

2 mmol 1-(2,6-bismethylphenyl)-4-(2-thienyl)-benzo[g]pyridazine, 1 mmol IrCl3.3H2O, ethylene glycol monomethyl ether (30 ml) and distilled water (10 ml) were stirred under nitrogen atmosphere at 110° C. for 24 h. After cooled to room temperature, suction filtered, washed with water, ethanol and n-hexane, and vacuum drying, a black Iridium dichloro-bridged intermediate was obtained. 1 mmol Iridium dichloro-bridged intermediate, 2.2 mmol 1-(2,6-bismethylphenyl)-4-(2-thienyl)-benzo[g]pyridazine and 9 mmol $Na_2CO_3$ were added to 10 ml ethylene glycol monoethyl ether, then the reaction was carried out at 130° C. for 12 h. Followed by suction filtration and silica gel column chromatography, a dark purple solid was obtained with a yield of 40%.

ESI-HRMS [m/z]: 1289[M+H]$^+$.

Elemental analysis ($C_{60}H_{33}IrN_6S_6$): Anal.Calcd: C, 67.11; H, 3.99; N, 6.52; Found: C, 67.13; H, 3.96; N, 6.62.

EXAMPLE 2

Preparation of Iridium Complex CT2

This example is basically the same as Example 1, except that the $R_1$ group in L ligand is different. 1-(2,3,4,5,6-pentatrifluoromethylphenyl)-4-(2-thienyl)-benzo[g]pyridazine is used instead of 1-(2,6-bismethylphenyl)-4-(2-thienyl)-benzo[g]pyridazine with a yield of 45%.

ESI-MS [m/z]: 2225 [M+H]$^+$.

Elemental analysis ($C_{81}H_{24}F_{45}IrN_6S_3$): Anal.Calcd: C, 43.74; H, 1.09; N, 3.78; Found: C, 43.72; H, 1.11; N, 3.74.

EXAMPLE 3

Preparation of Iridium Complex CT3

This example is basically the same as Example 1, except that the $R_1$ group in L ligand is different. 1-(2,3,4,6-tetratrifluoromethylphenyl)-4-(2-thienyl)-benzo[g]pyridazine is used instead of 1-(2,6-bismethylphenyl)-4-(2-thienyl)-benzo[g]pyridazine with a yield of 42%.

ESI-MS [m/z]: 2021 [M+H]$^+$.

Elemental analysis ($C_{78}H_{27}F_{36}IrN_6S_3$): Anal.Calcd: C, 46.37; H, 1.35; N, 4.16; Found: C, 46.35; H, 1.31; N, 4.19.

EXAMPLE 4

Preparation of Iridium Complex CT4

This example is basically the same as Example 1, except that the $R_1$ group in L ligand is different. 1-(2,3,4,5-tetratrifluoromethylphenyl)-4-(2-thienyl)-benzo[g]pyridazine is used instead of 1-(2,6-bismethylphenyl)-4-(2-thienyl)-benzo[g]pyridazine with a yield of 45%.

ESI-MS [m/z]: 2021 [M+H]$^+$.

Elemental analysis ($C_{78}H_{27}F_{36}IrN_6S_3$): Anal.Calcd: C, 46.37; H, 1.35; N, 4.16; Found: C, 46.39; H, 1.31; N, 4.20.

EXAMPLE 5

Preparation of Iridium Complex CT5

This example is basically the same as Example 1, except that the $R_1$ group in L ligand is different. 1-(2,3,5,6-tetratrifluoromethylphenyl)-4-(2-thienyl)-benzo[g]pyridazine is used instead of 1-(2,6-bismethylphenyl)-4-(2-thienyl)-benzo[g]pyridazine with a yield of 46%.

ESI-MS [m/z]: 2021 [M+H]$^+$.

Elemental analysis ($C_{78}H_{27}F_{36}IrN_6S_3$): Anal.Calcd: C, 46.37; H, 1.35; N, 4.16; Found: C, 46.32; H, 1.39; N, 4.11.

EXAMPLE 6

Preparation of Iridium Complex CT6

This example is basically the same as Example 1, except that the $R_1$ group in L ligand is different. 1-(2,4,6-tritrifluoromethylphenyl)-4-(2-thienyl)-benzo[g]pyridazine is used instead of 1-(2,6-bismethylphenyl)-4-(2-thienyl)-benzo[g]pyridazine with a yield of 40%.
ESI-MS [m/z]: 1817 [M+H]$^+$.
Elemental analysis ($C_{75}H_{30}F_{27}IrN_6S_3$): Anal.Calcd: C, 49.59; H, 1.66; N, 4.63; Found: C, 49.62; H, 1.59; N, 4.64.

EXAMPLE 7

Preparation of Iridium Complex CT7

This example is basically the same as Example 1, except that the $R_1$ group in L ligand is different. 1-(2,3,6-tritrifluoromethylphenyl)-4-(2-thienyl)-benzo[g]pyridazine is used instead of 1-(2,6-bismethylphenyl)-4-(2-thienyl)-benzo[g]pyridazine with a yield of 46%.
ESI-MS [m/z]: 1817 [M+H]$^+$.
Elemental analysis ($C_{75}H_{30}F_{27}IrN_6S_3$): Anal.Calcd: C, 49.59; H, 1.66; N, 4.63; Found: C, 49.60; H, 1.62; N, 4.65.

EXAMPLE 8

Preparation of Iridium Complex CT8

This example is basically the same as Example 1, except that the $R_1$ group in L ligand is different. 1-(2,3,4-tritrifluoromethylphenyl)-4-(2-thienyl)-benzo[g]pyridazine is used instead of 1-(2,6-bismethylphenyl)-4-(2-thienyl)-benzo[g]pyridazine with a yield of 43%.
ESI-MS [m/z]: 1817 [M+H]$^+$.
Elemental analysis ($C_{75}H_{30}F_{27}IrN_6S_3$): Anal.Calcd: C, 49.59; H, 1.66; N, 4.63; Found: C, 49.57; H, 1.59; N, 4.61.

EXAMPLE 9

Preparation of Iridium Complex CT9

This example is basically the same as Example 1, except that the $R_1$ group in L ligand is different. 1-(3,4,5-tritrifluoromethylphenyl)-4-(2-thienyl)-benzo[g]pyridazine is used instead of 1-(2,6-bismethylphenyl)-4-(2-thienyl)-benzo[g]pyridazine with a yield of 38%.
ESI-MS [m/z]: 1817 [M+H]$^+$.
Elemental analysis ($C_{75}H_{30}F_{27}IrN_6S_3$): Anal.Calcd: C, 49.59; H, 1.66; N, 4.63; Found: C, 49.58; H, 1.65; N, 4.58.

EXAMPLE 10

Preparation of Iridium Complex CT10

This example is basically the same as Example 1, except that the $R_1$ group in L ligand is different. 1-(2,3,5-tritrifluoromethylphenyl)-4-(2-thienyl)-benzo[g]pyridazine is used instead of 1-(2,6-bismethylphenyl)-4-(2-thienyl)-benzo[g]pyridazine with a yield of 38%.
ESI-MS [m/z]: 1817 [M+H]$^+$.
Elemental analysis ($C_{75}H_{30}F_{27}IrN_6S_3$): Anal.Calcd: C, 49.59; H, 1.66; N, 4.63; Found: C, 49.66; H, 1.57; N, 4.66.

EXAMPLE 11

Preparation of Iridium Complex CT11

This example is basically the same as Example 1, except that the $R_1$ group in L ligand is different. 1-(2,4,5-tritrifluoromethylphenyl)-4-(2-thienyl)-benzo[g]pyridazine is used instead of 1-(2,6-bismethylphenyl)-4-(2-thienyl)-benzo[g]pyridazine with a yield of 48%.
ESI-MS [m/z]: 1817 [M+H]$^+$.
Elemental analysis ($C_{75}H_{30}F_{27}IrN_6S_3$): Anal.Calcd: C, 49.59; H, 1.66; N, 4.63; Found: C, 49.55; H, 1.65; N, 4.63.

EXAMPLE 12

Preparation of Iridium Complex CT12

This example is basically the same as Example 1, except that the $R_1$ group in L ligand is different. 1-(2,4-bistrifluoromethylphenyl)-4-(2-thienyl)-benzo[g]pyridazine is used instead of 1-(2,6-bismethylphenyl)-4-(2-thienyl)-benzo[g]pyridazine with a yield of 50%.
ESI-MS [m/z]: 1613 [M+H]$^+$.
Elemental analysis ($C_{72}H_{33}F_{18}IrN_6S_3$): Anal.Calcd: C, 53.63; H, 2.06; N, 5.21; Found: C, 53.66; H, 2.04; N, 5.22.

EXAMPLE 13

Preparation of Iridium Complex CT13

This example is basically the same as Example 1, except that the $R_1$ group in L ligand is different. 1-(2,6-bistrifluoromethylphenyl)-4-(2-thienyl)-benzo[g]pyridazine is used instead of 1-(2,6-bismethylphenyl)-4-(2-thienyl)-benzo[g]pyridazine with a yield of 47%.
ESI-MS [m/z]: 1613 [M+H]$^+$.
Elemental analysis ($C_{72}H_{33}F_{18}IrN_6S_3$): Anal.Calcd: C, 53.63; H, 2.06; N, 5.21; Found: C, 53.64; H, 2.02; N, 5.25.

EXAMPLE 14

Preparation of Iridium Complex CT14

This example is basically the same as Example 1, except that the $R_1$ group in L ligand is different. 1-(2,5-bistrifluoromethylphenyl)-4-(2-thienyl)-benzo[g]pyridazine is used instead of 1-(2,6-bismethylphenyl)-4-(2-thienyl)-benzo[g]pyridazine with a yield of 49%.
ESI-MS [m/z]: 1613 [M+H]$^+$.
Elemental analysis ($C_{72}H_{33}F_{18}IrN_6S_3$): Anal.Calcd: C, 53.63; H, 2.06; N, 5.21; Found: C, 53.59; H, 2.07; N, 5.22.

EXAMPLE 15

Preparation of Iridium Complex CT15

This example is basically the same as Example 1, except that the $R_1$ group in L ligand is different. 1-(3,5-bistrifluoromethylphenyl)-4-(2-thienyl)-benzo[g]pyridazine is used instead of 1-(2,6-bismethylphenyl)-4-(2-thienyl)-benzo[g]pyridazine with a yield of 52%.
ESI-MS [m/z]: 1613 [M+H]$^+$.
Elemental analysis ($C_{72}H_{33}F_{18}IrN_6S_3$): Anal.Calcd: C, 53.63; H, 2.06; N, 5.21; Found: C, 53.63; H, 2.08; N, 5.20.

EXAMPLE 16

Preparation of Iridium Complex CT16

This example is basically the same as Example 1, except that the $R_1$ group in L ligand is different. 1-(3,4-bistrifluoromethylphenyl)-4-(2-thienyl)-benzo[g]pyridazine is used instead of 1-(2,6-bismethylphenyl)-4-(2-thienyl)-benzo[g]pyridazine with a yield of 54%.
ESI-MS [m/z]: 1613 [M+H]$^+$.
Elemental analysis ($C_{72}H_{33}F_{18}IrN_6S_3$): Anal.Calcd: C, 53.63; H, 2.06; N, 5.21; Found: C, 53.60; H, 2.02; N, 5.21.

EXAMPLE 17

Preparation of Iridium Complex CT17

This example is basically the same as Example 1, except that the $R_1$ group in L ligand is different. 1-(2,3-bistrifluoromethylphenyl)-4-(2-thienyl)-benzo[g]pyridazine is used instead of 1-(2,6-bismethylphenyl)-4-(2-thienyl)-benzo[g]pyridazine with a yield of 48%.

ESI-MS [m/z]: 1613 [M+H]$^+$.

Elemental analysis ($C_{72}H_{33}F_{18}IrN_6S_3$): Anal.Calcd: C, 53.63; H, 2.06; N, 5.21; Found: C, 53.62; H, 2.01; N, 5.26.

EXAMPLE 18

Preparation of Iridium Complex CT18

This example is basically the same as Example 1, except that the $R_1$ group in L ligand is different. 1-(2-pentafluoroethylphenyl)-4-(2-thienyl)-benzo[g]pyridazine is used instead of 1-(2,6-bismethylphenyl)-4-(2-thienyl)-benzo[g]pyridazine with a yield of 49%.

ESI-MS [m/z]: 1613 [M+H]$^+$.

Elemental analysis ($C_{72}H_{33}F_{18}IrN_6S_3$): Anal.Calcd: C, 53.63; H, 2.06; N, 5.21; Found: C, 53.69; H, 2.00; N, 5.22.

EXAMPLE 19

Preparation of Iridium Complex CT19

This example is basically the same as Example 1, except that the $R_1$ group in L ligand is different. 1-(3-trifluoromethylphenyl)-4-(2-thienyl)-benzo[g]pyridazine is used instead of 1-(2,6-bismethylphenyl)-4-(2-thienyl)-benzo[g]pyridazine with a yield of 54%.

ESI-MS [m/z]: 1409 [M+H]$^+$.

Elemental analysis ($C_{69}H_{36}F_9IrN_6S_3$) Anal.Calcd:C, 58.84; H, 2.58; N, 5.97; Found: C, 58.88; H, 2.55; N, 5.92.

EXAMPLE 20

Preparation of Iridium Complex CT20

This example is basically the same as Example 1, except that the $R_1$ group in L ligand is different. 1-(2-trifluoromethylphenyl)-4-(2-thienyl)-benzo[g]pyridazine is used instead of 1-(2,6-bismethylphenyl)-4-(2-thienyl)-benzo[g]pyridazine with a yield of 50%.

ESI-MS [m/z]: 1409 [M+H]$^+$.

Elemental analysis ($C_{69}H_{36}F_9IrN_6S_3$) Anal.Calcd:C, 58.82; H, 2.58; N, 5.97; Found: C, 58.88; H, 2.58; N, 5.96.

EXAMPLE 21

Preparation of Iridium Complex CT21

This example is basically the same as Example 1, except that the $R_1$ group in L ligand is different. 1-(4-trifluoromethylphenyl)-4-(2-thienyl)-benzo[g]pyridazine is used instead of 1-(2,6-bismethylphenyl)-4-(2-thienyl)-benzo[g]pyridazine with a yield of 52%.

ESI-MS [m/z]: 1409 [M+H]$^+$.

Elemental analysis ($C_{69}H_{36}F_9IrN_6S_3$) Anal.Calcd:C, 58.82; H, 2.58; N, 5.97; Found: C, 58.86; H, 2.55; N, 5.99.

EXAMPLE 22

Preparation of Iridium Complex CT22

This example is basically the same as Example 1, except that the $R_1$ group in L ligand is different. 1-(2,3,4,5,6-pentatrifluoromethylphenoxy)-4-(2-thienyl)-benzo[g]pyridazine is used instead of 1-(2,6-bismethylphenyl)-4-(2-thienyl)-benzo[g]pyridazine with a yield of 42%.

ESI-MS [m/z]: 2273 [M+H]$^+$.

Elemental analysis ($C_{81}H_{24}F_{45}IrN_6O_3S_3$): Anal.Calcd: C, 42.81; H, 1.06; N, 3.70; Found: C, 42.78; H, 1.09; N, 3.71.

EXAMPLE 23

Preparation of Iridium Complex CT23

This example is basically the same as Example 1, except that the $R_1$ group in L ligand is different. 1-(2,3,4,6-tetratrifluoromethylphenoxy)-4-(2-thienyl)-benzo[g]pyridazine is used instead of 1-(2,6-bismethylphenyl)-4-(2-thienyl)-benzo[g]pyridazine with a yield of 40%.

ESI-MS [m/z]: 2069 [M+H]$^+$.

Elemental analysis ($C_{78}H_{27}F_{36}IrN_6O_3S_3$): Anal.Calcd: C, 45.29; H, 1.32; N, 4.06; Found: C, 45.30; H, 1.29; N, 4.09.

EXAMPLE 24

Preparation of Iridium Complex CT24

This example is basically the same as Example 1, except that the $R_1$ group in L ligand is different. 1-(2,3,4,5-tetratrifluoromethylphenoxy)-4-(2-thienyl)-benzo[g]pyridazine is used instead of 1-(2,6-bismethylphenyl)-4-(2-thienyl)-benzo[g]pyridazine with a yield of 46%.

ESI-MS [m/z]: 2069 [M+H]$^+$.

Elemental analysis ($C_{78}H_{27}F_{36}IrN_6O_3S_3$): Anal.Calcd: C, 45.29; H, 1.32; N, 4.06; Found: C, 45.31; H, 1.31; N, 4.10.

EXAMPLE 25

Preparation of Iridium Complex CT25

This example is basically the same as Example 1, except that the $R_1$ group in L ligand is different. 1-(2,3,5,6-tetratrifluoromethylphenoxy)-4-(2-thienyl)-benzo[g]pyridazine is used instead of 1-(2,6-bismethylphenyl)-4-(2-thienyl)-benzo[g]pyridazine with a yield of 42%.

ESI-MS [m/z]: 2069 [M+H]$^+$.

Elemental analysis ($C_{78}H_{27}F_{36}IrN_6O_3S_3$): Anal.Calcd: C, 45.29; H, 1.32; N, 4.06; Found: C, 45.28; H, 1.30; N, 4.07.

EXAMPLE 26

Preparation of Iridium Complex CT26

This example is basically the same as Example 1, except that the $R_1$ group in L ligand is different. 1-(2,4,6-tritrifluoromethylphenoxy)-4-(2-thienyl)-benzo[g]pyridazine is used instead of 1-(2,6-bismethylphenyl)-4-(2-thienyl)-benzo[g]pyridazine with a yield of 46%.

ESI-MS [m/z]: 1865 [M+H]$^+$.

Elemental analysis ($C_{75}H_{30}F_{27}IrN_6O_3S_3$): Anal.Calcd: C, 48.32; H, 1.62; N, 4.51; Found: C, 48.33; H, 1.62; N, 4.52.

EXAMPLE 27

Preparation of Iridium Complex CT27

This example is basically the same as Example 1, except that the $R_1$ group in L ligand is different. 1-(2,3,6-tritrifluoromethylphenoxy)-4-(2-thienyl)-benzo[g]pyridazine is used instead of 1-(2,6-bismethylphenyl)-4-(2-thienyl)-benzo[g]pyridazine with a yield of 40%.

ESI-MS [m/z]: 1865 [M+H]$^+$.

Elemental analysis ($C_{75}H_{30}F_{27}IrN_6O_3S_3$): Anal.Calcd: C, 48.32; H, 1.62; N, 4.51; Found: C, 48.36; H, 1.60; N, 4.50.

EXAMPLE 28

Preparation of Iridium Complex CT28

This example is basically the same as Example 1, except that the $R_1$ group in L ligand is different. 1-(2,3,4-tritrifluoromethylphenoxy)-4-(2-thienyl)-benzo[g]pyridazine is used instead of 1-(2,6-bismethylphenyl)-4-(2-thienyl)-benzo[g]pyridazine with a yield of 46%.

ESI-MS [m/z]: 1865 [M+H]$^+$.

Elemental analysis ($C_{75}H_{30}F_{27}IrN_6O_3S_3$): Anal.Calcd: C, 48.32; H, 1.62; N, 4.51; Found: C, 48.31; H, 1.64; N, 4.50.

EXAMPLE 29

Preparation of Iridium Complex CT29

This example is basically the same as Example 1, except that the $R_1$ group in L ligand is different. 1-(3,4,5-tritrifluoromethylphenoxy)-4-(2-thienyl)-benzo[g]pyridazine is used instead of 1-(2,6-bismethylphenyl)-4-(2-thienyl)-benzo[g]pyridazine with a yield of 46%.

ESI-MS [m/z]: 1865 [M+H]$^+$.

Elemental analysis ($C_{75}H_{30}F_{27}IrN_6O_3S_3$): Anal.Calcd: C, 48.32; H, 1.62; N, 4.51; Found: C, 48.30; H, 1.61; N, 4.54.

EXAMPLE 30

Preparation of Iridium Complex CT30

This example is basically the same as Example 1, except that the $R_1$ group in L ligand is different. 1-(2,3,5-tritrifluoromethylphenoxy)-4-(2-thienyl)-benzo[g]pyridazine is used instead of 1-(2,6-bismethylphenyl)-4-(2-thienyl)-benzo[g]pyridazine with a yield of 42%.

ESI-MS [m/z]: 1865 [M+H]$^+$.

Elemental analysis ($C_{75}H_{30}F_{27}IrN_6O_3S_3$): Anal.Calcd: C, 48.32; H, 1.62; N, 4.51; Found: C, 48.32; H, 1.59; N, 4.52.

EXAMPLE 31

Preparation of Iridium Complex CT31

This example is basically the same as Example 1, except that the $R_1$ group in L ligand is different. 1-(2,4,5-tritrifluoromethylphenoxy)-4-(2-thienyl)-benzo[g]pyridazine is used instead of 1-(2,6-bismethylphenyl)-4-(2-thienyl)-benzo[g]pyridazine with a yield of 40%.

ESI-MS [m/z]: 1865 [M+H]$^+$.

Elemental analysis ($C_{75}H_{30}F_{27}IrN_6O_3S_3$): Anal.Calcd: C, 48.32; H, 1.62; N, 4.51; Found: C, 48.35; H, 1.58; N, 4.51.

EXAMPLE 32

Preparation of Iridium Complex CT32

This example is basically the same as Example 1, except that the $R_1$ group in L ligand is different. 1-(2,4-bistrifluoromethylphenoxy)-4-(2-thienyl)-benzo[g]pyridazine is used instead of 1-(2,6-bismethylphenyl)-4-(2-thienyl)-benzo[g]pyridazine with a yield of 46%.

ES I-MS [m/z]: 1661 [M+H]$^+$.

Elemental analysis ($C_{72}H_{33}F_{18}IrN_6O_3S_3$): Anal.Calcd: C, 52.08; H, 2.00; N, 5.06; Found: C, 52.04; H, 1.98; N, 5.08.

EXAMPLE 33

Preparation of Iridium Complex CT33

This example is basically the same as Example 1, except that the $R_1$ group in L ligand is different. 1-(2,6-bistrifluoromethylphenoxy)-4-(2-thienyl)-benzo[g]pyridazine is used instead of 1-(2,6-bismethylphenyl)-4-(2-thienyl)-benzo[g]pyridazine with a yield of 48%.

ES I-MS [m/z]: 1661 [M+H]$^+$.

Elemental analysis ($C_{72}H_{33}F_{18}IrN_6O_3S_3$): Anal.Calcd: C, 52.08; H, 2.00; N, 5.06; Found: C, 52.07; H, 2.02; N, 5.09.

EXAMPLE 34

Preparation of Iridium Complex CT34

This example is basically the same as Example 1, except that the $R_1$ group in L ligand is different. 1-(2,5-bistrifluoromethylphenoxy)-4-(2-thienyl)-benzo[g]pyridazine is used instead of 1-(2,6-bismethylphenyl)-4-(2-thienyl)-benzo[g]pyridazine with a yield of 45%.

ES I-MS [m/z]: 1661 [M+H]$^+$.

Elemental analysis ($C_{72}H_{33}F_{18}IrN_6O_3S_3$): Anal.Calcd: C, 52.08; H, 2.00; N, 5.06; Found: C, 52.09; H, 2.00; N, 5.05.

EXAMPLE 35

Preparation of Iridium Complex CT35

This example is basically the same as Example 1, except that the $R_1$ group in L ligand is different. 1-(3,5-bistrifluoromethylphenoxy)-4-(2-thienyl)-benzo[g]pyridazine is used instead of 1-(2,6-bismethylphenyl)-4-(2-thienyl)-benzo[g]pyridazine with a yield of 42%.

ES I-MS [m/z]: 1661 [M+H]$^+$.

Elemental analysis ($C_{72}H_{33}F_{18}IrN_6O_3S_3$): Anal.Calcd: C, 52.08; H, 2.00; N, 5.06; Found: C, 52.07; H, 2.02; N, 5.05.

EXAMPLE 36

Preparation of Iridium Complex CT36

This example is basically the same as Example 1, except that the $R_1$ group in L ligand is different. 1-(3,4-bistrifluoromethylphenoxy)-4-(2-thienyl)-benzo[g]pyridazine is used instead of 1-(2,6-bismethylphenyl)-4-(2-thienyl)-benzo[g]pyridazine with a yield of 45%.

ES I-MS [m/z]: 1661 [M+H]$^+$.

Elemental analysis ($C_{72}H_{33}F_{18}IrN_6O_3S_3$): Anal.Calcd: C, 52.08; H, 2.00; N, 5.06; Found: C, 52.08; H, 2.01; N, 5.09.

EXAMPLE 37

Preparation of Iridium Complex CT37

This example is basically the same as Example 1, except that the $R_1$ group in L ligand is different. 1-(2,3-bistrifluoromethylphenoxy)-4-(2-thienyl)-benzo[g]pyridazine is used instead of 1-(2,6-bismethylphenyl)-4-(2-thienyl)-benzo[g]pyridazine with a yield of 56%.

ES I-MS [m/z]: 1661 [M+H]$^+$.

Elemental analysis ($C_{72}H_{33}F_{18}IrN_6O_3S_3$): Anal.Calcd: C, 52.08; H, 2.00; N, 5.06; Found: C, 52.01; H, 1.99; N, 5.10.

EXAMPLE 38

Preparation of Iridium Complex CT38

This example is basically the same as Example 1, except that the $R_1$ group in L ligand is different. 1-(2-pentafluoroethylphenoxy)-4-(2-thienyl)-benzo[g]pyridazine is used instead of 1-(2,6-bismethylphenyl)-4-(2-thienyl)-benzo[g]pyridazine with a yield of 50%.

ES I-MS [m/z]: 1661 [M+H]$^+$.

Elemental analysis ($C_{72}H_{33}F_{18}IrN_6O_3S_3$): Anal.Calcd: C, 52.08; H, 2.00; N, 5.06; Found: C, 52.07; H, 2.04; N, 5.01.

EXAMPLE 39

Preparation of Iridium Complex CT39

This example is basically the same as Example 1, except that the $R_1$ group in L ligand is different. 1-(3-trifluoromethylphenoxy)-4-(2-thienyl)-benzo[g]pyridazine is used instead of 1-(2,6-bismethylphenyl)-4-(2-thienyl)-benzo[g]pyridazine with a yield of 55%.

ESI-MS [m/z]: 1457 [M+H]$^+$.

Elemental analysis ($C_{69}H_{36}F_9IrN_6O_3S_3$) Anal.Calcd:C, 56.90; H, 2.49; N, 5.77; Found: C, 56.92; H, 2.47; N, 5.77.

EXAMPLE 40

Preparation of Iridium Complex CT40

This example is basically the same as Example 1, except that the $R_1$ group in L ligand is different. 1-(2-trifluoromethylphenoxy)-4-(2-thienyl)-benzo[g]pyridazine is used instead of 1-(2,6-bismethylphenyl)-4-(2-thienyl)-benzo[g]pyridazine with a yield of 58%.

ESI-MS [m/z]: 1457 [M+H]$^+$.

Elemental analysis ($C_{69}H_{36}F_9IrN_6O_3S_3$) Anal.Calcd:C, 56.90; H, 2.49; N, 5.77; Found: C, 56.88; H, 2.51; N, 5.80.

EXAMPLE 41

Preparation of Iridium Complex CT41

This example is basically the same as Example 1, except that the $R_1$ group in L ligand is different. 1-(4-trifluoromethylphenoxy)-4-(2-thienyl)-benzo[g]pyridazine is used instead of 1-(2,6-bismethylphenyl)-4-(2-thienyl)-benzo[g]pyridazine with a yield of 50%.

ESI-MS [m/z]: 1457 [M+H]$^+$.

Elemental analysis ($C_{69}H_{36}F_9IrN_6O_3S_3$) Anal.Calcd:C, 56.90; H, 2.49; N, 5.77; Found: C, 56.89; H, 2.45; N, 5.82.

EXAMPLE 42

Preparation of Iridium Complex CT42

This example is basically the same as Example 1, except that the $R_1$ group in L ligand is different. 1-(2,6-bismethylphenoxy)-4-(2-thienyl)-benzo[g]pyridazine is used instead of 1-(2,6-bismethylphenyl)-4-(2-thienyl)-benzo[g]pyridazine with a yield of 60%.

ESI-MS [m/z]: 1337 [M+H]$^+$.

Elemental analysis ($C_{72}H_{51}IrN_6O_3S_3$): Anal.Calcd: C, 64.70; H, 3.85; N, 6.29; Found: C, 64.72; H, 3.82; N, 6.27.

EXAMPLE 43

Preparation of Iridium Complex CT43

This example is basically the same as Example 1, except that the $R_1$ group in L ligand is different. 1-(2-thienyl)-benzo[g]pyridazine is used instead of 1-(2,6-bismethylphenyl)-4-(2-thienyl)-benzo[g]pyridazine with a yield of 63%.

ESI-MS [m/z]: 977 [M+H]$^+$.

Elemental analysis ($C_{48}H_{27}IrN_6S_3$): Anal.Calcd: C, 59.06; H, 2.79; N, 8.61; Found: C, 59.05; H, 2.77; N, 8.65.

EXAMPLE 44

Preparation of Iridium Complex CT44

This example is basically the same as Example 1, except that the $R_1$ group in L ligand is different. 1-chloro-4-(2-thienyl)-benzo[g]pyridazine is used instead of 1-(2,6-bismethylphenyl)-4-(2-thienyl)-benzo[g]pyridazine with a yield of 70%.

ESI-MS [m/z]: 1079 [M+H]$^+$.

Elemental analysis ($C_{48}H_{24}Cl_3IrN_6S_3$): Anal.Calcd: C, 53.41; H, 2.24; N, 7.79; Found: C, 53.39; H, 2.25; N, 7.83.

EXAMPLE 45

Preparation of Iridium Complex CT45

This example is basically the same as Example 1, except that the $R_1$ group in L ligand is different. 1-bromo-4-(2-thienyl)-benzo[g]pyridazine is used instead of 1-(2,6-bismethylphenyl)-4-(2-thienyl)-benzo[g]pyridazine with a yield of 68%.

ESI-MS [m/z]: 1213 [M+H]$^+$.

Elemental analysis ($C_{48}H_{24}Br_3IrN_6S_3$): Anal.Calcd: C, 47.53; H, 1.99; N, 6.93; Found: C, 47.56; H, 2.01; N, 6.91.

EXAMPLE 46

Preparation of Iridium Complex CT46

This example is basically the same as Example 1, except that the $R_1$ group in L ligand is different. 1-(9-carbazolyl)-4-(2-thienyl)-benzo[g]pyridazine is used instead of 1-(2,6-bismethylphenyl)-4-(2-thienyl)-benzo[g]pyridazine with a yield of 52%.

ESI-MS [m/z]: 1472 [M+H]$^+$.

Elemental analysis ($C_{84}H_{48}IrN_9S_3$): Anal.Calcd: C, 68.55; H, 3.29; N, 8.57; Found: C, 68.59; H, 3.28; N, 8.59.

EXAMPLE 47

Preparation of Iridium Complex CT47

This example is basically the same as Example 1, except that the $R_1$ group in L ligand is different. 1-(9-(3,6-bis-tert-butylcarbazolyl)-4-(2-thienyl)-benzo[g]pyridazine is used instead of 1-(2,6-bismethylphenyl)-4-(2-thienyl)-benzo[g]pyridazine with a yield of 40%.

ESI-MS [m/z]: 1810 [M+H]$^+$.

Elemental analysis ($C_{108}H_{96}IrN_9S_3$): Anal.Calcd: C, 71.73; H, 5.35; N, 6.97; Found: C, 71.71; H, 5.39; N, 6.99.

EXAMPLE 48

Preparation of Iridium Complex CT48

This example is basically the same as Example 1, except that the $R_1$ group in L ligand is different. 1-(diphenylamino)-4-(2-thienyl)-benzo[g]pyridazine is used instead of 1-(2,6-bismethylphenyl)-4-(2-thienyl)-benzo[g]pyridazine with a yield of 46%.

ESI-MS [m/z]: 1478 [M+H]$^+$.

Elemental analysis ($C_{84}H_{54}IrN_9S_3$): Anal.Calcd: C, 68.27; H, 3.68; N, 8.53; Found: C, 68.29; H, 3.66; N, 8.56.

The following Examples 49 to 96 are the preparation methods of compounds CBT1 to CBT48.

EXAMPLE 49

Preparation of Iridium Complex CBT1

This example is basically the same as Example 1, except that the Ar and $R_1$ group in L ligand are different. 1,4-bis(2-benzo[b]thienyl)-benzo[g]pyridazine is used instead of 1-(2,6-bismethylphenyl)-4-(2-thienyl)-benzo[g]pyridazine with a yield of 35%.

ESI-MS [m/z]: 1523 [M+H]$^+$.

Elemental analysis ($C_{84}H_{45}IrN_6S_6$): Anal.Calcd: C, 66.25; H, 2.98; N, 5.52; Found: C, 66.23; H, 3.00; N, 5.51.

EXAMPLE 50

Preparation of Iridium Complex CBT2

This example is basically the same as Example 1, except that the Ar and $R_1$ group in L ligand are different. 1-(2,3,4,5,6-pentatrifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 35%.

ESI-MS [m/z]: 2376 [M+H]$^+$.

Elemental analysis ($C_{93}H_{30}F_{45}IrN_6S_3$): Anal.Calcd: C, 47.04; H, 1.27; N, 3.54; Found: C, 47.06; H, 1.26; N, 3.56.

EXAMPLE 51

Preparation of Iridium Complex CBT3

This example is basically the same as Example 1, except that the Ar and $R_1$ group in L ligand are different. 1-(2,3,4,6-tetratrifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 40%.

ESI-MS [m/z]: 2171 [M+H]$^+$.

Elemental analysis ($C_{90}H_{33}F_{36}IrN_6S_3$): Anal.Calcd: C, 49.80; H, 1.53; N, 3.87; Found: C, 49.85; H, 1.50; N, 3.88.

EXAMPLE 52

Preparation of Iridium Complex CBT4

This example is basically the same as Example 1, except that the Ar and $R_1$ group in L ligand are different. 1-(2,3,4,5-tetratrifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 45%.

ESI-MS [m/z]: 2171 [M+H]$^+$.

Elemental analysis ($C_{90}H_{33}F_{36}IrN_6S_3$): Anal.Calcd: C, 49.80; H, 1.53; N, 3.87; Found: C, 49.81; H, 1.49; N, 3.90.

EXAMPLE 53

Preparation of Iridium Complex CBT5

This example is basically the same as Example 1, except that the Ar and $R_1$ group in L ligand are different. 1-(2,3,5,6-tetratrifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 45%.

ESI-MS [m/z]: 2171 [M+H]$^+$.

Elemental analysis ($C_{90}H_{33}F_{36}IrN_6S_3$): Anal.Calcd: C, 49.80; H, 1.53; N, 3.87; Found: C, 49.79; H, 1.51; N, 3.89.

EXAMPLE 54

Preparation of Iridium Complex CBT6

This example is basically the same as Example 1, except that the Ar and $R_1$ group in L ligand are different. 1-(2,4,6-trifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 48%.

ESI-MS [m/z]: 1967 [M+H]$^+$.

Elemental analysis ($C_{87}H_{36}F_{27}IrN_6S_3$): Anal.Calcd: C, 53.13; H, 1.85; N, 4.27; Found: C, 53.12; H, 1.84; N, 4.30.

EXAMPLE 55

Preparation of Iridium Complex CBT7

This example is basically the same as Example 1, except that the Ar and $R_1$ group in L ligand are different. 1-(2,3,6-trifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 50%.

ESI-MS [m/z]: 1967 [M+H]$^+$.

Elemental analysis ($C_{87}H_{36}F_{27}IrN_6S_3$): Anal.Calcd: C, 53.13; H, 1.85; N, 4.27; Found: C, 53.11; H, 1.88; N, 4.31.

EXAMPLE 56

Preparation of Iridium Complex CBT8

This example is basically the same as Example 1, except that the Ar and $R_1$ group in L ligand are different. 1-(2,3,4-trifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 55%.

ESI-MS [m/z]: 1967 [M+H]$^+$.

Elemental analysis ($C_{87}H_{36}F_{27}IrN_6S_3$): Anal.Calcd: C, 53.13; H, 1.85; N, 4.27; Found: C, 53.10; H, 1.81; N, 4.28.

EXAMPLE 57

Preparation of Iridium Complex CBT9

This example is basically the same as Example 1, except that the Ar and $R_1$ group in L ligand are different. 1-(3,4,5-trifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 50%.

ESI-MS [m/z]: 1967 [M+H]$^+$.

Elemental analysis ($C_{87}H_{36}F_{27}IrN_6S_3$): Anal.Calcd: C, 53.13; H, 1.85; N, 4.27; Found: C, 53.11; H, 1.88; N, 4.27.

EXAMPLE 58

Preparation of Iridium Complex CBT10

This example is basically the same as Example 1, except that the Ar and $R_1$ group in L ligand are different. 1-(2,3,5-trifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 48%.

ESI-MS [m/z]: 1967 [M+H]$^+$.

Elemental analysis ($C_{87}H_{36}F_{27}IrN_6S_3$): Anal.Calcd: C, 53.13; H, 1.85; N, 4.27; Found: C, 53.15; H, 1.90; N, 4.22.

EXAMPLE 59

Preparation of Iridium Complex CBT11

This example is basically the same as Example 1, except that the Ar and $R_1$ group in L ligand are different. 1-(2,4,5-trifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 55%.

ESI-MS [m/z]: 1967 [M+H]$^+$.

Elemental analysis ($C_{87}H_{36}F_{27}IrN_6S_3$): Anal.Calcd: C, 53.13; H, 1.85; N, 4.27; Found: C, 53.18; H, 1.82; N, 4.27.

EXAMPLE 60

Preparation of Iridium Complex CBT12

This example is basically the same as Example 1, except that the Ar and $R_1$ group in L ligand are different. 1-(2,4-bistrifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 60%.

ESI-MS [m/z]: 1763 [M+H]$^+$.

Elemental analysis ($C_{84}H_{39}F_{18}IrN_6S_3$): Anal.Calcd: C, 57.24; H, 2.23; N, 4.77; Found: C, 57.28; H, 2.21; N, 4.75.

EXAMPLE 61

Preparation of Iridium Complex CBT13

This example is basically the same as Example 1, except that the Ar and $R_1$ group in L ligand are different. 1-(2,6-bistrifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 61%.

ESI-MS [m/z]: 1763 [M+H]$^+$.

Elemental analysis ($C_{84}H_{39}F_{18}IrN_6S_3$): Anal.Calcd: C, 57.24; H, 2.23; N, 4.77; Found: C, 57.21; H, 2.25; N, 4.78.

EXAMPLE 62

Preparation of Iridium Complex CBT14

This example is basically the same as Example 1, except that the Ar and $R_1$ group in L ligand are different. 1-(2,5-bistrifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 55%.

ESI-MS [m/z]: 1763 [M+H]$^+$.

Elemental analysis ($C_{84}H_{39}F_{18}IrN_6S_3$): Anal.Calcd: C, 57.24; H, 2.23; N, 4.77; Found: C, 57.24; H, 2.27; N, 4.80.

EXAMPLE 63

Preparation of Iridium Complex CBT15

This example is basically the same as Example 1, except that the Ar and $R_1$ group in L ligand are different. 1-(3,5-bistrifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 63%.

ESI-MS [m/z]: 1763 [M+H]$^+$.

Elemental analysis ($C_{84}H_{39}F_{18}IrN_6S_3$): Anal.Calcd: C, 57.24; H, 2.23; N, 4.77; Found: C, 57.28; H, 2.29; N, 4.71.

EXAMPLE 64

Preparation of Iridium Complex CBT16

This example is basically the same as Example 1, except that the Ar and $R_1$ group in L ligand are different. 1-(3,4-bistrifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 60%.

ESI-MS [m/z]: 1763 [M+H]$^+$.

Elemental analysis ($C_{84}H_{39}F_{18}IrN_6S_3$): Anal.Calcd: C, 57.24; H, 2.23; N, 4.77; Found: C, 57.20; H, 2.23; N, 4.78.

EXAMPLE 65

Preparation of Iridium Complex CBT17

This example is basically the same as Example 1, except that the Ar and $R_1$ group in L ligand are different. 1-(2,3-bistrifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 66%.

ESI-MS [m/z]: 1763 [M+H]$^+$.

Elemental analysis ($C_{84}H_{39}F_{18}IrN_6S_3$): Anal.Calcd: C, 57.24; H, 2.23; N, 4.77; Found: C, 57.28; H, 2.21; N, 4.75.

EXAMPLE 66

Preparation of Iridium Complex CBT18

This example is basically the same as Example 1, except that the Ar and $R_1$ group in L ligand are different. 1-(2-pentafluoroethylphenyl)-4-(2-benzo[b]thienyl)-benzo[g]pyridazine is used instead of 1-(2,6-bismethylphenyl)-4-(2-thienyl)-benzo[g]pyridazine with a yield of 60%.

ESI-MS [m/z]: 1763 [M+H]$^+$.

Elemental analysis ($C_{84}H_{39}F_{18}IrN_6S_3$): Anal.Calcd: C, 57.24; H, 2.23; N, 4.77; Found: C, 57.25; H, 2.25; N, 4.79.

EXAMPLE 67

Preparation of Iridium Complex CBT19

This example is basically the same as Example 1, except that the Ar and $R_1$ group in L ligand are different. 1-(3-trifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 65%.

ESI-MS [m/z]: 1559 [M+H]$^+$.
Elemental analysis ($C_{81}H_{42}F_9IrN_6S_3$) Anal.Calcd:C, 62.42; H, 2.72; N, 5.39; Found: C, 62.40; H, 2.72; N, 5.36.

EXAMPLE 68

Preparation of Iridium Complex CBT20

This example is basically the same as Example 1, except that the Ar and $R_1$ group in L ligand are different. 1-(2-trifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 69%.

ESI-MS [m/z]: 1559 [M+H]$^+$.
Elemental analysis ($C_{81}H_{42}F_9IrN_6S_3$) Anal.Calcd:C, 62.42; H, 2.72; N, 5.39; Found: C, 62.44; H, 2.71; N, 5.36.

EXAMPLE 69

Preparation of Iridium Complex CBT21

This example is basically the same as Example 1, except that the Ar and $R_1$ group in L ligand are different. 1-(4-trifluoromethylphenyl)-4-(2-benzo[b]thienyl)-benzo[g]pyridazine is used instead of 1-(2,6-bismethylphenyl)-4-(2-thienyl)-benzo[g]pyridazine with a yield of 66%.

ESI-MS [m/z]: 1559 [M+H]$^+$.
Elemental analysis ($C_{81}H_{42}F_9IrN_6S_3$) Anal.Calcd:C, 62.42; H, 2.72; N, 5.39; Found: C, 62.41; H, 2.75; N, 5.32.

EXAMPLE 70

Preparation of Iridium Complex CBT22

This example is basically the same as Example 1, except that the Ar and $R_1$ group in L ligand are different. 1-(2,3,4,5,6-pentatrifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 41%.

ESI-MS [m/z]: 2424 [M+H]$^+$.
Elemental analysis ($C_{93}H_{30}F_{45}IrN_6O_3S_3$) Anal.Calcd:C, 46.11; H, 1.25; N, 3.47; Found: C, 46.13; H, 1.25; N, 3.49.

EXAMPLE 71

Preparation of Iridium Complex CBT23

This example is basically the same as Example 1, except that the Ar and $R_1$ group in L ligand are different. 1-(2,3,4,6-tetratrifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 46%.

ESI-MS [m/z]: 2219 [M+H]$^+$.
Elemental analysis ($C_{90}H_{33}F_{36}IrN_6O_3S_3$): Anal.Calcd: C, 48.72; H, 1.50; N, 3.79; Found: C, 48.75; H, 1.49; N, 3.75.

EXAMPLE 72

Preparation of Iridium Complex CBT24

This example is basically the same as Example 1, except that the Ar and $R_1$ group in L ligand are different. 1-(2,3,4,5-tetratrifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 44%.

ESI-MS [m/z]: 2219 [M+H]$^+$.
Elemental analysis ($C_{90}H_{33}F_{36}IrN_6O_3S_3$): Anal.Calcd: C, 48.72; H, 1.50; N, 3.79; Found: C, 48.75; H, 1.47; N, 3.75.

EXAMPLE 73

Preparation of Iridium Complex CBT25

This example is basically the same as Example 1, except that the Ar and $R_1$ group in L ligand are different. 1-(2,3,5,6-tetratrifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 47%.

ESI-MS [m/z]: 2219 [M+H]$^+$.
Elemental analysis ($C_{90}H_{33}F_{36}IrN_6O_3S_3$): Anal.Calcd: C, 48.72; H, 1.50; N, 3.79; Found: C, 48.75; H, 1.49; N, 3.75.

EXAMPLE 74

Preparation of Iridium Complex CBT26

This example is basically the same as Example 1, except that the Ar and $R_1$ group in L ligand are different. 1-(2,4,6-tritrifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 52%.

ESI-MS [m/z]: 2015 [M+H]$^+$.
Elemental analysis ($C_{87}H_{36}F_{27}IrN_6O_3S_3$): Anal.Calcd: C, 51.87; H, 1.80; N, 4.17; Found: C, 51.88; H, 1.82; N, 4.15.

EXAMPLE 75

Preparation of Iridium Complex CBT27

This example is basically the same as Example 1, except that the Ar and $R_1$ group in L ligand are different. 1-(2,3,6-tritrifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 51%.

ESI-MS [m/z]: 2015 [M+H]$^+$.
Elemental analysis ($C_{87}H_{36}F_{27}IrN_6O_3S_3$): Anal.Calcd: C, 51.87; H, 1.80; N, 4.17; Found: C, 51.85; H, 1.88; N, 4.15.

EXAMPLE 76

Preparation of Iridium Complex CBT28

This example is basically the same as Example 1, except that the Ar and $R_1$ group in L ligand are different. 1-(2,3,4-tritrifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 56%.

ESI-MS [m/z]: 2015 [M+H]$^+$.
Elemental analysis ($C_{87}H_{36}F_{27}IrN_6O_3S_3$): Anal.Calcd: C, 51.87; H, 1.80; N, 4.17; Found: C, 51.81; H, 1.84; N, 4.15.

EXAMPLE 77

Preparation of Iridium Complex CBT29

This example is basically the same as Example 1, except that the Ar and $R_1$ group in L ligand are different. 1-(3,4,5-tritrifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 55%.
ESI-MS [m/z]: 2015 [M+H]$^+$.
Elemental analysis ($C_{87}H_{36}F_{27}IrN_6O_3S_3$): Anal.Calcd: C, 51.87; H, 1.80; N, 4.17; Found: C, 51.88; H, 1.85; N, 4.14.

EXAMPLE 78

Preparation of Iridium Complex CBT30

This example is basically the same as Example 1, except that the Ar and $R_1$ group in L ligand are different. 1-(2,3,5-tritrifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 54%.
ESI-MS [m/z]: 2015 [M+H]$^+$.
Elemental analysis ($C_{87}H_{36}F_{27}IrN_6O_3S_3$): Anal.Calcd: C, 51.87; H, 1.80; N, 4.17; Found: C, 51.89; H, 1.84; N, 4.11.

EXAMPLE 79

Preparation of Iridium Complex CBT31

This example is basically the same as Example 1, except that the Ar and $R_1$ group in L ligand are different. 1-(2,4,5-tritrifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 60%.
ESI-MS [m/z]: 2015 [M+H]$^+$.
Elemental analysis ($C_{87}H_{36}F_{27}IrN_6O_3S_3$): Anal.Calcd: C, 51.87; H, 1.80; N, 4.17; Found: C, 51.87; H, 1.81; N, 4.15.

EXAMPLE 80

Preparation of Iridium Complex CBT32

This example is basically the same as Example 1, except that the Ar and $R_1$ group in L ligand are different. 1-(2,4-bistrifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 59%.
ESI-MS [m/z]: 1811 [M+H]$^+$.
Elemental analysis ($C_{84}H_{39}F_{18}IrN_6O_3S_3$): Anal.Calcd: C, 55.72; H, 2.17; N, 4.64; Found: C, 55.75; H, 2.19; N, 4.65.

EXAMPLE 81

Preparation of Iridium Complex CBT33

This example is basically the same as Example 1, except that the Ar and $R_1$ group in L ligand are different. 1-(2,6-bistrifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 66%.
ESI-MS [m/z]: 1811 [M+H]$^+$.
Elemental analysis ($C_{84}H_{39}F_{18}IrN_6O_3S_3$): Anal.Calcd: C, 55.72; H, 2.17; N, 4.64; Found: C, 55.74; H, 2.11; N, 4.66.

EXAMPLE 82

Preparation of Iridium Complex CBT34

This example is basically the same as Example 1, except that the Ar and $R_1$ group in L ligand are different. 1-(2,5-bistrifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 60%.
ESI-MS [m/z]: 1811 [M+H]$^+$.
Elemental analysis ($C_{84}H_{39}F_{18}IrN_6O_3S_3$): Anal.Calcd: C, 55.72; H, 2.17; N, 4.64; Found: C, 55.71; H, 2.15; N, 4.68.

EXAMPLE 83

Preparation of Iridium Complex CBT35

This example is basically the same as Example 1, except that the Ar and $R_1$ group in L ligand are different. 1-(3,5-bistrifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 64%.
ESI-MS [m/z]: 1811 [M+H]$^+$.
Elemental analysis ($C_{84}H_{39}F_{18}IrN_6O_3S_3$): Anal.Calcd: C, 55.72; H, 2.17; N, 4.64; Found: C, 55.77; H, 2.16; N, 4.61.

EXAMPLE 84

Preparation of Iridium Complex CBT36

This example is basically the same as Example 1, except that the Ar and $R_1$ group in L ligand are different. 1-(3,4-bistrifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 60%.
ESI-MS [m/z]: 1811 [M+H]$^+$.
Elemental analysis ($C_{84}H_{39}F_{18}IrN_6O_3S_3$): Anal.Calcd: C, 55.72; H, 2.17; N, 4.64; Found: C, 55.74; H, 2.17; N, 4.62.

EXAMPLE 85

Preparation of Iridium Complex CBT37

This example is basically the same as Example 1, except that the Ar and $R_1$ group in L ligand are different. 1-(2,3-bistrifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 64%.
ESI-MS [m/z]: 1811 [M+H]$^+$.
Elemental analysis ($C_{84}H_{39}F_{18}IrN_6O_3S_3$): Anal.Calcd: C, 55.72; H, 2.17; N, 4.64; Found: C, 55.77; H, 2.20; N, 4.60.

EXAMPLE 86

Preparation of Iridium Complex CBT38

This example is basically the same as Example 1, except that the Ar and $R_1$ group in L ligand are different. 1-(2-pentafluoroethylphenoxy)-4-(2-benzo[b]thienyl)-benzo[g]pyridazine is used instead of 1-(2,6-bismethylphenyl)-4-(2-thienyl)-benzo[g]pyridazine with a yield of 60%.
ESI-MS [m/z]: 1811 [M+H]$^+$
Elemental analysis ($C_{84}H_{39}F_{18}IrN_6O_3S_3$): Anal.Calcd: C, 55.72; H, 2.17; N, 4.64; Found: C, 55.71; H, 2.20; N, 4.69.

EXAMPLE 87

Preparation of Iridium Complex CBT39

This example is basically the same as Example 1, except that the Ar and $R_1$ group in L ligand are different. 1-(3-trifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 64%.

ESI-MS [m/z]: 1607 [M+H]$^+$.
Elemental analysis ($C_{81}H_{42}F_9IrN_6O_3S_3$) Anal.Calcd:C, 60.55; H, 2.64; N, 5.23; Found: C, 60.59; H, 2.61; N, 5.22.

EXAMPLE 88

Preparation of Iridium Complex CBT40

This example is basically the same as Example 1, except that the Ar and $R_1$ group in L ligand are different. 1-(2-trifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 61%.

ESI-MS [m/z]: 1607 [M+H]$^+$.
Elemental analysis ($C_{81}H_{42}F_9IrN_6O_3S_3$) Anal.Calcd:C, 60.55; H, 2.64; N, 5.23; Found: C, 60.51; H, 2.68; N, 5.23.

EXAMPLE 89

Preparation of Iridium Complex CBT41

This example is basically the same as Example 1, except that the Ar and $R_1$ group in L ligand are different. 1-(4-trifluoromethylphenoxy)-4-(2-benzo[b]thienyl)-benzo[g]pyridazine is used instead of 1-(2,6-bismethylphenyl)-4-(2-thienyl)-benzo[g]pyridazine with a yield of 55%.

ESI-MS [m/z]: 1607 [M+H]$^+$.
Elemental analysis ($C_{81}H_{42}F_9IrN_6O_3S_3$) Anal.Calcd:C, 60.55; H, 2.64; N, 5.23; Found: C, 60.54; H, 2.63; N, 5.24.

EXAMPLE 90

Preparation of Iridium Complex CBT42

This example is basically the same as Example 1, except that the Ar and $R_1$ group in L ligand are different. 1-(2,6-bismethylphenoxy)-4-(2-benzo[b]thienyl)-benzo[g]pyridazine is used instead of 1-(2,6-bismethylphenyl)-4-(2-thienyl)-benzo[g]pyridazine with a yield of 62%.

ESI-MS [m/z]: 1487 [M+H]$^+$.
Elemental analysis ($C_{84}H_{57}IrN_6O_3S_3$): Anal.Calcd: C, 67.86; H, 3.86; N, 5.65; Found: C, 67.88; H, 3.80; N, 5.66.

EXAMPLE 91

Preparation of Iridium Complex CBT43

This example is basically the same as Example 1, except that the Ar and $R_1$ group in L ligand are different. 1-(2-benzo[b]thienyl)-benzo[g]pyridazine is used instead of 1-(2,6-bismethylphenyl)-4-(2-thienyl)-benzo[g]pyridazine with a yield of 70%.

ESI-MS [m/z]: 1127 [M+H]$^+$.
Elemental analysis ($C_{60}H_{33}IrN_6S_3$): Anal.Calcd: C, 63.98; H, 2.95; N, 7.46; Found: C, 63.99; H, 2.96; N, 7.50.

EXAMPLE 92

Preparation of Iridium Complex CBT44

This example is basically the same as Example 1, except that the Ar and $R_1$ group in L ligand are different. 1-chloro-4-(2-benzo[b]thienyl)-benzo[g]pyridazine is used instead of 1-(2,6-bismethylphenyl)-4-(2-thienyl)-benzo[g]pyridazine with a yield of 60%.

ESI-MS [m/z]: 1229 [M+H]$^+$.
Elemental analysis ($C_{60}H_{30}Cl_3IrN_6S_3$): Anal.Calcd: C, 58.61; H, 2.46; N, 6.83; Found: C, 58.62; H, 2.44; N, 6.80.

EXAMPLE 93

Preparation of Iridium Complex CBT45

This example is basically the same as Example 1, except that the Ar and $R_1$ group in L ligand are different. 1-bromo-4-(2-benzo[b]thienyl)-benzo[g]pyridazine is used instead of 1-(2,6-bismethylphenyl)-4-(2-thienyl)-benzo[g]pyridazine with a yield of 62%.

ESI-MS [m/z]: 1363 [M+H]$^+$.
Elemental analysis ($C_{60}H_{30}Br_3IrN_6S_3$): Anal.Calcd: C, 52.87; H, 2.22; N, 6.17; Found: C, 52.82; H, 2.25; N, 6.14.

EXAMPLE 94

Preparation of Iridium Complex CBT46

This example is basically the same as Example 1, except that the Ar and $R_1$ group in L ligand are different. 1-(9-carbazolyl)-4-(2-benzo[b]thienyl)-benzo[g]pyridazine is used instead of 1-(2,6-bismethylphenyl)-4-(2-thienyl)-benzo[g]pyridazine with a yield of 45%.

ESI-MS [m/z]: 1623 [M+H]$^+$.
Elemental analysis ($C_{96}H_{54}IrN_9S_3$): Anal.Calcd: C, 71.09; H, 3.36; N, 7.77; Found: C, 71.08; H, 3.35; N, 7.80.

EXAMPLE 95

Preparation of Iridium Complex CBT47

This example is basically the same as Example 1, except that the Ar and $R_1$ group in L ligand are different. 1-(9-(3,6-bis-tert-butylcarbazolyl))-4-(2-benzo[b]thienyl)-benzo[g]pyridazine is used instead of 1-(2,6-bismethylphenyl)-4-(2-thienyl)-benzo[g]pyridazine with a yield of 40%.

ESI-MS [m/z]: 1960 [M+H]$^+$.
Elemental analysis ($C_{120}H_{102}IrN_9S_3$):Anal.Calcd:C, 73.59; H, 5.25; N, 6.44; Found: C, 73.60; H, 5.25; N, 6.42.

EXAMPLE 96

Preparation of Iridium Complex CBT48

This example is basically the same as Example 1, except that the Ar and $R_1$ group in L ligand are different. 1-(diphenylamino)-4-(2-benzo[b]thienyl)-benzo[g]pyridazine is used instead of 1-(2,6-bismethylphenyl)-4-(2-thienyl)-benzo[g]pyridazine with a yield of 49%.

ESI-MS [m/z]: 1629 [M+H]$^+$.
Elemental analysis ($C_{96}H_{60}IrN_9S_3$): Anal.Calcd: C, 70.83; H, 3.71; N, 7.74; Found: C, 70.86; H, 3.75; N, 7.77.

The following Examples 97 to 144 are the preparation methods of compounds CBF1 to CBF48.

EXAMPLE 97

Preparation of Iridium Complex CBF1

This example is basically the same as Example 1, except that the Ar and $R_1$ group in L ligand are different. 1,4-bis (2-benzo[b]furanyl)-benzo[g]pyridazine is used instead of 1-(2,6-bismethylphenyl)-4-(2-thienyl)-benzo[g]pyridazine with a yield of 33%.

ESI-MS [m/z]: 1427 [M+H]$^+$.

Elemental analysis ($C_{84}H_{45}IrN_6O_6$): Anal.Calcd: C, 70.72; H, 3.18; N, 5.89; Found: C, 70.70; H, 3.24; N, 5.82.

EXAMPLE 98

Preparation of Iridium Complex CBF2

This example is basically the same as Example 1, except that the Ar and $R_1$ group in L ligand are different. 1-(2,3,4,5,6-pentatrifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 43%.

ESI-MS [m/z]: 2327 [M+H]$^+$.

Elemental analysis ($C_{93}H_{30}F_{45}IrN_6O_3$): Anal.Calcd: C, 48.01; H, 1.30; N, 3.61; Found: C, 47.89; H, 1.32; N, 3.69.

EXAMPLE 99

Preparation of Iridium Complex CBF3

This example is basically the same as Example 1, except that the Ar and $R_1$ group in L ligand are different. 1-(2,3,4,6-tetratrifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 34%.

ESI-MS [m/z]: 2123 [M+H]$^+$.

Elemental analysis ($C_{90}H_{33}F_{36}IrN_6O_3$): Anal.Calcd: C, 50.93; H, 1.57; N, 3.96; Found: C, 51.02; H, 1.54; N, 3.92.

EXAMPLE 100

Preparation of Iridium Complex CBF4

This example is basically the same as Example 1, except that the Ar and $R_1$ group in L ligand are different. 1-(2,3,4,5-tetratrifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 34%.

ESI-MS [m/z]: 2123 [M+H]$^+$.

Elemental analysis ($C_{90}H_{33}F_{36}IrN_6O_3$): Anal.Calcd: C, 50.93; H, 1.57; N, 3.96; Found: C, 50.83; H, 1.50; N, 4.08.

EXAMPLE 101

Preparation of Iridium Complex CBF5

This example is basically the same as Example 1, except that the Ar and $R_1$ group in L ligand are different. 1-(2,3,5,6-tetratrifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 35%.

ESI-MS [m/z]: 2123 [M+H]$^+$.

Elemental analysis ($C_{90}H_{33}F_{36}IrN_6O_3$): Anal.Calcd: C, 50.93; H, 1.57; N, 3.96; Found: C, 51.10; H, 1.48; N, 3.94.

EXAMPLE 102

Preparation of Iridium Complex CBF6

This example is basically the same as Example 1, except that the Ar and $R_1$ group in L ligand are different. 1-(2,4,6-tritrifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 45%.

ESI-MS [m/z]: 1919 [M+H]$^+$.

Elemental analysis ($C_{87}H_{36}F_{27}IrN_6O_3$): Anal.Calcd: C, 54.47; H, 1.89; N, 4.38; Found: C, 54.39; H, 1.94; N, 4.51.

EXAMPLE 103

Preparation of Iridium Complex CBF7

This example is basically the same as Example 1, except that the Ar and $R_1$ group in L ligand are different. 1-(2,3,6-tritrifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 45%.

ESI-MS [m/z]: 1919 [M+H]$^+$.

Elemental analysis ($C_{87}H_{36}F_{27}IrN_6O_3$): Anal.Calcd: C, 54.47; H, 1.89; N, 4.38; Found: C, 54.50; H, 1.84; N, 4.24.

EXAMPLE 104

Preparation of Iridium Complex CBF8

This example is basically the same as Example 1, except that the Ar and $R_1$ group in L ligand are different. 1-(2,3,4-tritrifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 42%.

ESI-MS [m/z]: 1919 [M+H]$^+$.

Elemental analysis ($C_{87}H_{36}F_{27}IrN_6O_3$): Anal.Calcd: C, 54.47; H, 1.89; N, 4.38; Found: C, 54.37; H, 1.72; N, 4.49.

EXAMPLE 105

Preparation of Iridium Complex CBF9

This example is basically the same as Example 1, except that the Ar and $R_1$ group in L ligand are different. 1-(3,4,5-tritrifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 33%.

ESI-MS [m/z]: 1919 [M+H]$^+$.

Elemental analysis ($C_{87}H_{36}F_{27}IrN_6O_3$): Anal.Calcd: C, 54.47; H, 1.89; N, 4.38; Found: C, 54.63; H, 1.99; N, 4.21.

EXAMPLE 106

Preparation of Iridium Complex CBF10

This example is basically the same as Example 1, except that the Ar and $R_1$ group in L ligand are different. 1-(2,3,5-tritrifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 34%.

ESI-MS [m/z]: 1919 [M+H]$^+$.

Elemental analysis ($C_{87}H_{36}F_{27}IrN_6O_3$): Anal.Calcd: C, 54.47; H, 1.89; N, 4.38; Found: C, 54.42; H, 1.75; N, 4.45.

EXAMPLE 107

Preparation of Iridium Complex CBF11

This example is basically the same as Example 1, except that the Ar and $R_1$ group in L ligand are different. 1-(2,4,5-tritrifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 45%.

ESI-MS [m/z]: 1919 [M+H]$^+$.

Elemental analysis ($C_{87}H_{36}F_{27}IrN_6O_3$): Anal.Calcd: C, 54.47; H, 1.89; N, 4.38; Found: C, 54.49; H, 1.80; N, 4.31.

EXAMPLE 108

Preparation of Iridium Complex CBF12

This example is basically the same as Example 1, except that the Ar and $R_1$ group in L ligand are different. 1-(2,4-bistrifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 43%.

ESI-MS [m/z]: 1715 [M+H]$^+$.

Elemental analysis ($C_{84}H_{39}F_{18}IrN_6O_3$): Anal.Calcd: C, 58.85; H, 2.29; N, 4.90; Found: C, 58.78; H, 2.31; N, 4.84.

EXAMPLE 109

Preparation of Iridium Complex CBF13

This example is basically the same as Example 1, except that the Ar and $R_1$ group in L ligand are different. 1-(2,6-bistrifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 43%.

ESI-MS [m/z]: 1715 [M+H]$^+$.

Elemental analysis ($C_{84}H_{39}F_{18}IrN_6O_3$): Anal.Calcd: C, 58.85; H, 2.29; N, 4.90; Found: C, 58.89; H, 2.34; N, 5.03.

EXAMPLE 110

Preparation of Iridium Complex CBF14

This example is basically the same as Example 1, except that the Ar and $R_1$ group in L ligand are different. 1-(2,5-bistrifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 45%.

ESI-MS [m/z]: 1715 [M+H]$^+$.

Elemental analysis ($C_{84}H_{39}F_{18}IrN_6O_3$): Anal.Calcd: C, 58.85; H, 2.29; N, 4.90; Found: C, 58.94; H, 2.21; N, 4.95.

EXAMPLE 111

Preparation of Iridium Complex CBF15

This example is basically the same as Example 1, except that the Ar and $R_1$ group in L ligand are different. 1-(3,5-bistrifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 43%.

ESI-MS [m/z]: 1715 [M+H]$^+$.

Elemental analysis ($C_{84}H_{39}F_{18}IrN_6O_3$): Anal.Calcd: C, 58.85; H, 2.29; N, 4.90; Found: C, 58.79; H, 2.26; N, 4.83.

EXAMPLE 112

Preparation of Iridium Complex CBF16

This example is basically the same as Example 1, except that the Ar and $R_1$ group in L ligand are different. 1-(3,4-bistrifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 34%.

ESI-MS [m/z]: 1715 [M+H]$^+$.

Elemental analysis ($C_{84}H_{39}F_{18}IrN_6O_3$): Anal.Calcd: C, 58.85; H, 2.29; N, 4.90; Found: C, 58.81; H, 2.18; N, 4.87.

EXAMPLE 113

Preparation of Iridium Complex CBF17

This example is basically the same as Example 1, except that the Ar and $R_1$ group in L ligand are different. 1-(2,3-bistrifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 36%.

ESI-MS [m/z]: 1715 [M+H]$^+$.

Elemental analysis ($C_{84}H_{39}F_{18}IrN_6O_3$): Anal.Calcd: C, 58.85; H, 2.29; N, 4.90; Found: C, 58.81; H, 2.36; N, 4.76.

EXAMPLE 114

Preparation of Iridium Complex CBF18

This example is basically the same as Example 1, except that the Ar and $R_1$ group in L ligand are different. 1-(2-pentafluoroethylphenyl)-4-(2-benzo[b]furanyl)-benzo[g]pyridazine is used instead of 1-(2,6-bismethylphenyl)-4-(2-thienyl)-benzo[g]pyridazine with a yield of 37%.

ESI-MS [m/z]: 1715 [M+H]$^+$.

Elemental analysis ($C_{84}H_{39}F_{18}IrN_6O_3$): Anal.Calcd: C, 58.85; H, 2.29; N, 4.90; Found: C, 58.90; H, 2.41; N, 4.98.

EXAMPLE 115

Preparation of Iridium Complex CBF19

This example is basically the same as Example 1, except that the Ar and $R_1$ group in L ligand are different. 1-(3-trifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 37%.

ESI-MS [m/z]: 1511 [M+H]$^+$.

Elemental analysis ($C_{81}H_{42}F_9IrN_6O_3$):Anal.Calcd:C, 64.41; H, 2.80; N, 5.56; Found: C, 64.34; H, 2.75; N, 5.63.

EXAMPLE 116

Preparation of Iridium Complex CBF20

This example is basically the same as Example 1, except that the Ar and $R_1$ group in L ligand are different. 1-(2-trifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 35%.

ESI-MS [m/z]: 1511 [M+H]$^+$.

Elemental analysis ($C_{81}H_{42}F_9IrN_6O_3$):Anal.Calcd:C, 64.41; H, 2.80; N, 5.56; Found: C, 64.45; H, 2.91; N, 5.54.

EXAMPLE 117

Preparation of Iridium Complex CBF21

This example is basically the same as Example 1, except that the Ar and $R_1$ group in L ligand are different. 1-(4-trifluoromethylphenyl)-4-(2-benzo[b]furanyl)-benzo[g]pyridazine is used instead of 1-(2,6-bismethylphenyl)-4-(2-thienyl)-benzo[g]pyridazine with a yield of 35%.
ESI-MS [m/z]: 1511 [M+H]$^+$.
Elemental analysis $(C_{81}H_{42}F_9IrN_6O_3)$:Anal.Calcd:C, 64.41; H, 2.80; N, 5.56; Found: C, 64.52; H, 2.89; N, 5.50.

EXAMPLE 118

Preparation of Iridium Complex CBF22

This example is basically the same as Example 1, except that the Ar and $R_1$ group in L ligand are different. 1-(2,3,4,5,6-pentatrifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 46%.
ESI-MS [m/z]: 2375 [M+H]$^+$.
Elemental analysis $(C_{93}H_{30}F_{45}IrN_6O_6)$: Anal.Calcd: C, 47.04; H, 1.27; N, 3.54; Found: C, 46.98; H, 1.33; N, 3.48.

EXAMPLE 119

Preparation of Iridium Complex CBF23

This example is basically the same as Example 1, except that the Ar and $R_1$ group in L ligand are different. 1-(2,3,4,6-tetratrifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 42%.
ESI-MS [m/z]: 2171 [M+H]$^+$.
Elemental analysis $(C_{90}H_{33}F_{36}IrN_6O_6)$: Anal.Calcd: C, 49.80; H, 1.53; N, 3.87; Found: C, 49.86; H, 1.59; N, 3.81.

EXAMPLE 120

Preparation of Iridium Complex CBF24

This example is basically the same as Example 1, except that the Ar and $R_1$ group in L ligand are different. 1-(2,3,4,5-tetratrifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 44%.
ESI-MS [m/z]: 2171 [M+H]$^+$.
Elemental analysis $(C_{90}H_{33}F_{36}IrN_6O_6)$: Anal.Calcd: C, 49.80; H, 1.53; N, 3.87; Found: C, 49.77; H, 1.61; N, 3.96.

EXAMPLE 121

Preparation of Iridium Complex CBF25

This example is basically the same as Example 1, except that the Ar and $R_1$ group in L ligand are different. 1-(2,3,5,6-tetratrifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 43%.
ESI-MS [m/z]: 2171 [M+H]$^+$.
Elemental analysis $(C_{90}H_{33}F_{36}IrN_6O_6)$: Anal.Calcd: C, 49.80; H, 1.53; N, 3.87; Found: C, 49.84; H, 1.60; N, 3.99.

EXAMPLE 122

Preparation of Iridium Complex CBF26

This example is basically the same as Example 1, except that the Ar and $R_1$ group in L ligand are different. 1-(2,4,6-tritrifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 33%.
ESI-MS [m/z]: 1967 [M+H]$^+$.
Elemental analysis $(C_{87}H_{36}F_{27}IrN_6O_6)$: Anal.Calcd: C, 53.14; H, 1.85; N, 4.27; Found: C, 53.10; H, 1.91; N, 4.23.

EXAMPLE 123

Preparation of Iridium Complex CBF27

This example is basically the same as Example 1, except that the Ar and $R_1$ group in L ligand are different. 1-(2,3,6-tritrifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 36%.
ESI-MS [m/z]: 1967 [M+H]$^+$.
Elemental analysis $(C_{87}H_{36}F_{27}IrN_6O_6)$: Anal.Calcd: C, 53.14; H, 1.85; N, 4.27; Found: C, 53.21; H, 1.88; N, 4.36.

EXAMPLE 124

Preparation of Iridium Complex CBF28

This example is basically the same as Example 1, except that the Ar and $R_1$ group in L ligand are different. 1-(2,3,4-tritrifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 38%.
ESI-MS [m/z]: 1967 [M+H]$^+$.
Elemental analysis $(C_{87}H_{36}F_{27}IrN_6O_6)$: Anal.Calcd: C, 53.14; H, 1.85; N, 4.27; Found: C, 53.24; H, 1.79; N, 4.20.

EXAMPLE 125

Preparation of Iridium Complex CBF29

This example is basically the same as Example 1, except that the Ar and $R_1$ group in L ligand are different. 1-(3,4,5-tritrifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 38%.
ESI-MS [m/z]: 1967 [M+H]$^+$.
Elemental analysis $(C_{87}H_{36}F_{27}IrN_6O_6)$: Anal.Calcd: C, 53.14; H, 1.85; N, 4.27; Found: C, 53.22; H, 1.81; N, 4.33.

EXAMPLE 126

Preparation of Iridium Complex CBF30

This example is basically the same as Example 1, except that the Ar and $R_1$ group in L ligand are different. 1-(2,3,5-tritrifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 42%.
ESI-MS [m/z]: 1967 [M+H]$^+$.
Elemental analysis $(C_{87}H_{36}F_{27}IrN_6O_6)$: Anal.Calcd: C, 53.14; H, 1.85; N, 4.27; Found: C, 53.08; H, 1.91; N, 4.24.

EXAMPLE 127

Preparation of Iridium Complex CBF31

This example is basically the same as Example 1, except that the Ar and $R_1$ group in L ligand are different. 1-(2,4,5-tritrifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 43%.

ESI-MS [m/z]: 1967 [M+H]$^+$.

Elemental analysis ($C_{87}H_{36}F_{27}IrN_6O_6$): Anal.Calcd: C, 53.14; H, 1.85; N, 4.27; Found: C, 53.06; H, 1.89; N, 4.15.

EXAMPLE 128

Preparation of Iridium Complex CBF32

This example is basically the same as Example 1, except that the Ar and $R_1$ group in L ligand are different. 1-(2,4-bistrifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 43%.

ESI-MS [m/z]: 1763 [M+H]$^+$.

Elemental analysis ($C_{84}H_{39}F_{18}IrN_6O_6$): Anal.Calcd: C, 57.24; H, 2.23; N, 4.77; Found: C, 57.18; H, 2.21; N, 4.82.

EXAMPLE 129

Preparation of Iridium Complex CBF33

This example is basically the same as Example 1, except that the Ar and $R_1$ group in L ligand are different. 1-(2,6-bistrifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 44%.

ESI-MS [m/z]: 1763 [M+H]$^+$.

Elemental analysis ($C_{84}H_{39}F_{18}IrN_6O_6$): Anal.Calcd: C, 57.24; H, 2.23; N, 4.77; Found: C, 57.29; H, 2.16; N, 4.75.

EXAMPLE 130

Preparation of Iridium Complex CBF34

This example is basically the same as Example 1, except that the Ar and $R_1$ group in L ligand are different. 1-(2,5-bistrifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 41%.

ESI-MS [m/z]: 1763 [M+H]$^+$.

Elemental analysis ($C_{84}H_{39}F_{18}IrN_6O_6$): Anal.Calcd: C, 57.24; H, 2.23; N, 4.77; Found: C, 57.27; H, 2.30; N, 4.68.

EXAMPLE 131

Preparation of Iridium Complex CBF35

This example is basically the same as Example 1, except that the Ar and $R_1$ group in L ligand are different. 1-(3,5-bistrifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 41%.

ESI-MS [m/z]: 1763 [M+H]$^+$.

Elemental analysis ($C_{84}H_{39}F_{18}IrN_6O_6$): Anal.Calcd: C, 57.24; H, 2.23; N, 4.77; Found: C, 57.31; H, 2.29; N, 4.73.

EXAMPLE 132

Preparation of Iridium Complex CBF36

This example is basically the same as Example 1, except that the Ar and $R_1$ group in L ligand are different. 1-(3,4-bistrifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 41%.

ESI-MS [m/z]: 1763 [M+H]$^+$.

Elemental analysis ($C_{84}H_{39}F_{18}IrN_6O_6$): Anal.Calcd: C, 57.24; H, 2.23; N, 4.77; Found: C, 57.19; H, 2.18; N, 4.80.

EXAMPLE 133

Preparation of Iridium Complex CBF37

This example is basically the same as Example 1, except that the Ar and $R_1$ group in L ligand are different. 1-(2,3-bistrifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 41%.

ESI-MS [m/z]: 1763 [M+H]$^+$.

Elemental analysis ($C_{84}H_{39}F_{18}IrN_6O_6$): Anal.Calcd: C, 57.24; H, 2.23; N, 4.77; Found: C, 57.27; H, 2.11; N, 4.85.

EXAMPLE 134

Preparation of Iridium Complex CBF38

This example is basically the same as Example 1, except that the Ar and $R_1$ group in L ligand are different. 1-(2-pentafluoroethylphenoxy)-4-(2-benzo[b]furanyl)-benzo[g]pyridazine is used instead of 1-(2,6-bismethylphenyl)-4-(2-thienyl)-benzo[g]pyridazine with a yield of 41%.

ESI-MS [m/z]: 1763 [M+H]$^+$.

Elemental analysis ($C_{84}H_{39}F_{18}IrN_6O_6$): Anal.Calcd: C, 57.24; H, 2.23; N, 4.77; Found: C, 57.41; H, 2.19; N, 4.68.

EXAMPLE 135

Preparation of Iridium Complex CBF39

This example is basically the same as Example 1, except that the Ar and $R_1$ group in L ligand are different. 1-(3-trifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 40%.

ESI-MS [m/z]: 1559 [M+H]$^+$.

Elemental analysis ($C_{81}H_{42}F_9IrN_6O_6$):Anal.Calcd:C, 62.43; H, 2.72; N, 5.39; Found: C, 62.39; H, 2.71; N, 5.48.

EXAMPLE 136

Preparation of Iridium Complex CBF40

This example is basically the same as Example 1, except that the Ar and $R_1$ group in L ligand are different. 1-(2-trifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 40%.

ESI-MS [m/z]: 1559 [M+H]$^+$.

Elemental analysis ($C_{81}H_{42}F_9IrN_6O_6$):Anal.Calcd:C, 62.43; H, 2.72; N, 5.39; Found: C, 62.48; H, 2.75; N, 5.34.

EXAMPLE 137

Preparation of Iridium Complex CBF41

This example is basically the same as Example 1, except that the Ar and $R_1$ group in L ligand are different. 1-(4-trifluoromethylphenoxy)-4-(2-benzo[b]furanyl)-benzo[g]pyridazine is used instead of 1-(2,6-bismethylphenyl)-4-(2-thienyl)-benzo[g]pyridazine with a yield of 40%.

ESI-MS [m/z]: 1559 [M+H]$^+$.

Elemental analysis ($C_{81}H_{42}F_9IrN_6O_6$):Anal.Calcd:C, 62.43; H, 2.72; N, 5.39; Found: C, 62.37; H, 2.81; N, 5.33.

EXAMPLE 138

Preparation of Iridium Complex CBF42

This example is basically the same as Example 1, except that the Ar and $R_1$ group in L ligand are different. 1-(2,6-bismethylphenoxy)-4-(2-benzo[b]furanyl)-benzo[g]pyridazine is used instead of 1-(2,6-bismethylphenyl)-4-(2-thienyl)-benzo[g]pyridazine with a yield of 40%.

ESI-MS [m/z]: 1439 [M+H]$^+$.

Elemental analysis ($C_{84}H_{57}IrN_6O_6$): Anal.Calcd: C, 70.13; H, 3.99; N, 5.84; Found: C, 70.09; H, 4.04; N, 5.81.

EXAMPLE 139

Preparation of Iridium Complex CBF43

This example is basically the same as Example 1, except that the Ar and $R_1$ group in L ligand are different. 1-(2-benzo[b]furanyl)-benzo[g]pyridazine is used instead of 1-(2,6-bismethylphenyl)-4-(2-thienyl)-benzo[g]pyridazine with a yield of 40%.

ESI-MS [m/z]: 1079 [M+H]$^+$.

Elemental analysis ($C_{60}H_{33}IrN_6O_3$): Anal.Calcd: C, 66.84; H, 3.09; N, 7.79; Found: C, 66.71; H, 3.05; N, 7.85.

EXAMPLE 140

Preparation of Iridium Complex CBF44

This example is basically the same as Example 1, except that the Ar and $R_1$ group in L ligand are different. 1-chloro-4-(2-benzo[b]furanyl)-benzo[g]pyridazine is used instead of 1-(2,6-bismethylphenyl)-4-(2-thienyl)-benzo[g]pyridazine with a yield of 40%.

ESI-MS [m/z]: 1182 [M+H]$^+$.

Elemental analysis ($C_{60}H_{30}Cl_3IrN_6O_3$) Anal.Calcd:C, 60.99; H, 2.56; N, 7.11; Found: C, 60.93; H, 2.64; N, 7.15.

EXAMPLE 141

Preparation of Iridium Complex CBF45

This example is basically the same as Example 1, except that the Ar and $R_1$ group in L ligand are different. 1-bromo-4-(2-benzo[b]furanyl)-benzo[g]pyridazine is used instead of 1-(2,6-bismethylphenyl)-4-(2-thienyl)-benzo[g]pyridazine with a yield of 40%.

ESI-MS [m/z]: 1316 [M+H]$^+$.

Elemental analysis ($C_{60}H_{30}Br_3IrN_6O_3$): Anal.Calcd: C, 54.81; H, 2.30; N, 6.39; Found: C, 54.87; H, 2.26; N, 6.47.

EXAMPLE 142

Preparation of Iridium Complex CBF46

This example is basically the same as Example 1, except that the Ar and $R_1$ group in L ligand are different. 1-(9-carbazolyl)-4-(2-benzo[b]furanyl)-benzo[g]pyridazine is used instead of 1-(2,6-bismethylphenyl)-4-(2-thienyl)-benzo[g]pyridazine with a yield of 40%.

ESI-MS [m/z]: 1574 [M+H]$^+$.

Elemental analysis ($C_{96}H_{54}IrN_9O_3$): Anal.Calcd: C, 73.27; H, 3.46; N, 8.01; Found: C, 73.23; H, 3.52; N, 7.94.

EXAMPLE 143

Preparation of Iridium Complex CBF47

This example is basically the same as Example 1, except that the Ar and $R_1$ group in L ligand are different. 1-(9-(3,6-bis-tert-butylcarbazolyl)-4-(2-benzo[b]furanyl)-benzo[g]pyridazine is used instead of 1-(2,6-bismethylphenyl)-4-(2-thienyl)-benzo[g]pyridazine with a yield of 39%.

ESI-MS [m/z]: 1911 [M+H]$^+$.

Elemental analysis ($C_{120}H_{102}IrN_9O_3$):Anal.Calcd:C, 75.45; H, 5.38; N, 6.60; Found: C, 75.41; H, 5.49; N, 6.56.

EXAMPLE 144

Preparation of Iridium Complex CBF48

This example is basically the same as Example 1, except that the Ar and $R_1$ group in L ligand are different. 1-(diphenylamino)-4-(2-benzo[b]furanyl)-benzo[g]pyridazine is used instead of 1-(2,6-bismethylphenyl)-4-(2-thienyl)-benzo[g]pyridazine with a yield of 35%.

ESI-MS [m/z]: 1580 [M+H]$^+$.

Elemental analysis ($C_{96}H_{60}IrN_9O_3$): Anal.Calcd: C, 72.99; H, 3.83; N, 7.98; Found: C, 73.01; H, 3.92; N, 8.04.

The following Examples 145 to 192 are the preparation methods of compounds CP1 to CP48.

EXAMPLE 145

Preparation of Iridium Complex CP1

This example is basically the same as Example 1, except that the Ar and $R_1$ group in L ligand are different. 1-(2,6-bismethylphenyl)-4-phenyl-benzo[g]pyridazine is used instead of 1-(2,6-bismethylphenyl)-4-(2-thienyl)-benzo[g]pyridazine with a yield of 35%.

ESI-MS [m/z]: 1271 [M+H]$^+$.

Elemental analysis ($C_{72}H_{45}IrN_6$):Anal.Calcd:C, 73.73; H, 4.52; N, 6.61; Found: C, 73.76; H, 4.55; N, 6.10.

EXAMPLE 146

Preparation of Iridium Complex CP2

This example is basically the same as Example 1, except that the Ar and $R_1$ group in L ligand are different. 1-(2,3,4,5,6-pentatrifluoromethylphenyl)-4-phenyl-benzo[g]pyridazine is used instead of 1-(2,6-bismethylphenyl)-4-(2-thienyl)-benzo[g]pyridazine with a yield of 30%.

ESI-MS [m/z]: 2207 [M+H]$^+$.

Elemental analysis ($C_{87}H_{30}F_{45}IrN_6$): Anal.Calcd: C, 47.36; H, 1.37; N, 3.81; Found: C, 47.35; H, 1.40; N, 3.85.

EXAMPLE 147

Preparation of Iridium Complex CP3

This example is basically the same as Example 1, except that the Ar and $R_1$ group in L ligand are different. 1-(2,3,4,6-tetratrifluoromethylphenyl)-4-phenyl-benzo[g]pyridazine is used instead of 1-(2,6-bismethylphenyl)-4-(2-thienyl)-benzo[g]pyridazine with a yield of 35%.

ESI-MS [m/z]: 2003 [M+H]$^+$.

Elemental analysis ($C_{84}H_{33}F_{36}IrN_6$): Anal.Calcd: C, 50.39; H, 1.66; N, 4.20; Found: C, 50.37; H, 1.70; N, 4.16.

EXAMPLE 148

Preparation of Iridium Complex CP4

This example is basically the same as Example 1, except that the Ar and $R_1$ group in L ligand are different. 1-(2,3,4,5-tetratrifluoromethylphenyl)-4-phenyl-benzo[g]pyridazine is used instead of 1-(2,6-bismethylphenyl)-4-(2-thienyl)-benzo[g]pyridazine with a yield of 35%.

ESI-MS [m/z]: 2003 [M+H]$^+$.

Elemental analysis ($C_{84}H_{33}F_{36}IrN_6$): Anal.Calcd: C, 50.39; H, 1.66; N, 4.20; Found: C, 50.35; H, 1.64; N, 4.21.

EXAMPLE 149

Preparation of Iridium Complex CP5

This example is basically the same as Example 1, except that the Ar and $R_1$ group in L ligand are different. 1-(2,3,5,6-tetratrifluoromethylphenyl)-4-phenyl-benzo[g]pyridazine is used instead of 1-(2,6-bismethylphenyl)-4-(2-thienyl)-benzo[g]pyridazine with a yield of 36%.

ESI-MS [m/z]: 2003 [M+H]$^+$.

Elemental analysis ($C_{84}H_{33}F_{36}IrN_6$): Anal.Calcd: C, 50.39; H, 1.66; N, 4.20; Found: C, 50.38; H, 1.65; N, 4.24.

EXAMPLE 150

Preparation of Iridium Complex CP6

This example is basically the same as Example 1, except that the Ar and $R_1$ group in L ligand are different. 1-(2,4,6-tritrifluoromethylphenyl)-4-phenyl-benzo[g]pyridazine is used instead of 1-(2,6-bismethylphenyl)-4-(2-thienyl)-benzo[g]pyridazine with a yield of 30%.

ESI-MS [m/z]: 1799 [M+H]$^+$.

Elemental analysis ($C_{81}H_{36}F_{27}IrN_6$): Anal.Calcd: C, 54.10; H, 2.02; N, 4.67; Found: C, 54.11; H, 2.03; N, 4.70.

EXAMPLE 151

Preparation of Iridium Complex CP7

This example is basically the same as Example 1, except that the Ar and $R_1$ group in L ligand are different. 1-(2,3,6-tritrifluoromethylphenyl)-4-phenyl-benzo[g]pyridazine is used instead of 1-(2,6-bismethylphenyl)-4-(2-thienyl)-benzo[g]pyridazine with a yield of 32%.

ESI-MS [m/z]: 1799 [M+H]$^+$.

Elemental analysis ($C_{81}H_{36}F_{27}IrN_6$): Anal.Calcd: C, 54.10; H, 2.02; N, 4.67; Found: C, 54.15; H, 2.07; N, 4.73.

EXAMPLE 152

Preparation of Iridium Complex CP8

This example is basically the same as Example 1, except that the Ar and $R_1$ group in L ligand are different. 1-(2,3,4-tritrifluoromethylphenyl)-4-phenyl-benzo[g]pyridazine is used instead of 1-(2,6-bismethylphenyl)-4-(2-thienyl)-benzo[g]pyridazine with a yield of 35%.

ESI-MS [m/z]: 1799 [M+H]$^+$.

Elemental analysis ($C_{81}H_{36}F_{27}IrN_6$): Anal.Calcd: C, 54.10; H, 2.02; N, 4.67; Found: C, 54.16; H, 2.01; N, 4.62.

EXAMPLE 153

Preparation of Iridium Complex CP9

This example is basically the same as Example 1, except that the Ar and $R_1$ group in L ligand are different. 1-(3,4,5-tritrifluoromethylphenyl)-4-phenyl-benzo[g]pyridazine is used instead of 1-(2,6-bismethylphenyl)-4-(2-thienyl)-benzo[g]pyridazine with a yield of 38%.

ESI-MS [m/z]: 1799 [M+H]$^+$.

Elemental analysis ($C_{81}H_{36}F_{27}IrN_6$): Anal.Calcd: C, 54.10; H, 2.02; N, 4.67; Found: C, 54.08; H, 1.99; N, 4.70.

EXAMPLE 154

Preparation of Iridium Complex CP10

This example is basically the same as Example 1, except that the Ar and $R_1$ group in L ligand are different. 1-(2,3,5-tritrifluoromethylphenyl)-4-phenyl-benzo[g]pyridazine is used instead of 1-(2,6-bismethylphenyl)-4-(2-thienyl)-benzo[g]pyridazine with a yield of 38%.

ESI-MS [m/z]: 1799 [M+H]$^+$.

Elemental analysis ($C_{81}H_{36}F_{27}IrN_6$): Anal.Calcd: C, 54.10; H, 2.02; N, 4.67; Found: C, 54.09; H, 2.05; N, 4.71.

EXAMPLE 155

Preparation of Iridium Complex CP11

This example is basically the same as Example 1, except that the Ar and $R_1$ group in L ligand are different. 1-(2,4,5-tritrifluoromethylphenyl)-4-phenyl-benzo[g]pyridazine is used instead of 1-(2,6-bismethylphenyl)-4-(2-thienyl)-benzo[g]pyridazine with a yield of 30%.

ESI-MS [m/z]: 1799 [M+H]$^+$.

Elemental analysis ($C_{81}H_{36}F_{27}IrN_6$): Anal.Calcd: C, 54.10; H, 2.02; N, 4.67; Found: C, 54.14; H, 2.00; N, 4.70.

EXAMPLE 156

Preparation of Iridium Complex CP12

This example is basically the same as Example 1, except that the Ar and $R_1$ group in L ligand are different. 1-(2,4-bistrifluoromethylphenyl)-4-phenyl-benzo[g]pyridazine is used instead of 1-(2,6-bismethylphenyl)-4-(2-thienyl)-benzo[g]pyridazine with a yield of 33%.

ESI-MS [m/z]: 1595 [M+H]$^+$.

Elemental analysis ($C_{78}H_{39}F_{18}IrN_6$): Anal.Calcd: C, 58.76; H, 2.47; N, 5.27; Found: C, 58.75; H, 2.50; N, 5.25.

EXAMPLE 157

Preparation of Iridium Complex CP13

This example is basically the same as Example 1, except that the Ar and $R_1$ group in L ligand are different. 1-(2,6-bistrifluoromethylphenyl)-4-phenyl-benzo[g]pyridazine is used instead of 1-(2,6-bismethylphenyl)-4-(2-thienyl)-benzo[g]pyridazine with a yield of 36%.

ESI-MS [m/z]: 1595 [M+H]$^+$.

Elemental analysis ($C_{78}H_{39}F_{18}IrN_6$): Anal.Calcd: C, 58.76; H, 2.47; N, 5.27; Found: C, 58.71; H, 2.52; N, 5.27.

EXAMPLE 158

Preparation of Iridium Complex CP14

This example is basically the same as Example 1, except that the Ar and $R_1$ group in L ligand are different. 1-(2,5-bistrifluoromethylphenyl)-4-phenyl-benzo[g]pyridazine is used instead of 1-(2,6-bismethylphenyl)-4-(2-thienyl)-benzo[g]pyridazine with a yield of 32%.

ESI-MS [m/z]: 1595 [M+H]$^+$.

Elemental analysis ($C_{78}H_{39}F_{18}IrN_6$): Anal.Calcd: C, 58.76; H, 2.47; N, 5.27; Found: C, 58.79; H, 2.44; N, 5.22.

EXAMPLE 159

Preparation of Iridium Complex CP15

This example is basically the same as Example 1, except that the Ar and $R_1$ group in L ligand are different. 1-(3,5-bistrifluoromethylphenyl)-4-phenyl-benzo[g]pyridazine is used instead of 1-(2,6-bismethylphenyl)-4-(2-thienyl)-benzo[g]pyridazine with a yield of 35%.

ESI-MS [m/z]: 1595 [M+H]$^+$.

Elemental analysis ($C_{78}H_{39}F_{18}IrN_6$): Anal.Calcd: C, 58.76; H, 2.47; N, 5.27; Found: C, 58.71; H, 2.49; N, 5.25.

EXAMPLE 160

Preparation of Iridium Complex CP16

This example is basically the same as Example 1, except that the Ar and $R_1$ group in L ligand are different. 1-(3,4-bistrifluoromethylphenyl)-4-phenyl-benzo[g]pyridazine is used instead of 1-(2,6-bismethylphenyl)-4-(2-thienyl)-benzo[g]pyridazine with a yield of 30%.

ESI-MS [m/z]: 1595 [M+H]$^+$.

Elemental analysis ($C_{78}H_{39}F_{18}IrN_6$): Anal.Calcd: C, 58.76; H, 2.47; N, 5.27; Found: C, 58.76; H, 2.47; N, 5.29.

EXAMPLE 161

Preparation of Iridium Complex CP17

This example is basically the same as Example 1, except that the Ar and $R_1$ group in L ligand are different. 1-(2,3-bistrifluoromethylphenyl)-4-phenyl-benzo[g]pyridazine is used instead of 1-(2,6-bismethylphenyl)-4-(2-thienyl)-benzo[g]pyridazine with a yield of 35%.

ESI-MS [m/z]: 1595 [M+H]$^+$.

Elemental analysis ($C_{78}H_{39}F_{18}IrN_6$): Anal.Calcd: C, 58.76; H, 2.47; N, 5.27; Found: C, 58.70; H, 2.44; N, 5.32.

EXAMPLE 162

Preparation of Iridium Complex CP18

This example is basically the same as Example 1, except that the Ar and $R_1$ group in L ligand are different. 1-(2-pentafluoroethylphenyl)-4-phenyl-benzo[g]pyridazine is used instead of 1-(2,6-bismethylphenyl)-4-(2-thienyl)-benzo[g]pyridazine with a yield of 34%.

ESI-MS [m/z]: 1595 [M+H]$^+$.

Elemental analysis ($C_{78}H_{39}F_{18}IrN_6$): Anal.Calcd: C, 58.76; H, 2.47; N, 5.27; Found: C, 58.75; H, 2.45; N, 5.36.

EXAMPLE 163

Preparation of Iridium Complex CP19

This example is basically the same as Example 1, except that the Ar and $R_1$ group in L ligand are different. 1-(3-trifluoromethylphenyl)-4-phenyl-benzo[g]pyridazine is used instead of 1-(2,6-bismethylphenyl)-4-(2-thienyl)-benzo[g]pyridazine with a yield of 35%.

ESI-MS [m/z]: 1391 [M+H]$^+$.

Elemental analysis ($C_{75}H_{42}F_9IrN_6$): Anal.Calcd: C, 64.79; H, 3.04; N, 6.04; Found: C, 64.80; H, 3.08; N, 6.00.

EXAMPLE 164

Preparation of Iridium Complex CP20

This example is basically the same as Example 1, except that the Ar and $R_1$ group in L ligand are different. 1-(2-trifluoromethylphenyl)-4-phenyl-benzo[g]pyridazine is used instead of 1-(2,6-bismethylphenyl)-4-(2-thienyl)-benzo[g]pyridazine with a yield of 35%.

ESI-MS [m/z]: 1391 [M+H]$^+$.

Elemental analysis (C75H42F9IrN6): Anal.Calcd: C, 64.79; H, 3.04; N, 6.04; Found: C, 64.74; H, 3.00; N, 6.10.

EXAMPLE 165

Preparation of Iridium Complex CP21

This example is basically the same as Example 1, except that the Ar and $R_1$ group in L ligand are different. 1-(4-trifluoromethylphenyl)-4-phenyl-benzo[g]pyridazine is used instead of 1-(2,6-bismethylphenyl)-4-(2-thienyl)-benzo[g]pyridazine with a yield of 31%.

ESI-MS [m/z]: 1391 [M+H]$^+$.

Elemental analysis ($C_{75}H_{42}F_9IrN_6$): Anal.Calcd: C, 64.79; H, 3.04; N, 6.04; Found: C, 64.75; H, 3.04; N, 6.11.

EXAMPLE 166

Preparation of Iridium Complex CP22

This example is basically the same as Example 1, except that the Ar and $R_1$ group in L ligand are different. 1-(2,3,4,5,6-pentatrifluoromethylphenoxy)-4-phenyl-benzo[g]pyridazine is used instead of 1-(2,6-bismethylphenyl)-4-(2-thienyl)-benzo[g]pyridazine with a yield of 35%.

ESI-MS [m/z]: 2255 [M+H]$^+$.

Elemental analysis ($C_{87}H_{30}F_{45}IrN_6O_3$): Anal.Calcd: C, 46.35; H, 1.34; N, 3.73; Found: C, 46.33; H, 1.37; N, 3.70.

EXAMPLE 167

Preparation of Iridium Complex CP23

This example is basically the same as Example 1, except that the Ar and $R_1$ group in L ligand are different. 1-(2,3,4,6-tetratrifluoromethylphenoxy)-4-phenyl-benzo[g]pyridazine is used instead of 1-(2,6-bismethylphenyl)-4-(2-thienyl)-benzo[g]pyridazine with a yield of 30%.
ESI-MS [m/z]: 2051 [M+H]$^+$.
Elemental analysis ($C_{84}H_{33}F_{36}IrN_6O_3$): Anal.Calcd: C, 49.21; H, 1.62; N, 4.10; Found: C, 49.26; H, 1.65; N, 4.11.

EXAMPLE 168

Preparation of Iridium Complex CP24

This example is basically the same as Example 1, except that the Ar and $R_1$ group in L ligand are different. 1-(2,3,4,5-tetratrifluoromethylphenoxy)-4-phenyl-benzo[g]pyridazine is used instead of 1-(2,6-bismethylphenyl)-4-(2-thienyl)-benzo[g]pyridazine with a yield of 36%.
ESI-MS [m/z]: 2051 [M+H]$^+$.
Elemental analysis ($C_{84}H_{33}F_{36}IrN_6O_3$): Anal.Calcd: C, 49.21; H, 1.62; N, 4.10; Found: C, 49.19; H, 1.59; N, 4.17.

EXAMPLE 169

Preparation of Iridium Complex CP25

This example is basically the same as Example 1, except that the Ar and $R_1$ group in L ligand are different. 1-(2,3,5,6-tetratrifluoromethylphenoxy)-4-phenyl-benzo[g]pyridazine is used instead of 1-(2,6-bismethylphenyl)-4-(2-thienyl)-benzo[g]pyridazine with a yield of 30%.
ESI-MS [m/z]: 2051 [M+H]$^+$.
Elemental analysis ($C_{84}H_{33}F_{36}IrN_6O_3$): Anal.Calcd: C, 49.21; H, 1.62; N, 4.10; Found: C, 49.17; H, 1.66; N, 4.10.

EXAMPLE 170

Preparation of Iridium Complex CP26

This example is basically the same as Example 1, except that the Ar and $R_1$ group in L ligand are different. 1-(2,4,6-tritrifluoromethylphenoxy)-4-phenyl-benzo[g]pyridazine is used instead of 1-(2,6-bismethylphenyl)-4-(2-thienyl)-benzo[g]pyridazine with a yield of 38%.
ESI-MS [m/z]: 1847 [M+H]$^+$.
Elemental analysis ($C_{81}H_{36}F_{27}IrN_6O_3$): Anal.Calcd: C, 52.69; H, 1.97; N, 4.55; Found: C, 52.65; H, 1.99; N, 4.59.

EXAMPLE 171

Preparation of Iridium Complex CP27

This example is basically the same as Example 1, except that the Ar and $R_1$ group in L ligand are different. 1-(2,3,6-tritrifluoromethylphenoxy)-4-phenyl-benzo[g]pyridazine is used instead of 1-(2,6-bismethylphenyl)-4-(2-thienyl)-benzo[g]pyridazine with a yield of 32%.
ESI-MS [m/z]: 1847 [M+H]$^+$.
Elemental analysis ($C_{81}H_{36}F_{27}IrN_6O_3$): Anal.Calcd: C, 52.69; H, 1.97; N, 4.55; Found: C, 52.67; H, 1.95; N, 4.57.

EXAMPLE 172

Preparation of Iridium Complex CP28

This example is basically the same as Example 1, except that the Ar and $R_1$ group in L ligand are different. 1-(2,3,4-tritrifluoromethylphenoxy)-4-phenyl-benzo[g]pyridazine is used instead of 1-(2,6-bismethylphenyl)-4-(2-thienyl)-benzo[g]pyridazine with a yield of 32%.
ESI-MS [m/z]: 1847 [M+H]$^+$.
Elemental analysis ($C_{81}H_{36}F_{27}IrN_6O_3$): Anal.Calcd: C, 52.69; H, 1.97; N, 4.55; Found: C, 52.64; H, 1.92; N, 4.59.

EXAMPLE 173

Preparation of Iridium Complex CP29

This example is basically the same as Example 1, except that the Ar and $R_1$ group in L ligand are different. 1-(3,4,5-tritrifluoromethylphenoxy)-4-phenyl-benzo[g]pyridazine is used instead of 1-(2,6-bismethylphenyl)-4-(2-thienyl)-benzo[g]pyridazine with a yield of 32%.
ESI-MS [m/z]: 1847 [M+H]$^+$.
Elemental analysis ($C_{81}H_{36}F_{27}IrN_6O_3$): Anal.Calcd: C, 52.69; H, 1.97; N, 4.55; Found: C, 52.72; H, 2.00; N, 4.50.

EXAMPLE 174

Preparation of Iridium Complex CP30

This example is basically the same as Example 1, except that the Ar and $R_1$ group in L ligand are different. 1-(2,3,5-tritrifluoromethylphenoxy)-4-phenyl-benzo[g]pyridazine is used instead of 1-(2,6-bismethylphenyl)-4-(2-thienyl)-benzo[g]pyridazine with a yield of 38%.
ESI-MS [m/z]: 1847 [M+H]$^+$.
Elemental analysis ($C_{81}H_{36}F_{27}IrN_6O_3$): Anal.Calcd: C, 52.69; H, 1.97; N, 4.55; Found: C, 52.70; H, 1.94; N, 4.55.

EXAMPLE 175

Preparation of Iridium Complex CP31

This example is basically the same as Example 1, except that the Ar and $R_1$ group in L ligand are different. 1-(2,4,5-tritrifluoromethylphenoxy)-4-phenyl-benzo[g]pyridazine is used instead of 1-(2,6-bismethylphenyl)-4-(2-thienyl)-benzo[g]pyridazine with a yield of 34%.
ESI-MS [m/z]: 1847 [M+H]$^+$.
Elemental analysis ($C_{81}H_{36}F_{27}IrN_6O_3$): Anal.Calcd: C, 52.69; H, 1.97; N, 4.55; Found: C, 52.63; H, 1.99; N, 4.54.

EXAMPLE 176

Preparation of Iridium Complex CP32

This example is basically the same as Example 1, except that the Ar and $R_1$ group in L ligand are different. 1-(2,4-bistrifluoromethylphenoxy)-4-phenyl-benzo[g]pyridazine is used instead of 1-(2,6-bismethylphenyl)-4-(2-thienyl)-benzo[g]pyridazine with a yield of 34%.
ES I-MS [m/z]: 1643 [M+H]$^+$.
Elemental analysis ($C_{78}H_{39}F_{18}IrN_6O_3$): Anal.Calcd: C, 57.04; H, 2.39; N, 5.12; Found: C, 56.99; H, 2.42; N, 5.09.

EXAMPLE 177

Preparation of Iridium Complex CP33

This example is basically the same as Example 1, except that the Ar and $R_1$ group in L ligand are different. 1-(2,6-bistrifluoromethylphenoxy)-4-phenyl-benzo[g]pyridazine is used instead of 1-(2,6-bismethylphenyl)-4-(2-thienyl)-benzo[g]pyridazine with a yield of 38%.
ES I-MS [m/z]: 1643 [M+H]$^+$.
Elemental analysis ($C_{78}H_{39}F_{18}IrN_6O_3$): Anal.Calcd: C, 57.04; H, 2.39; N, 5.12; Found: C, 57.01; H, 2.44; N, 5.08.

EXAMPLE 178

Preparation of Iridium Complex CP34

This example is basically the same as Example 1, except that the Ar and $R_1$ group in L ligand are different. 1-(2,5-bistrifluoromethylphenoxy)-4-phenyl-benzo[g]pyridazine is used instead of 1-(2,6-bismethylphenyl)-4-(2-thienyl)-benzo[g]pyridazine with a yield of 32%.
ES I-MS [m/z]: 1643 [M+H]$^+$.
Elemental analysis ($C_{78}H_{39}F_{18}IrN_6O_3$): Anal.Calcd: C, 57.04; H, 2.39; N, 5.12; Found: C, 57.05; H, 2.36; N, 5.15.

EXAMPLE 179

Preparation of Iridium Complex CP35

This example is basically the same as Example 1, except that the Ar and $R_1$ group in L ligand are different. 1-(3,5-bistrifluoromethylphenoxy)-4-phenyl-benzo[g]pyridazine is used instead of 1-(2,6-bismethylphenyl)-4-(2-thienyl)-benzo[g]pyridazine with a yield of 34%.
ES I-MS [m/z]: 1643 [M+H]$^+$.
Elemental analysis ($C_{78}H_{39}F_{18}IrN_6O_3$): Anal.Calcd: C, 57.04; H, 2.39; N, 5.12; Found: C, 57.06; H, 2.37; N, 5.11.

EXAMPLE 180

Preparation of Iridium Complex CP36

This example is basically the same as Example 1, except that the Ar and $R_1$ group in L ligand are different. 1-(3,4-bistrifluoromethylphenoxy)-4-phenyl-benzo[g]pyridazine is used instead of 1-(2,6-bismethylphenyl)-4-(2-thienyl)-benzo[g]pyridazine with a yield of 39%.
ES I-MS [m/z]: 1643 [M+H]$^+$.
Elemental analysis ($C_{78}H_{39}F_{18}IrN_6O_3$): Anal.Calcd: C, 57.04; H, 2.39; N, 5.12; Found: C, 57.05; H, 2.37; N, 5.16.

EXAMPLE 181

Preparation of Iridium Complex CP37

This example is basically the same as Example 1, except that the Ar and $R_1$ group in L ligand are different. 1-(2,3-bistrifluoromethylphenoxy)-4-phenyl-benzo[g]pyridazine is used instead of 1-(2,6-bismethylphenyl)-4-(2-thienyl)-benzo[g]pyridazine with a yield of 39%.
ES I-MS [m/z]: 1643 [M+H]$^+$.
Elemental analysis ($C_{78}H_{39}F_{18}IrN_6O_3$): Anal.Calcd: C, 57.04; H, 2.39; N, 5.12; Found: C, 57.07; H, 2.35; N, 5.13.

EXAMPLE 182

Preparation of Iridium Complex CP38

This example is basically the same as Example 1, except that the Ar and $R_1$ group in L ligand are different. 1-(2-pentafluoroethylphenoxy)-4-phenyl-benzo[g]pyridazine is used instead of 1-(2,6-bismethylphenyl)-4-(2-thienyl)-benzo[g]pyridazine with a yield of 39%.
ES I-MS [m/z]: 1643 [M+H]$^+$.
Elemental analysis ($C_{78}H_{39}F_{18}IrN_6O_3$): Anal.Calcd: C, 57.04; H, 2.39; N, 5.12; Found: C, 57.01; H, 2.38; N, 5.16.

EXAMPLE 183

Preparation of Iridium Complex CP39

This example is basically the same as Example 1, except that the Ar and $R_1$ group in L ligand are different. 1-(3-trifluoromethylphenoxy)-4-phenyl-benzo[g]pyridazine is used instead of 1-(2,6-bismethylphenyl)-4-(2-thienyl)-benzo[g]pyridazine with a yield of 39%.
ESI-MS [m/z]: 1439 [M+H]$^+$.
Elemental analysis ($C_{75}H_{42}F_9IrN_6O_3$):Anal.Calcd:C, 62.63; H, 2.94; N, 5.84; Found: C, 62.65; H, 2.90; N, 5.84.

EXAMPLE 184

Preparation of Iridium Complex CP40

This example is basically the same as Example 1, except that the Ar and $R_1$ group in L ligand are different. 1-(2-trifluoromethylphenoxy)-4-phenyl-benzo[g]pyridazine is used instead of 1-(2,6-bismethylphenyl)-4-(2-thienyl)-benzo[g]pyridazine with a yield of 32%.
ESI-MS [m/z]: 1439 [M+H]$^+$.
Elemental analysis ($C_{75}H_{42}F_9IrN_6O_3$):Anal.Calcd:C, 62.63; H, 2.94; N, 5.84; Found: C, 62.60; H, 2.98; N, 5.81.

EXAMPLE 185

Preparation of Iridium Complex CP41

This example is basically the same as Example 1, except that the Ar and $R_1$ group in L ligand are different. 1-(4-trifluoromethylphenoxy)-4-phenyl-benzo[g]pyridazine is used instead of 1-(2,6-bismethylphenyl)-4-(2-thienyl)-benzo[g]pyridazine with a yield of 38%.
ESI-MS [m/z]: 1439 [M+H]$^+$.
Elemental analysis ($C_{75}H_{42}F_9IrN_6O_3$):Anal.Calcd:C, 62.63; H, 2.94; N, 5.84; Found: C, 62.66; H, 2.92; N, 5.88.

EXAMPLE 186

Preparation of Iridium Complex CP42

This example is basically the same as Example 1, except that the Ar and $R_1$ group in L ligand are different. 1-(2,6-bismethylphenoxy)-4-phenyl-benzo[g]pyridazine is used instead of 1-(2,6-bismethylphenyl)-4-(2-thienyl)-benzo[g]pyridazine with a yield of 35%.
ESI-MS [m/z]: 1319 [M+H]$^+$.
Elemental analysis ($C78H57IrN_6O_3$): Anal.Calcd: C, 71.05; H, 4.36; N, 6.37; Found: C, 71.05; H, 4.33; N, 6.38.

EXAMPLE 187

Preparation of Iridium Complex CP43

This example is basically the same as Example 1, except that the Ar and $R_1$ group in L ligand are different. 1-phenyl-benzo[g]pyridazine is used instead of 1-(2,6-bismethylphenyl)-4-(2-thienyl)-benzo[g]pyridazine with a yield of 35%.
ESI-MS [m/z]: 959 [M+H]$^+$.
Elemental analysis ($C_{54}H_{33}IrN_6$):Anal.Calcd:C, 67.69; H, 3.47; N, 8.77; Found: C, 67.70; H, 3.50; N, 8.74.

EXAMPLE 188

Preparation of Iridium Complex CP44

This example is basically the same as Example 1, except that the Ar and $R_1$ group in L ligand are different. 1-chloro-4-phenyl-benzo[g]pyridazine is used instead of 1-(2,6-bismethylphenyl)-4-(2-thienyl)-benzo[g]pyridazine with a yield of 30%.
ESI-MS [m/z]: 1061 [M+H]$^+$.
Elemental analysis ($C_{54}H_{30}Cl_3IrN_6$): Anal.Calcd: C, 61.10; H, 2.85; N, 7.92; Found: C, 61.07; H, 2.86; N, 7.95.

EXAMPLE 189

Preparation of Iridium Complex CP45

This example is basically the same as Example 1, except that the Ar and $R_1$ group in L ligand are different. 1-bromo-4-phenyl-benzo[g]pyridazine is used instead of 1-(2,6-bismethylphenyl)-4-(2-thienyl)-benzo[g]pyridazine with a yield of 35%.
ESI-MS [m/z]: 1195 [M+H]$^+$.
Elemental analysis ($C_{54}H_{30}Br_3IrN_6$): Anal.Calcd: C, 54.28; H, 2.53; N, 7.03; Found: C, 54.25; H, 2.59; N, 7.00.

EXAMPLE 190

Preparation of Iridium Complex CP46

This example is basically the same as Example 1, except that the Ar and $R_1$ group in L ligand are different. 1-(9-carbazolyl)-4-phenyl-benzo[g]pyridazine is used instead of 1-(2,6-bismethylphenyl)-4-(2-thienyl)-benzo[g]pyridazine with a yield of 38%.
ES I-MS [m/z]: 1454 [M+H]$^+$.
Elemental analysis ($C_{90}H_{54}IrN_9$):Anal.Calcd:C, 74.36; H, 3.74; N, 8.67; Found: C, 74.35; H, 3.72; N, 8.66.

EXAMPLE 191

Preparation of Iridium Complex CP47

This example is basically the same as Example 1, except that the Ar and $R_1$ group in L ligand are different. 1-(9-(3,6-bis-tert-butylcarbazolyl))-4-phenyl-benzo[g]pyridazine is used instead of 1-(2,6-bismethylphenyl)-4-(2-thienyl)-benzo[g]pyridazine with a yield of 32%.
ESI-MS [m/z]: 1792 [M+H]$^+$.
Elemental analysis ($C_{114}H_{102}IrN_9$): Anal.Calcd: C, 76.48; H, 5.74; N, 7.04; Found: C, 76.50; H, 5.77; N, 7.03.

EXAMPLE 192

Preparation of Iridium Complex CP48

This example is basically the same as Example 1, except that the Ar and $R_1$ group in L ligand are different. 1-(diphenylamino)-4-phenyl-benzo[g]pyridazine is used instead of 1-(2,6-bismethylphenyl)-4-(2-thienyl)-benzo[g]pyridazine with a yield of 30%.
ES I-MS [m/z]: 1460 [M+H]$^+$.
Elemental analysis ($C_{90}H_{60}IrN_9$):Anal.Calcd:C, 74.05; H, 4.14; N, 8.64; Found: C, 74.06; H, 4.15; N, 8.63.

Compound Application Implementation

The iridium complexes in this invention can be applied as luminescent materials in organic electroluminescent devices, that is, OLED devices.

Referring to FIG. 1, this present invention further provides a type of organic electroluminescent devices 10 comprising anode 120, hole transport layer 130, organic light-emitting layer 140, electron transport layer 160, and cathode 170. Organic light-emitting layer 140 includes iridium complexes. Anode 120, hole transport layer 130, organic light-emitting layer 140, electron transport layer 160, and cathode 170 are sequentially stacked.

Anode 120 is used to inject holes into hole transport layer 130, and anode 120 is composed of conductive materials, which may be selected from one or more of indium tin oxide (ITO), indium zinc oxide (IZO), tin dioxide ($SnO_2$), zinc oxide (ZnO), silver, aluminum, gold, platinum, and palladium.

Hole transport layer 130 is used to transport holes from anode 120 to organic light-emitting layer 140. The material of hole transport layer 130 has a high hole mobility, and may be selected from one or more of phthalocyanine compounds and aromatic amine compounds, for example, 4,4'-bis[N-(1-naphthyl)-N-phenylamino]biphenyl (NPB), N,N'-bis(3-methylphenyl)-N,N'-diphenylbiphenyl (TPD), 1,3,5-tris(3-methyldiphenylamino)benzene (m-MTDATA) or polyvinylcarbazole (PVK) and etc.

Organic light-emitting layer 140 can emit deep red or near-infrared light. Organic light-emitting layer 140 includes a host material and one of the iridium complexes in this present invention. The host material generates excitons by receiving holes and electrons, and then transfers the energy of the excitons to the iridium complexes in this present invention, and the iridium complexes emit light by means of energy transfer through forming excitons. The amount of Iridium Complexes in this present invention in organic light-emitting layer 140 of the OLED devices can be adjusted according to actual needs.

Host materials may be selected from one or more of carbazole-containing conjugated small molecules, arylsilicon-based small molecules, and metal complexes, for example, polyvinylcarbazole/2-(4-biphenyl)-5-phenyloxadiazole (PVK/PBD), 4,4'-(N,N'-dicarbazolyl)-biphenyl (CBP), 8-hydroxyquinoline aluminum ($Alq_3$), gallium dinuclear complex $Ga_2(saph)_2q_2$ or bis(10-hydroxybenzo[h]quinoline)indole ($Bebq_2$), 2-(12-phenylindole[2,3-a]carbazole)-4,6-diphenyl Base-1,3,5-triazine (DIC-TRZ) and etc.

Electron transport layer 160 is used to transport electrons from cathode 170 to organic light-emitting layer 140. The material of electron transport layer 160 has high electron mobility, and may be selected from one or more of oxazole compounds, metal complexes, quinoline compounds, porphyrin compounds, diazonium derivatives, and phenanthroline derivatives, for example, 8-hydroxyquinoline aluminum (Alq3) and its derivatives, and etc.

Cathode 170 is used to inject electrons into electron transport layer 160. The material of cathode 170 may be metals or alloys with a low work function such as lithium, magnesium, aluminum, calcium, aluminum lithium alloy, magnesium silver alloy, magnesium indium alloy, or an electrode layer where metal and metal fluoride are alternately formed.

Organic electroluminescent devices 10 may further include a hole blocking layer 150 for blocking the transport of holes to electron transport layer 160, thereby improving carrier transport efficiency and achieving highly efficient luminescence efficiency. Hole blocking layer 150 may be disposed between organic light-emitting layer 140 and electron transport layer 160. The material of hole blocking layer 150 may be selected from one or more of 2,9-dimethyl-4,7-diphenyl-1,10-phenanthroline (BCP), 4,7-diphenyl-1,10-phenanthroline (BPhen), 1,3,5-tris(2-N-phenylbenzimidazolyl)benzene (TPBi) and 3-(4-diphenyl)-5-(4-tert-butylphenyl)-4-(4-ethylphenyl)-1,2,4-triazole (TAZ). The material of hole blocking layer 150 may also be the same as the material of electron transport layer 160.

Organic electroluminescent devices 10 may further include a substrate 110 for carrying anode 120, hole transport layer 130, organic light-emitting layer 140, electron transport layer 160, and cathode 170. Substrate 110 is a transparent material such as glass or plastic. Substrate 110 can have a smooth surface for easy handling.

It can be understood that organic electroluminescent devices 10 may further include one or two intermediate layers such as hole injection layer, electron injection layer, electron blocking layer, and etc.

The following Examples 193 to 194 show the preparation of organic electroluminescent devices 10, which are OLED-1, OLED-2, and OLED-3, respectively.

EXAMPLE 193

Preparation of OLED-1

The glass plate coated with ITO transparent conductive layer was sonicated in a detergent, rinsed in deionized water, ultrasonically degreased in a mixed solvent of acetone and ethanol, baked in a clean environment to completely remove water, cleaned by ultraviolet light and ozone, and the surface of ITO transparent conductive layer was bombarded with a low energy cation beam to obtain the glass plate with anode 120, wherein the ITO transparent conductive layer was anode 120.

The glass plate with anode 120 was placed in a vacuum chamber vacuumed to $1\times10^{-5}\sim9\times10^{-3}$ Pa. NPB was vacuum-deposited on anode 120 as hole transport layer 130, and the evaporation rate was 0.1 nm/s, the thickness of deposited film was 40 nm.

A DIC-TRZ film doped with iridium complex CT34 was vacuum-deposited on the surface of hole transport layer 130 away from the glass plate as organic light-emitting layer 140. The vapor deposition rate ratio of Iridium Complex CT34 and DIC-TRZ was 1:10, and the doping concentration of CT34 in DIC-TRZ was 10 wt %. The total vapor deposition rate was 0.1 nm/s, and the total thickness of deposited film was 20 nm.

A TPBi layer was vacuum-deposited on organic light-emitting layer 140 as electron transport layer 160. The evaporation rate was 0.1 nm/s, and the total thickness of deposited film was 30 nm. Mg and Ag alloy layer and Ag layer were sequentially vacuum-deposited on the surface of electron transport layer 160 away from organic light-emitting layer 140 as cathode 170. The evaporation rate of Mg and Ag alloy layer was 2.0-3.0 nm/s, and the thickness was 100 nm. The evaporation rate of Ag layer was 0.3 nm/s, and the thickness was 100 nm.

EXAMPLE 194

Preparation of OLED-2

This example is basically the same as Example 193, except that the iridium complex is CT12.

EXAMPLE 195

Preparation of OLED-3

This example is basically the same as Example 193, except that the luminescent dye is Ir(mpbqx-g)$_2$acac in existing technology. The chemical structure of Ir(mpbqx-g)$_2$acac is shown as follows:

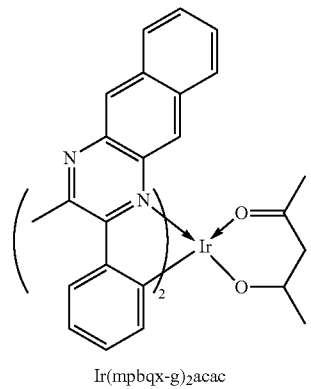

Ir(mpbqx-g)$_2$acac

The properties of the OLED-1, OLED-2 and OLED-3 are shown in detail in Table 1.

| Number | Structure Composition | PL Peak Wavelength nm | Radiance W/m$^2$ (20 V) | Maximum EQE % |
|---|---|---|---|---|
| OLED-1 | ITO/NPB (40 nm)/DIC-TRZ: 10 wt % CT34 (20 nm)/TPBi (30 nm)/Mg: Ag (100 nm)/Ag (100 nm) | 750 | 45.4 | 5.0 |
| OLED-2 | ITO/NPB (40 nm)/DIC-TRZ: 10 wt % CT12 (20 nm)/TPBi (30 nm)/Mg: Ag (150 nm)/Ag (100 nm) | 760 | 41.8 | 4.5 |
| OLED-3 | ITO/NPB (40 nm)/DIC-TRZ: 10 wt % Ir(mpbqx-g)$_2$acac (20 nm)/TPBi (30 nm)/Mg: Ag (150 nm)/Ag (100 nm) | 780 | 18.1 | 2.2 |

In Table 1, "ITO/NPB (40 nm)/DIC-TRZ: 10 wt % CT34 (20 nm)/TPBi (30 nm)/Mg: Ag (100 nm)/Ag (100 nm)" means that NPB formed a film with a thickness of 40 nm; DIC-TRZ and 10 wt % CT34 formed a film with a thickness of 20 nm; TPBi formed a film with a thickness of 30 nm; Mg: Ag formed a film with a thickness of 100 nm; Ag formed a film with a thickness of 100 nm. By analogy, the meanings of other parts in structure composition of Table 1 can be known, and will not be described again.

FIGS. 2 to 5 are characterization diagrams of OLED-2, from which the PL peak wavelength, current density, radiance, and maximum external quantum efficiency can be known, separately. From FIG. 5, it can be known that the maximum external quantum efficiency of OLED-2 can reach 4.5%. Under the condition of large current density, OLED-2 can still maintain a high external quantum efficiency, and the effect of efficiency roll-off is very low.

Therefore, from Table 1 and FIGS. 2 to 4, organic electroluminescent device 10 can emit light from deep red to near-infrared region, and the radiance of device 10 is above 40 W/m$^2$ (15V). Meanwhile, it has a high luminescence efficiency and the effect of efficiency roll-off is very low. Compared with previously reported hetero-coordinated Ir(mpbqx-g)$_2$acac based divices, the iridium complexes based devices in this invention have higher irradiance and external quantum efficiency, which are more than twice of Ir(mpbqx-g)$_2$acac based divices.

It can be seen from the above examples that the application of Iridium Complexes to organic electroluminescent devices in this present invention has the following advantages: first, near-infrared region emission can be emitted; second, high quantum efficiency can be achieved; third, higher radiation can be achieved; fourth, efficiency roll-off effect can be significantly suppressed, and the devices can be used under high current density.

The preferred embodiments in this present invention have been described above in detail, but this present invention is not limited to the specific details of above embodiments. Within the scope of technical idea in this present invention, various simple modifications of technical solutions can be made in this present invention, and these simple variants are all fall within the scope of protection in this present invention.

It should be further noted that specific technical features described in aboved specific embodiments may be combined in any suitable pattern without contradiction. In order to avoid unnecessary repetition, this present invention will not be further described in various possible combinations.

In addition, any combination of various embodiments in this invention can be made, as long as it does not deviate from the idea in this invention, and it should be regarded as disclosure of this invention.

The invention claimed is:

1. An iridium complex with a molecular formula of L$_3$Ir, wherein:
   Ir is the central atom and L is a ligand;
   the structural formula of the iridium complex is represented in formula (I):

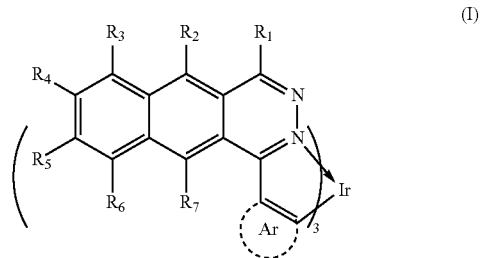

in formula (I), Ar is selected from the group consisting of substituted or unsubstituted aryl groups with 6 to 30 carbon atoms and substituted or unsubstituted heterocyclic aryl groups with 4 to 30 carbon atoms;
   R$_1$ is selected from group consisting of: substituted thiophene, substituted benzothiophene, substituted benzene, substituted naphthalene, substituted anthracene, substituted phenanthrene, substituted pyrene, substituted furan, substituted benzofuran, substituted thiazole, substituted benzothiazole, substituted isothiazole, substituted benzisothiazole, substituted pyrrole, substituted benzopyrrole, substituted imidazole, substituted benzimidazole, substituted pyrazole, substituted benzopyrazole, substituted oxazole, substituted benzoxazole, substituted isoxazole, substituted benzisoxazole, substituted pyridine, substituted pyrimidine, substituted benzopyrimidine, substituted pyrazine, substituted benzopyrazine, substituted pyridazine, substituted benzopyridazine, substituted quinoline, substituted isoquinoline, substituted purine, substituted pteridine, substituted indole, substituted carbazole, substituted diphenylamine, substituted phenoxy, substituted diphenylboron, substituted diphenylphosphine, substituted diphenylphosphine oxide, and substituted triphenylsilicon;
   R$_2$ to R$_7$ are each independently selected from hydrogen atoms, halogen atoms, cyano groups, nitro groups, hydroxyl groups, substituted or unsubstituted alkyl or cycloalkyl groups with 1 to 30 carbon atoms, fluoroalkyl groups, chloroalkyl groups, alkoxy groups, thioalkoxy groups, carboxyl groups with 1 to 30 carbon atoms, ester groups with 1 to 30 carbon atoms, acyl groups with 1 to 30 carbon atoms, substituted or unsubstituted amino groups with 1 to 30 carbon atoms, substituted or unsubstituted aryl groups with 6 to 30 carbon atoms, or substituted or unsubstituted heterocyclic aryl groups with 4 to 30 carbon atoms;
   the above heterocyclic aryl group means a monocyclic or fused ring aryl group containing one or more hetero atoms selected from the group consisting of B, N, O, S, P, P=O, Si and P with 4 to 30 ring carbon atoms; and
   the substituent groups on aryl or R$_1$ to R$_7$ are independently selected from F, Cl, Br, I, CHO, CN, unsubstituted alkyl or cycloalkyl groups with 1 to 30 carbon atoms, fluoroalkyl groups, alkoxy groups or thioalkoxy groups.

2. The iridium complex according to claim 1, in formula (I), wherein:
Ar is selected from the group consisting of substituted or unsubstituted aryl groups with 6 to 18 carbon atoms, and substituted or unsubstituted heterocyclic aryl groups with 4 to 18 carbon atoms;
$R_2$ to $R_7$ are each independently selected from hydrogen atoms, halogen atoms, hydroxyl groups, substituted or unsubstituted alkyl or cycloalkyl groups with 1 to 20 carbon atoms, fluoroalkyl groups, chloroalkyl groups, alkoxy groups, thioalkoxy groups, carboxyl groups with 1 to 20 carbon atoms, ester groups with 1 to 20 carbon atoms, acyl groups with 1 to 20 carbon atoms, substituted or unsubstituted amino groups with 1 to 20 carbon atoms, substituted or unsubstituted aryl groups with 6 to 18 carbon atoms, or substituted or unsubstituted heterocyclic aryl groups with 4 to 18 carbon atoms; and
the substituent groups on aryl or $R_1$ to $R_7$ are independently selected from F, Cl, Br, unsubstituted alkyl or cycloalkyl groups with 1 to 20 carbon atoms, fluoroalkyl groups, alkoxy groups or thioalkoxy groups.

3. An organic electroluminescent device comprising one or more of the iridium complexes according to claim 2.

4. The iridium complex according to claim 1, in formula (I), wherein:
wherein Ar is substituted or unsubstituted and is selected from the group consisting of: thiophene, benzothiophene, benzene, naphthalene, anthracene, phenanthrene, pyrene, furan, benzofuran, thiazole, benzothiazole, isothiazole, benzoisothiazole, pyrrole, benzopyrrole, imidazole, benzimidazole, pyrazole, benzopyrazole, oxazole, benzoxazole, isoxazole, benzisoxazole, pyridine, pyrimidine, benzopyrimidine, pyrazine, benzopyrazine, pyridazine, benzopyridazine, quinoline, isoquinoline, purine, pteridine, and indole;
$R_2$ to $R_7$ are each independently hydrogen or $R_2$ to $R_7$ are each independently substituted or unsubstituted and are selected from the group consisting of: thiophene, benzothiophene, benzene, naphthalene, anthracene, phenanthrene, pyrene, furan, benzofuran, thiazole, benzothiazole, isothiazole, benzisothiazole, pyrrole, benzopyrrole, imidazole, benzimidazole, pyrazole, benzopyrazole, oxazole, benzoxazole, isoxazole, benzisoxazole, pyridine, pyrimidine, benzopyrimidine, pyrazine, benzopyrazine, pyridazine, benzopyridazine, quinoline, isoquinoline, purine, pteridine, indole, carbazole, diphenylamine, phenoxy, diphenylboron, diphenylphosphine, diphenylphosphine oxide, and triphenyl silicon; and
the substituent groups on aryl or $R_1$ to $R_7$ are independently selected from F, Cl, unsubstituted alkyl or cycloalkyl groups with 1 to 10 carbon atoms, fluoroalkyl groups, alkoxy groups or thioalkoxy groups.

5. An organic electroluminescent device comprising one or more of the iridium complexes according to claim 4.

6. The iridium complex according to claim 1, in formula (I), wherein:
wherein Ar is substituted or unsubstituted and is selected from the group consisting of: thiophene, benzothiophene, benzene, naphthalene, anthracene, phenanthrene, pyrene, furan, benzofuran, thiazole, benzothiazole, isothiazole, benzoisothiazole, pyrrole, benzopyrrole, imidazole, benzimidazole, pyrazole, benzopyrazole, oxazole, benzoxazole, isoxazole, benzisoxazole, pyridine, pyrimidine, benzopyrimidine, pyrazine, benzopyrazine, pyridazine, benzopyridazine, quinoline, isoquinoline, purine, pteridine, and indole;
$R_2$ to $R_7$ are hydrogen atoms; $R_1$ is selected from the group consisting of: substituted thiophene, substituted benzothiophene, substituted benzene, substituted naphthalene, substituted anthracene, substituted phenanthrene, substituted pyrene, substituted furan, substituted benzofuran, substituted thiazole, substituted benzothiazole, substituted isothiazole, substituted benzisothiazole, substituted pyrrole, substituted benzopyrrole, substituted imidazole, substituted benzimidazole, substituted pyrazole, substituted benzopyrazole, substituted oxazole, substituted benzoxazole, substituted isoxazole, substituted benzisoxazole, substituted pyridine, substituted pyrimidine, substituted benzopyrimidine, substituted pyrazine, substituted benzopyrazine, substituted pyridazine, substituted benzopyridazine, substituted quinoline, substituted isoquinoline, substituted purine, substituted pteridine, substituted indole, substituted carbazole, substituted diphenylamine, substituted phenoxy, substituted diphenylboron, substituted diphenyl phosphine, substituted diphenylphosphine oxide, and substituted triphenylsilicon; and
the substituent groups on aryl is independently selected from F, Cl, unsubstituted alkyl or cycloalkyl groups with 1 to 10 carbon atoms, fluoroalkyl groups, alkoxy groups or thioalkoxy groups.

7. An organic electroluminescent device comprising one or more of the application of iridium complexes according to claim 6.

8. The iridium complex according to claim 1, selected from the following specific structural formulas:

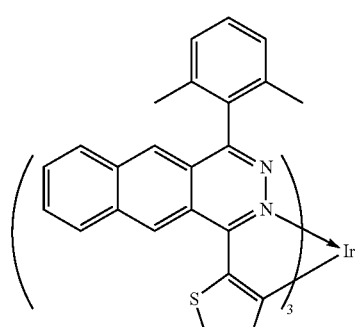

CT1

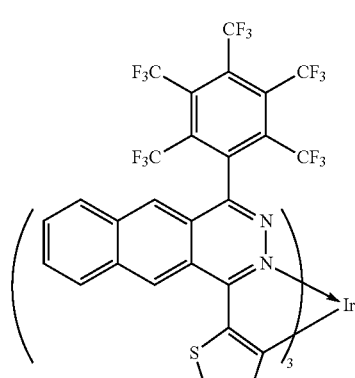

CT2

CT3
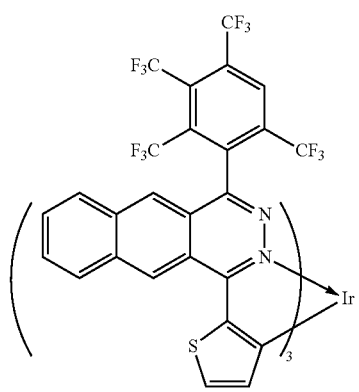
CT4
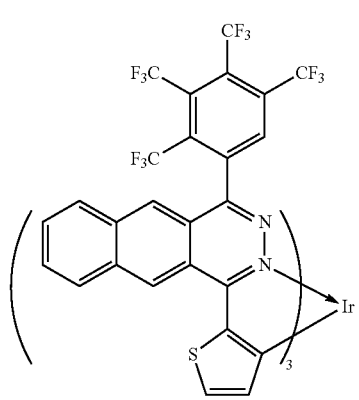
CT5
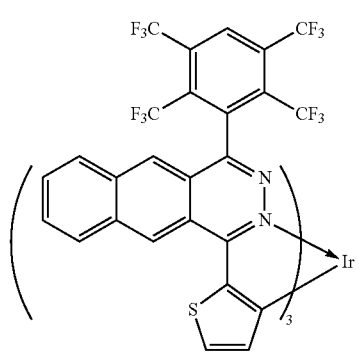
CT6
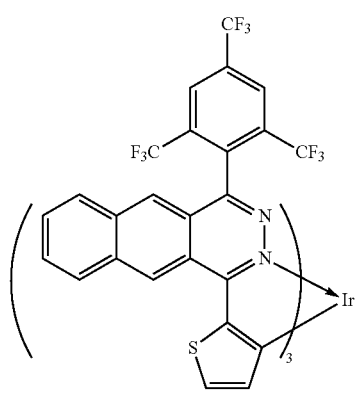
CT7
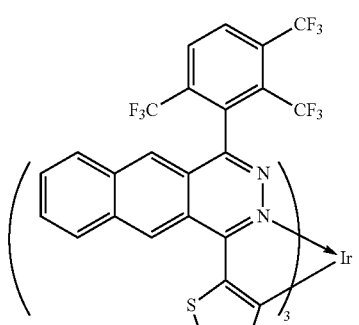
CT8
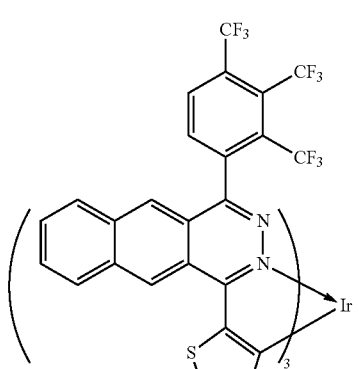
CT9
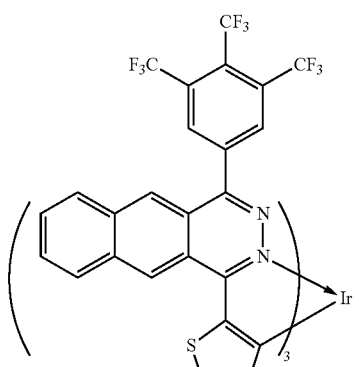
CT10
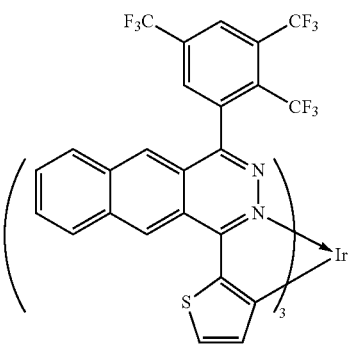

CT11
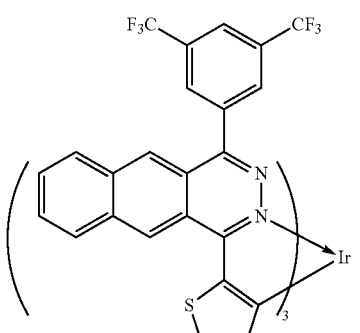
CT15
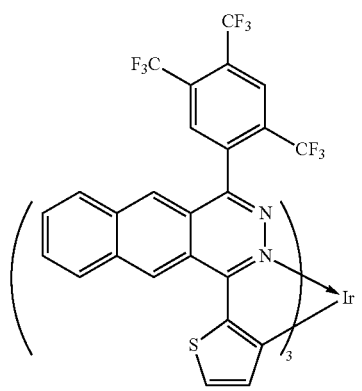
CT12
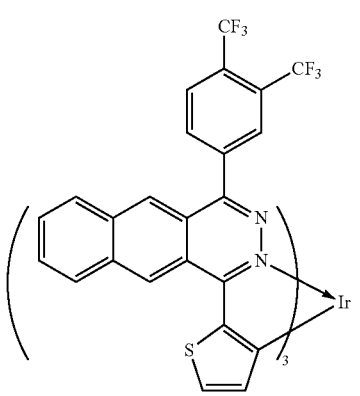
CT16
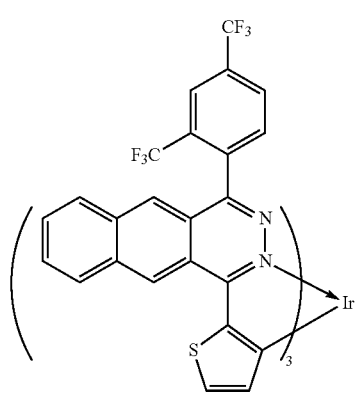
CT13
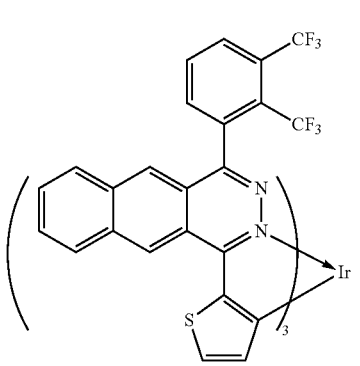
CT17
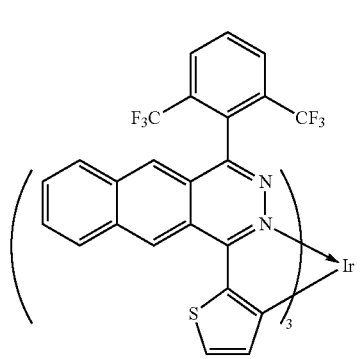
CT14
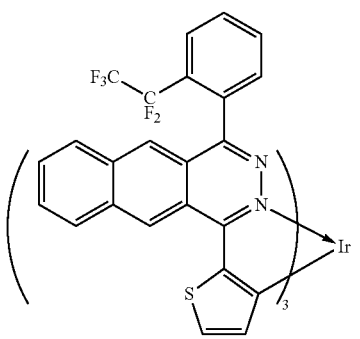
CT18

CT19
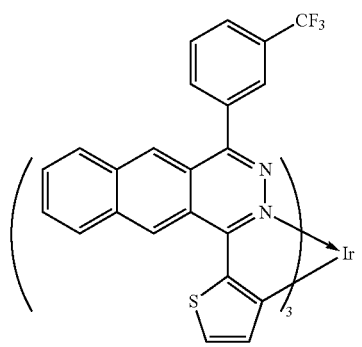
CT20
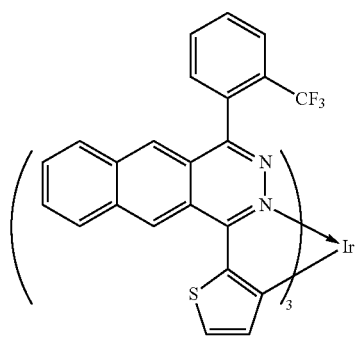
CT21
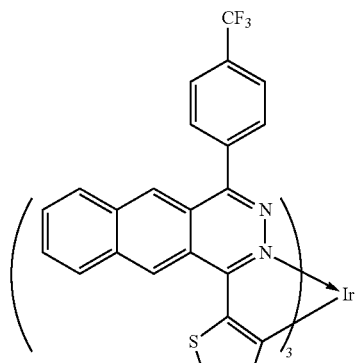
CT22
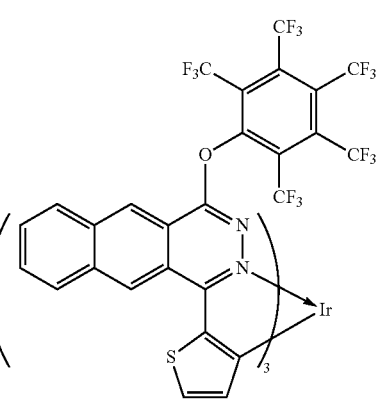
CT23
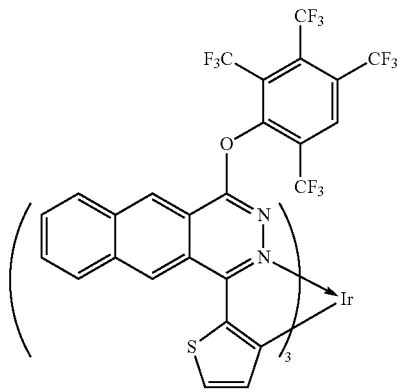
CT24
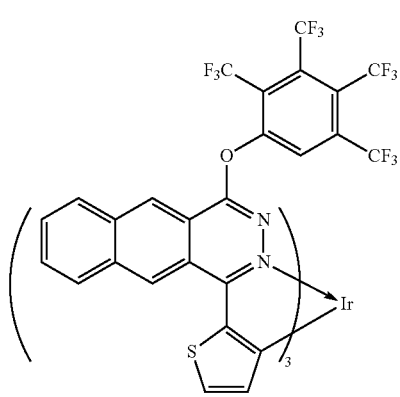
CT25
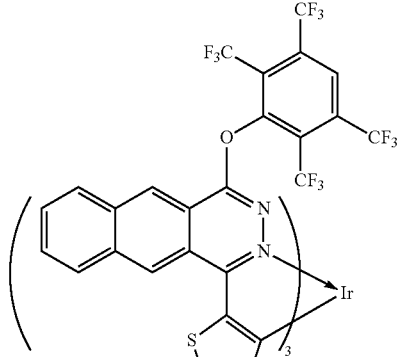
CT26
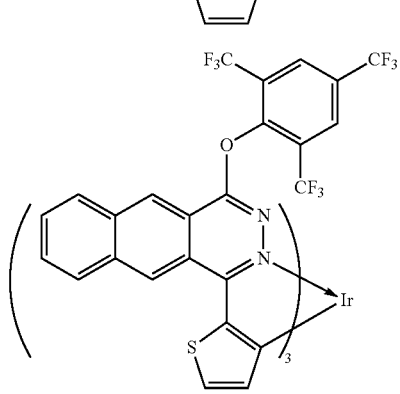

CT27 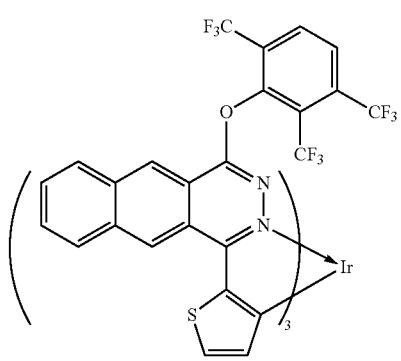
CT28 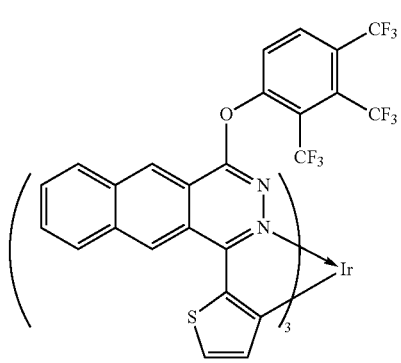
CT29 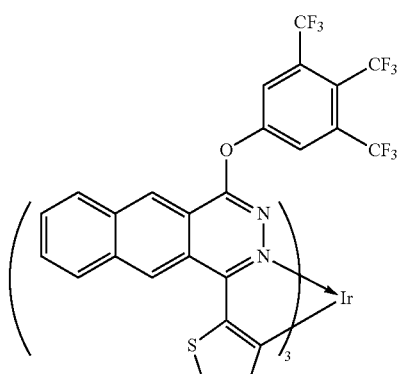
CT30 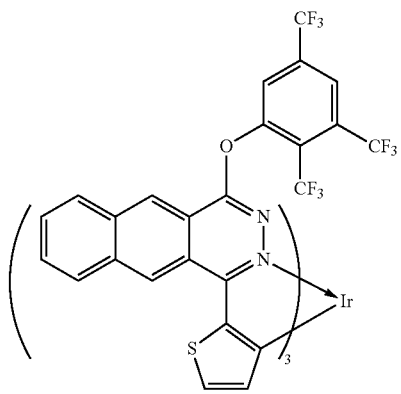
CT31 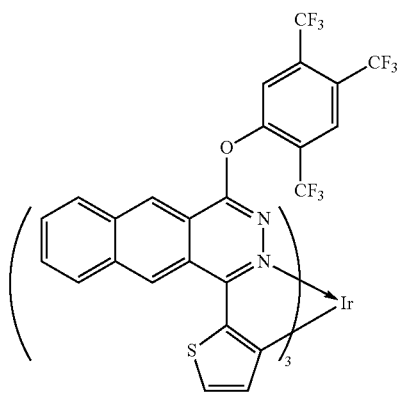
CT32 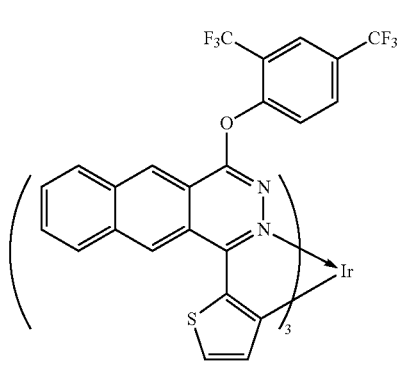
CT33 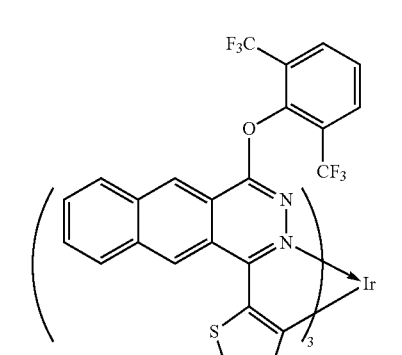
CT34 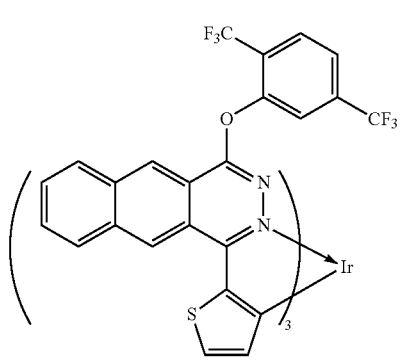

CT35 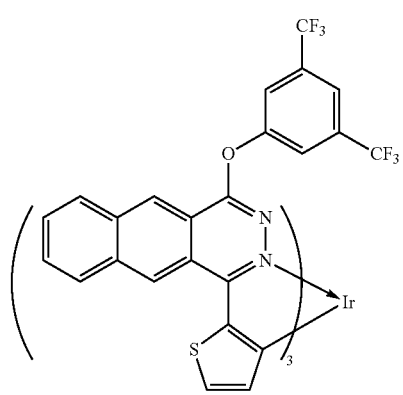
CT36 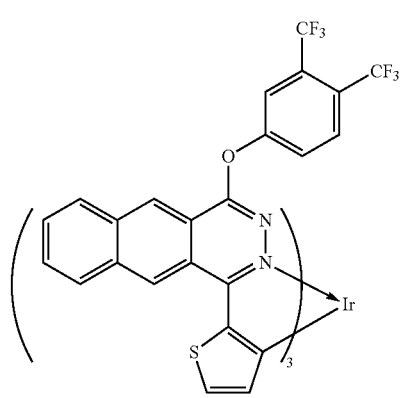
CT37 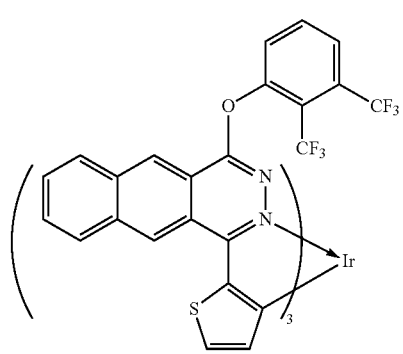
CT38 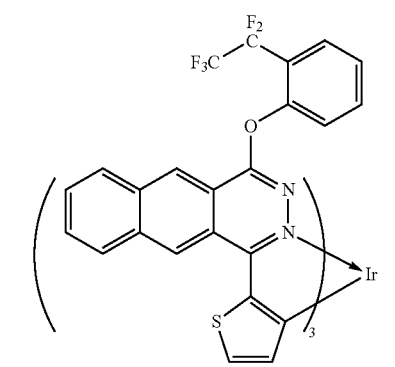
CT39 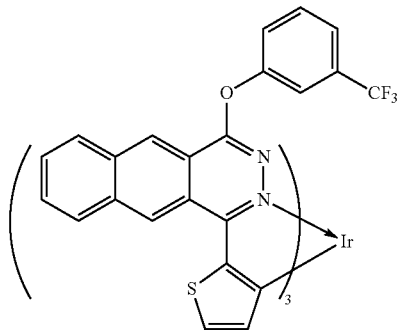
CT40 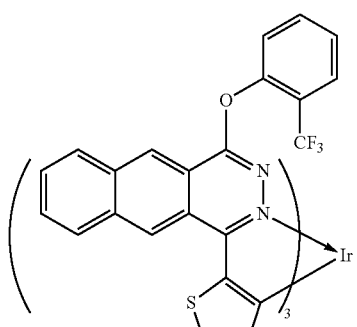
CT41 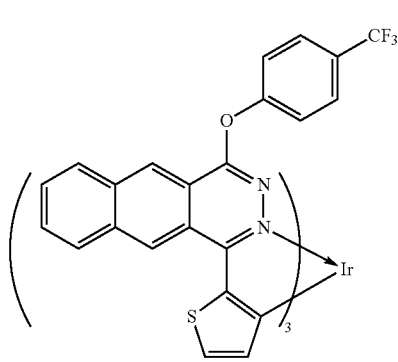
CT42 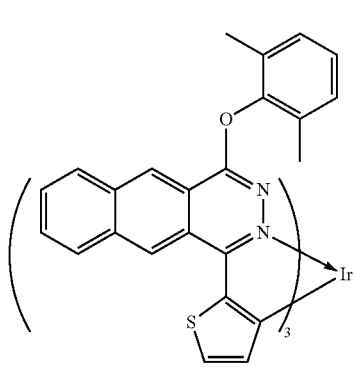

CT47
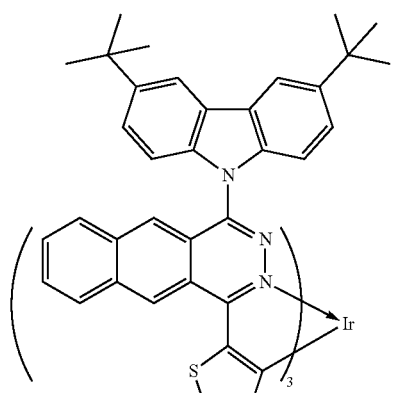
CBT2
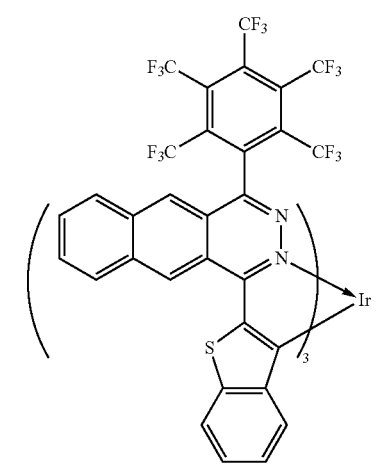
CBT3
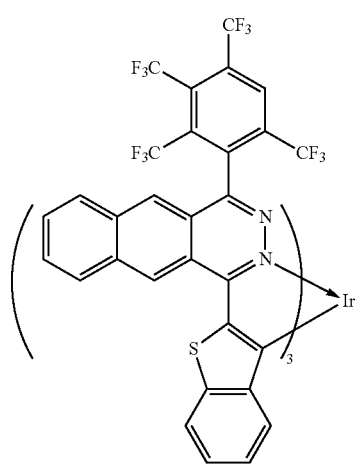
CBT4
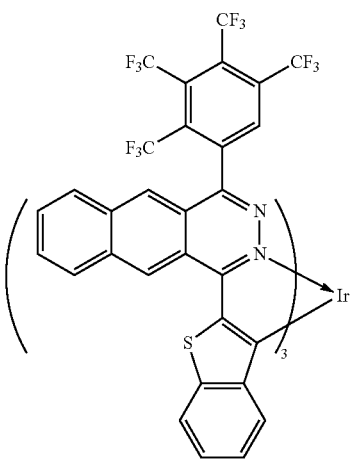
CBT5
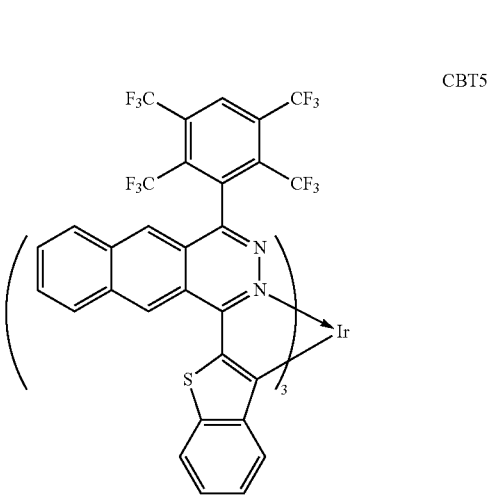
CBT6
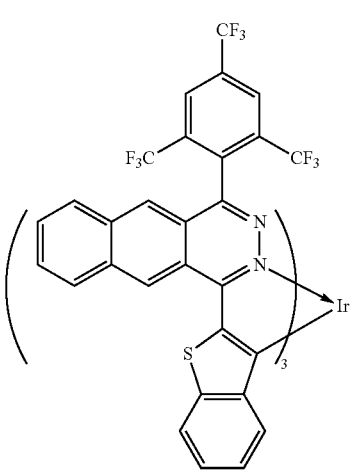

-continued
CBT7
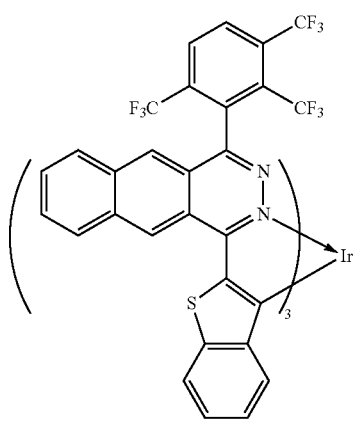
CBT8
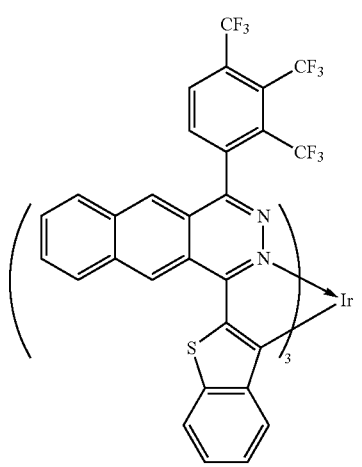
CBT9
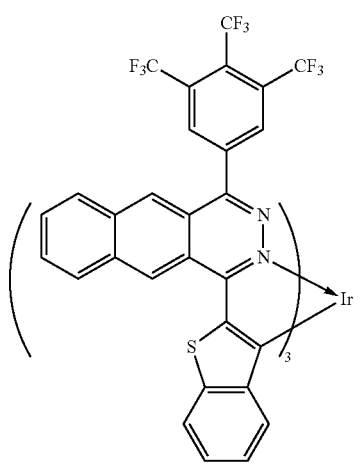
-continued
CBT10
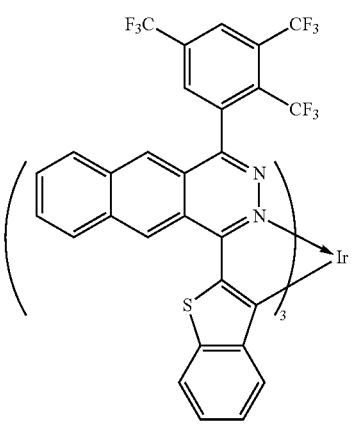
CBT11
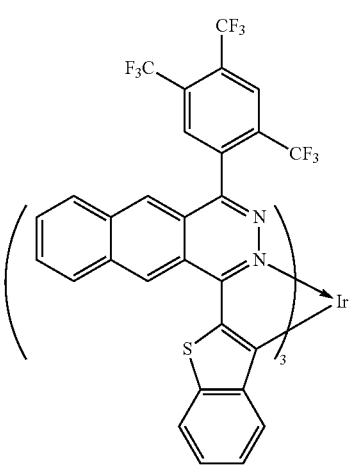
CBT12
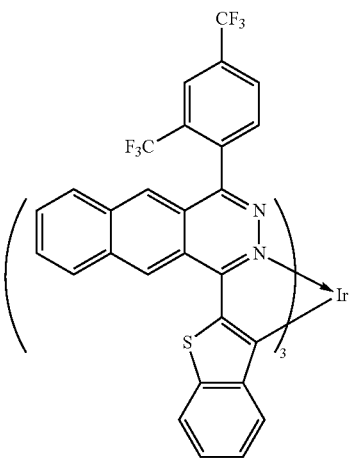

CBT13
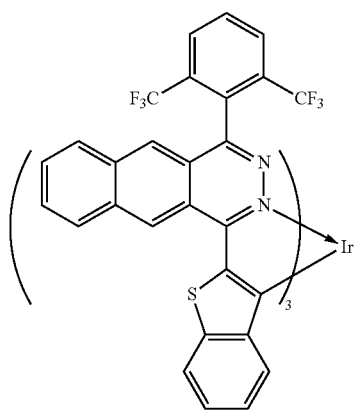
CBT14
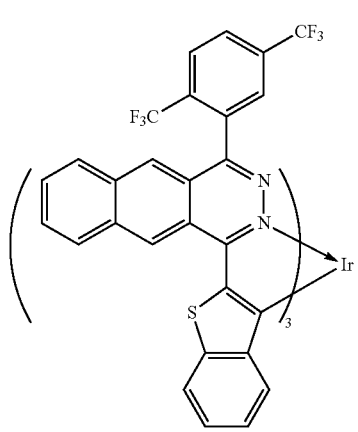
CBT15
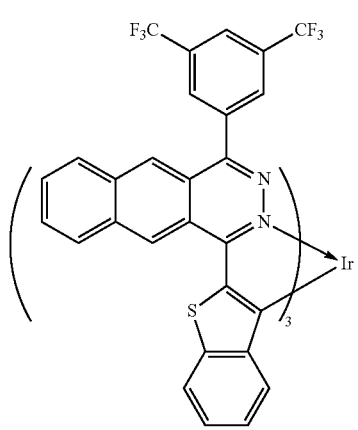
CBT16
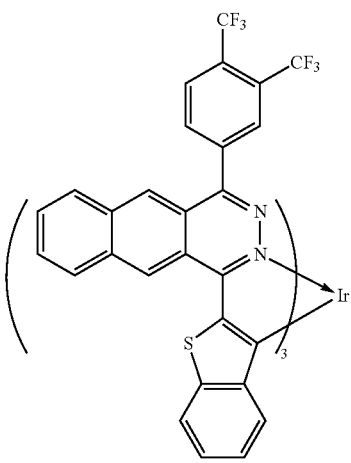
CBT17
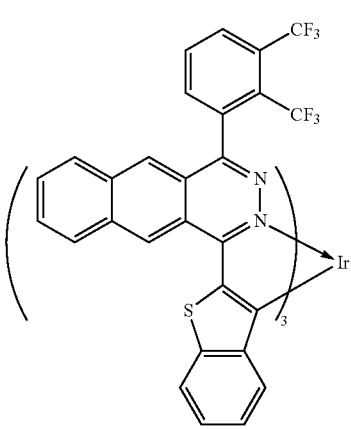
CBT18
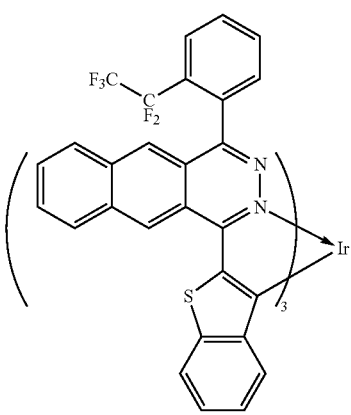

CBT19
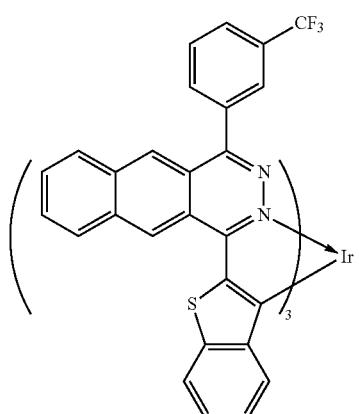
CBT20
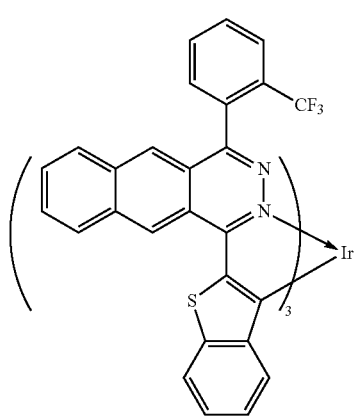
CBT21
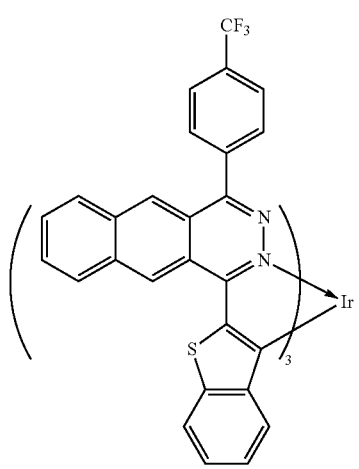
CBT22
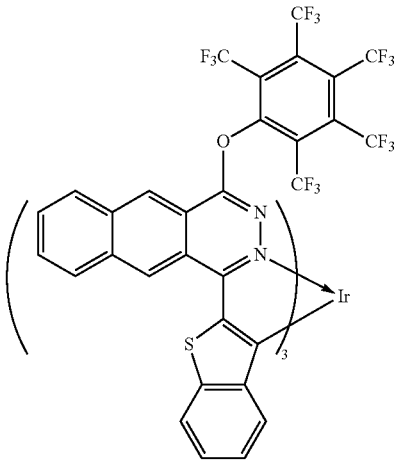
CBT23
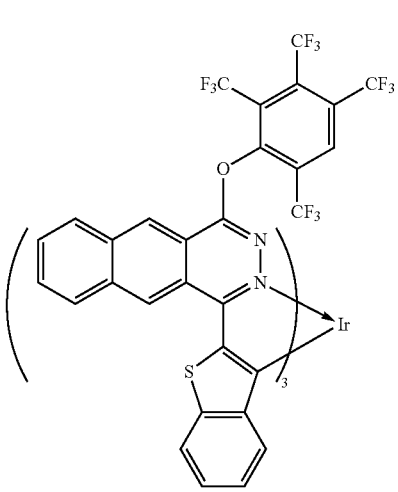
CBT24
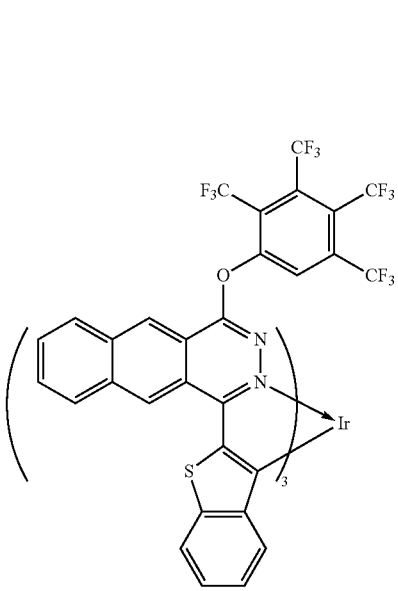

CBT25
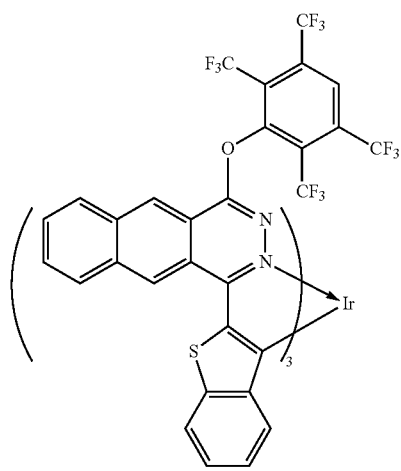
CBT26
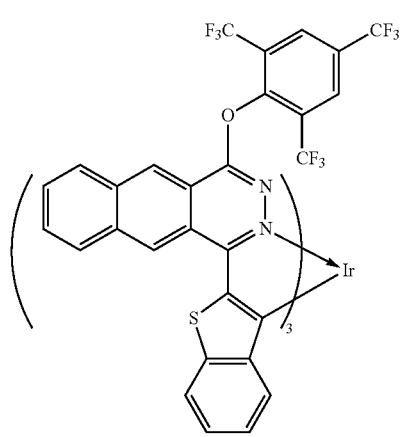
CBT27
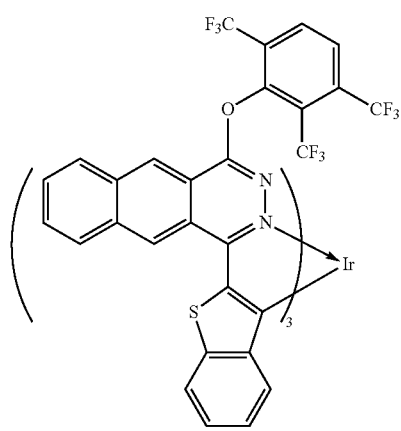
CBT28
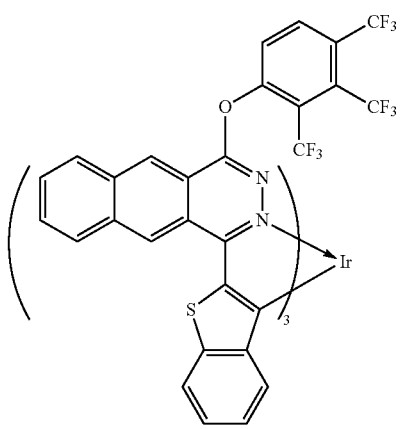
CBT29
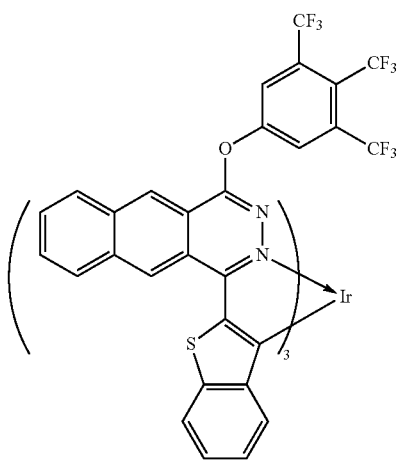
CBT30
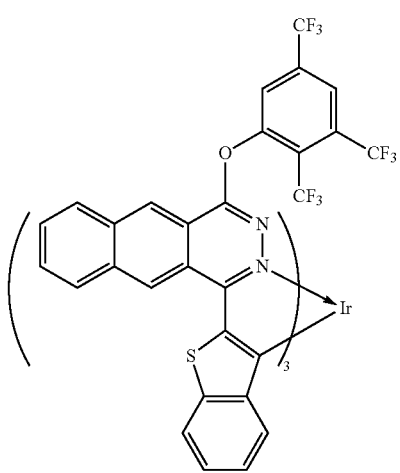

CBT31
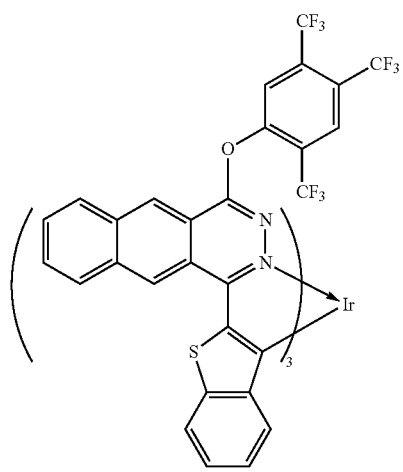
CBT32
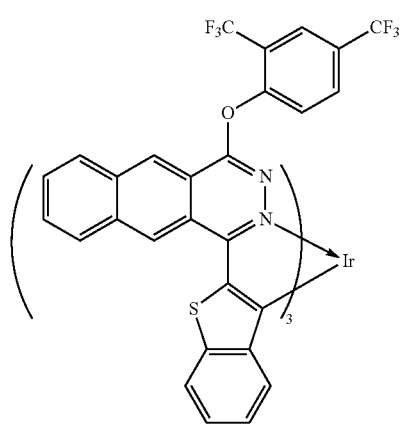
CBT33
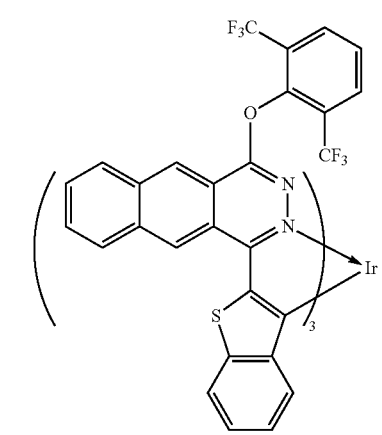
CBT34
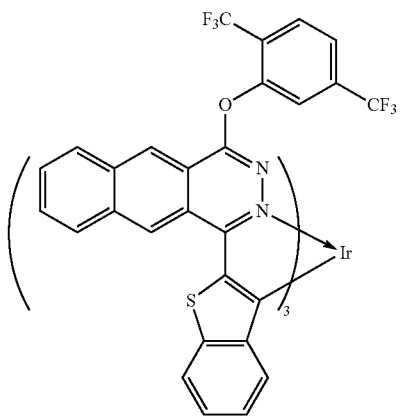
CBT35
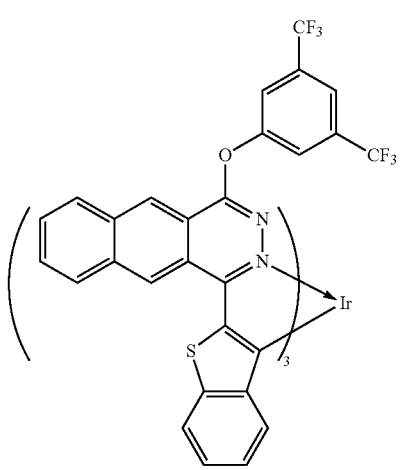
CBT36
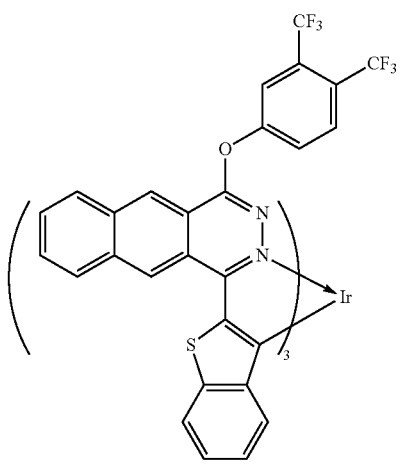

CBT37 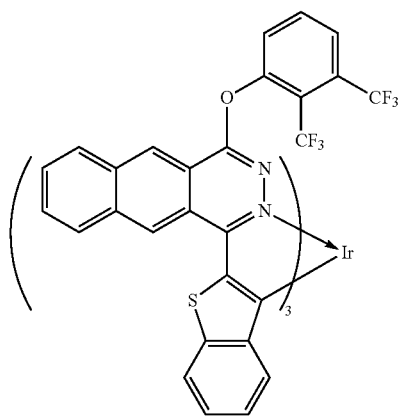
CBT40 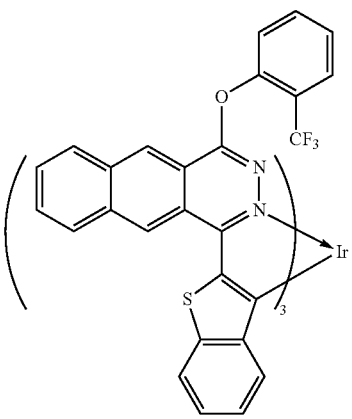
CBT38 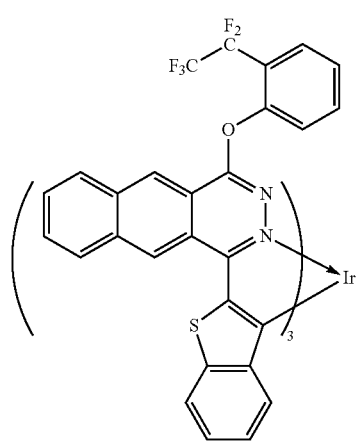
CBT41 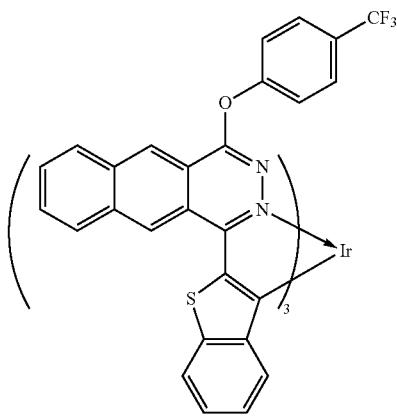
CBT39 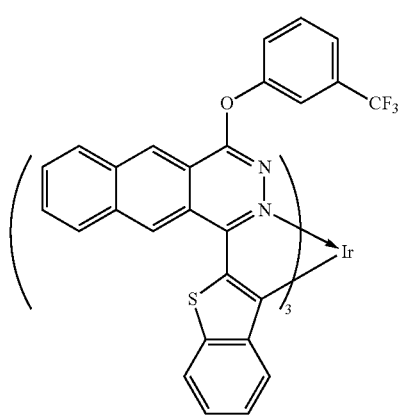
CBT42 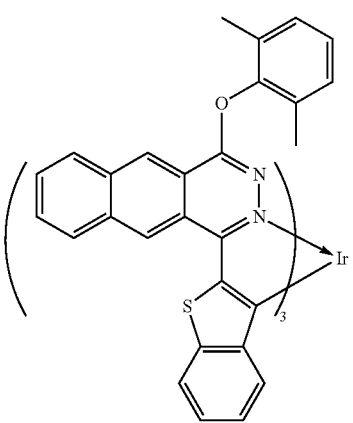

CBT47
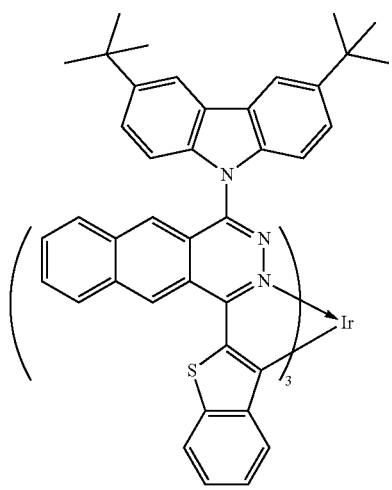
CBF2
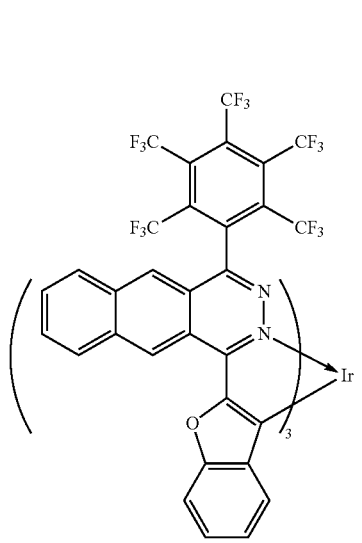
CBF3
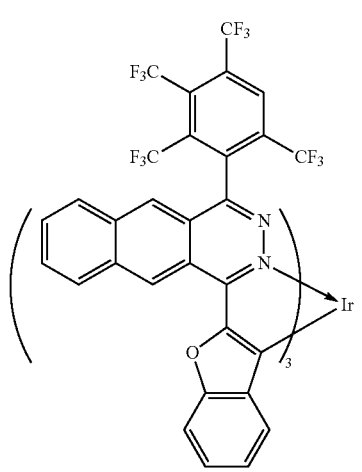
CBF4
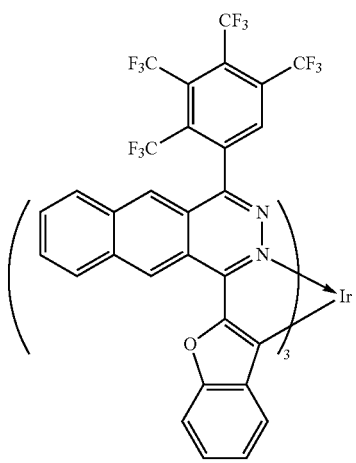
CBF5
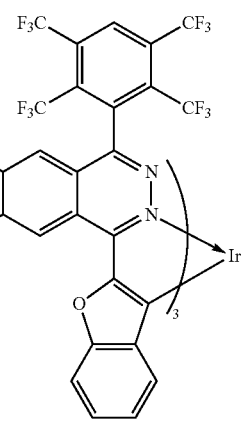
CBF6
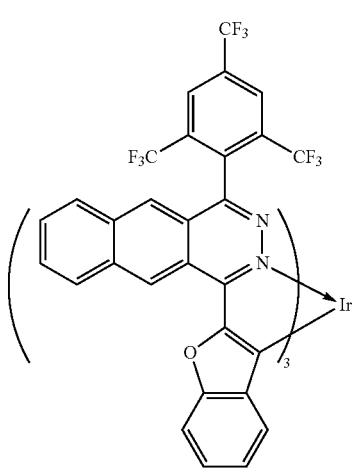

CBF7
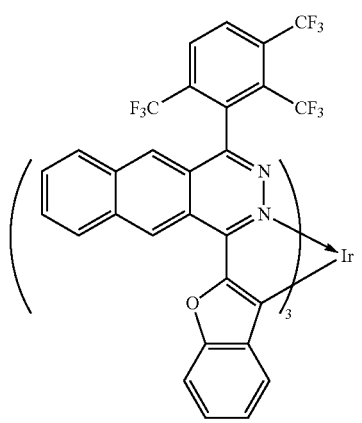
CBF8
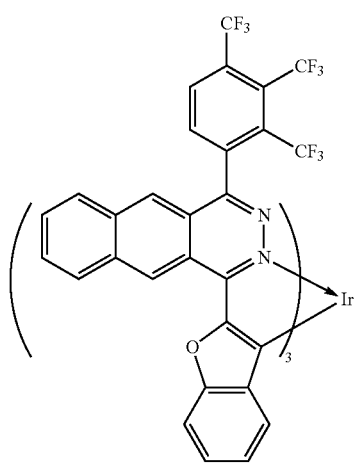
CBF9
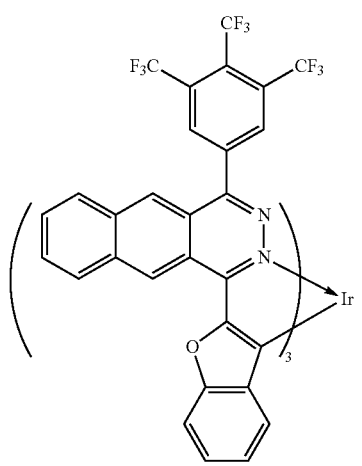
CBF10
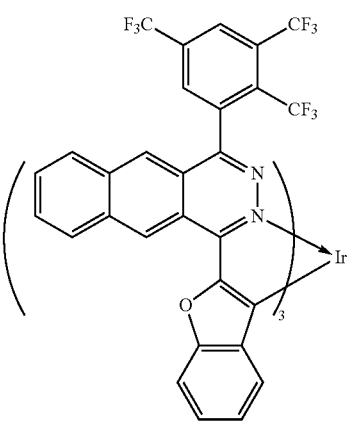
CBF11
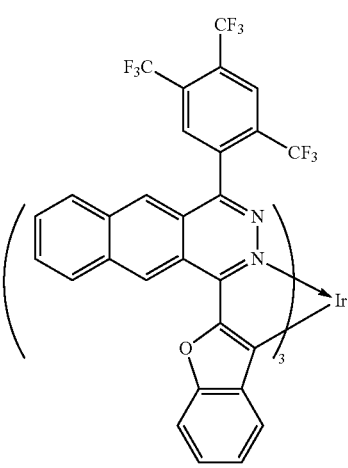
CBF12
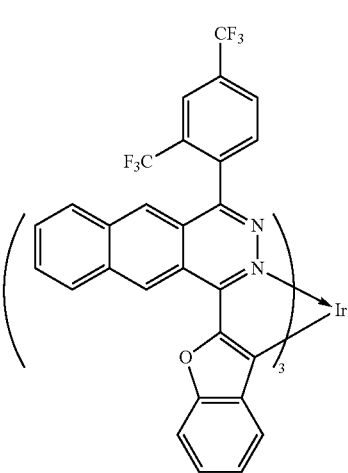

CBF13
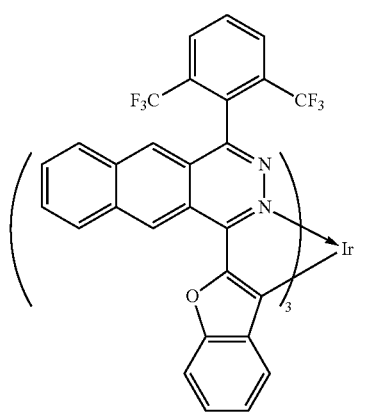
CBF14
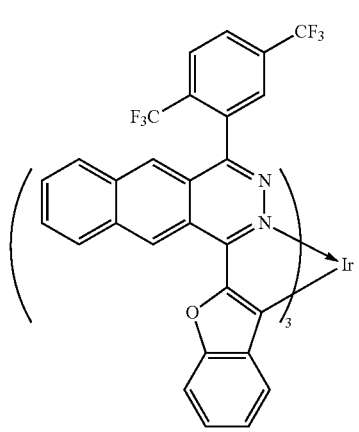
CBF15
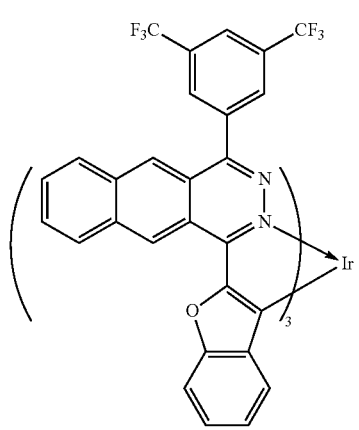
CBF16
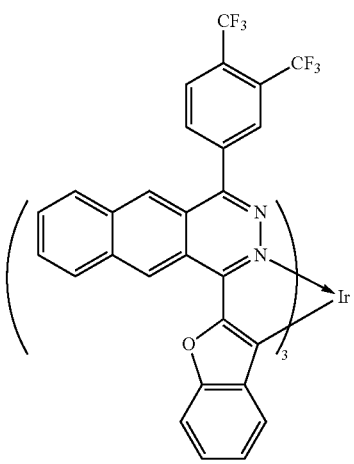
CBF17
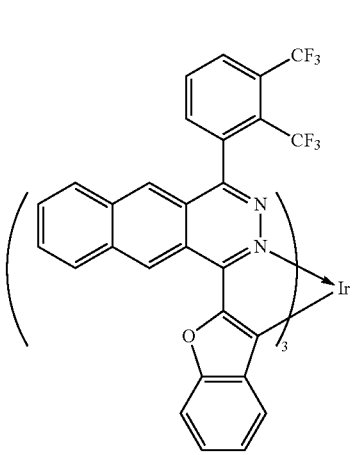
CBF18
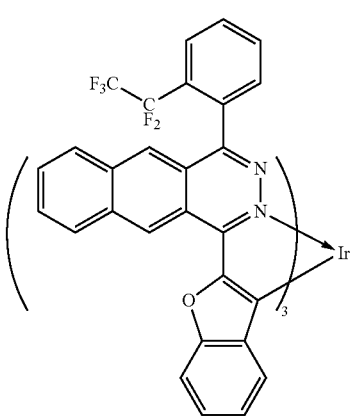

CBF19
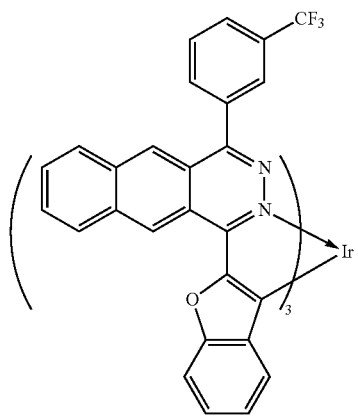
CBF20
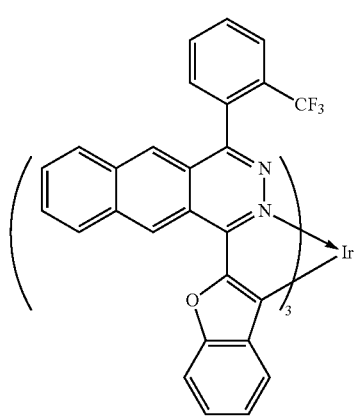
CBF21
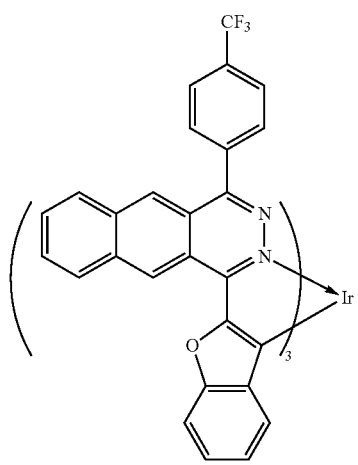
CBF22
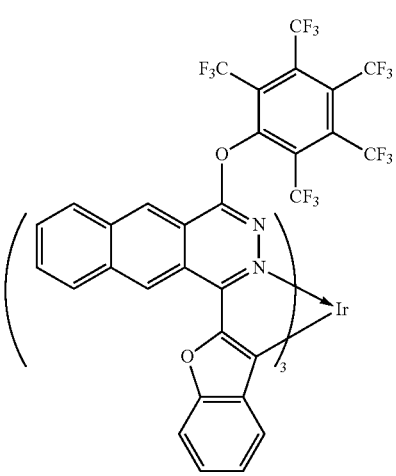
CBF23
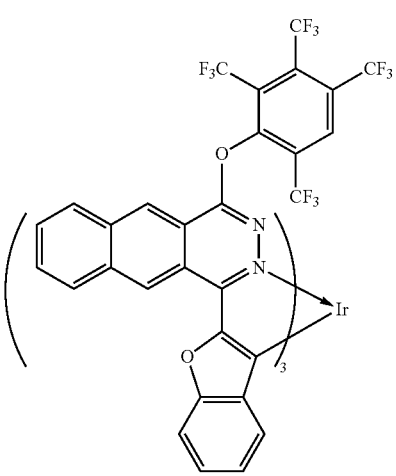
CBF24
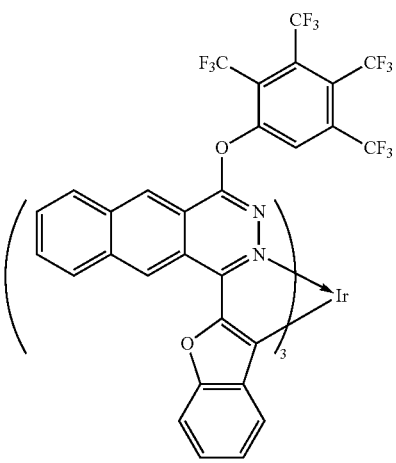

CBF25
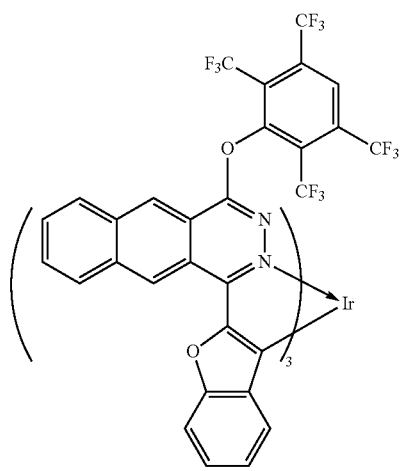
CBF26
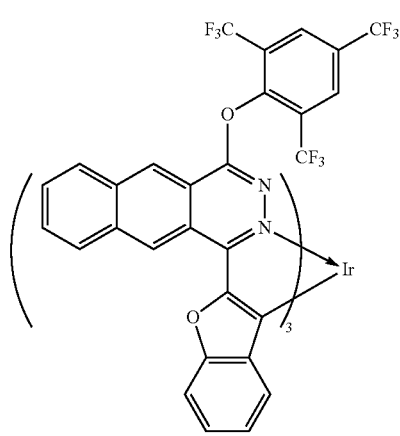
CBF27
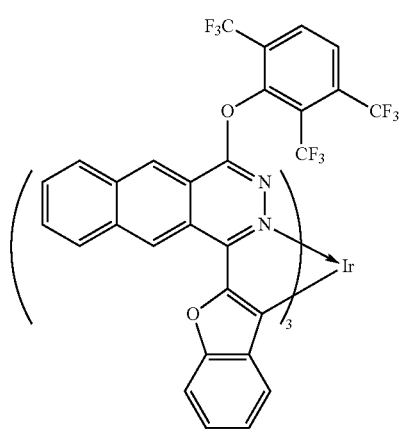
CBF28
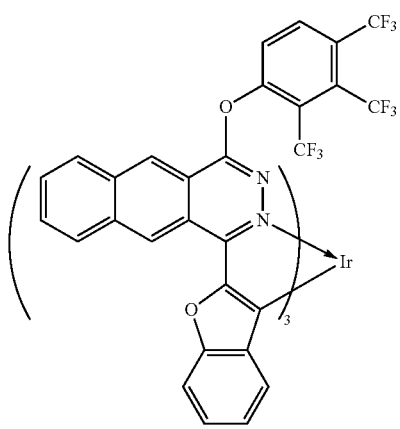
CBF29
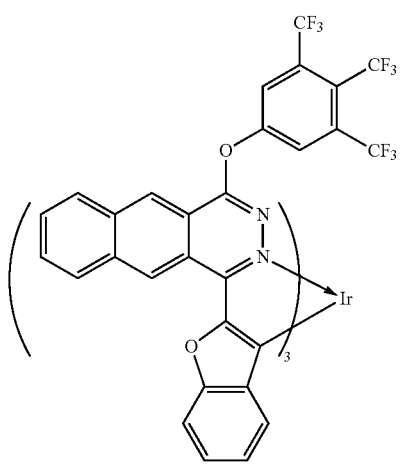
CBF30
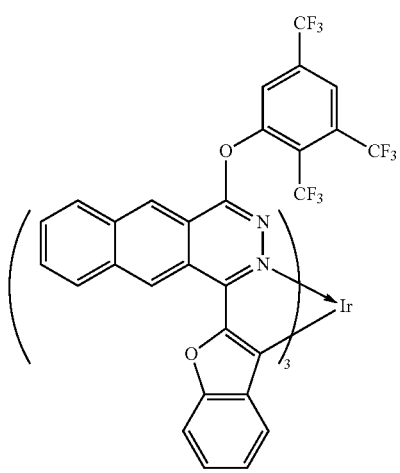

CBF31
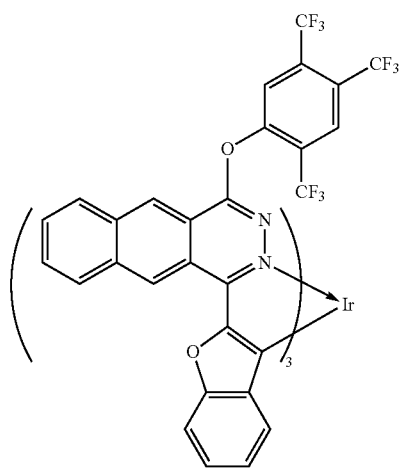
CBF32
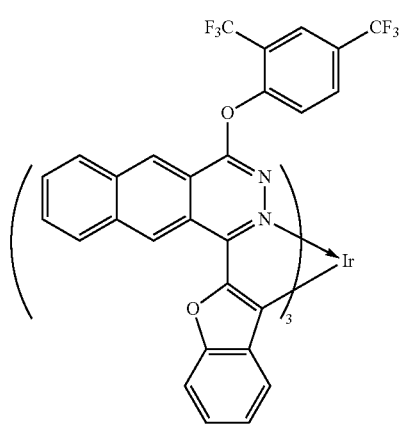
CBF33
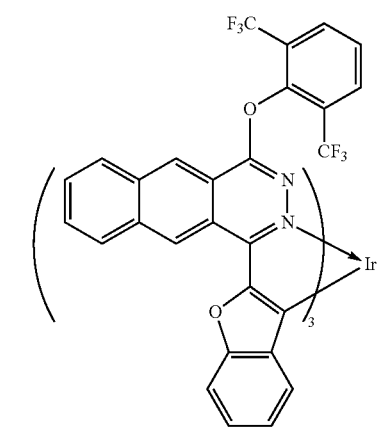
CBF34
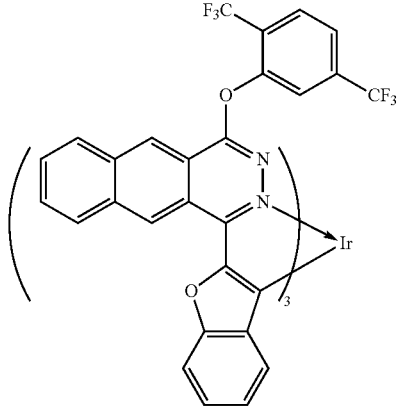
CBF35
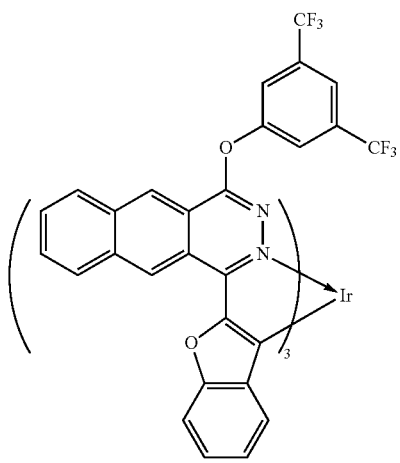
CBF36
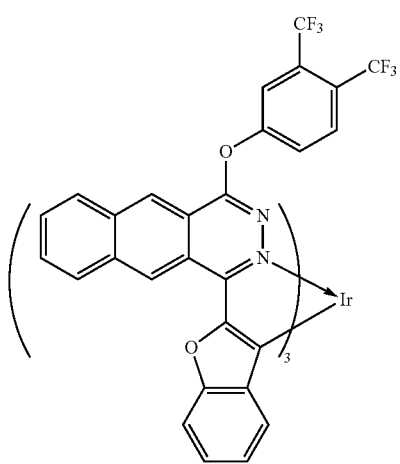

CBF37
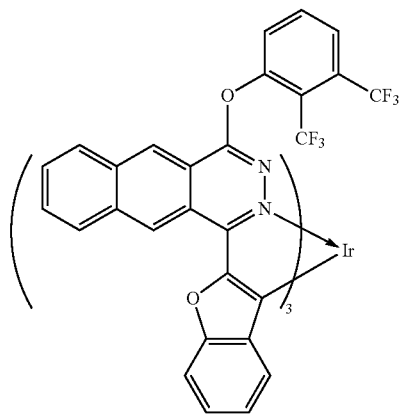
CBF38
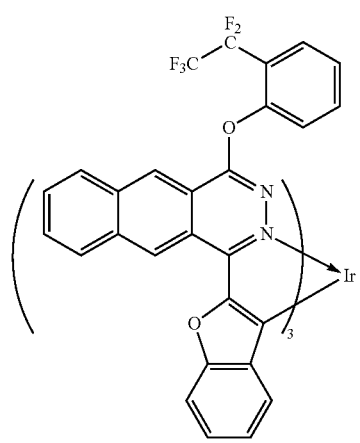
CBF39
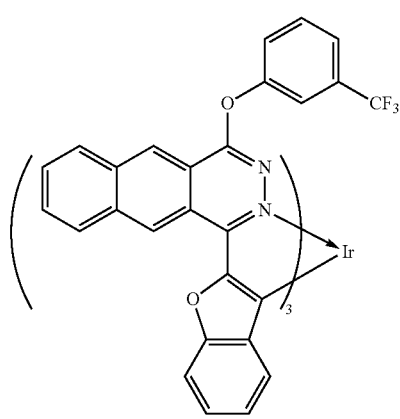
CBF40
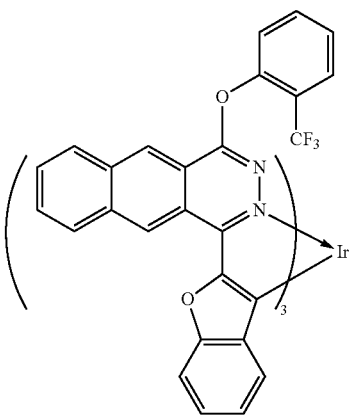
CBF41
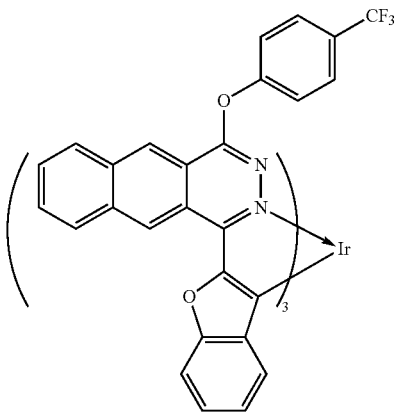
CBF42
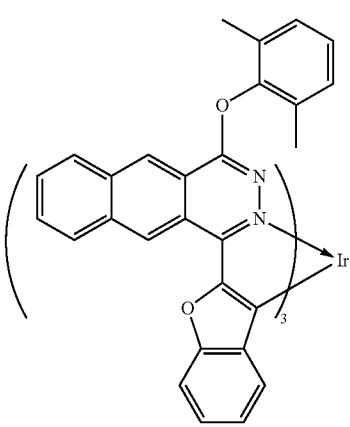

CBF47
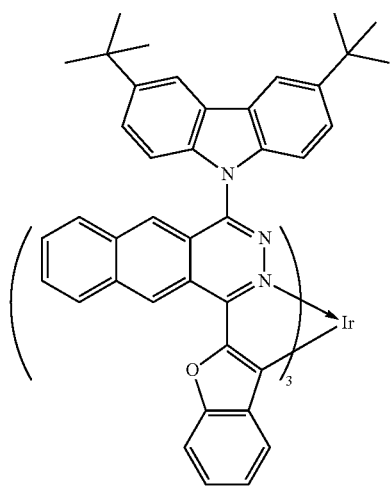
CP1
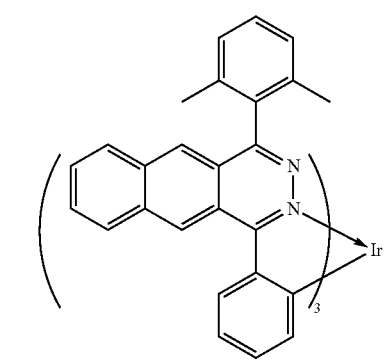
CP2
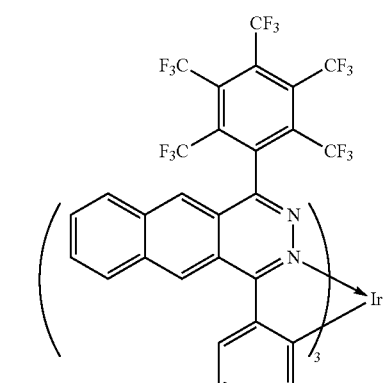
CP3
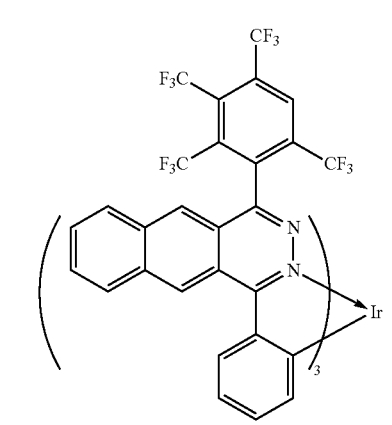
CP4
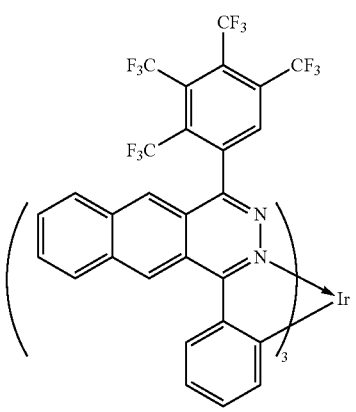
CP5
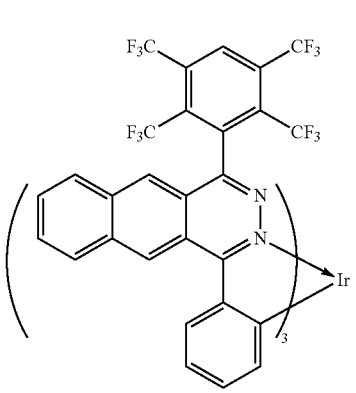
CP6
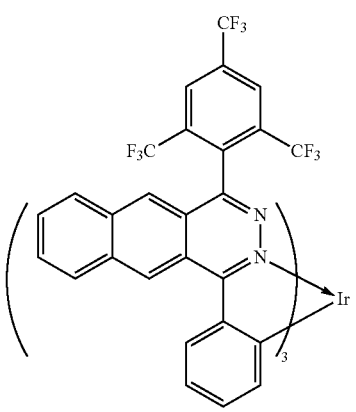
CP7
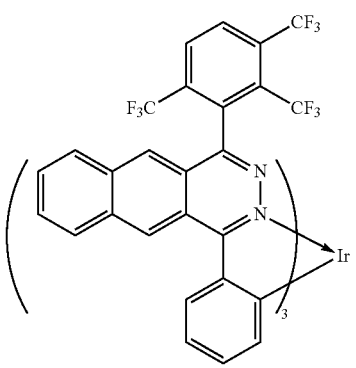

-continued
CP8
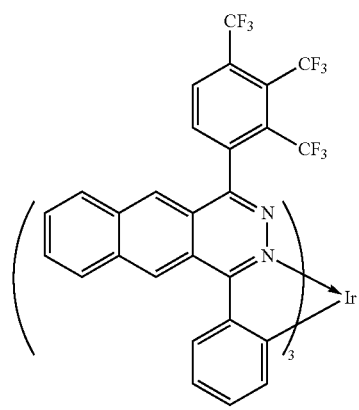
CP9
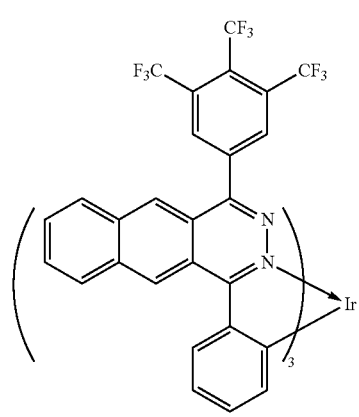
CP10
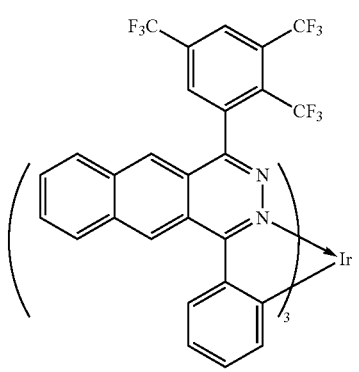
CP11
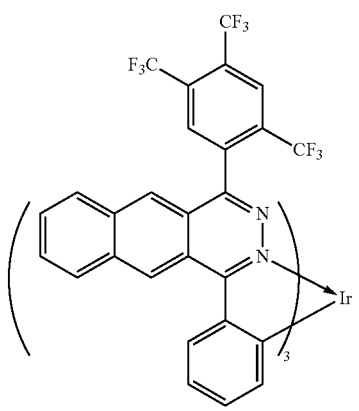
-continued
CP12
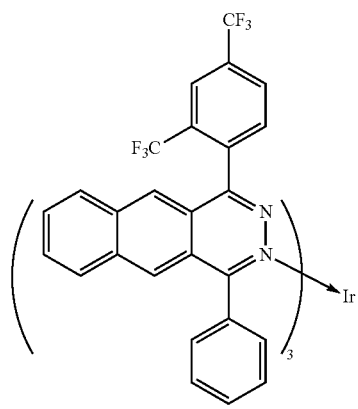
CP13
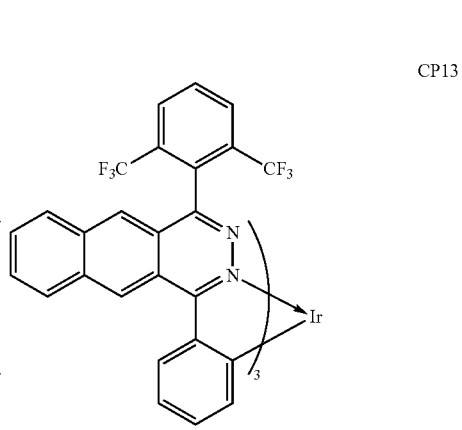
CP14
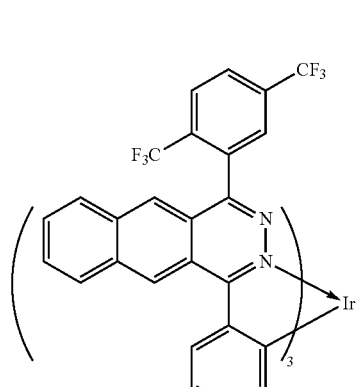
CP15
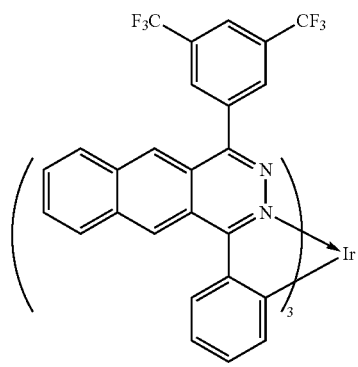

CP16
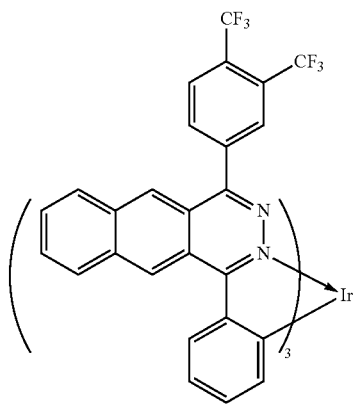
CP17
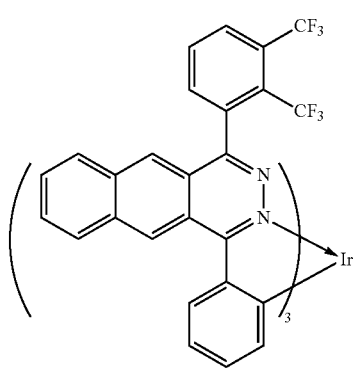
CP18
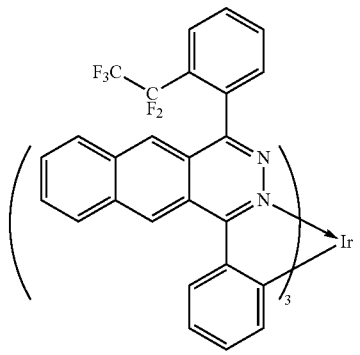
CP19
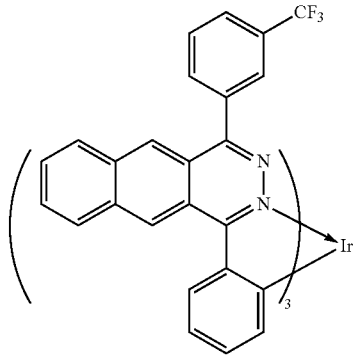
CP20
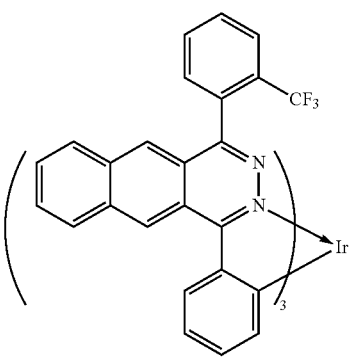
CP21
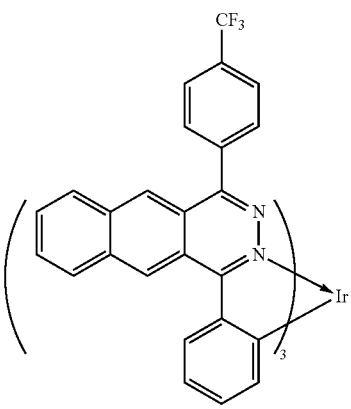
CP22
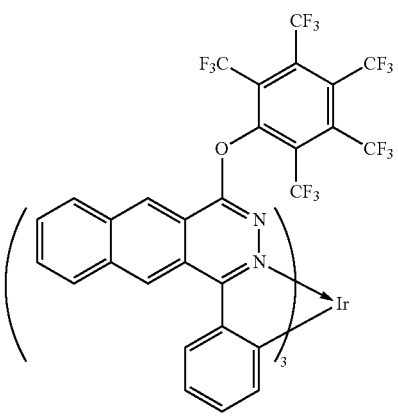
CP23
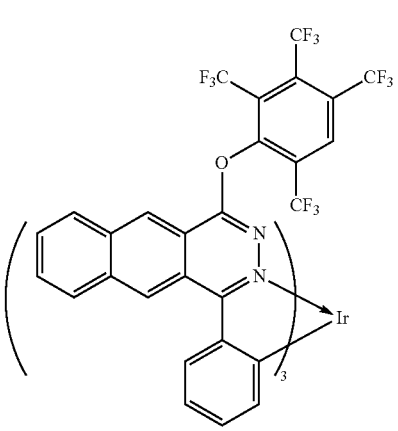

CP24
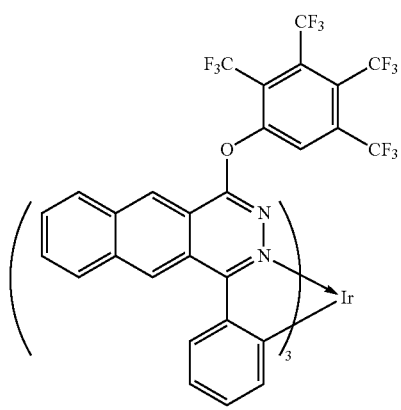
CP25
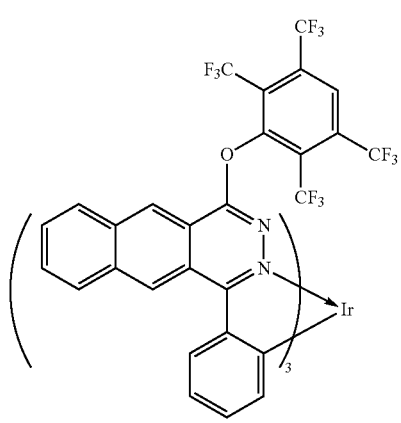
CP26
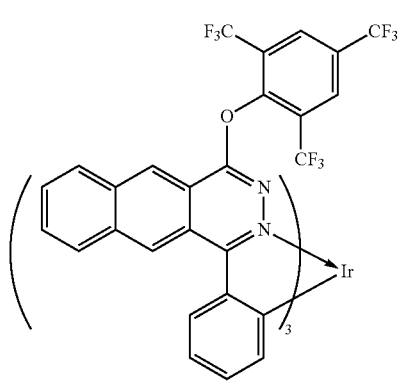
CP27
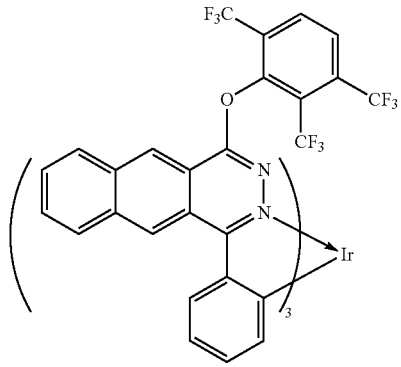
CP28
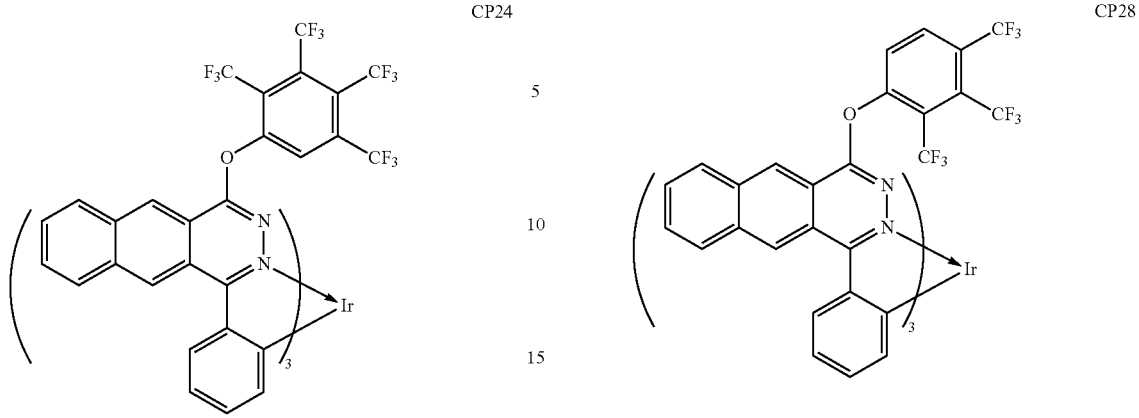
CP29
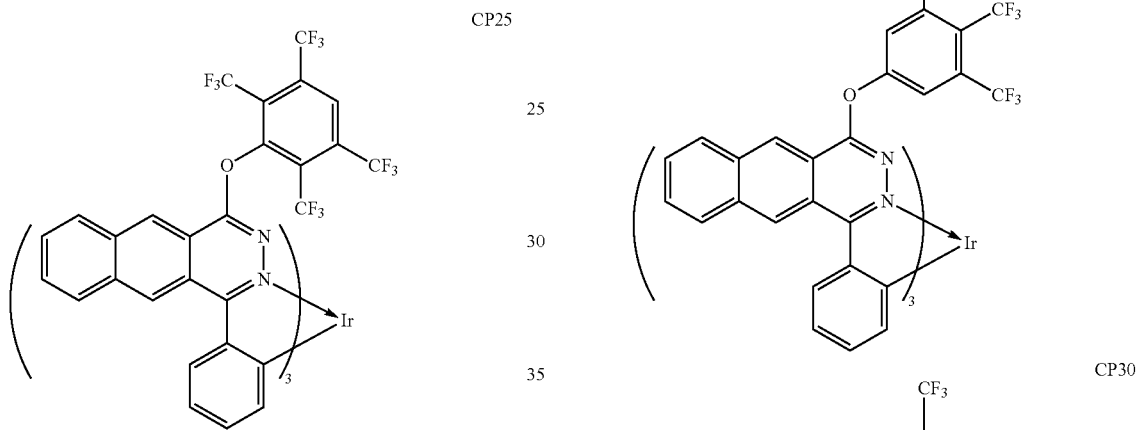
CP30
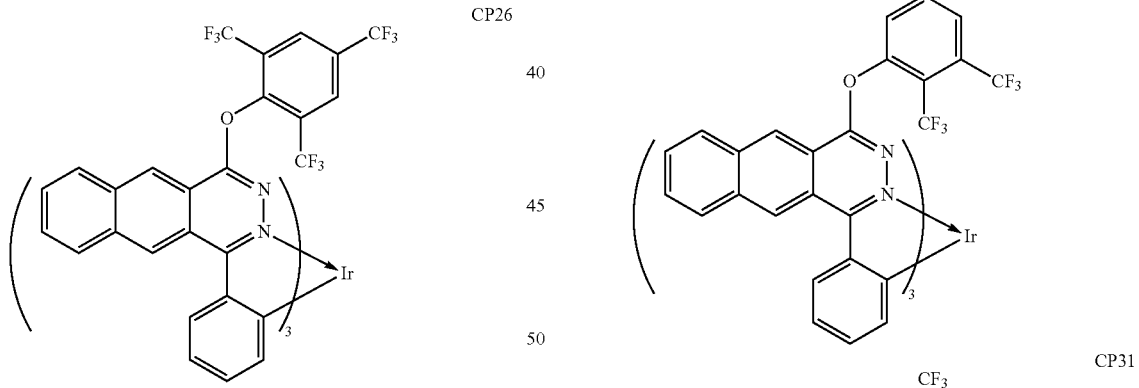
CP31
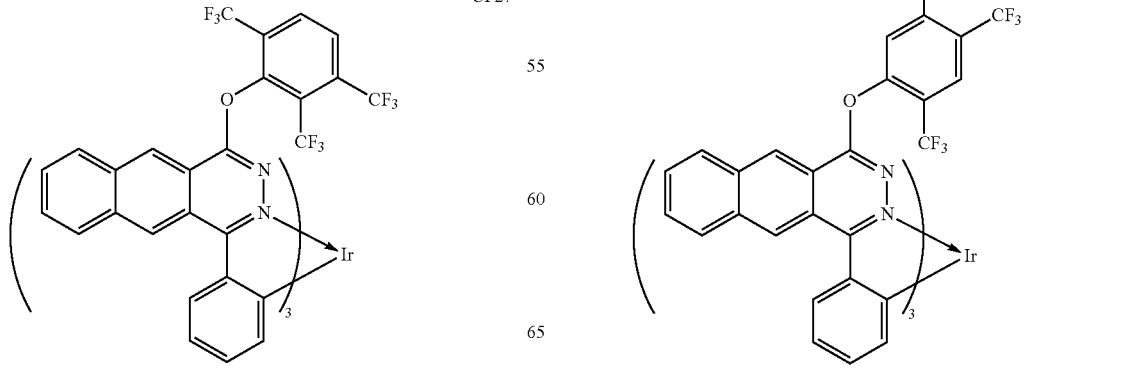

-continued
CP32
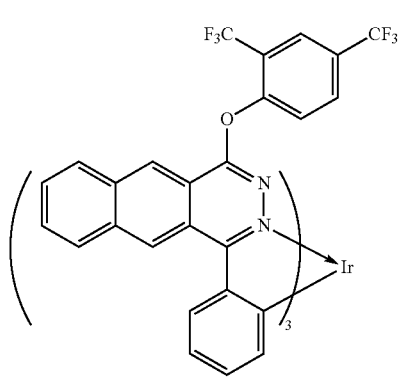
CP33
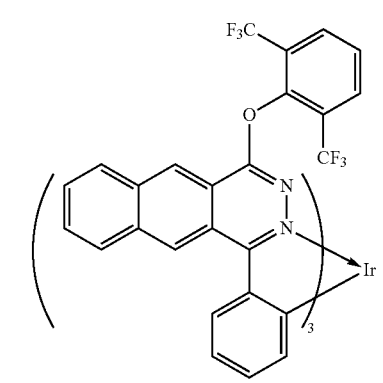
CP34
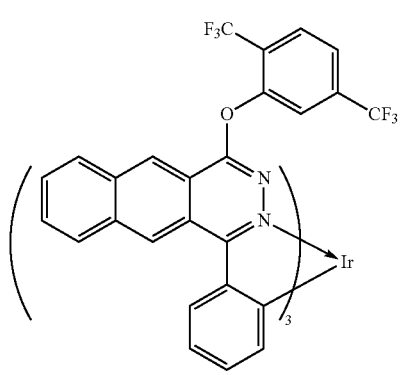
CP35
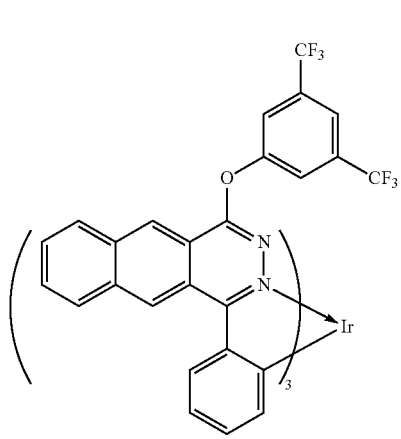
-continued
CP36
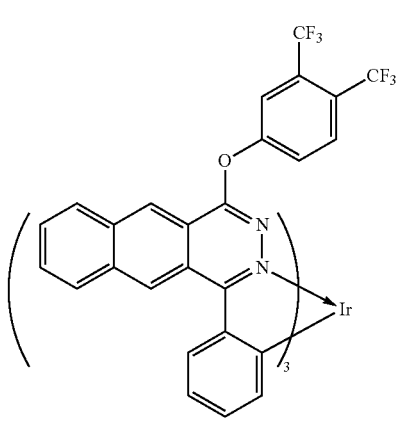
CP37
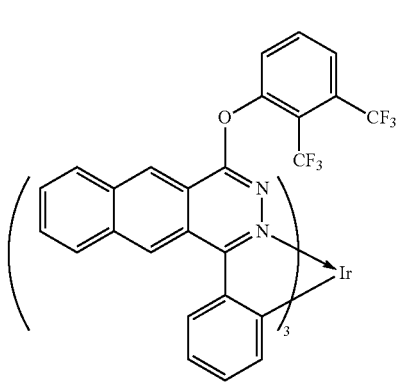
CP38
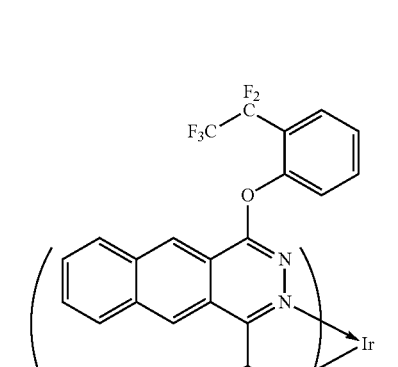
CP39
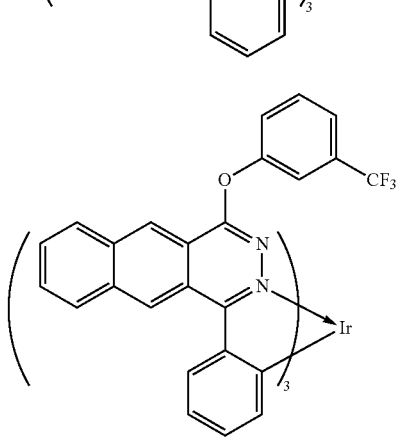

-continued

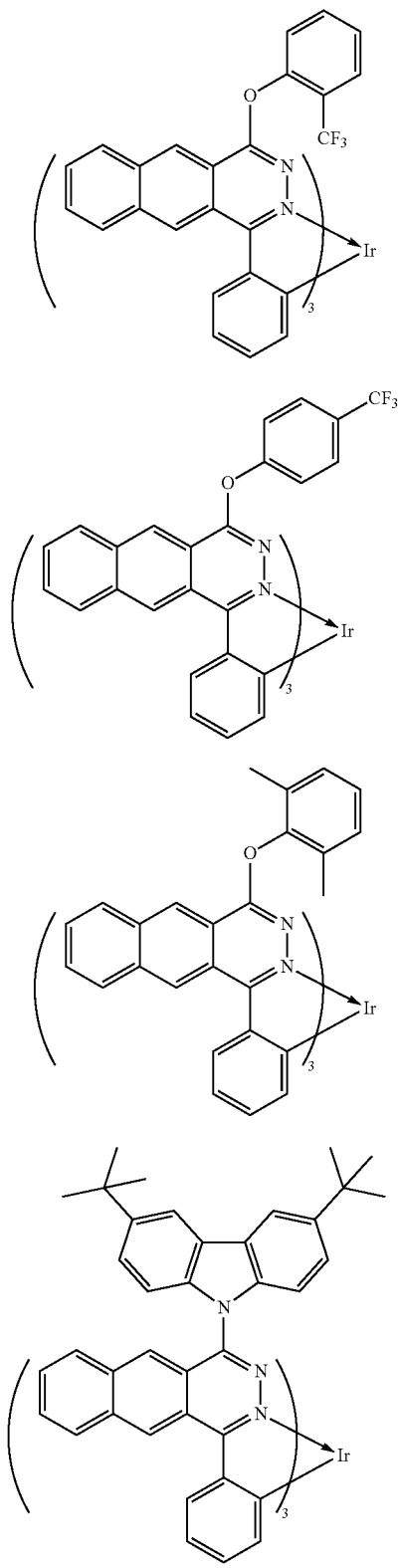

CP40

CP41

CP42

CP47

9. An organic electroluminescent device comprising one or more of the iridium complexes according to claim 8.

10. An organic electroluminescent device comprising one or more of the iridium complexes according to claim 1.

11. An organic electroluminescent device, comprising:
a first electrode, a second electrode, and one or more organic layers between the first electrode and the second electrode, wherein:
the one more organic layers comprise an iridium complex given by general formula (I), which have a molecular formula of $L_3Ir$, wherein Ir is the central metal atom and L is the ligand:

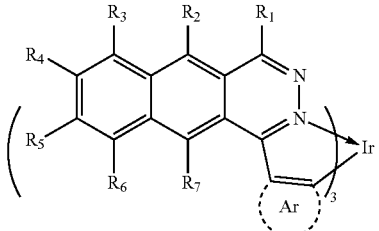

(I)

in formula (I), Ar is selected from substituted or unsubstituted aryl groups with 6 to 30 carbon atoms, and substituted or unsubstituted heterocyclic aryl groups with 4 to 30 carbon atoms;

$R_1$ is selected from group consisting of: substituted thiophene, substituted benzothiophene, substituted benzene, substituted naphthalene, substituted anthracene, substituted phenanthrene, substituted pyrene, substituted furan, substituted benzofuran, substituted thiazole, substituted benzothiazole, substituted isothiazole, substituted benzisothiazole, substituted pyrrole, substituted benzopyrrole, substituted imidazole, substituted benzimidazole, substituted pyrazole, substituted benzopyrazole, substituted oxazole, substituted benzoxazole, substituted isoxazole, substituted benzisoxazole, substituted pyridine, substituted pyrimidine, substituted benzopyrimidine, substituted pyrazine, substituted benzopyrazine, substituted pyridazine, substituted benzopyridazine, substituted quinoline, substituted isoquinoline, substituted purine, substituted pteridine, substituted indole, substituted carbazole, substituted diphenylamine, substituted phenoxy, substituted diphenyl boron, substituted diphenylphosphine, substituted diphenylphosphine oxide, and substituted triphenyl silicon; and $R_2$ to $R_7$ can each be independently selected from hydrogen atoms, halogen atoms, cyano groups, nitro groups, hydroxyl groups, substituted or unsubstituted alkyl or cycloalkyl groups with 1 to 30 carbon atoms, fluoroalkyl groups, chloroalkyl groups, alkoxy groups, thioalkoxy groups, carboxyl groups with 1 to 30 carbon atoms, ester groups with 1 to 30 carbon atoms, acyl groups with 1 to 30 carbon atoms, substituted or unsubstituted amino groups with 1 to 30 carbon atoms, substituted or unsubstituted aryl groups with 6 to 30 carbon atoms, or substituted or unsubstituted heterocyclic aryl groups with 4 to 30 carbon atoms;

the above heterocyclic aryl group means a monocyclic or fused ring aryl group containing one or more hetero atoms selected from the group consisting of B, N, O, S, P, P=O, Si and P with 4 to 30 ring carbon atoms; and the substituent group on above-mentioned Ar or $R_1$ to $R_7$ is independently selected from F, Cl, Br, I, CHO, CN, unsubstituted alkyl or cycloalkyl groups with 1 to 30 carbon atoms, fluoroalkyl groups, alkoxy groups, or thioalkoxy groups.

12. The organic electroluminescent device according to claim 11, wherein the iridium complex is selected from the following specific structural formulas:
CT1
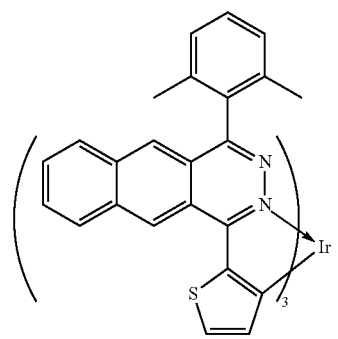
CT2
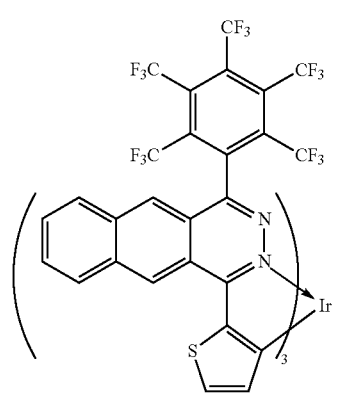
CT3
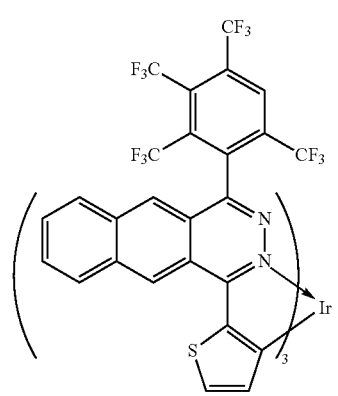
CT4
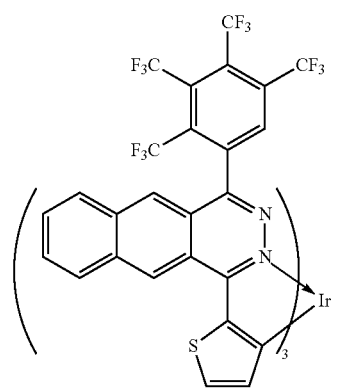
-continued
CT5
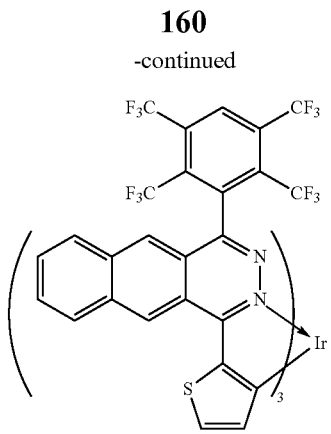
CT6
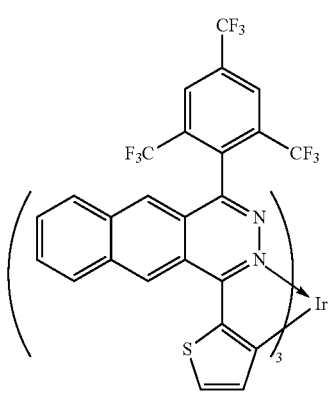
CT7
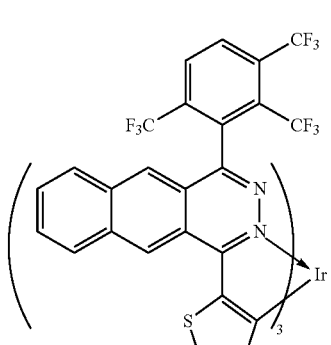
CT8
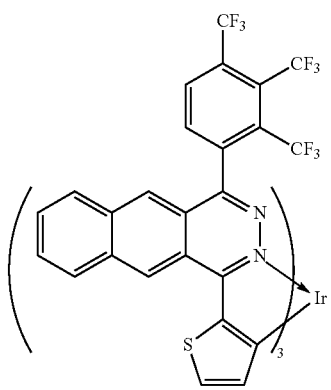

CT9
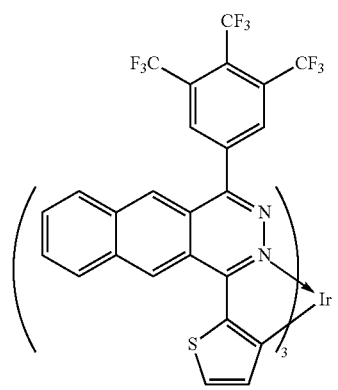
CT10
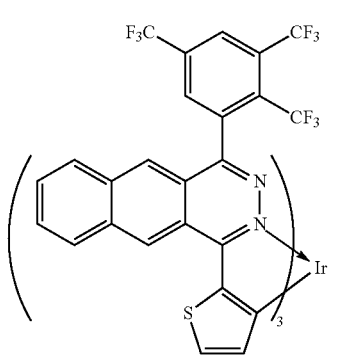
CT11
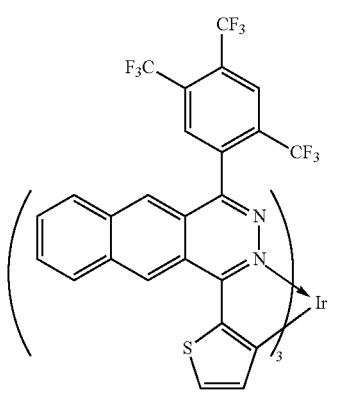
CT12
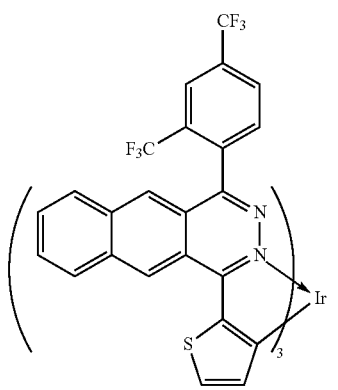
CT13
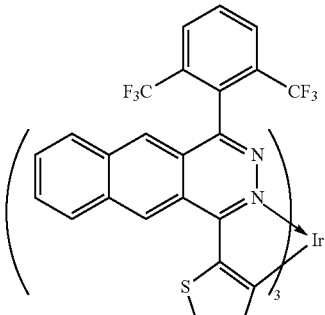
CT14
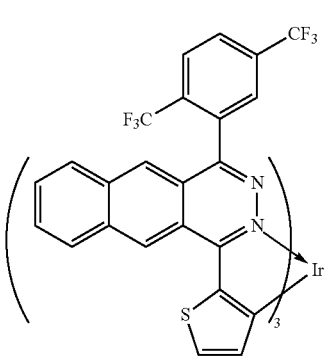
CT15
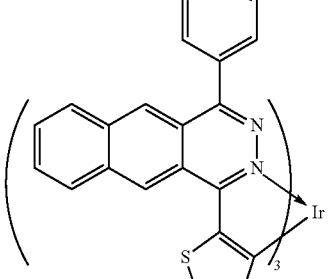
CT16
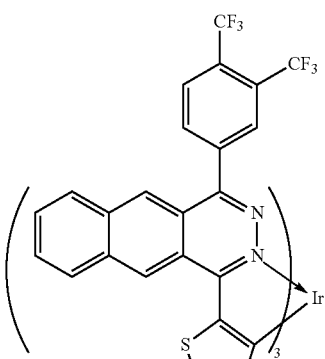

CT17 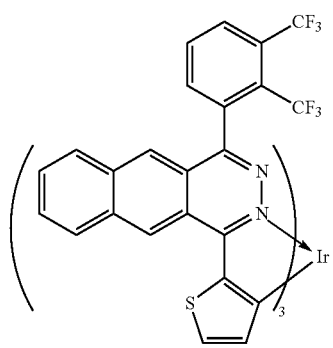
CT18 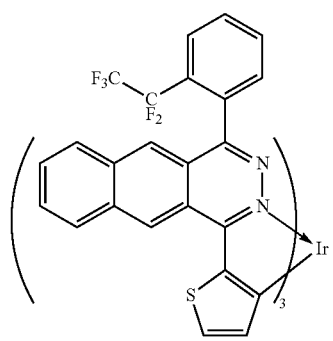
CT19 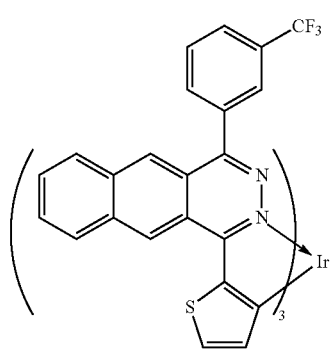
CT20 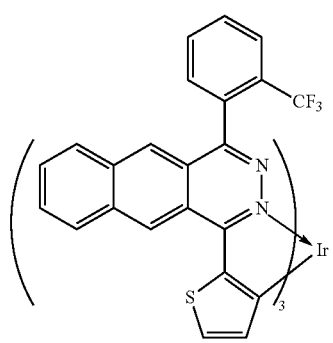
CT21 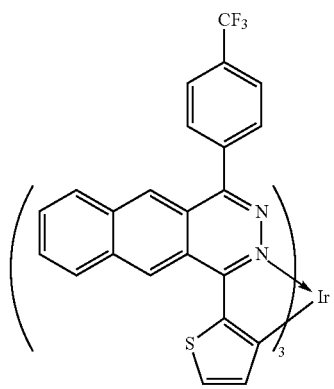
CT22 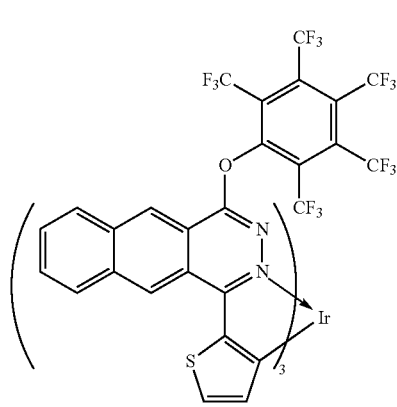
CT23 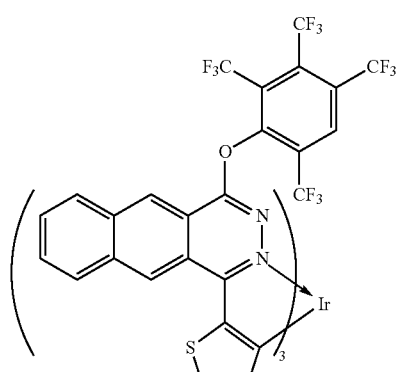
CT24 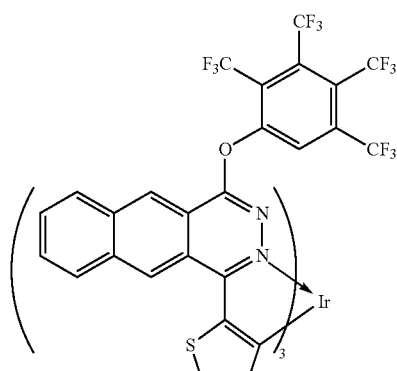

CT25 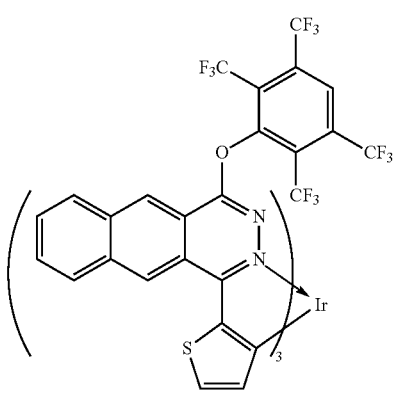
CT29 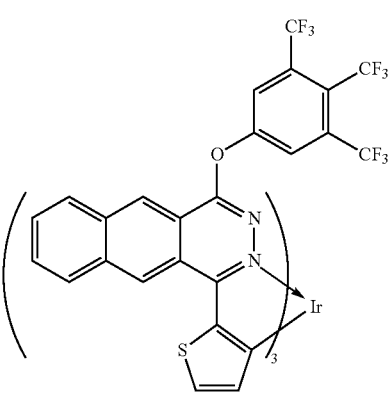
CT26 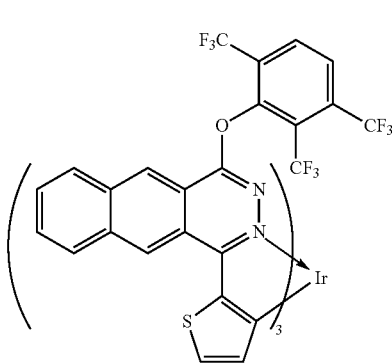
CT30 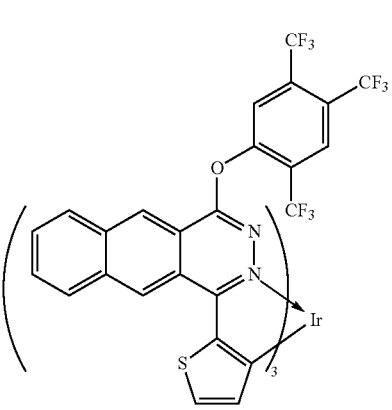
CT27 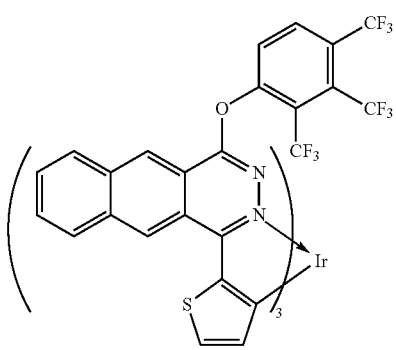
CT31 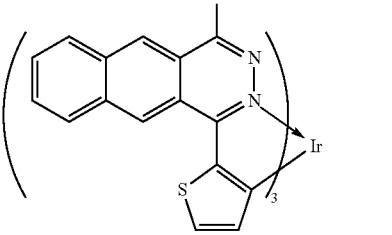
CT28
CT32

CT33
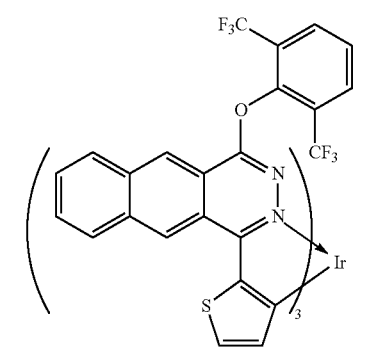
CT34
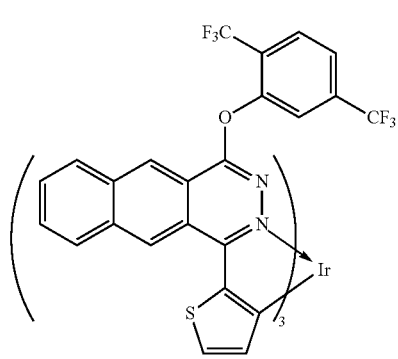
CT35
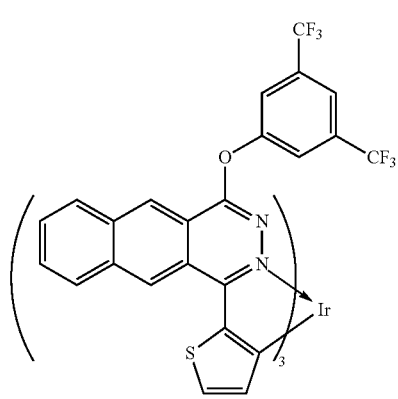
CT36
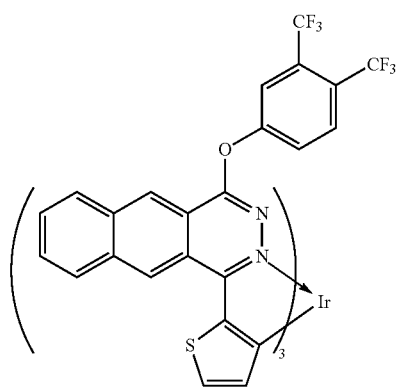
CT37
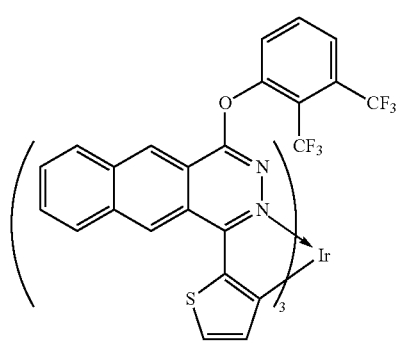
CT38
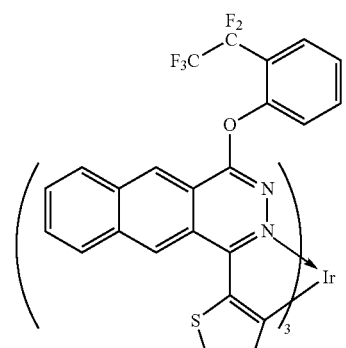
CT39
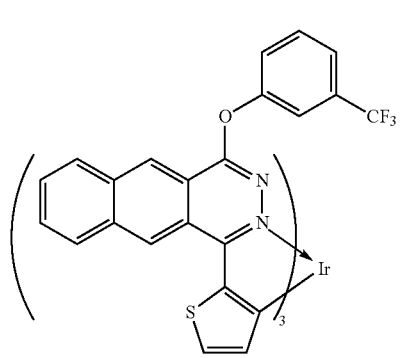
CT40
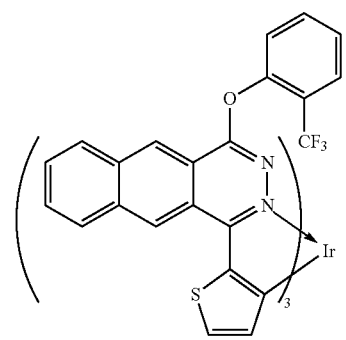

-continued
CT41
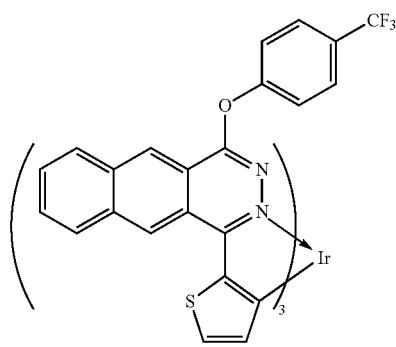
CT42
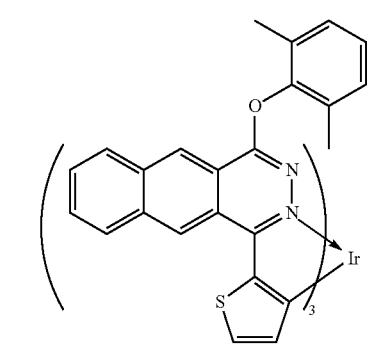
CT47
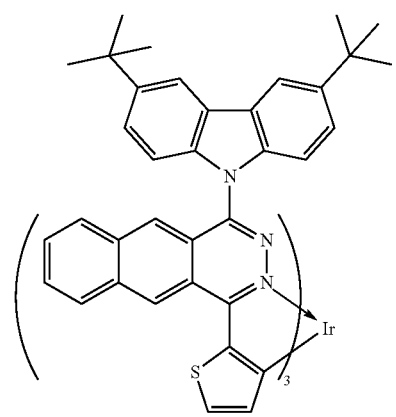
CBT2
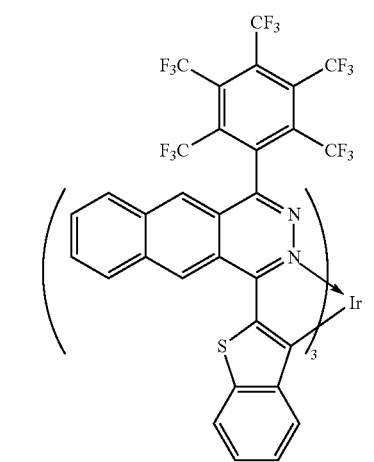
-continued
CBT3
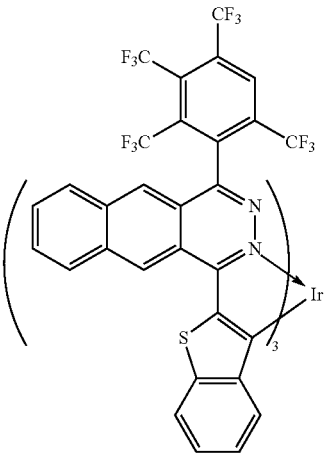
CBT4
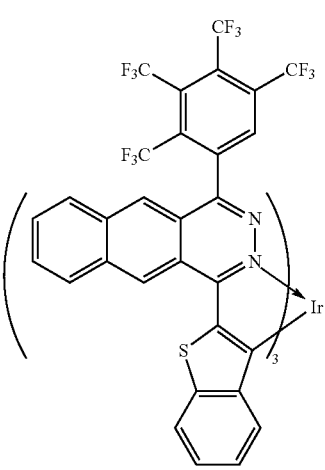
CBT5
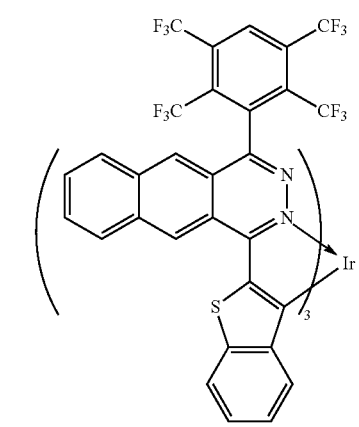

-continued
CBT6
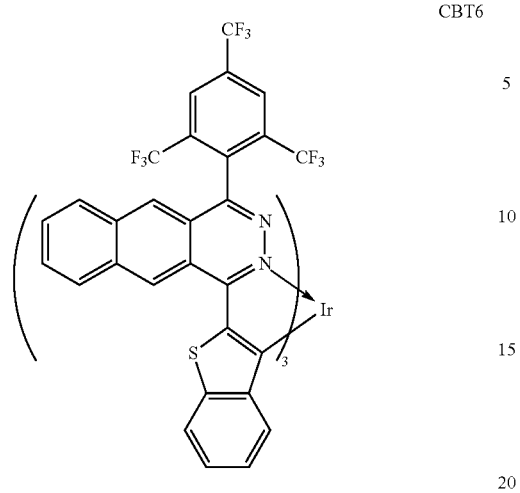
CBT7
CBT8
-continued
CBT9
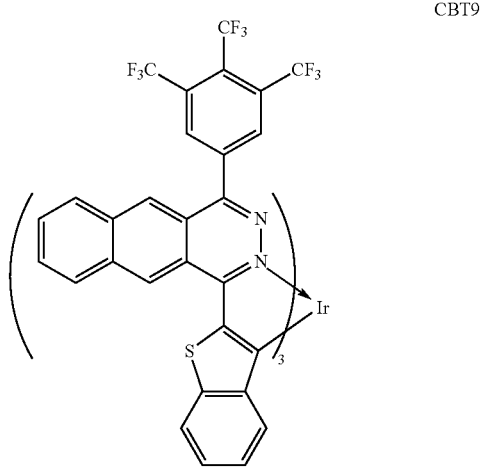
CBT10
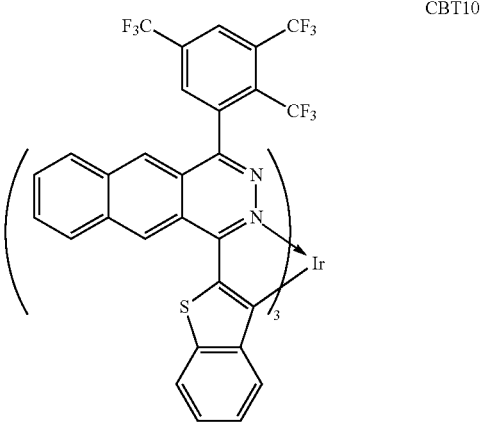
CBT11
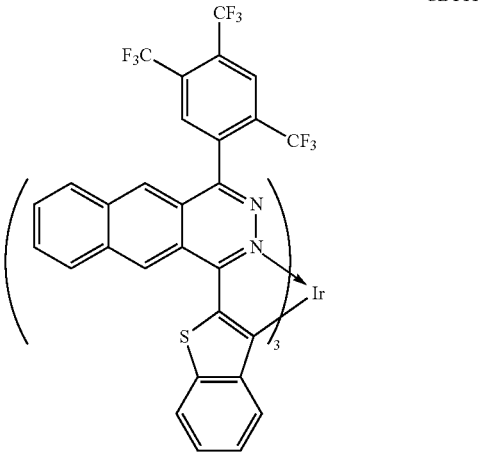

-continued
CBT12
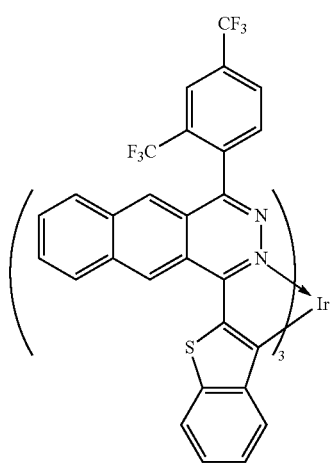
CBT15
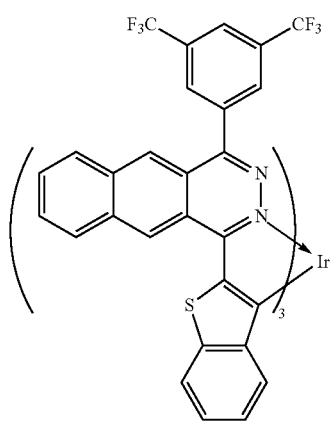
CBT13
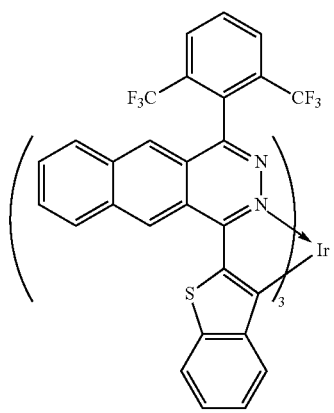
CBT16
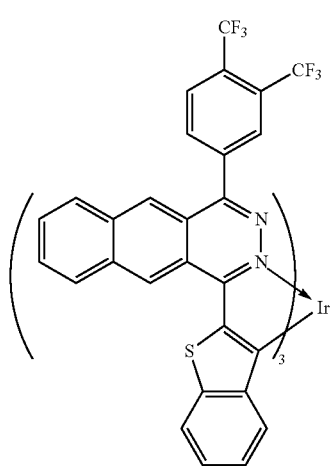
CBT14
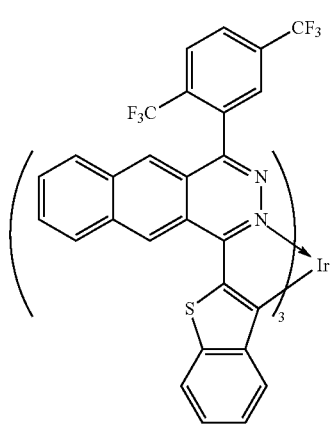
CBT17

CBT18
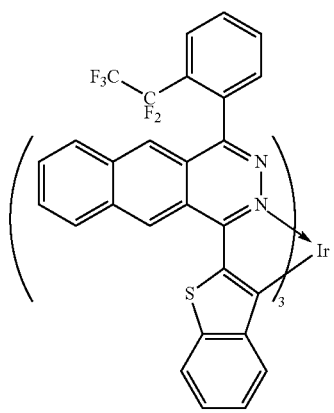
CBT19
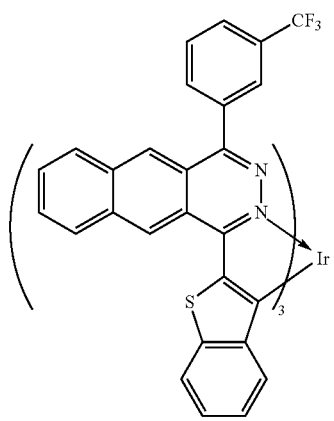
CBT20
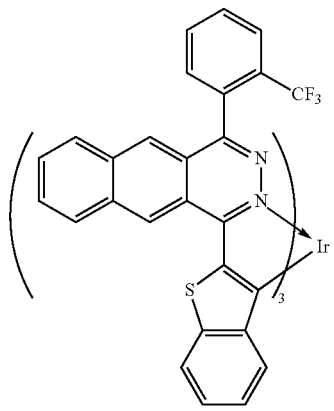
CBT21
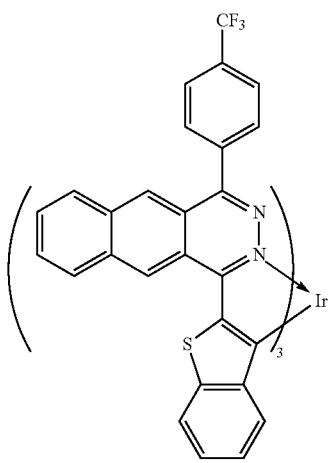
CBT22
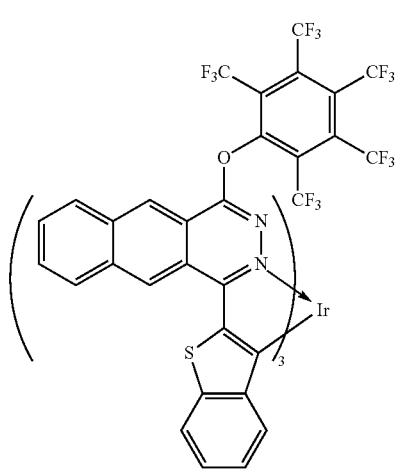
CBT23
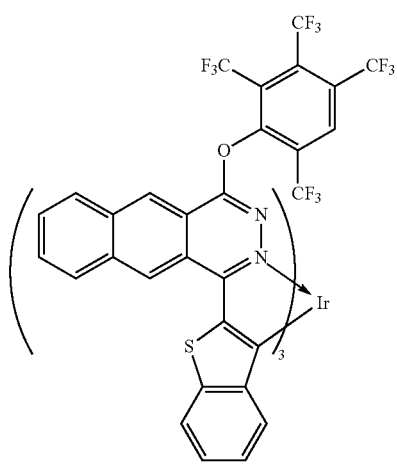

-continued
CBT24
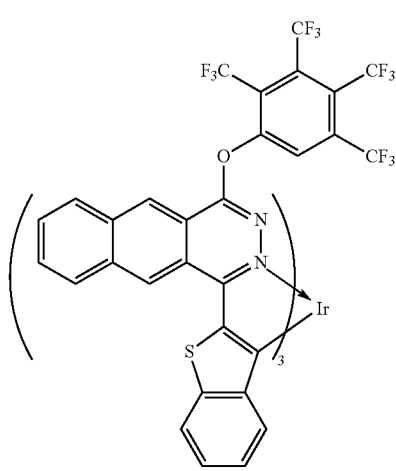
CBT25
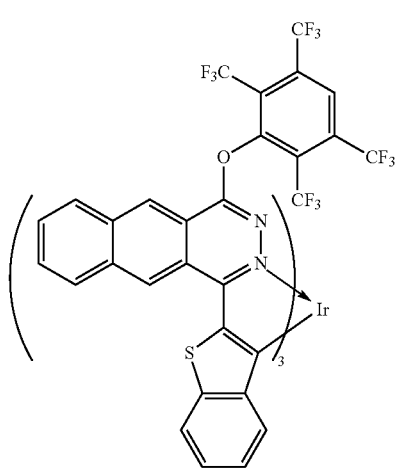
CBT26
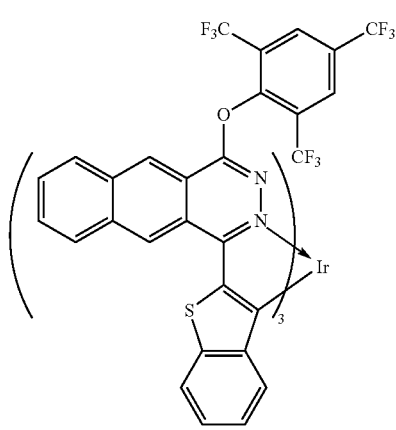
-continued
CBT27
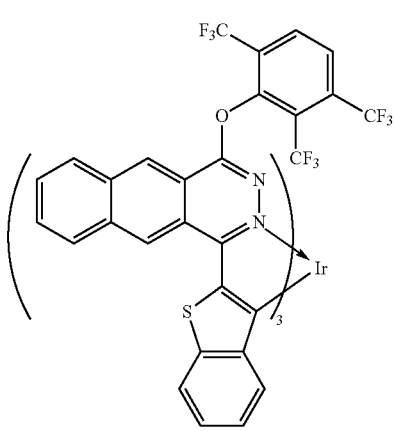
CBT28
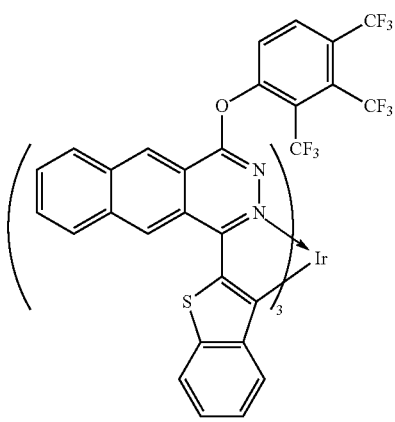
CBT29
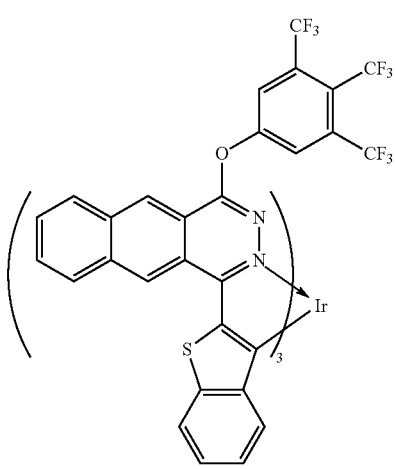

-continued
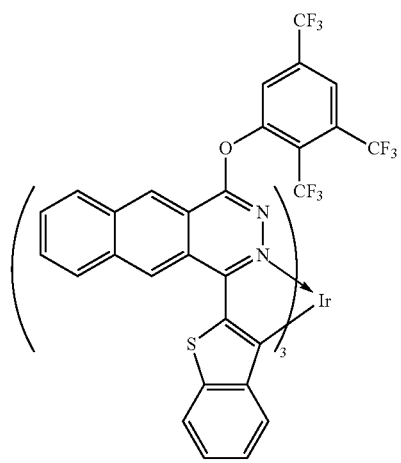
CBT30
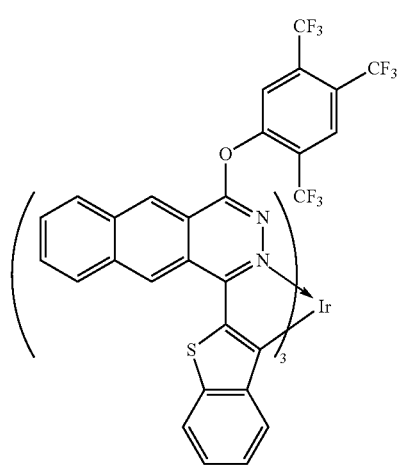
CBT31
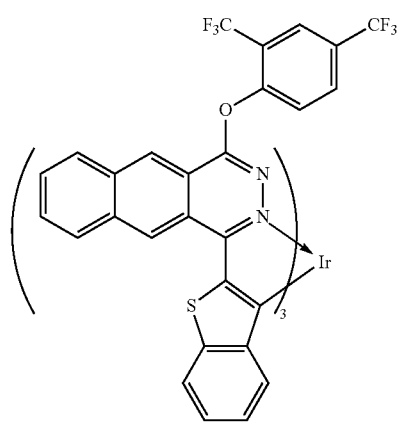
CBT32
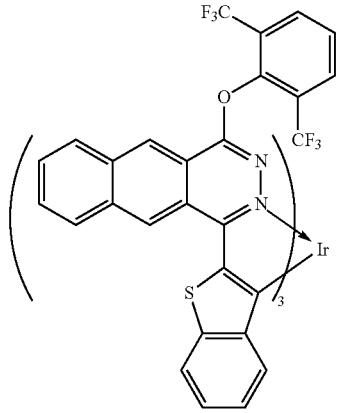
CBT33
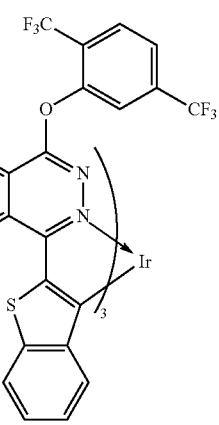
CBT34
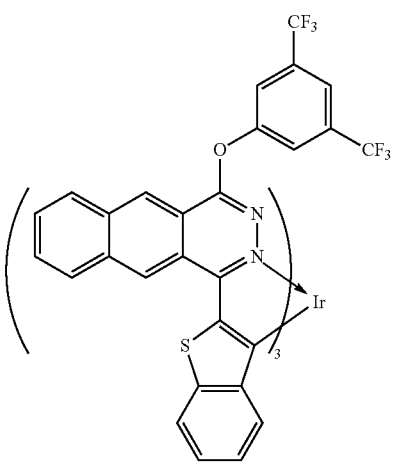
CBT35

CBT36
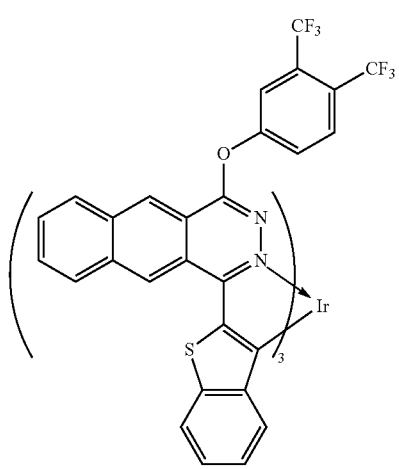
CBT37
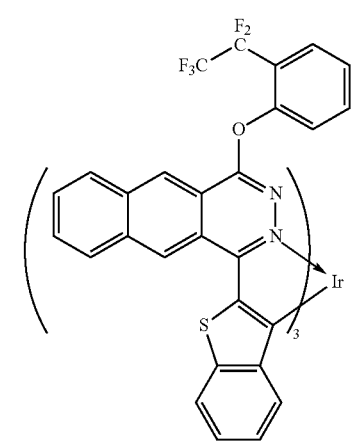
CBT38
CBT39
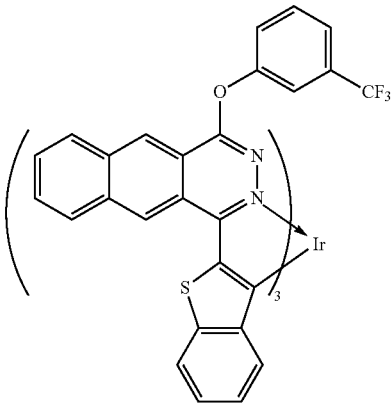
CBT40
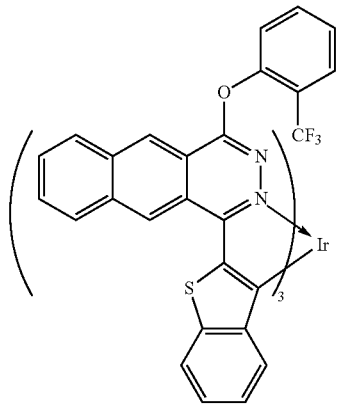
CBT41
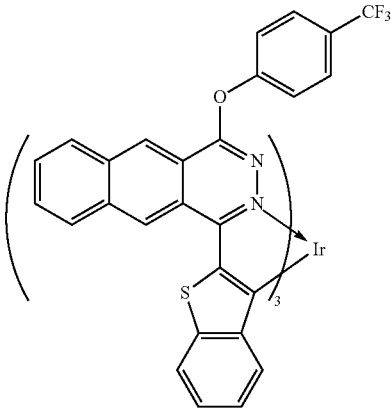
CBT42
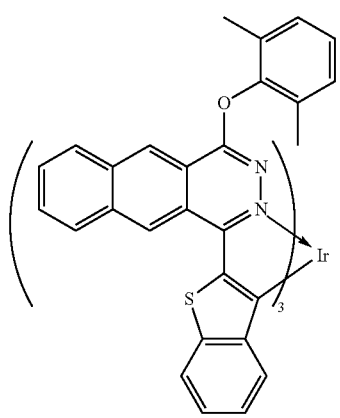

-continued
CBT47
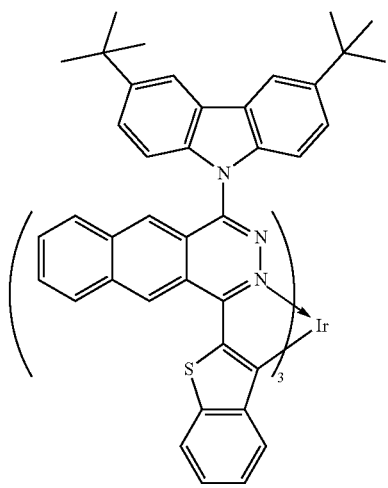
CBF2
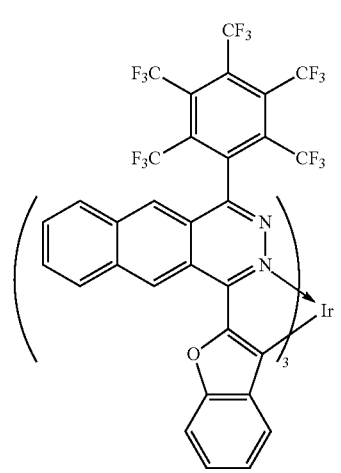
CBF3
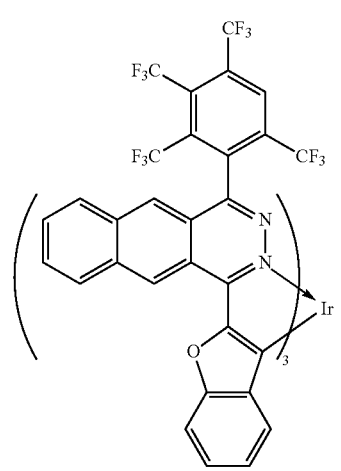
-continued
CBF4
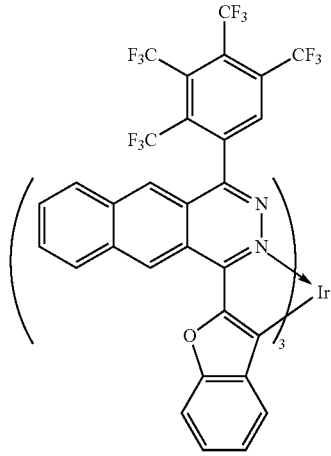
CBF5
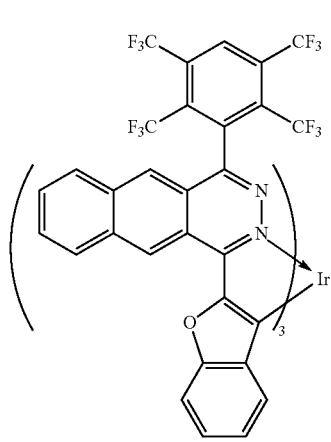
CBF6
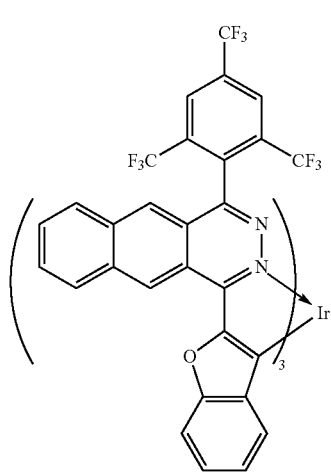

-continued
CBF7
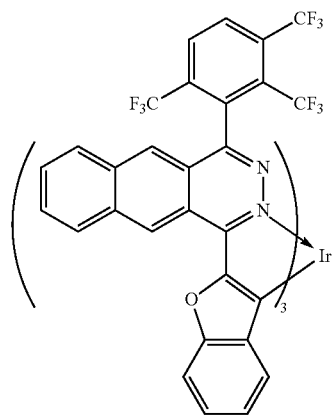
CBF8
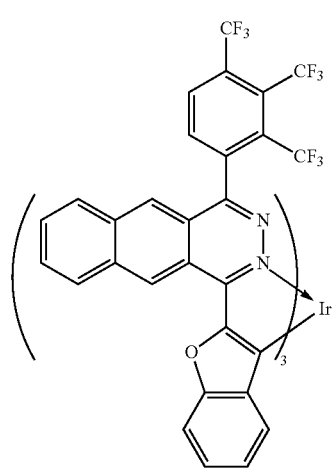
CBF9
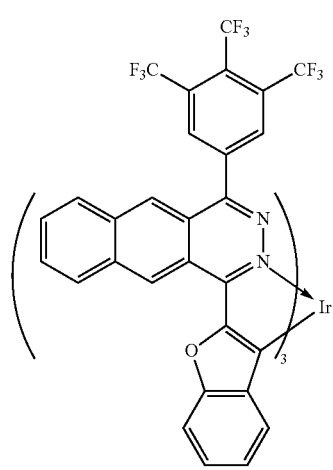
-continued
CBF10
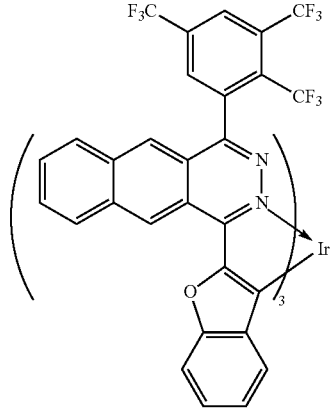
CBF11
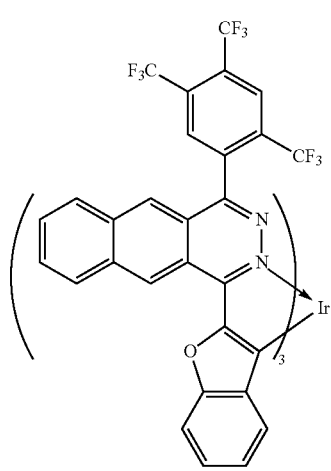
CBF12
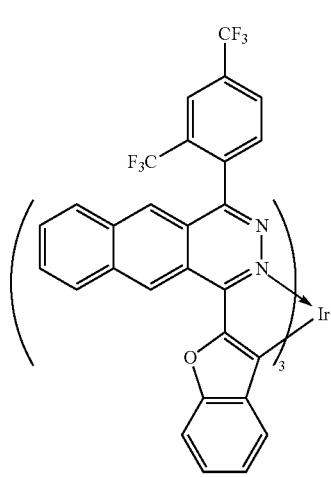

-continued
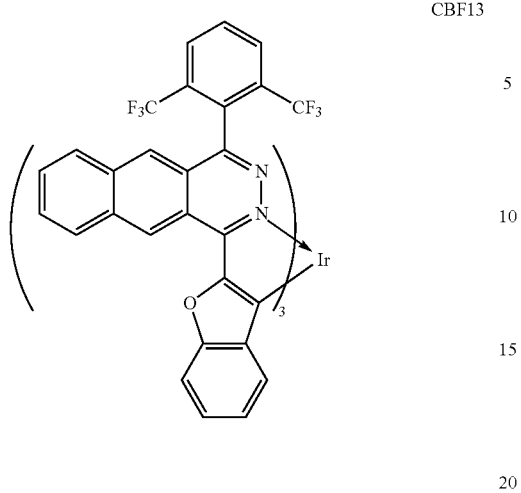
CBF13
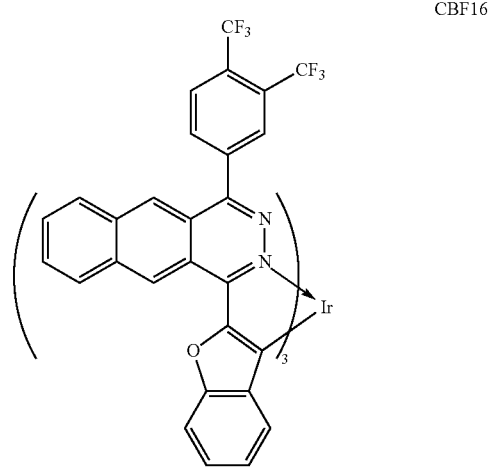
CBF16
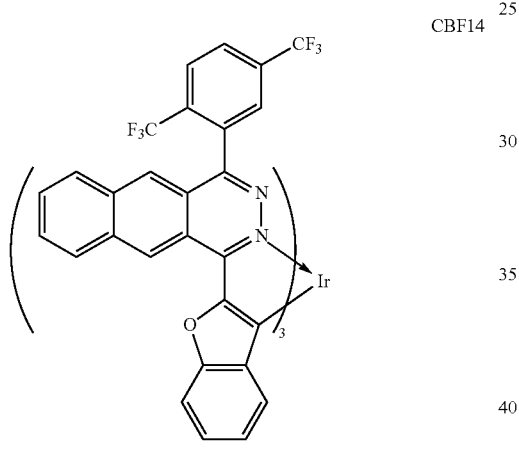
CBF14
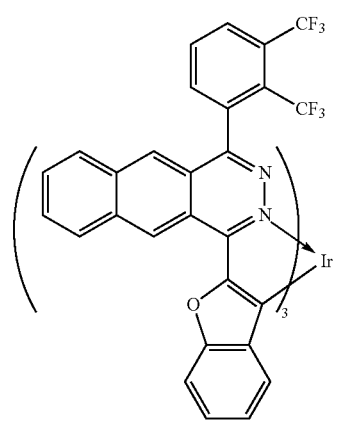
CBF17
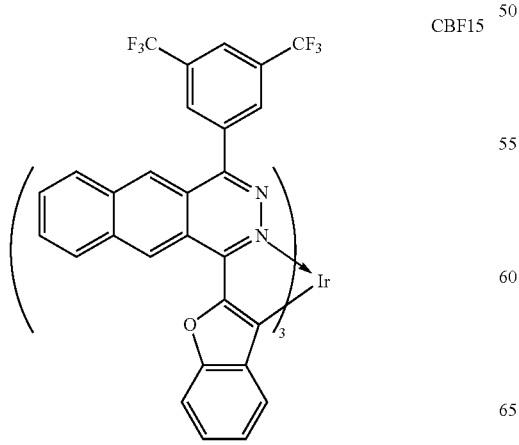
CBF15
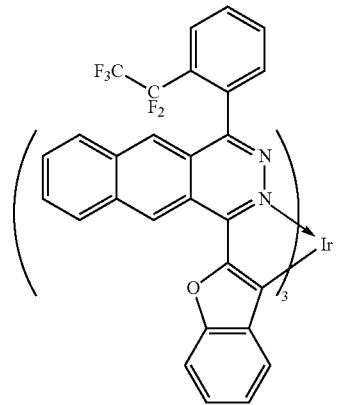
CBF18

-continued
CBF19
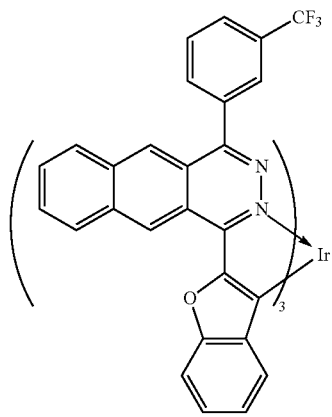
CBF20
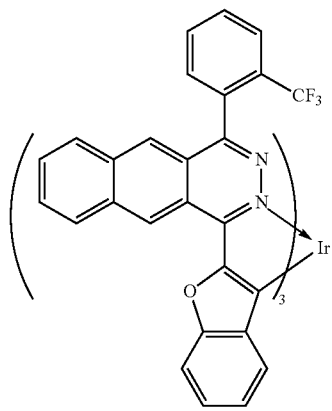
CBF21
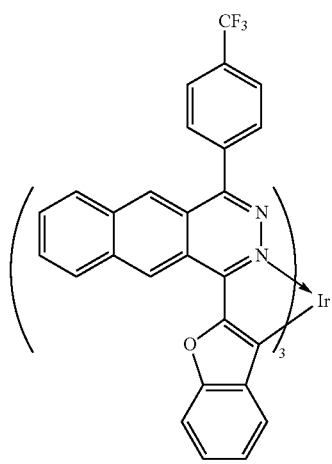
-continued
CBF22
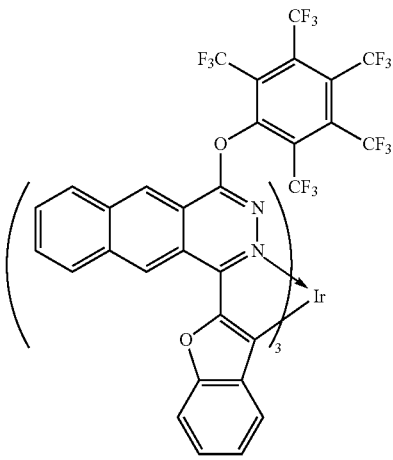
CBF23
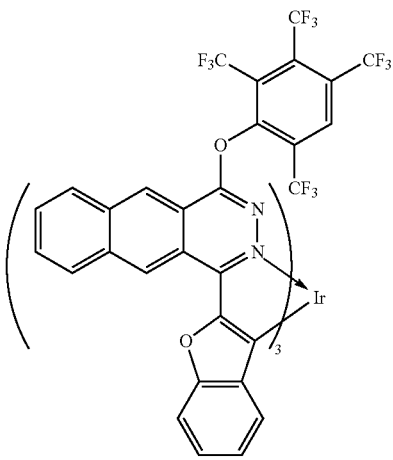
CBF24
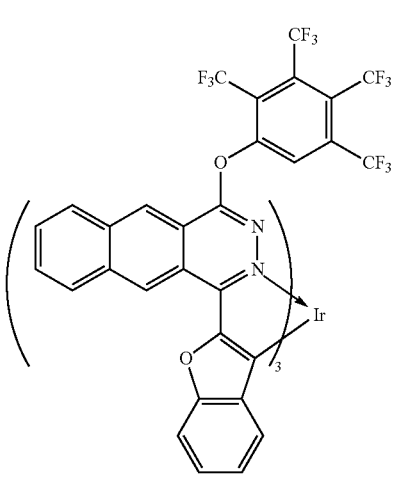

CBF25
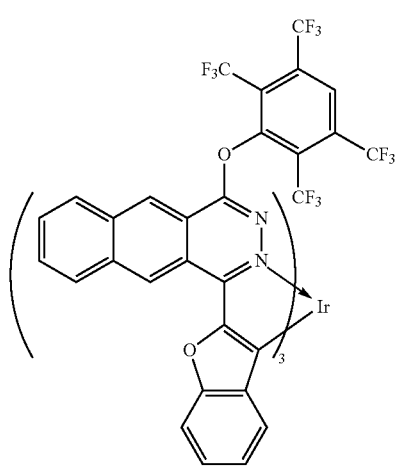
CBF26
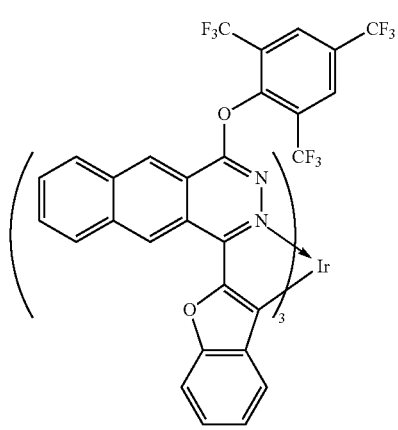
CBF27
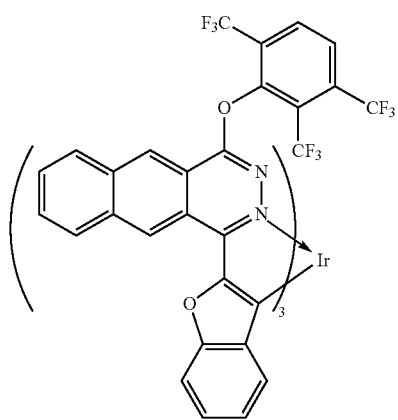
CBF28
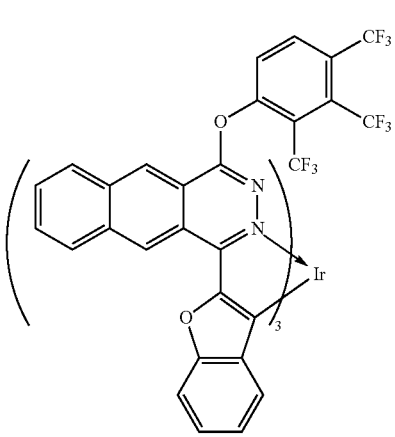
CBF29
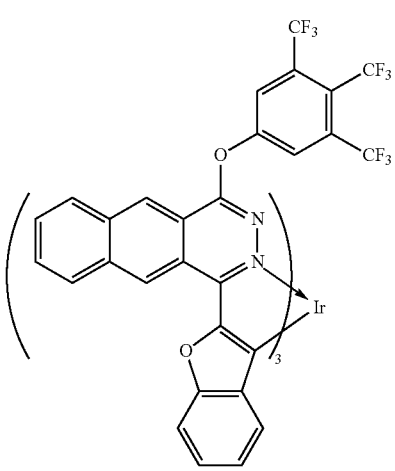
CBF30
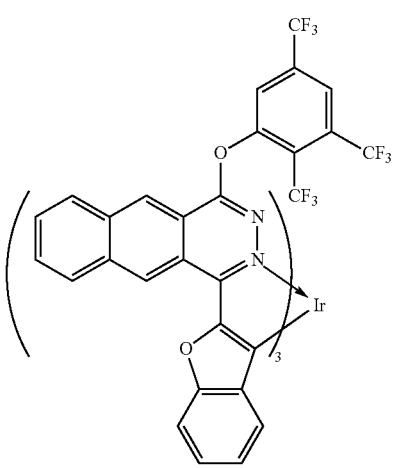

-continued
CBF31
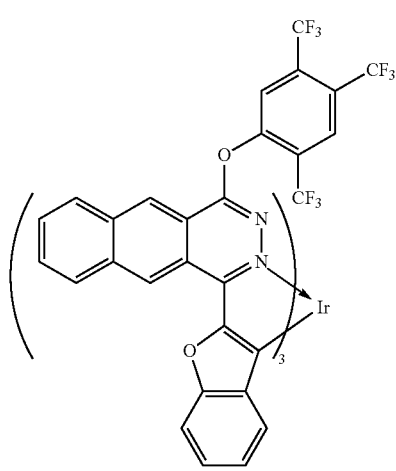
CBF32
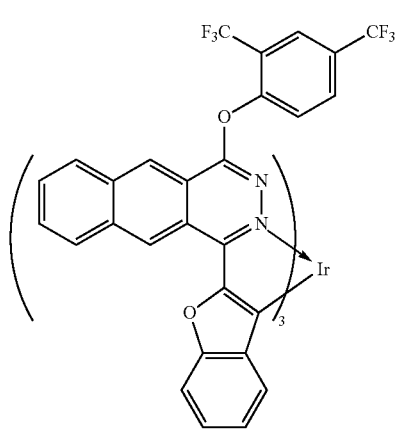
CBF33
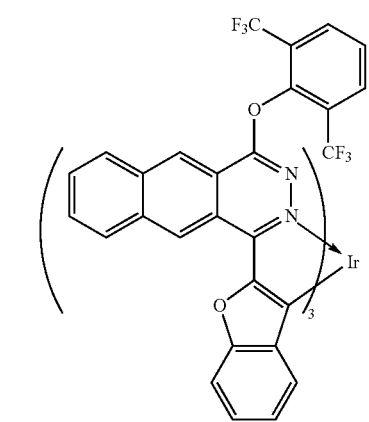
-continued
CBF34
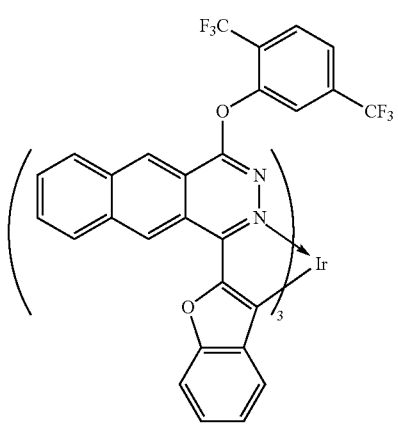
CBF35
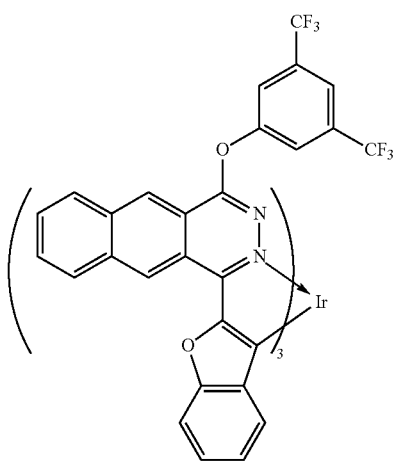
CBF36
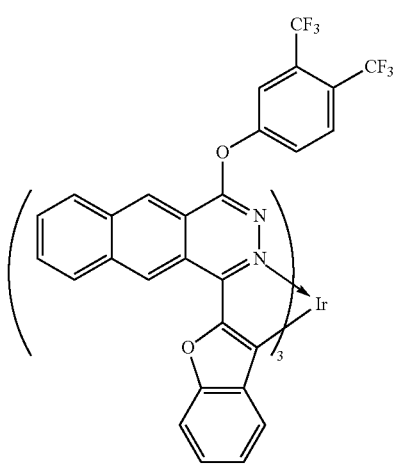

CBF37
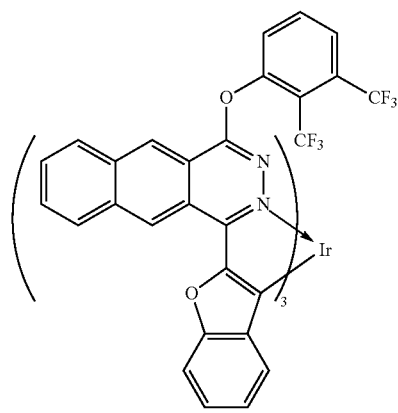
CBF38
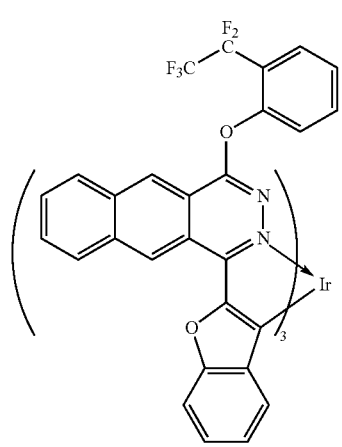
CBF39
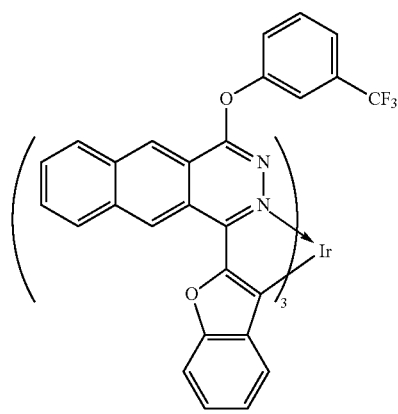
CBF40
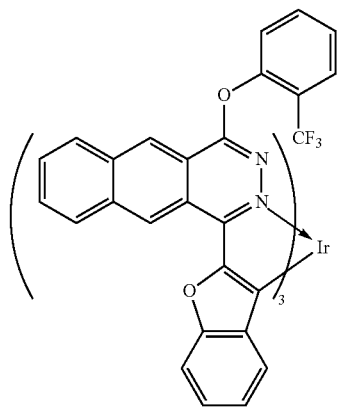
CBF41
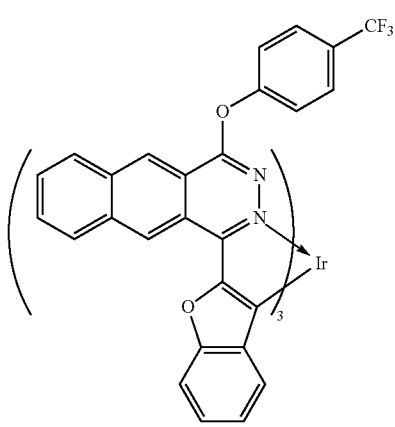
CBF42
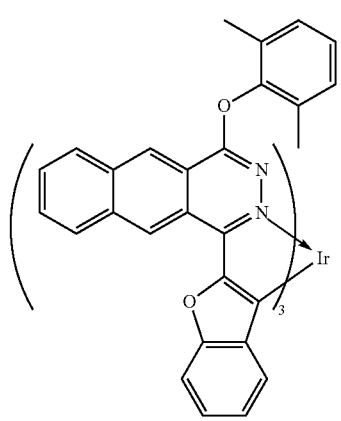

197
-continued
CBF47
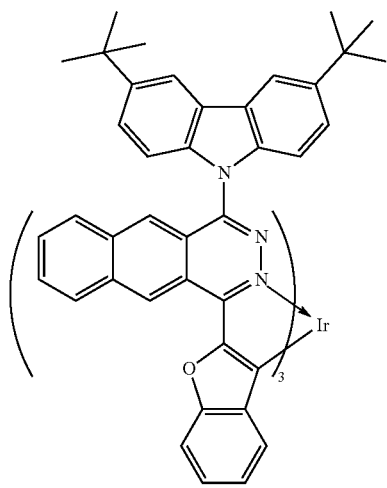
CP1
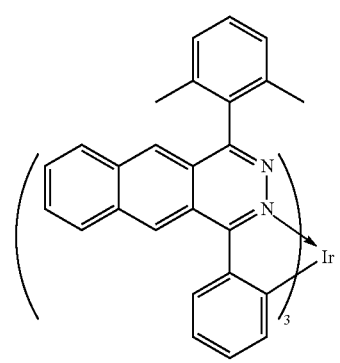
CP2
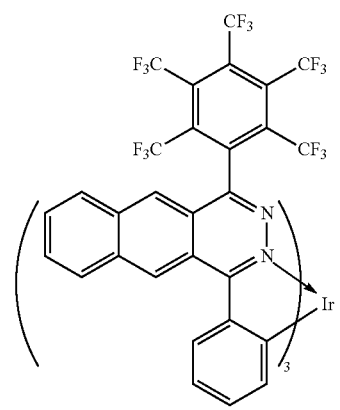
CP3
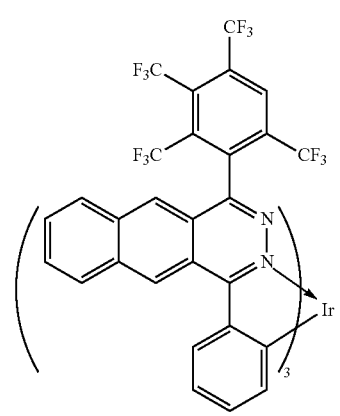
198
-continued
CP4
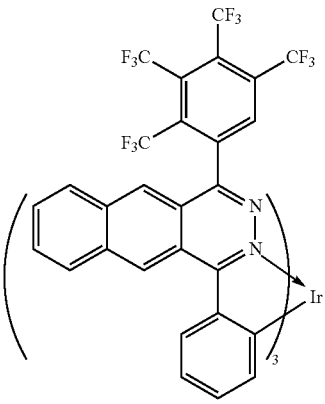
CP5
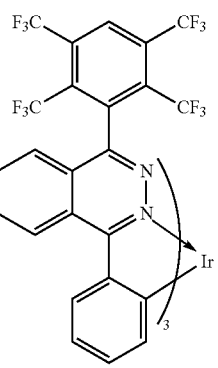
CP6
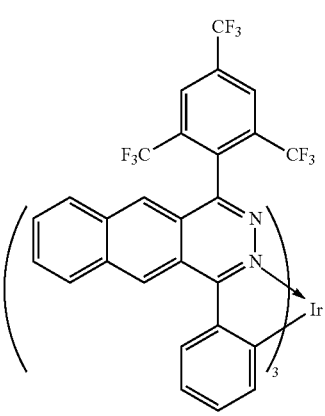
CP7
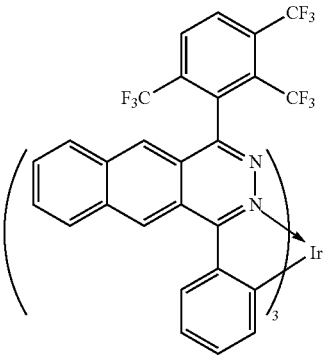

-continued
CP8
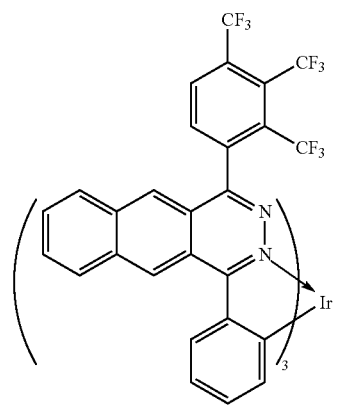
CP9
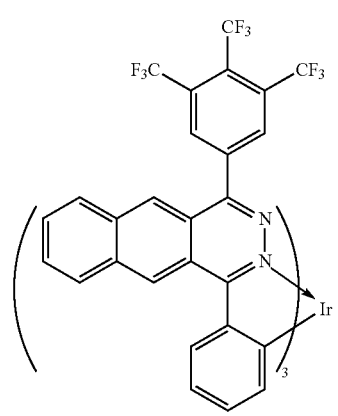
CP10
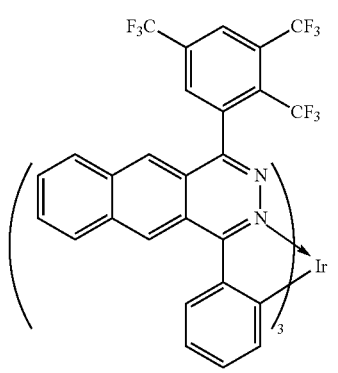
CP11
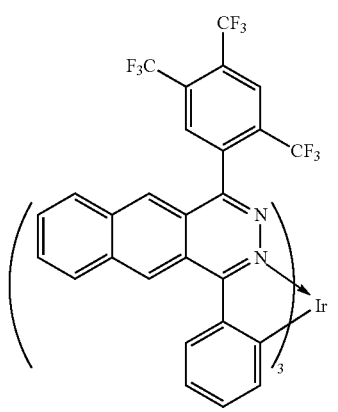
-continued
CP12
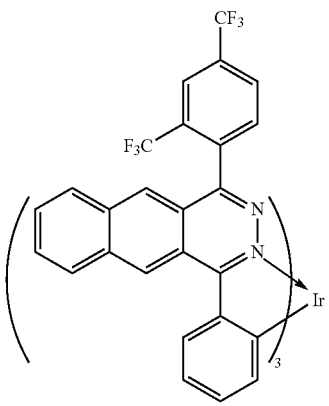
CP13
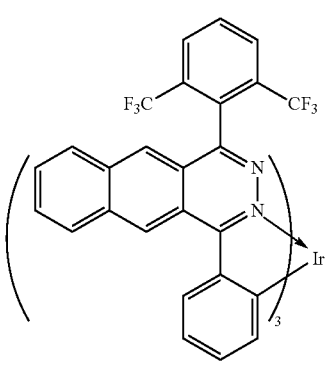
CP14
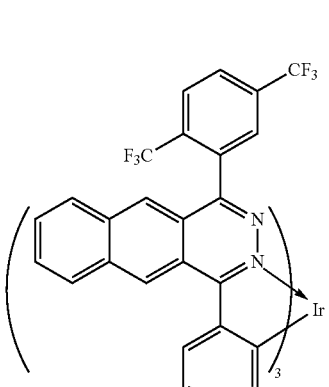
CP15
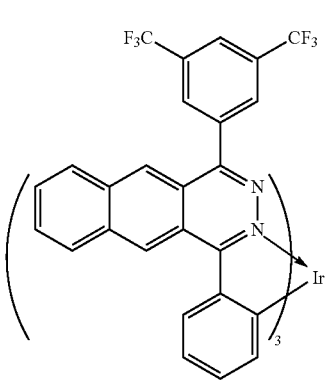

CP16
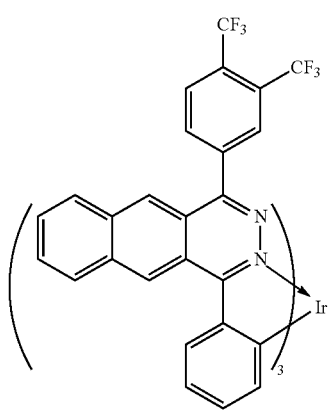
CP17
CP18
CP19
CP20
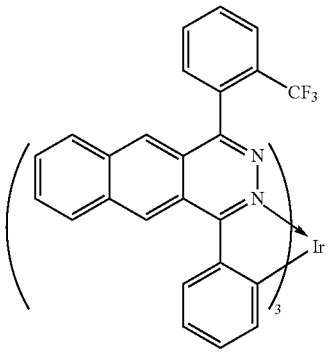
CP21
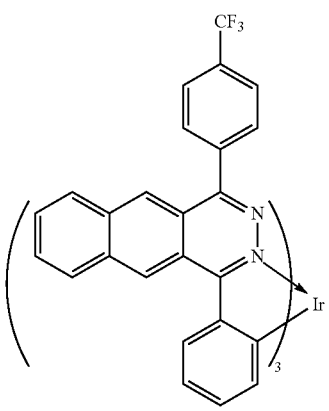
CP22
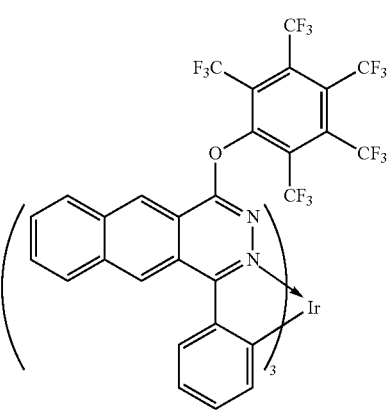
CP23
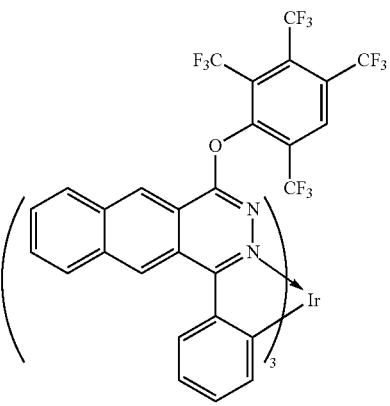

-continued
CP24
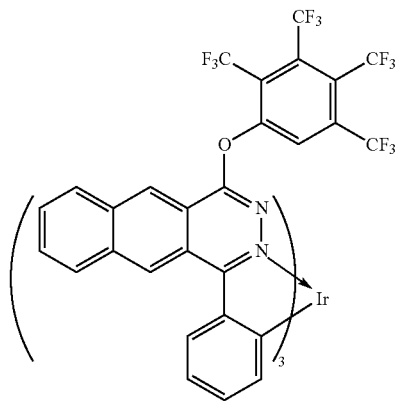
CP25
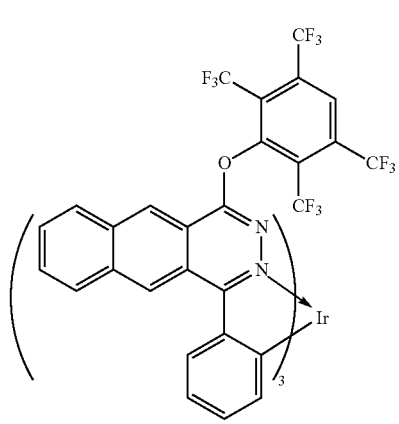
CP26
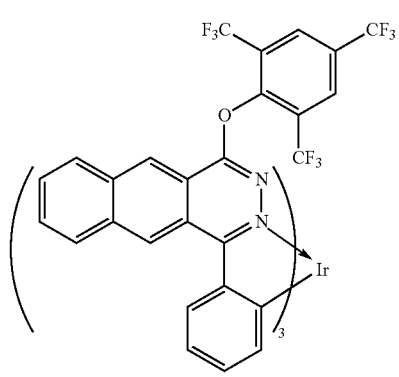
CP27
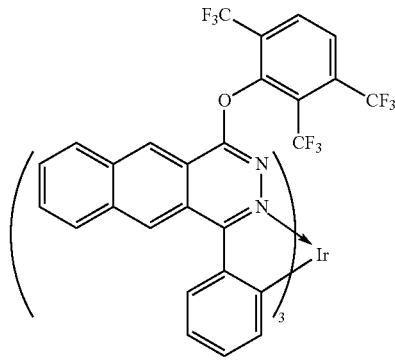
-continued
CP28
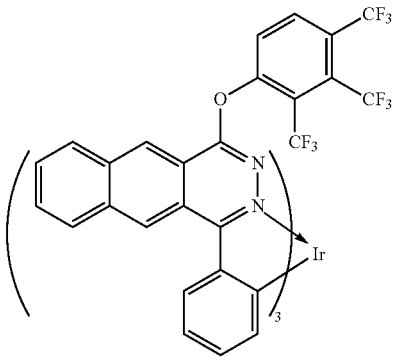
CP29
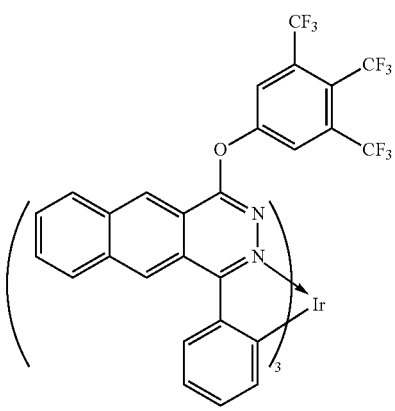
CP30
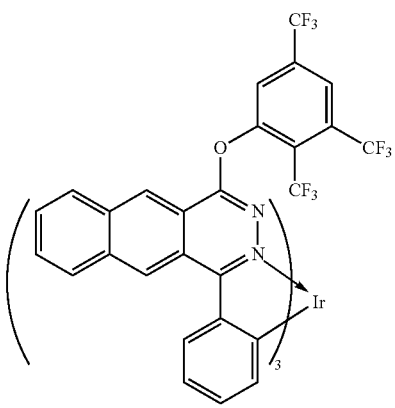
CP31
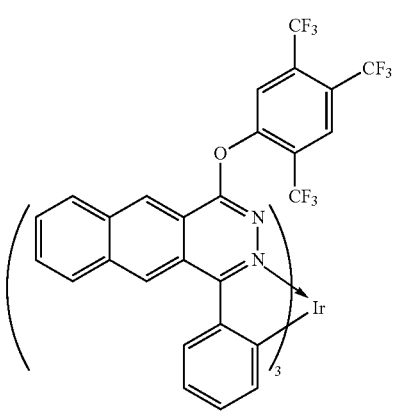

CP32
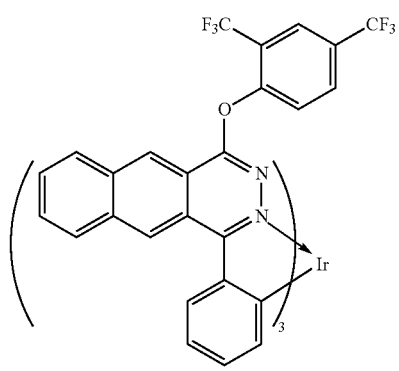
CP33
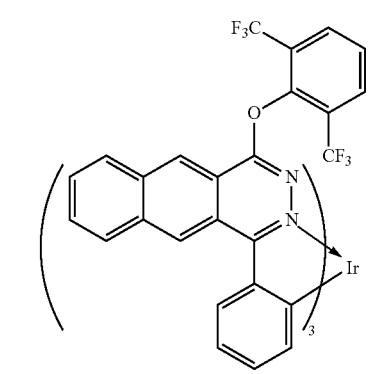
CP34
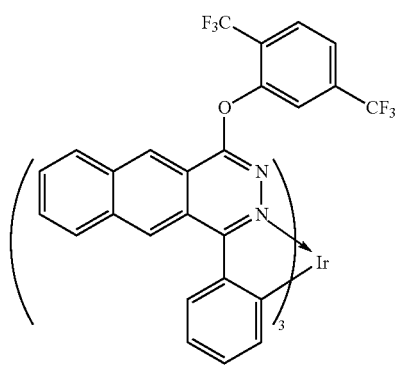
CP35
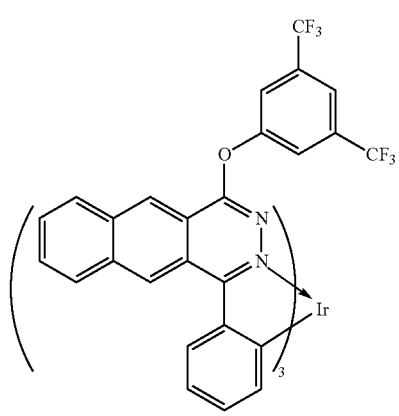
CP36
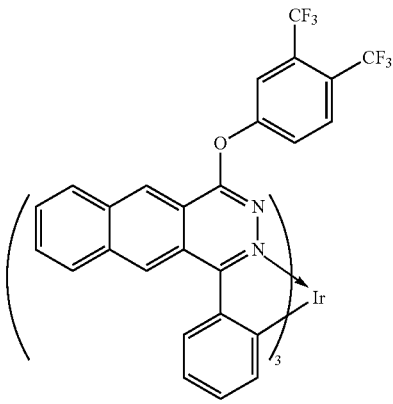
CP37
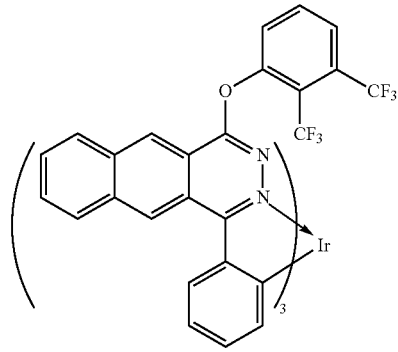
CP38
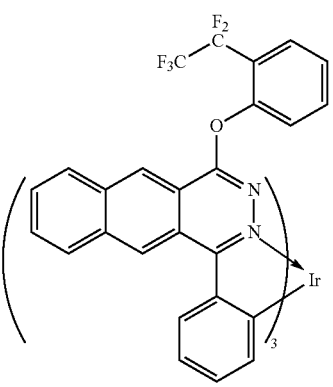
CP39
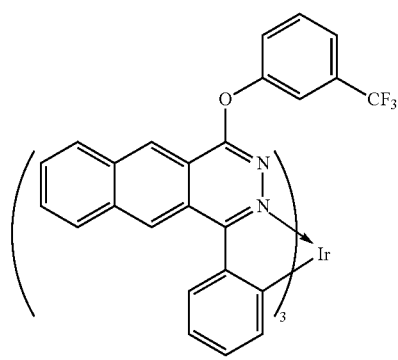

-continued
CP40
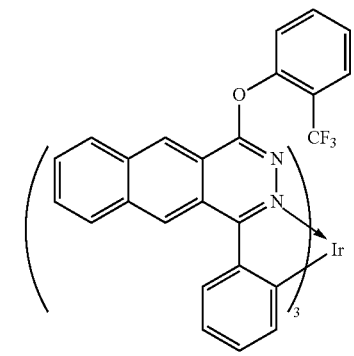
CP41
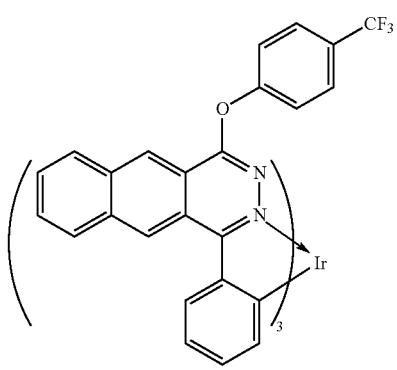
-continued
CP42
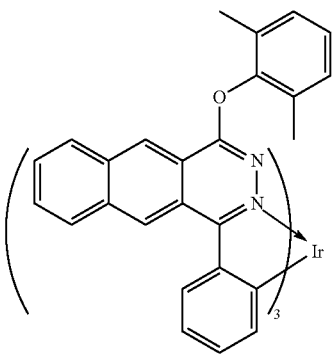
CP47
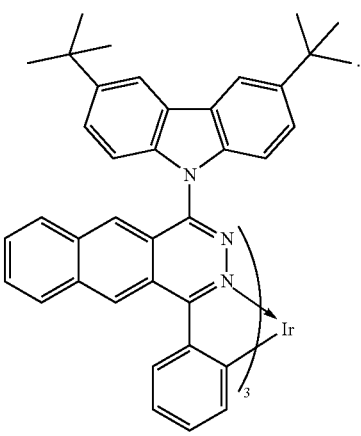
* * * * *